US010730915B2

(12) United States Patent
Gudkov et al.

(10) Patent No.: US 10,730,915 B2
(45) **Date of Patent: *Aug. 4, 2020**

(54) FLAGELLIN-BASED AGENTS AND USES INCLUDING EFFECTIVE VACCINATION

(71) Applicant: Genome Protection, Inc., Buffalo, NY (US)

(72) Inventors: Andrei V. Gudkov, Buffalo, NY (US); Vadim Mett, Buffalo, NY (US); Vadim Krivokrysenko, Buffalo, NY (US)

(73) Assignee: Genome Protection, Inc., Buffalo, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/414,403

(22) Filed: May 16, 2019

(65) Prior Publication Data

US 2019/0315810 A1 Oct. 17, 2019

Related U.S. Application Data

(63) Continuation of application No. 15/500,133, filed as application No. PCT/US2015/042887 on Jul. 30, 2015, now Pat. No. 10,336,793.

(60) Provisional application No. 62/117,366, filed on Feb. 17, 2015, provisional application No. 62/110,744, filed on Feb. 2, 2015, provisional application No. 62/031,116, filed on Jul. 30, 2014.

(51) Int. Cl.

| | |
|---|---|
| ***A61K 39/00*** | (2006.01) |
| ***A61K 49/00*** | (2006.01) |
| ***A61K 39/39*** | (2006.01) |
| ***C07K 14/195*** | (2006.01) |
| ***A61K 38/16*** | (2006.01) |
| ***A61K 39/02*** | (2006.01) |
| ***A61K 45/06*** | (2006.01) |

(52) U.S. Cl.

CPC .......... *C07K 14/195* (2013.01); *A61K 38/164* (2013.01); *A61K 39/0013* (2013.01); *A61K 39/02* (2013.01); *A61K 39/39* (2013.01); *A61K 45/06* (2013.01); *A61K 2039/55505* (2013.01); *A61K 2039/55516* (2013.01); *A61K 2039/55583* (2013.01); *A61K 2039/55594* (2013.01); *A61K 2039/57* (2013.01); *A61K 2039/575* (2013.01); *C07K 2319/00* (2013.01); *C07K 2319/21* (2013.01); *Y02A 50/388* (2018.01); *Y02A 50/39* (2018.01); *Y02A 50/466* (2018.01); *Y02A 50/484* (2018.01)

(58) Field of Classification Search

CPC ......... A61K 39/00; A61K 49/00; A61K 39/39
USPC ......................... 424/9.2, 184.1, 185.1, 234.1
See application file for complete search history.

(56) References Cited

U.S. PATENT DOCUMENTS

| | | | |
|---|---|---|---|
| 4,554,101 | A | 11/1985 | Hopp |
| 5,399,494 | A | 3/1995 | Kaper et al. |
| 5,693,476 | A | 12/1997 | Scheller |
| 6,130,082 | A | 10/2000 | Majarian et al. |
| 7,404,963 | B2 | 7/2008 | Sotomayor et al. |
| 7,638,485 | B2 | 12/2009 | Gudkov |
| 7,794,731 | B2 | 9/2010 | Mizel et al. |
| 8,007,812 | B2 | 8/2011 | Gudkov et al. |
| 8,106,005 | B2 | 1/2012 | Gudkov |
| 8,287,882 | B2 | 10/2012 | Gudkov et al. |
| 8,324,163 | B2 | 12/2012 | Gudkov et al. |
| 8,580,321 | B2 | 11/2013 | Gudkov et al. |
| 2002/0009747 | A1 | 1/2002 | Miller et al. |
| 2003/0044429 | A1 | 3/2003 | Aderem et al. |
| 2005/0147627 | A1 | 7/2005 | Aderem et al. |
| 2005/0266391 | A1 | 12/2005 | Bennett et al. |
| 2006/0275255 | A1 | 12/2006 | Gudkov |
| 2007/0202551 | A1 | 8/2007 | Gudkov |
| 2007/0269406 | A1 | 11/2007 | Ichim |
| 2008/0124361 | A1 | 5/2008 | Mizel et al. |
| 2008/0182797 | A1 | 7/2008 | Nudler et al. |
| 2009/0011982 | A1 | 1/2009 | Gudkov et al. |
| 2009/0081157 | A1 | 3/2009 | Kornbluth et al. |
| 2009/0123467 | A1 | 5/2009 | Bedi et al. |
| 2009/0175880 | A1 | 7/2009 | Keler et al. |
| 2009/0246303 | A1 | 10/2009 | Gudkov et al. |
| 2010/0056454 | A1 | 3/2010 | Gudkov |
| 2011/0206699 | A1 | 8/2011 | Hossain et al. |
| 2011/0319595 | A1 | 12/2011 | Gudkov et al. |
| 2012/0208871 | A1 | 8/2012 | Gudkov et al. |
| 2013/0004515 | A1 | 1/2013 | Gudkov et al. |
| 2013/0324462 | A1 | 12/2013 | Gudkov et al. |

FOREIGN PATENT DOCUMENTS

| | | |
|---|---|---|
| WO | 1992005816 | 4/1992 |
| WO | 1993018150 | 9/1993 |
| WO | 1999029312 | 6/1999 |
| WO | 2001040280 | 6/2001 |
| WO | 2001055210 | 8/2001 |
| WO | 2002044363 | 6/2002 |
| WO | 2003027251 | 4/2003 |

(Continued)

OTHER PUBLICATIONS

Coffman et al., "Vaccine Adjuvants: Putting Innate Immunity to Work," Immunity, 2010, vol. 33, No. 4, pp. 492-503.

(Continued)

*Primary Examiner* — Rodney P Swartz

(74) *Attorney, Agent, or Firm* — Morgan, Lewis & Bockius LLP

(57) ABSTRACT

The present invention relates to, in part, compositions comprising improved flagellin derived constructs and methods of using for vaccination, including adjuvants comprising flagellin-based agents.

16 Claims, 18 Drawing Sheets

Specification includes a Sequence Listing.

(56) References Cited

FOREIGN PATENT DOCUMENTS

| | | |
|---|---|---|
| WO | 2003028659 | 4/2003 |
| WO | 2004086039 | 10/2004 |
| WO | 2005056041 | 6/2005 |
| WO | 2005056042 | 6/2005 |
| WO | 2005056054 | 6/2005 |
| WO | 2005056055 | 6/2005 |
| WO | 2005057218 | 6/2005 |
| WO | 2006066214 | 6/2006 |
| WO | 2006069198 | 6/2006 |
| WO | 2007030581 | 3/2007 |
| WO | 2008157473 | 12/2008 |
| WO | 2009102818 | 8/2009 |
| WO | 2010040096 A2 | 4/2010 |
| WO | 2010133885 | 11/2010 |
| WO | 2011027222 | 3/2011 |
| WO | 2011044246 | 4/2011 |

OTHER PUBLICATIONS

International Search Report and Written Opinion, Application No. PCT/US2015/042887, dated Dec. 3, 2015, 9 pages.
Alavanja M. CR. "Biologic damage resulting from exposure to tobacco smoke from radon: implication for preventive interventions" Oncogene 21:7365-7375 (2002).
Andreassen C. N. et al. "Chemical radioprotection: a critical review of amifostine as a cytoprotector in radiotherapy" Seminars in Radiation Oncology 13(1):62-72 (2003).
Androstenediol and Androstenedione Wikipedia (online). URL: < http://en. wikipedia.org/wiki/Androstenediol> [Retrieved from the Internet: Dec. 5, 2006] 4 pages.
Bachmann M. F. et al. "Recall proliferation potential of memory CD8+ T cells and antiviral protection" The Journal of Immunology 175:4677-4685 (2005).
Ben-Yedidia T. et al. "Intranasal administration of peptide vaccine protects human/mouse radiation chimera from influenza infection" International Immunology 11(7):1043-1051 (1998).
Booth D. et. al. "Transforming growth factor-B3 protects murine small intestinal crypt stem cells and animal survival after irradiation possibly by reducing stem-cell cycling" Int. J. Cancer 86(1):53-59 (2000).
Borges H. L. et al. "DNA damage-induced cell death: lessons from the central nervous system" Cell Research 18:17-26 (2008).
Bulinski J. C. et al. "Overexpression of MAP4 inhibits organelle motility and trafficking in vivo" Journal of Cell Sciences 110:3055-3064 (1997).
Burdelya L. G. et al. "An agonist of toll-like receptor 5 has radioprotective activity in mouse and primate models" Science 320:226-230 (2008).
Cai et al. "Activation of toll-like receptor 5 on breast cancer cells by flagellin suppresses cell proliferation and tumor growth" Cancer Res 71 (7): 2466-2475 2011.
Cai et al. "Activation of toll-like receptor 5 on breast cancer cells by flagellin suppresses tumor development and growth" Cancer Res 70: #3819 Apr. 2010.
Carnes B. A. et al. "Mortality of atomic bomb survivors predicted from laboratory animals" Radiation Research 160(2):159-167 (2003) Abstract.
Caron G. et. al. "Direct stimulation of human T cells via TLR5 and TLR7/8: Flagellin and R-848 up-regulate proliferation and IFN-y production by memory CD4+ T cells" The Journal of Immunology 175(3):1551-1557 (2005).
Dummer et al. "An exploratory study of systemic administration of the toll-like receptor-7 agonist 852A in patients with refractory metastic melanoma" Clin Cancer Res 14(3): 856-864 2008.
Eaves-Pyles T. D. et al. "*Salmonella flagellin*-dependent proinflammatory responses are localized to the conserved amino and carboxyl regions of the protein" The Journal of Immunology 167(12):7009-7016 (2001).
Eaves-Pyles T. et al. "Flagellin a novel mediator of *Salmonella*-induced epithelial activation and systemic inflammation: IKBa degradation induction of nitric oxide synthase induction of proinflammatory mediators and cardiovascular dysfunction" The Journal of Immunology 166(2):1248-1260 (2001).
Efferson C. L. et al. "Stimulation of human T cells by an influenza A vector expressing a CTL epitope from the HER-2/neu protooncogene results in higher numbers of antigen-specific TCRhi cells than stimulation with peptide. Divergent roles of IL-2 and IL-15" Anticancer Research 25:715-724 (2005).
Egan L. J. et al. "IkB-kinase13-dependent NF-k13 activation provides radioprotection to the intestinal epithelium" PNAS 101(8):2452-2457 (2004).
Elewaut D. et al. "NF-KB is a central regulator of the intestinal epithelial cell innate immune response induced by infection with enteroinvasive bacteria" The Journal of Immunology 163:1457-1466 (1999).
Etter et al. "The combination of chemotherapy and intraperitoneal MegaFas ligand improves treatment of ovarian carcinoma" Gynecologic Oncol 107: 14-21 2007.
Foldes G. et al. "Toll-like receptor modulation in cardiovascular disease: a target for intervention?" Expert Opinion on Investigational Drugs 15(8):857-871 (2006).
Fukuzawa N. et al. "A TLR5 agonist inhibits acute renal ischemic failure" The Journal of Immunology 187:3831-3839 (2011).
GenBank databases NCBI Accession No. M84972 Apr. 26, 1993 [online] [retrieved on Sep. 29, 2011] Retrieved from the Internet: <URL: http://www.ncbi.nlm.nih.gov/nuccore/M84972>.
Gewirtz A.T. et. al. "Cutting edge: Bacterial flagellin activates basolaterally expressed TLR5 to induce epithelial proinflammatory gene expression" The Journal of Immunology 167(4):1882-1885 (2001).
Grdina D. J. et al. "Relationships between cytoprotection and mutation prevention by WR-1065" Military Medicine 167(2):51-53 (2002).
Guan K. L. et al. "Eukaryotic proteins expressed in *Escherichia coli*: an improved thrombin cleavage and purification procedure of fusion proteins with glutathione S-transferase" Analytical Biochemistry 192:262-267 (1991).
Gudkov A. V. et al. "The role of p53 in determining sensitivity to radiotherapy" Nat. Rev. Cancer 3:117-129 (2003).
Guicciardi et al., Life and Death by Death Receptors, FASEB J, 2009, vol. 23, No. 6, pp. 1625-1637.
Haimovitz-Friedman A. et al. "Ionizing radiation acts on cellular membranes to generate ceramide and apoptosis" J. Exp. Med. 180:525-535 (1994).
Hall "Physics and Chemisty of Radiation Absorption" Radiobiology for the Radiobiologist pp. 5-15 5th ed. Lippincott Williams and Wilkins Philadelphia PA (2000).
Herbert J. M. et al. "Involvement of u-PA in the anti-apoptotic activity of TGF-beta for vascular smooth muscle cells" FEBS Letters 413(3):401-404 (1997).
Honko A. N. et al. "Effects of flagellin on innate and adaptive immunity" Immunologic Research 33(1):83-101 (2005).
Jung C. W. et al. "Antiproliferative effect of a vitamin D3 analog EB1089 on HL-60 cells by the induction of TGF-beta receptor" Leukemia Research 23(12):1105-1112 (1999).
Kemp G. et al. "Amifostine pretreatment for protection against cyclophosphamide-induced and cisplatininduced toxicities: results of a randomized control in patients with advanced ovarian cancer" Journal of Clinical Oncolouv 14(7)2101-2112 (1996).
Krieg A.M. "Development of TLR9 agonists for cancer therapy" J Clinical Invest 117(5): 1184-1194 2007.
Kyte J. et al. "A simple method for displaying the hydropathic character of a protein" J. Mol. Biol. 157:105-132 (1982).
Lehnert B. E. et al. "A new mechanism for DNA alterations induced by alpha particles such as those emitted by radon and radon progeny" Environmental Health Perspectives 105(5):1095-1101 (1997).
Leigh et al. "A Flagellin-Derived Toll-Like Receptor 5 Agonist Stimulates Cytotoxic Lymphocyte-Mediated Tumor Immunity" PLOS ONE Jan. 2014 vol. 9 Issue 1 pp. 1-10.
Li G. et al. "A special issue on DNA damage responses and genome maintenance" Cell Research 18(1):1-2 (2008).

(56) References Cited

OTHER PUBLICATIONS

Li J. et al."Evolutionary origin and radiation of the avian-adapted non-motile salmonellae" Journal of Medical Microbiology 38(2):129-139 (1993).
McQuiston J. R. et al. "Sequencing and comparative analysis of flagellin genes fliC fljB and flpA from *Salmonella*" Journal of Clinical Microbiology 42(5):1923-1932 (2004).
Melby T. E. et al. "The symmetrical structure of structural maintenance of chromosomes (SMC) and MukB proteins: Long antiparallel coiled coils folded at a flexible hinge" The Journal of Cell Biology 142(6):1595-1604 (1998).
Mercurio F. et al. "NF-kB as a primary regulator of the stress response" Oncogene 18:6163-6171 (1999).
Murley J. S. et al. "Delayed cytoprotection after enhancement of Sod2 (MnSOD) gene expression in SA-NH mouse sarcoma cells exposed to WR-1065 the active metabolite of amifostine" Radiation Research 158(1):101-109 (2002).
Murley J. S. et al. "Delayed radioprotection by NFKB-mediated induction of Sod2 (MnSOD) in SA-NH tumor cells after exposure to clinically used thiol-containing drugs" Radiation Research 162(5):536-546 (2004).
Mutlu-Turkoglu U. et al. "The effect of selenium and/or vitamin E treatments on radiation-induced intestinal injury in rats" Life Sciences 66(20):1905-1913 (2000).
Neish A. S. "TLRS in the Gut. II. Flagellin-induced inflammation and antiapoptosis" American Journal of Physiology: Gastrointestinal and Liver Physiology 292(2):G462-G466 (2006).
Newton S. M. C. et al. "Immune response to cholera toxin epitope inserted in *Salmonella flagellin*" Science 244:70-72 (1989).
Offringa "Tumour immunology—Exploitation of the weapon of immune destruction for cancer therapy: taking aim before firing" Current Opinion in Immunology 2005 17:159-162.
Panda D. et al. "Stabilization of microtubule dynamics by estramustine by binding to a novel site in tubulin: A possible mechanistic basis for its antitumor action" Proc. Natl. Acad. Sci. USA 94(20):10560-10564 (1997).
Pashenkov et al. "Phase II trial of a toll-like receptor 9-activating oligonucleotide in patients with metastic melanoma" J Clin Oncol 24: 5716-5724 2006.
Patchen M. L. "Amifostine plus granulocyte colony-stimulating factor therapy enhances recovery from supralethal radiation exposures: preclinical experience in animals models" European Journal of Cancer 31A(1):S17-521 (1995).
Rensing-Ehl et al., Local Fas/APO-1 )(CD95) Ligand-Mediated Tumor Cell Killing in vivo, Eur J Immunol, 1995, vol. 25, pp. 2253-2258.
Rhee et al. "Toll-like receptor 5 engagement modulates tumor development and growth in a mouse xenograft model of human colon cancer" Gastroenterology Aug. 2008; 135(2): 518-528.
Samatey F. A. et al. "Structure of the bacterial flagellar protofilament and implications for a switch for supercoiling" Nature 410:331-337 (2001).
Satyamitra M. et al. "In vivo postirradiation protection by a vitamin E analog a-TMG" Radiation Research 160(6):655-661 (2003).
Schmidt et al. "Intratumoural injection of the toll-like receptor-2/6 agonist 'macrophage-activating lipopeptide-2' in patients with pancreatic carcinoma: a phase I/II trial" Brit J Cancer 97: 598-604 2007.
Sebastiani G. et. al. "Cloning and characterization of the murine Toll-like Receptor 5 (Tlr5) gene: sequence and mRNA expression studies in *Salmonella*-susceptible MOLF/Ei mice" Genomics 64(3):230-240 (2000).
Seed T. et al. "New strategies for the prevention of radiation injury: possible implications for countering radiation hazards of long-term space travel" Journal of Radiation Research 43:S239-S244 (2002).
Selander R. K. et al. "Molecular evolutionary genetics of the cattle-adapted serovar *Salmonella dublin*" Journal of Bacteriology 174(11):3587-3592 (1992).
Service R. F. "Tumor-Killer Made; How Does It Work?" Science 274:2009 (1996).
Sfondrini et al. "Antitumor Activity of the TLR-5 Ligand Flagellin in Mouse Models of Cancer" The Journal of Immunology 2006 176:6624-6630.
Smith K. D. et al. "Toll-like receptor 5 recognizes a conserved site on flagellin required for protofilament formation and bacterial motility" Nature Immunology 4(12):1247-1253 (2003).
Song et al. "Flagellin promotes the proliferation of gastric cancers via the Toll-like receptor 5" Int J Mol Med 28:115-119 2011.
Spadaro J. A. et al. "Radioprotectant combinations spare radiation-induced damage to the physis more than fractionation alone" Int. J. Radiat. Biol. 81(10):759-765 (2005) Abstract.
Sredni B. et al. "The immunomodulator AS101 administered orally as a chemoprotective and radioprotective agent" Int. J. Immunopharmacol. 14(4):613-619 (1992).
Streeter P. R. et al. "Activation of the G-CSF and Flt-3 receptors protects hematopoietic stem cells from lethal irradiation" Experimental Hematology 31(11):1119-1125 (2003).
Symon Z. et al. "Selective radioprotection of hepatocytes by systemic and portal vein infusions of amifostine in a rat liver tumor model" Int. J. Radiation Oncology Biol. Phys. 50(2):473-478 (2001).
Tallant T. et al. "Flagellin acting via TLR5 is the major activator of key signaling pathways leading to NF-KB and proinflammatory gene program activation in intestinal epithelial cells" BMC Microbiology 4(1):33 (2004).
Timmer et al. "Fas receptor-mediated apoptosis: a clinical application?" J Pathol 196: 125-134 2002.
Trauth et al. "Monoclonal antibody-mediated tumor regression by induction of apoptosis" Science 245: 301-305 1989.
Tsujimoto H. et al. "Flagellin enhances NK cell proliferation and activation directly and through dendritic cell—NK cell interactions" Journal of Leukocyte Biology 78(4):888-897 (2005).
Vasquez R. J. et al. "Nanomolar concentrations of nocodazole alter microtubule dynamic instability in vivo and in vitro" Molecular Biology of the Cell 8(6):973-985 (1997).
Vijay-Kumar et al. "Flagellin Treatment Protects against Chemicals Bacteria Viruses and Radiation" The Journal of Immunology 2008 180:8280-8285.
Waddick K. G. et al. "In vitro and in vivo antileukemic activity of B43-pokeweed antiviral protein against radiation-resistant human B-cell precursor leukemia cells" Blood 86(11):4228-4233 (1995).
Watson A. J. et al. "Lessons from genetically engineered animal models. VII. Apoptosis in intestinal epithelium: lessons from transgenic and knockout mice" Am. J. Physiol. Gastrointest. Liver Physiol. 278(1):G1-G5 (2000).
Wheeler C. M. "Preventative vaccines for cervial cancer" Salud Publica de Mexico 39(4) (1997) 9 pages.
Whitnall M. H. et al. "In vivo radioprotection by 5-androstenediol: stimulation of the innate immune system" Radiation Research 156(3):283-293 (2001).
Wolska et al. "Toll-like receptors and their role in carcinogensis and anti-tumor treatment" Cell Mol Biol Letters 14:248-272 2009.
Wong G. H. W. "Protective roles of cytokines against radiation: induction of mitochondrial MnSOD" Biochimica et Biophysica Acta 1271:205-209 (1995).
Yang et al. "Antigen replacement of domains D2 and D3 in flagellin promotes mucosal IgA production and attenuates flagellin-induced inflammatory response after intranasal immunization" Human Vaccines and Immunotherap 9:5 1084-1092 2013.

FIG. 1A

```
                 |         |         |         |         |         |         |
Q53970    1 MAQVINTNSLSLLTQNNLNKSQSSLSSAIERLSSGLRINSAKDDAAGQAIANRFTSNIKGLTQASRNAND
P72151    1 MALTVNTNIASLNTQRNLNASSNDLNTSLQRLTTGYRINSAKDDAAGLQISNRLSNQISGLNVATRNAND
Q5X5M6    1 MAQVINTNVASLTAQRNLGVSGNMMQTSIQRLSSGLRINSAKDDAAGLAISQRMTAQIRGMNQAVRNAND
Q6VMV6    1 MAQVINTNSLSLLTQNNLNKSQSSLSSAIERLSSGLRINSAKDDAAGQAIANRFTANIKGLTQASRNAND
P13713    1 MAQVINTNSLSLMAQNNLNKSQSSLGTAIERLSSGLRINSAKDDAAGQAISNRFTANIKGLTQASRNAND
Q93RK8    1 --MRINHNIAALNTSRQLNAGSNSAAKNMEKLSSGLRINRAGDDAAGLAISEKMRSQIRGLDMASKNAQD
Q02551    1 --MKVNTNIISLKTQEYLRKNNEGMTQAQRRLASGKRINSSLDDAAGLAVVTRMNVKSTGLDAASKNSSM
Q09012    1 MAQVINTNSLSLLTQNNLNKSQSSLSSAIERLSSGLRINSAKDDAAGQAIANRFTANIKGLTQASRNAND
Q8GNT8    1 MAQVINTNSLSLMAQNNLNKSQSALGTAIERLSSGLRINSAKDDAAGQAISNRFTANINGLTQASRNAND
Q9FAE7    1 MASTINTNVSSLTAQRNLSLSQSSLNTSIQRLSSGLRINSAKDDAAGLAISERFTSQIRGLNQAVRNAND
Q8ZF76    1 MA-VINTNSLSLLTQNNLNKSQSSLGTAIERLSSGLRINSAKDDAAGQAIANRFTSNIKGLTQAARNAND
Q7N5J4    1 MAQVINTNSLSLLTQNNLNRSQGTLGSAIERLSSGLRINSAKDDAAGQAIANRFTANVRGLTQAARNAND
O33578    1 -MTTINTNIGAIAAQANMTKVNDQFNTAMTRLSTGLRINAAKDDAAGMAIGEKMTAQVMGLNQAIRNAQD
Q56826    1 MASVINTNDSALLAQNNLTKSKGILGSAIERLSSGLRINSAKDDAAGQAIANRFTANVKGLTQAARNAND
P42273    1 MAQVINTNYLSLVTQNNLNRSQSALGNAIERLSSGMRINSAKDDAAGQAIANRFTSNINGLTQASRNAND
O31059    1 --MVVQHNMQAANASRMLGITTGDQSKSTEKLSSGFKINRAADDAAGLSISEKMRKQIRGLDQASTNASD
Q7VZC2    1 MAAVINTNYLSLVAQNNLNKSQSALGSAIERLSSGLRINSAKDDAAGQAIANRFTANVKGLTQAARNAND
Q9F4A4    1 --MIINHNMNALNAHRNMMGNIATAGKSMEKLSSGLRINRAGDDAAGLAISEKMRGQIRGLDQASRNAQD
Q8P9C4    1 MAQVINTNVMSLNAQRNLNTNSSSMALSIQQLSSGKRITSASVDAAGLAISERFTTQIRGLDVASRNAND
Q82UA3    1 MPQVINTNIASLNAQRNLNVSQNSLSTALQRLSSGLRINSAKDDAAGLAISERMTSQIRGMNQAARNAND
Q84IC5    1 -GFRINTNGASLNAQVNAGLNSRNLDSSLARLSSGLRINSAADDASGLAIADSLKTQANSLGQAINNAND
                 :: *  :  :                 :*::* :*. :  **:*  :    :  :  .:  *  *:.
```

C=indicates a conserved amino acid important for TLR5 activity

FIG. 1A (continued)

```
                      |        |       |        |       |        |       |
Q53970    71  GISIAQTTEGALNEINNNLQRVRELSVQATNGTNSDSDLKSIQDEIQQRLEEIDRVSNQTQFNGVKVLSQ
P72151    71  GISLAQTAEGALQQSTNILQRIRDLALQSANGSNSDADRAALQKEVAAQQAELTRISDTTTFGGRKLLDG
Q5X5M6    71  GISLAQVAEGAMQETTNILQRMRELSVQAANSTNNSSDRASIQSEISQLKSELERIAQNTEFNGQRILDG
Q6VMV6    71  GISVAQTTEGALNEINNNLQRVRELTVQATNGTNSDSDLSSIQAEITQRLEEIDRVSEQTQFNGVKVLAE
P13713    71  GISLAQTTEGALNEVNDNLQNIRRLTVQAQNGSNSTSDLKSIQDEITQRLSEINRISEQTDFNGVKVLSS
Q93RK8    69  GISLIQTSEGALNETHSILQRMSELATQAANDTNTDSDRSELQKEMDQLASEVTRISTDTEFNTKKLLDG
Q02551    71  GIDLLQTADSALSSMSSILQRMRQLAVQSSNGSFSDEDRKQYTAEFGSLIKELDHVADTTNYNNIKLLDQ
Q09012    69  GISVAQTTEGALSEINNNLQRIRELSVQATNGTNSDSDLNSIQDEITQRLSEIDRVSNQTQFNGVKVLAS
Q8GNT8    71  GISLAQTTEGALNEVNDNLQNIRRLTVQAQNGSNSSSDLQSIQDEITQRLSEIDRISQQTDFNGVKVLSK
Q9FAE7    71  GISLAQTAEGALKSTGDILQRVRELAVQSANATNSSGDRKAIQAEVGQLLSEMDRIAGNTEFNGQKLLDG
Q8ZF76    70  GISIAQTTEGSLNEINNNLQRVRELTVQAQNGSNSSSDLDSIQDEISLRLAEIDRVSDQTQFNGKKVLAE
Q7N5J4    71  GISIAQTTEGALNEINTNLQRIRELTVQSQNGSNSESDIKSIQEEVTQRLKEIDRISEQTQFNGVRVLRE
O33578    70  GKNLVDTTEGAHVEVSSMLQRLRELAVQSSNDTNTAADRGSLAAEGKQLIAEINRVAESTTFNGMKVLDG
Q56826    71  GISIAQTTEGALNEINNNLQRIRELTVQSENGSNSKSDLDSIQKEVTQRLEEIDRISTQTQFNGIKVLNG
P42273    71  GISVSQTTEGALNEINNNLQRIRELTVQAKNGTNSNSDINSIQNEVNQRLDEINRVSEQTQFNGVKVLSG
O31059    69  GISAVQTAEGALTEVHSMLQRMNELAVQAANGTNSESDRSSIQDEINQLTTEIDRVAETTKFNETYLLKG
Q7VZC2    71  GISIAQTTEGALNEINNNLQRIRELTVQASNGTNSASDIDSIQQEVNQRLEEINRIAEQTDFNGIKVLKS
Q9F4A4    69  GISLIQTAEGALAETHSILQRMRELSVQSANDTNVAVDRTAIQDEINSLTEEINRISGDTEFNTQKLLDG
Q8P9C4    71  GISLAQTAEGAMVEIGNNLQRIRELSVQSANATNSATDREALNSEVKQLTSEIDRVANQTSFNGTKLLNG
Q82UA3    71  GISLAQTAEGALVEIGNNLQRIRELAVQSANATNSEDDREALQKEVTQLIDEIQRVGEQTSFNGTKLLDG
Q84IC5    70  ANSMLQIADKAMDEQLKILDTIKVKATQAAQDGQTAKTRAMIQGEINKLMEELDNIANTTTYNGKQLLSG
                           *         *              *     *. .   *.    .*
                              CCC  C C  C           C
```

C=indicates a conserved amino acid important for TLR5 activity

FIG. 1A (continued)

```
                         |                        |       |                |
Q53970  141  DNQ-MK--IQVGANDG---------------ETITIDLQ----------KID-VKSLG----LDGFN
P72151  141  SFGTTS--FQVGSNAY---------------ETIDISLQNASASAIGSYQVG-SNGAGTVASVAGTA
Q5X5M6  141  SFSGAS--FQVGANSN---------------QTINFSIG----------SIK-ASSIGGIATATGTE
Q6VMV6  141  NNE-MK--IQVGANDG---------------ETITINLA----------KID-AKTLG----LDGFN
P13713  141  DQK-LT--IQVGANDG---------------ETTDIDLK----------KID-AKQLG----MDTF-
Q93RK8  139  TAQNLT--FQIGANEG---------------QTMSLSIN----------KMD-SE---------SLK
Q02551  139  TATGAATQVSIQASDKAN-------------DLINIDLFNAKGLSAGTITLGSGSTVAGYSALSVAD
Q09012  141  DQT-MK--IQVGANDG---------------ETIEIALD----------KID-AKTLG----LDNFS
Q8GNT8  141  DQK-LT--IQVGANDG---------------ETIDIDLK----------NIN-AQSLG----LDKFN
Q9FAE7  141  SFGSAT--FQVGANAN---------------QTITATTGNFRTNNY-GAQLT-ASASG--AATSGAS
Q8ZF76  140  NTT-MS--IQVGANDG---------------ETIDINLQ----------KID-SKSLG----LGSYS
Q7N5J4  141  DSK-MT--IQVGANDN---------------EVIDIDLK----------KID-KEALN----LGKFT
O33578  140  SFTGKQ--LQIGADSG---------------QTMAINVDSAAATDIGAHKISSASTVVADAALTDTT
Q56826  141  DVTEMK--IQVGANDN---------------ETIGIKLG----------KIN-SEKLN----LKEFS
P42273  141  EKSKMT--IQVGTNDN---------------EVIEFNLD----------KID-NDTLG----VASDK
O31059  139  GNGDRT--VRVYAHDAGLVGSLSQNTTKATFQMRKLEIGDSYTIGGTTYKIG-AETVK--EAMTALK
Q7VZC2  141  NATDMTLSIQVGAKDN---------------ETIDIKID----------RNS-NWNLY----DAVGT
Q9F4A4  139  GFKG-E--FQIGANSN---------------QTVKLDIG----------NMS-AA---------SLG
Q8P9C4  139  DFSGAL--FQVGADAG---------------QTIGINS---------IVDAN-VDSLG--KANFAAS
Q82UA3  141  SFASQI--FQVGANEG---------------ETIDFTD-----------------------------
Q84IC5  140  SFSNAQ--FQIGDKAN---------------QTVNATIG----------STN-SAKVGQTRFETGAV
```

C=indicates a conserved amino acid important for TLR5 activity

FIG. 1B

```
                  |         |           |         |         |           |         |         |         |
Q53970    410     PLASIDSALSKVDAVRSSLGAIQNRFDSAITNLGNTVTNLNSARSRIEDADYATEVSNMSKAQILQQAGTSVLAQANQVPQNVLSLLR--
P72151    401     AIAVVDNALAAIDAQRADLGAVQNRFKNTIDNLTNISENATNARSRIKDTDFAAETAALSKNQVLQQAGTAILAQANQLPQAVLSLLR--
Q5X5M6    387     AIKRIDAALNSVNSNRANMGALQNRFESTIANLQNVSDNLSAARSRIQDADYAAEMASLTKNQILQQAGTAMLAQANSLPQSVLSLLGR-
Q6VMV6    400     PLETIDKALAKVDNLRSDLGAVQNRFDSAITNLGNTVNNLSSARSRIRDADYATEVSNMSRAQILQQAGTSVLAQANQTTQNVLSLLQG-
P13713    264     PLATLDKALAQVDGLRSSLGAVQNRFDSVINNLNSTVNNLSASQSRIQDADYATEVSNMSRANILQQAGTSVLAQANQSTQNVLSLLR--
Q93RK8    245     ALTTIXTAIDTVSSERAKLGAVQNRLEHTINNLGTSSENLTSABSRIRDVDMASEMMEYTKNNILTQASQAMLAQANQQPQQVLQLLKG-
Q02551    481     VIGLADAALTKIMKQRADMGAYYNRLEYTAKGLMGAYENMQASESRIRDADMAEEVVSLTTKQILVQSGTAMLAQANMKPNSVLKLLQQI
Q09012    437     PLSKLDEALAKVDKLRSSLGAVQNRFDSAITNLGNTVNDLSSARSRIEDADYATEVSNMSRAQILQQAGTSVLAQANQTTQNVLSLLR--
Q8GNT8    329     PLATLDKALSQVDILRSGLGAVQNRFDSVINNLNSTVNNLSASRSRIQDADYATEVSNMSRAQILQQAGTSVLAQANQSTQNVLSLLR--
Q9FAE7    405     ALKIIDAALSAVNQQRASFGALQSRFETTVNNLQSTSENMSASRSRIQDADFAAETANLSRSQILQQAGTAMVAQANQLPQGVLSLLK--
Q8ZF76    282     PLETLDDAIKQVDGLRSSLGAVQNRFESAVTNLNNTVTNLTSARSRIEDADYATEVSNMSRAQILQQAGTSVLSQANQVPQTVLSLLN--
Q7N5J4    268     PLETLDSALAQVDSLRSSLGAIQNRLESTVNNLNNTVNNLSAARSRIEDADYATEVSNMSRGQILQQAGTAVLAQAMQVPQNVMSLLR--
O33578    405     AIGVIDVALSKISQSRSELGAVSNRLDSTISNLTNISTSVQAAKSQVMDADFAAESTNLARSQILSQASTAMLAQANSSKQNVLSLLRG-
Q56826    226     PLDTLDKALAQVDDNRSSLGAVQNRLESTVNNLNNTVNNLSAARSRIEDADYAVEVSNMSRGQILQQAGTSVLAQANQVPQTVLSLLR--
P42273    280     ALATLDNAISKVDESRSKLGAIQNRFQSTINNLNNTVNNLSASRSRILDADYATEVSNMSKNQILQQAGTAVLAQANQVPQTVLSLLR--
O31059    385     AIDAISDALAKVSAQRSALGSIQNRLEHSIANLDNVVENTNAAESRIRDTDMADEMVTYSKNNILMQAGQSMLAQANQATQGVLSILQ--
Q7VZC2    304     ALSKLDDAMKAVDEQRSSLGAIQNRFESTVANLNNTITNLSAARSRIEDSDYATEVSNMTKNQILQQAGTSVLAQANQVPQNVLSLLR--
Q9F4A4    326     SIKTINSAIEQVSTQRSKLGAVQNRLEHTINNLNTSSENLTAAESRVRDVDMAKEMMAFSKNNILSQAAQAMLGQANQQPQGVLQLLR--
Q8P9C4    312     ALEIVDKALTSVNSSRADMGAVQNRFTSTLANLAATSENLTASRSRIADTDYAKTTAELTRTQILQQAGTAMLAQAKSVPQNVLSLLQ--
Q82UA3    192     ----IDDALKIVNSTRADLGAIQNRFSSAIANLQTSAENLSASRSRIQDADFAAETAALTRAQILQQAGVAMLSQANALPNNVLSLLR--
Q84IC5    403     VMDIADTAIANLDTIRANIGATQNQITSTINNISVTQVNVKAAESQIRDVDFASEKSANYSKANILAQSGSYAMAQANAASQNVLRLLQ--
                             *:  :   *: :*:  .::      .:      .     :.*:: * * *        :  ::* *:.    :.**:   : *: :*
                          CC  C     C     C     C
```

C=indicates a conserved amino acid important for TLR5 activity

FIG. 2
A.
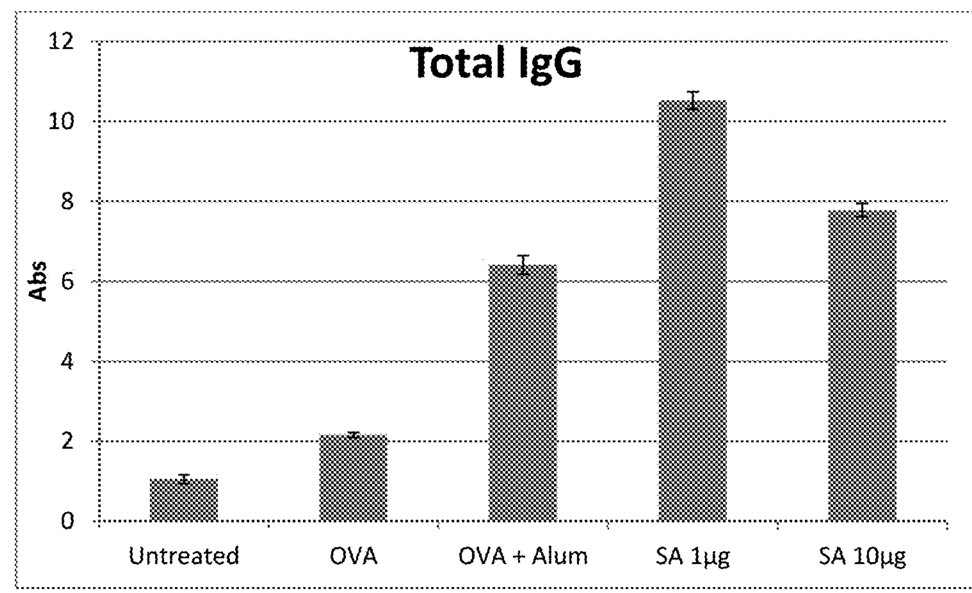
B.
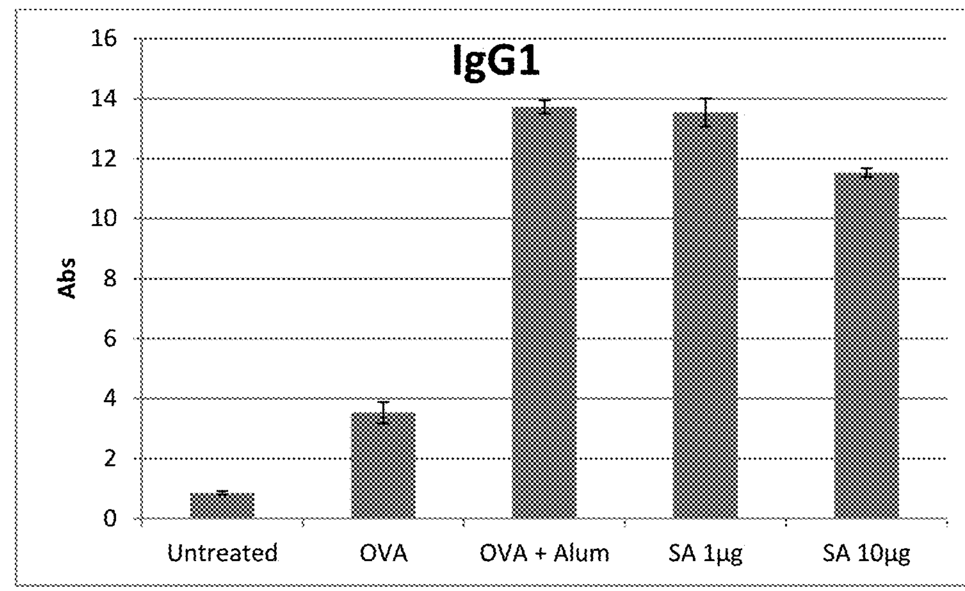

FIG. 2 (CONT.)
C.
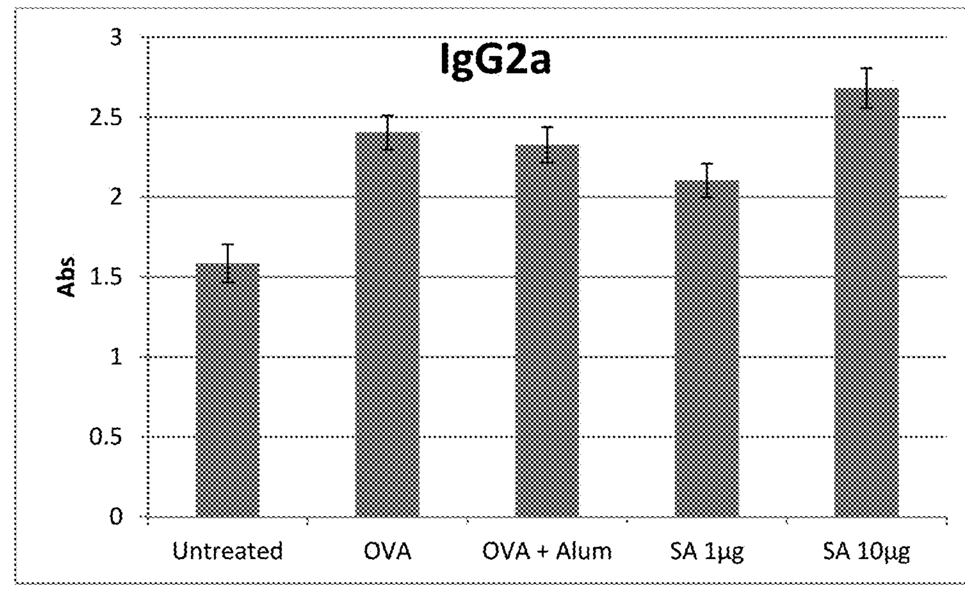
D.
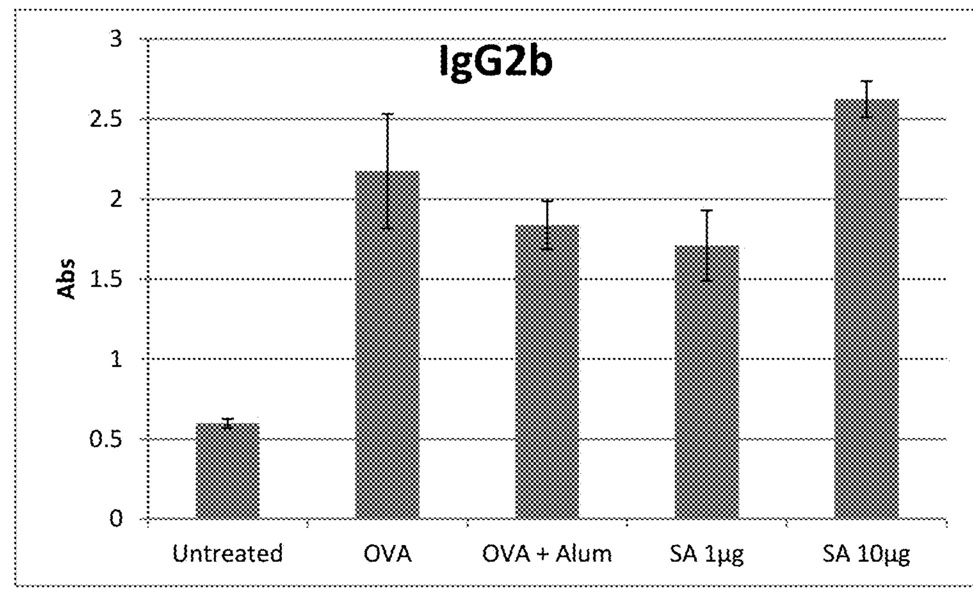

E.

FIG. 3
A.
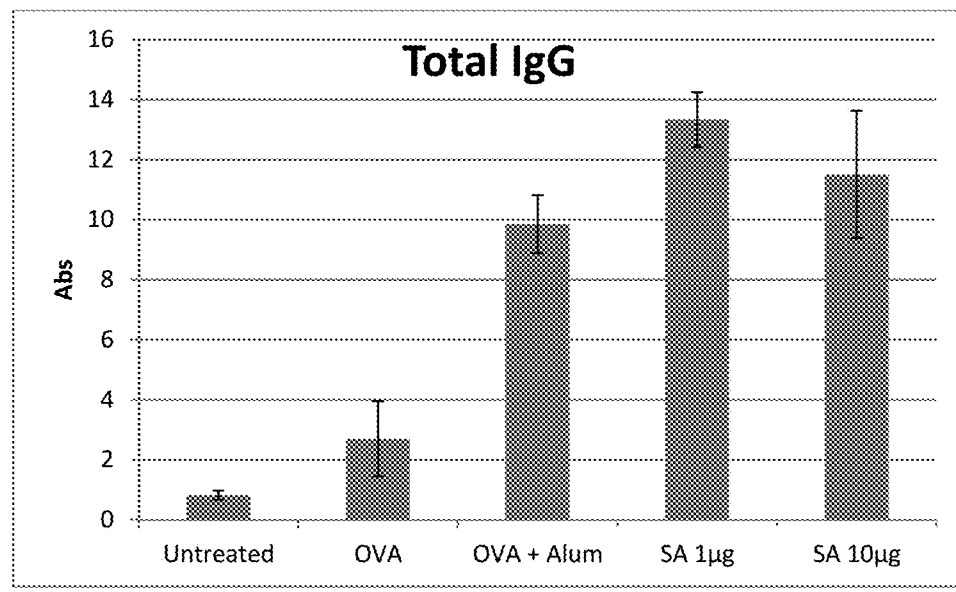
B.
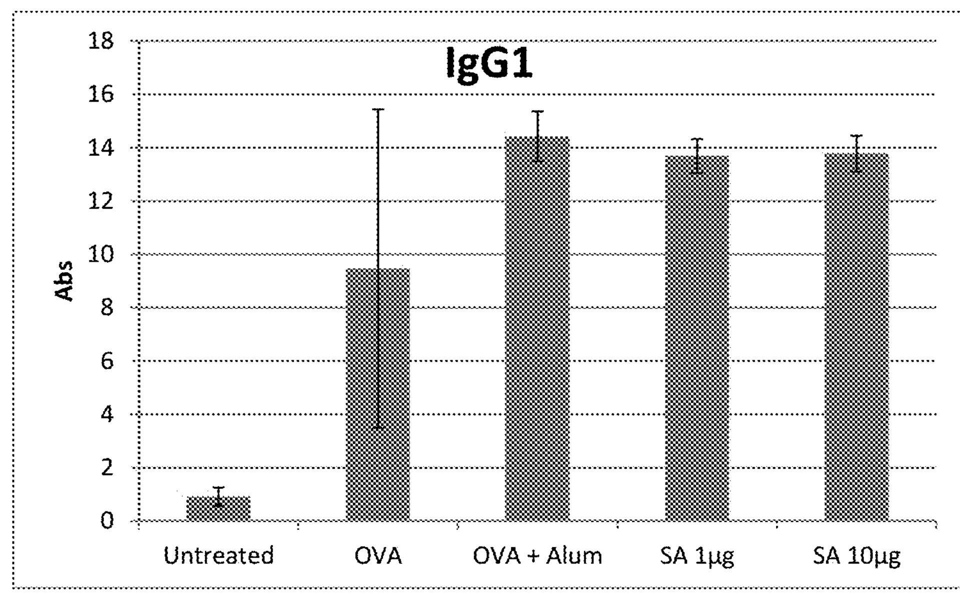

FIG. 3 (CONT.)
C.
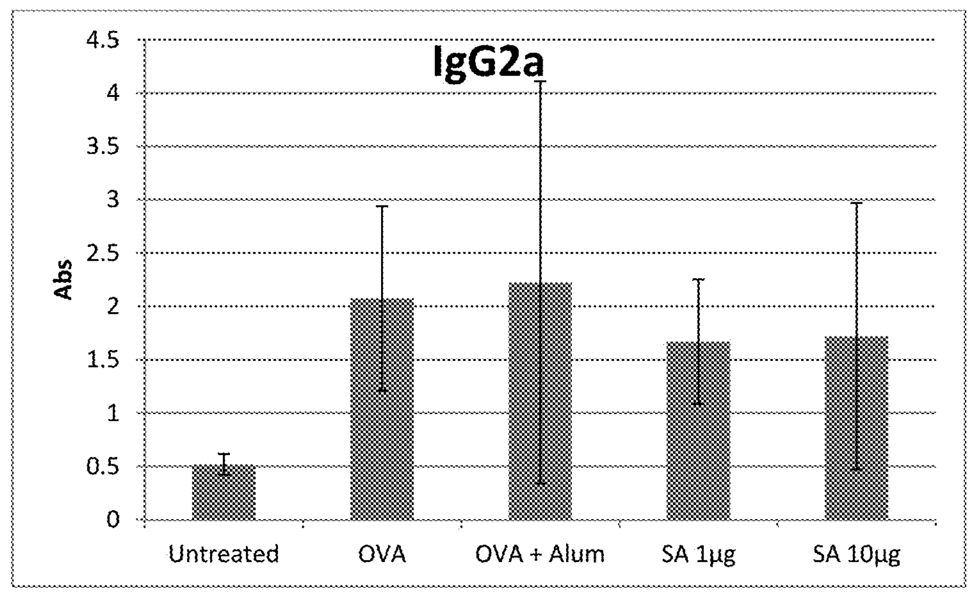
D.
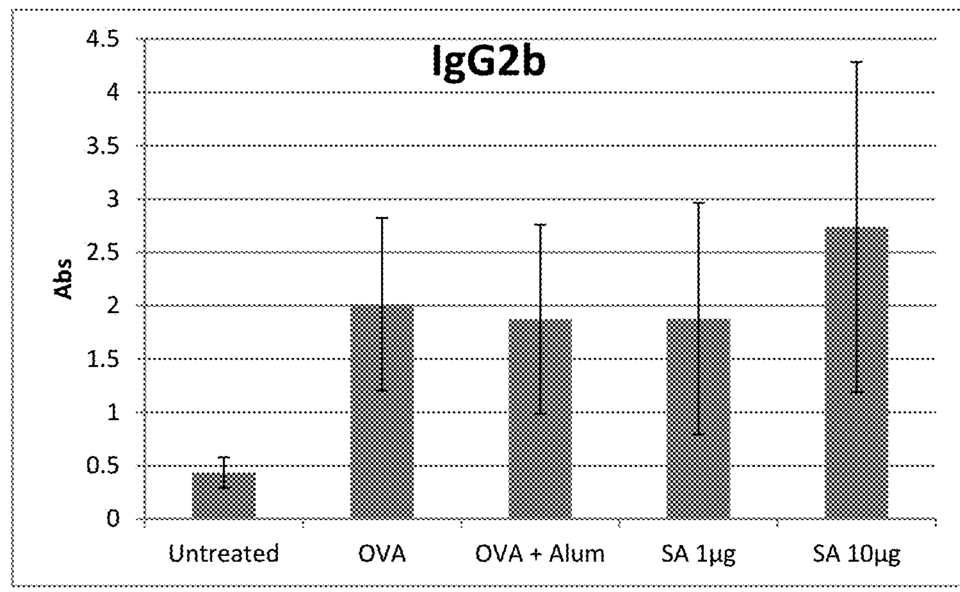

E.

FIG. 4
A.
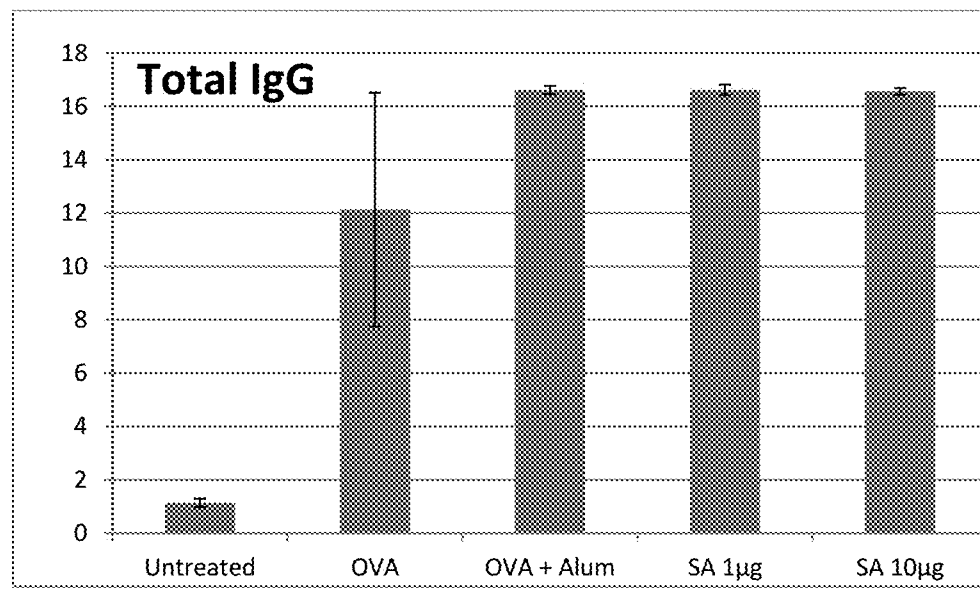
B
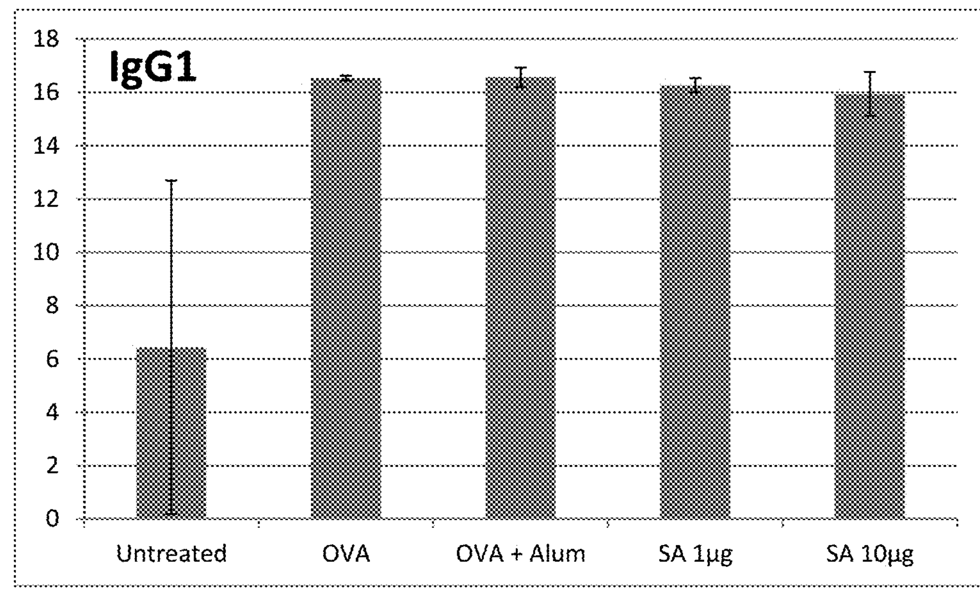

FIG. 4 (CONT.)
C.
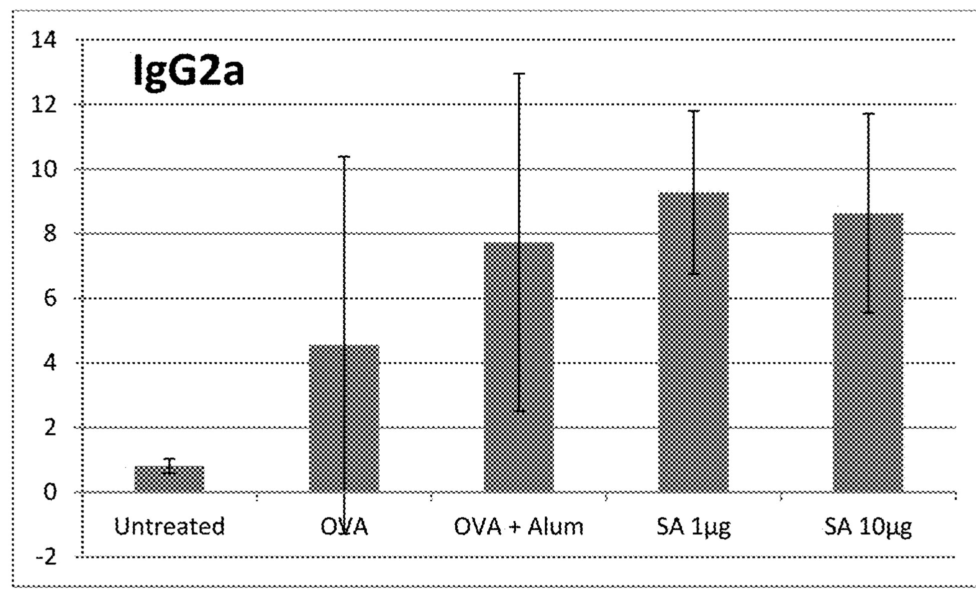
D.
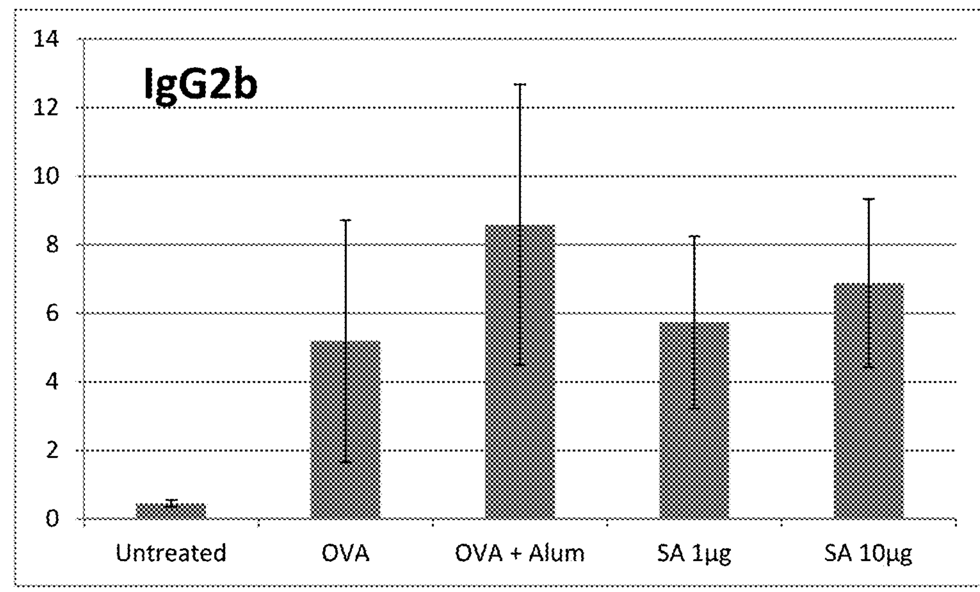

E.

FIG. 11
A.
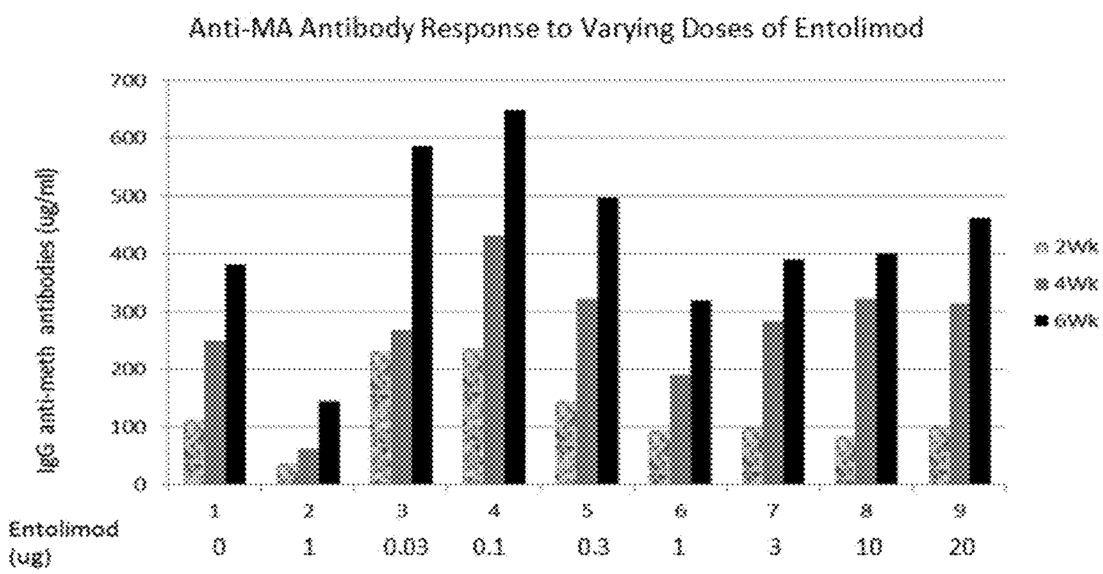
B.
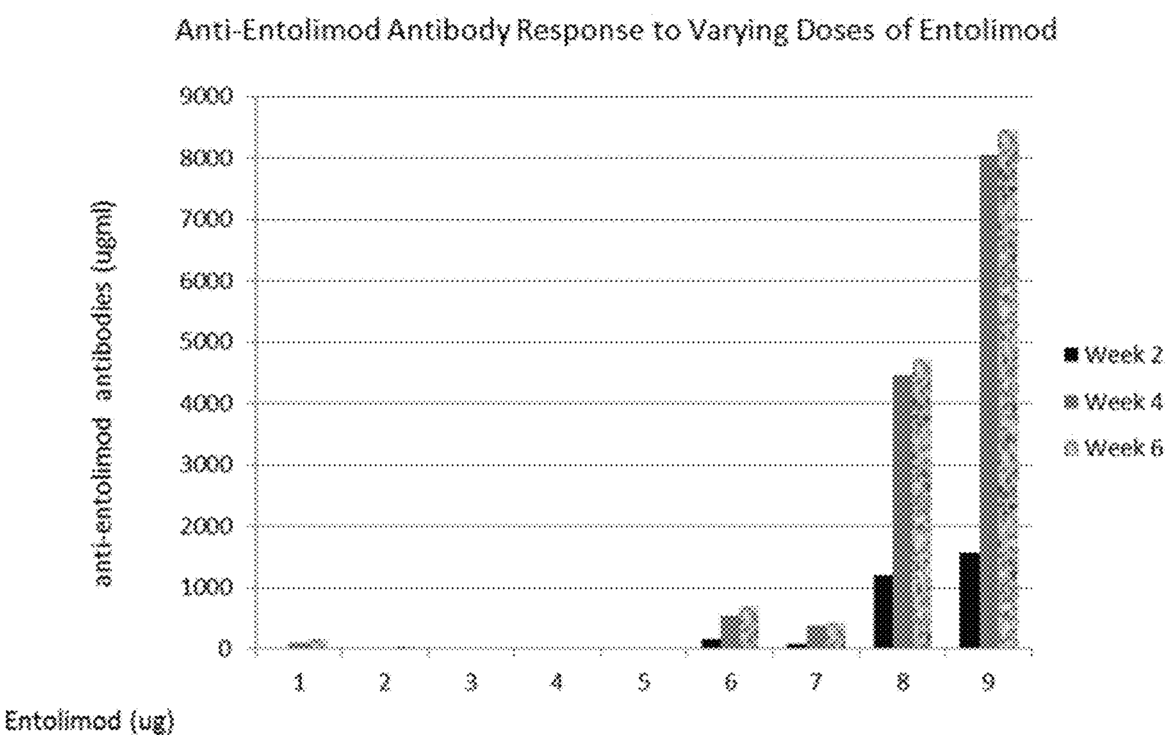

SEQUENCE LISTING

```
<160> NUMBER OF SEQ ID NOS: 294

<210> SEQ ID NO 1
<211> LENGTH: 505
<212> TYPE: PRT
<213> ORGANISM: Salmonella dublin

<400> SEQUENCE: 1

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ser
                85                  90                  95

Val Gln Ala Thr Asn Gly Thr Asn Ser Asp Ser Asp Leu Lys Ser Ile
            100                 105                 110

Gln Asp Glu Ile Gln Gln Arg Leu Glu Glu Ile Asp Arg Val Ser Asn
        115                 120                 125

Gln Thr Gln Phe Asn Gly Val Lys Val Leu Ser Gln Asp Asn Gln Met
    130                 135                 140
```

```
Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Gly Pro Lys Glu Ala Thr Val Gly Asp Leu Lys Ser Ser Phe Lys Asn
            180                 185                 190

Val Thr Gly Tyr Asp Thr Tyr Ala Ala Gly Ala Asp Lys Tyr Arg Val
        195                 200                 205

Asp Ile Asn Ser Gly Ala Val Val Thr Asp Ala Ala Ala Pro Asp Lys
    210                 215                 220

Val Tyr Val Asn Ala Ala Asn Gly Gln Leu Thr Thr Asp Asp Ala Glu
225                 230                 235                 240

Asn Asn Thr Ala Val Asp Leu Phe Lys Thr Thr Lys Ser Thr Ala Gly
                245                 250                 255

Thr Ala Glu Ala Lys Ala Ile Ala Gly Ala Ile Lys Gly Gly Lys Glu
            260                 265                 270

Gly Asp Thr Phe Asp Tyr Lys Gly Val Thr Phe Thr Ile Asp Thr Lys
        275                 280                 285

Thr Gly Asp Asp Gly Asn Gly Lys Val Ser Thr Thr Ile Asn Gly Glu
    290                 295                 300

Lys Val Thr Leu Thr Val Ala Asp Ile Ala Thr Gly Ala Ala Asp Val
305                 310                 315                 320

Asn Ala Ala Thr Leu Gln Ser Ser Lys Asn Val Tyr Thr Ser Val Val
                325                 330                 335

Asn Gly Gln Phe Thr Phe Asp Asp Lys Thr Lys Asn Glu Ser Ala Lys
            340                 345                 350

Leu Ser Asp Leu Glu Ala Asn Asn Ala Val Lys Gly Glu Ser Lys Ile
        355                 360                 365

Thr Val Asn Gly Ala Glu Tyr Thr Ala Asn Ala Thr Gly Asp Lys Ile
    370                 375                 380

Thr Leu Ala Gly Lys Thr Met Phe Ile Asp Lys Thr Ala Ser Gly Val
385                 390                 395                 400

Ser Thr Leu Ile Asn Glu Asp Ala Ala Ala Ala Lys Lys Ser Thr Ala
                405                 410                 415

Asn Pro Leu Ala Ser Ile Asp Ser Ala Leu Ser Lys Val Asp Ala Val
            420                 425                 430

Arg Ser Ser Leu Gly Ala Ile Gln Asn Arg Phe Asp Ser Ala Ile Thr
        435                 440                 445

Asn Leu Gly Asn Thr Val Thr Asn Leu Asn Ser Ala Arg Ser Arg Ile
    450                 455                 460

Glu Asp Ala Asp Tyr Ala Thr Glu Val Ser Asn Met Ser Lys Ala Gln
465                 470                 475                 480

Ile Leu Gln Gln Ala Gly Thr Ser Val Leu Ala Gln Ala Asn Gln Val
                485                 490                 495

Pro Gln Asn Val Leu Ser Leu Leu Arg
            500                 505
```

<210> SEQ ID NO 2
<211> LENGTH: 329
<212> TYPE: PRT
<213> ORGANISM: Artificial Sequence
<220> FEATURE:
<223> OTHER INFORMATION: Synthetic sequence

<400> SEQUENCE: 2

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Asp Val Lys Ser Leu Gly Leu Asp Gly Phe Asn Val
        195                 200                 205

Asn Ser Pro Gly Ile Ser Gly Gly Gly Gly Gly Ile Leu Asp Ser Met
    210                 215                 220

Gly Thr Leu Ile Asn Glu Asp Ala Ala Ala Ala Lys Lys Ser Thr Ala
225                 230                 235                 240

Asn Pro Leu Ala Ser Ile Asp Ser Ala Leu Ser Lys Val Asp Ala Val
                245                 250                 255

Arg Ser Ser Leu Gly Ala Ile Gln Asn Arg Phe Asp Ser Ala Ile Thr
            260                 265                 270

Asn Leu Gly Asn Thr Val Thr Asn Leu Asn Ser Ala Arg Ser Arg Ile
        275                 280                 285

Glu Asp Ala Asp Tyr Ala Thr Glu Val Ser Asn Met Ser Lys Ala Gln
    290                 295                 300

Ile Leu Gln Gln Ala Gly Thr Ser Val Leu Ala Gln Ala Asn Gln Val
305                 310                 315                 320

Pro Gln Asn Val Leu Ser Leu Leu Arg
                325
```

<210> SEQ ID NO 3
<211> LENGTH: 21
<212> TYPE: DNA
<213> ORGANISM: Artificial Sequence
<220> FEATURE:
<223> OTHER INFORMATION: Synthetic sequence

<400> SEQUENCE: 3
taatacgact cactataggg g 21

<210> SEQ ID NO 4
<211> LENGTH: 20

<212> TYPE: DNA
<213> ORGANISM: Artificial Sequence
<220> FEATURE:
<223> OTHER INFORMATION: Synthetic sequence

<400> SEQUENCE: 4
attgcgcaga ccactgaagg 20

<210> SEQ ID NO 5
<211> LENGTH: 6
<212> TYPE: PRT
<213> ORGANISM: Artificial Sequence
<220> FEATURE:
<223> OTHER INFORMATION: Synthetic sequence

<400> SEQUENCE: 5

Leu Val Pro Arg Gly Ser
1 5

<210> SEQ ID NO 6
<211> LENGTH: 5
<212> TYPE: PRT
<213> ORGANISM: Artificial Sequence
<220> FEATURE:
<223> OTHER INFORMATION: Synthetic sequence

<400> SEQUENCE: 6

Asp Asp Asp Asp Lys
1 5

<210> SEQ ID NO 7
<211> LENGTH: 13
<212> TYPE: PRT
<213> ORGANISM: Artificial Sequence
<220> FEATURE:
<223> OTHER INFORMATION: Synthetic sequence

<400> SEQUENCE: 7

Ser Ser Gly Leu Arg Ile Asn Ser Ala Lys Asp Asp Ala
1 5 10

<210> SEQ ID NO 8
<211> LENGTH: 6
<212> TYPE: PRT
<213> ORGANISM: Artificial Sequence
<220> FEATURE:
<223> OTHER INFORMATION: Synthetic sequence

<400> SEQUENCE: 8

Glu Asp Ala Asp Tyr Ala
1 5

<210> SEQ ID NO 9
<211> LENGTH: 14
<212> TYPE: PRT
<213> ORGANISM: Artificial Sequence
<220> FEATURE:
<223> OTHER INFORMATION: Synthetic sequence

<400> SEQUENCE: 9

Ala Ala Ser Ala Gly Ala Gly Gln Gly Gly Gly Gly Ser Gly
1 5 10

<210> SEQ ID NO 10
<211> LENGTH: 14
<212> TYPE: PRT
<213> ORGANISM: Artificial Sequence

```
<220> FEATURE:
<223> OTHER INFORMATION: Synthetic sequence

<400> SEQUENCE: 10

Glu Gly Lys Ser Ser Gly Ser Gly Ser Glu Ser Lys Ser Thr
1               5                   10


<210> SEQ ID NO 11
<211> LENGTH: 22
<212> TYPE: PRT
<213> ORGANISM: Artificial Sequence
<220> FEATURE:
<223> OTHER INFORMATION: Synthetic sequence

<400> SEQUENCE: 11

Gly Gly Gly Arg Thr Ser Ser Ser Ala Ala Ser Ala Gly Ala Gly Gln
1               5                   10                  15

Gly Gly Gly Gly Ser Gly
            20


<210> SEQ ID NO 12
<211> LENGTH: 4
<212> TYPE: PRT
<213> ORGANISM: Artificial Sequence
<220> FEATURE:
<223> OTHER INFORMATION: Synthetic sequence

<400> SEQUENCE: 12

Gly Pro Ser Gly
1


<210> SEQ ID NO 13
<211> LENGTH: 12
<212> TYPE: PRT
<213> ORGANISM: Artificial Sequence
<220> FEATURE:
<223> OTHER INFORMATION: Synthetic sequence

<400> SEQUENCE: 13

Gly Ser Ala Gly Ser Ala Ala Gly Ser Gly Glu Phe
1               5                   10


<210> SEQ ID NO 14
<211> LENGTH: 4
<212> TYPE: PRT
<213> ORGANISM: Artificial Sequence
<220> FEATURE:
<223> OTHER INFORMATION: Synthetic sequence

<400> SEQUENCE: 14

Gly Ser Pro Gly
1


<210> SEQ ID NO 15
<211> LENGTH: 18
<212> TYPE: PRT
<213> ORGANISM: Artificial Sequence
<220> FEATURE:
<223> OTHER INFORMATION: Synthetic sequence

<400> SEQUENCE: 15

Lys Glu Ser Gly Ser Val Ser Ser Glu Gln Leu Ala Gln Phe Arg Ser
1               5                   10                  15

Leu Asp
```

<210> SEQ ID NO 16
<211> LENGTH: 16
<212> TYPE: PRT
<213> ORGANISM: Artificial Sequence
<220> FEATURE:
<223> OTHER INFORMATION: Synthetic sequence

<400> SEQUENCE: 16

```
Ser Pro Gly Ile Ser Gly Gly Gly Gly Gly Ile Leu Asp Ser Met Gly
1               5                   10                  15
```

<210> SEQ ID NO 17
<211> LENGTH: 300
<212> TYPE: PRT
<213> ORGANISM: Artificial Sequence
<220> FEATURE:
<223> OTHER INFORMATION: Synthetic sequence

<400> SEQUENCE: 17

```
Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Ser Gly Leu Arg Ile Asn Ser Ala Lys Asp Asp
        35                  40                  45

Ala Ala Gly Gln Ala Ile Ala Asn Arg Phe Thr Ser Asn Ile Lys Gly
    50                  55                  60

Leu Thr Gln Ala Ser Arg Asn Ala Asn Asp Gly Ile Ser Ile Ala Gln
65                  70                  75                  80

Thr Thr Glu Gly Ala Leu Asn Glu Ile Asn Asn Asn Leu Gln Arg Val
                85                  90                  95

Arg Glu Leu Ser Val Gln Ala Thr Asn Gly Thr Asn Ser Asp Ser Asp
            100                 105                 110

Leu Lys Ser Ile Gln Asp Glu Ile Gln Gln Arg Leu Glu Glu Ile Asp
        115                 120                 125

Arg Val Ser Asn Gln Thr Gln Phe Asn Gly Val Lys Val Leu Ser Gln
    130                 135                 140

Asp Asn Gln Met Lys Ile Gln Val Gly Ala Asn Asp Gly Glu Thr Ile
145                 150                 155                 160

Thr Ile Asp Leu Gln Lys Ile Asp Val Lys Ser Leu Gly Leu Asp Gly
                165                 170                 175

Phe Asn Val Asn Ser Pro Gly Ile Ser Gly Gly Gly Gly Gly Ile Leu
            180                 185                 190

Asp Ser Met Gly Thr Leu Ile Asn Glu Asp Ala Ala Ala Ala Lys Lys
        195                 200                 205

Ser Thr Ala Asn Pro Leu Ala Ser Ile Asp Ser Ala Leu Ser Lys Val
    210                 215                 220

Asp Ala Val Arg Ser Ser Leu Gly Ala Ile Gln Asn Arg Phe Asp Ser
225                 230                 235                 240

Ala Ile Thr Asn Leu Gly Asn Thr Val Thr Asn Leu Asn Ser Ala Arg
                245                 250                 255

Ser Arg Ile Glu Asp Ala Asp Tyr Ala Thr Glu Val Ser Asn Met Ser
            260                 265                 270

Lys Ala Gln Ile Leu Gln Gln Ala Gly Thr Ser Val Leu Ala Gln Ala
        275                 280                 285

Asn Gln Val Pro Gln Asn Val Leu Ser Leu Leu Arg
    290                 295                 300
```

<210> SEQ ID NO 18
<211> LENGTH: 48
<212> TYPE: DNA
<213> ORGANISM: Artificial Sequence
<220> FEATURE:
<223> OTHER INFORMATION: Synthetic sequence

<400> SEQUENCE: 18
gcagattctg cagcaggctg gttgataatc tggcgcaggc taaccagg 48

<210> SEQ ID NO 19
<211> LENGTH: 60
<212> TYPE: DNA
<213> ORGANISM: Artificial Sequence
<220> FEATURE:
<223> OTHER INFORMATION: Synthetic sequence

<400> SEQUENCE: 19
tctaaagcgc agattctgca gcaggctggt acttccgttc tggcgcaggc taaccaggtt 60

<210> SEQ ID NO 20
<211> LENGTH: 48
<212> TYPE: DNA
<213> ORGANISM: Artificial Sequence
<220> FEATURE:
<223> OTHER INFORMATION: Synthetic sequence

<400> SEQUENCE: 20
cctggttagc ctgcgccaga ttatcaacca gcctgctgca gaatctgc 48

<210> SEQ ID NO 21
<211> LENGTH: 936
<212> TYPE: DNA
<213> ORGANISM: Artificial Sequence
<220> FEATURE:
<223> OTHER INFORMATION: Synthetic sequence

<400> SEQUENCE: 21
taatacgact cactataggg gaattgtgag cggataacaa ttcccctcta gaataatttt 60
gtttaacttt aagaaggaga tatacatatg cggggttctc atcatcatca tcatcatggt 120
atggctagca tgactggtgg acagcaaatg ggtcgggatc tgtacgacct ggttccgcgc 180
ggtagcgcga aggatccgtc tggtctgcgt atcaacagcg cgaaagacga tgcggcaggc 240
caggcgattg ctaaccgctt cacttctaat atcaaaggtc tgactcaggc ttcccgtaac 300
gctaacgacg gcatttctat tgcgcagacc actgaaggtg cgctgaatga aatcaacaac 360
aacctgcagc gtgtgcgtga gttgtctgtt caggccacta acgggactaa ctctgattcc 420
gatctgaaat ctatccagga tgaaattcag caacgtctgg aagaaatcga tcgcgtttct 480
aatcagactc aatttaacgg tgttaaagtc ctgtctcagg acaaccagat gaaaatccag 540
gttggtgcta acgatggtga aaccattacc atcgatctgc aaaaaattga tgtgaaaagc 600
cttggccttg atgggttcaa tgttaattcc ccgggaattt ccggtggtgg tggtggaatt 660
ctagactcca tgggtacatt aatcaatgaa gacgctgccg cagccaagaa aagtaccgct 720
aacccactgg cttcaattga ttctgcattg tcaaaagtgg acgcagttcg ttcttctctg 780
ggggcaattc aaaaccgttt tgattcagcc attaccaacc ttggcaatac ggtaaccaat 840
ctgaactccg cgcgtagccg tatcgaagat gctgactatg caacggaagt ttctaatatg 900
tctaaagcgc agattctgca gcaggctggt tgataa 936

```
<210> SEQ ID NO 22
<211> LENGTH: 281
<212> TYPE: PRT
<213> ORGANISM: Artificial Sequence
<220> FEATURE:
<223> OTHER INFORMATION: Synthetic sequence

<400> SEQUENCE: 22

Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Ser Gly Leu Arg Ile Asn Ser Ala Lys Asp Asp
        35                  40                  45

Ala Ala Gly Gln Ala Ile Ala Asn Arg Phe Thr Ser Asn Ile Lys Gly
    50                  55                  60

Leu Thr Gln Ala Ser Arg Asn Ala Asn Asp Gly Ile Ser Ile Ala Gln
65                  70                  75                  80

Thr Thr Glu Gly Ala Leu Asn Glu Ile Asn Asn Asn Leu Gln Arg Val
                85                  90                  95

Arg Glu Leu Ser Val Gln Ala Thr Asn Gly Thr Asn Ser Asp Ser Asp
            100                 105                 110

Leu Lys Ser Ile Gln Asp Glu Ile Gln Gln Arg Leu Glu Glu Ile Asp
        115                 120                 125

Arg Val Ser Asn Gln Thr Gln Phe Asn Gly Val Lys Val Leu Ser Gln
    130                 135                 140

Asp Asn Gln Met Lys Ile Gln Val Gly Ala Asn Asp Gly Glu Thr Ile
145                 150                 155                 160

Thr Ile Asp Leu Gln Lys Ile Asp Val Lys Ser Leu Gly Leu Asp Gly
                165                 170                 175

Phe Asn Val Asn Ser Pro Gly Ile Ser Gly Gly Gly Gly Gly Ile Leu
            180                 185                 190

Asp Ser Met Gly Thr Leu Ile Asn Glu Asp Ala Ala Ala Ala Lys Lys
        195                 200                 205

Ser Thr Ala Asn Pro Leu Ala Ser Ile Asp Ser Ala Leu Ser Lys Val
    210                 215                 220

Asp Ala Val Arg Ser Ser Leu Gly Ala Ile Gln Asn Arg Phe Asp Ser
225                 230                 235                 240

Ala Ile Thr Asn Leu Gly Asn Thr Val Thr Asn Leu Asn Ser Ala Arg
                245                 250                 255

Ser Arg Ile Glu Asp Ala Asp Tyr Ala Thr Glu Val Ser Asn Met Ser
            260                 265                 270

Lys Ala Gln Ile Leu Gln Gln Ala Gly
        275                 280


<210> SEQ ID NO 23
<211> LENGTH: 329
<212> TYPE: PRT
<213> ORGANISM: Artificial Sequence
<220> FEATURE:
<223> OTHER INFORMATION: Synthetic sequence

<400> SEQUENCE: 23

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30
```

```
Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ser
                85                  90                  95

Val Gln Ala Thr Asn Gly Thr Asn Ser Asp Ser Asp Leu Lys Ser Ile
            100                 105                 110

Gln Asp Glu Ile Gln Gln Arg Leu Glu Glu Ile Asp Arg Val Ser Asn
        115                 120                 125

Gln Thr Gln Phe Asn Gly Val Lys Val Leu Ser Gln Asp Asn Gln Met
    130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Ser Pro Gly Ile Ser Gly Gly Gly Gly Gly Ile Leu Asp Ser Met Gly
            180                 185                 190

Thr Leu Ile Asn Glu Asp Ala Ala Ala Ala Lys Lys Ser Thr Ala Asn
        195                 200                 205

Pro Leu Ala Ser Ile Asp Ser Ala Leu Ser Lys Val Asp Ala Val Arg
    210                 215                 220

Ser Ser Leu Gly Ala Ile Gln Asn Arg Phe Asp Ser Ala Ile Thr Asn
225                 230                 235                 240

Leu Gly Asn Thr Val Thr Asn Leu Asn Ser Ala Arg Ser Arg Ile Glu
                245                 250                 255

Asp Ala Asp Tyr Ala Thr Glu Val Ser Asn Met Ser Lys Ala Gln Ile
            260                 265                 270

Leu Gln Gln Ala Gly Thr Ser Val Leu Ala Gln Ala Asn Gln Val Pro
        275                 280                 285

Gln Asn Val Leu Ser Leu Leu Val Pro Arg Gly Ser His His His His
    290                 295                 300

His His Gly Met Ala Ser Met Thr Gly Gly Gln Gln Met Gly Arg Asp
305                 310                 315                 320

Leu Tyr Asp Asp Asp Asp Lys Asp Pro
                325
```

<210> SEQ ID NO 24
<211> LENGTH: 1005
<212> TYPE: DNA
<213> ORGANISM: Artificial Sequence
<220> FEATURE:
<223> OTHER INFORMATION: Synthetic sequence

<400> SEQUENCE: 24

```
atggcacaag tcattaatac aaacagcctg tcgctgttga cccagaataa cctgaacaaa      60

tctcagtcct cactgagttc cgctattgag cgtctgtcct ctggtctgcg tatcaacagc     120

gcgaaagacg atgcggcagg ccaggcgatt gctaaccgct tcacttctaa tatcaaaggt     180

ctgactcagg cttcccgtaa cgctaacgac ggcatttcta ttgcgcagac cactgaaggt     240

gcgctgaatg aaatcaacaa caacctgcag cgtgtgcgtg agttgtctgt tcaggccact     300

aacgggacta actctgattc cgatctgaaa tctatccagg atgaaattca gcaacgtctg     360
```

```
gaagaaatcg atcgcgtttc taatcagact caatttaacg gtgttaaagt cctgtctcag    420

gacaaccaga tgaaaatcca ggttggtgct aacgatggtg aaaccattac catcgatctg    480

caaaaaattg atgtgaaaag ccttggcctt gatgggttca atgttaattc cccgggaatt    540

tccggtggtg gtggtggaat tctagactcc atgggtacat taatcaatga agacgctgcc    600

gcagccaaga aaagtaccgc taacccactg gcttcaattg attctgcatt gtcaaaagtg    660

gacgcagttc gttcttctct gggggcaatt caaaaccgtt ttgattcagc cattaccaac    720

cttggcaata cggtaaccaa tctgaactcc gcgcgtagcc gtatcgaaga tgctgactat    780

gcaacggaag tttctaatat gtctaaagcg cagattctgc agcaggctgg tacttccgtt    840

ctggcgcagg ctaaccaggt tccgcaaaac gtcctctctt tactggttcc gcggggttct    900

catcatcatc atcatcatgg tatggctagc atgactggtg gacagcaaat gggtcgggat    960

ctgtacgacg atgacgataa ggatccgtaa gtcgacaagc ttgcg                   1005
```

```
<210> SEQ ID NO 25
<211> LENGTH: 31
<212> TYPE: DNA
<213> ORGANISM: Artificial Sequence
<220> FEATURE:
<223> OTHER INFORMATION: Synthetic sequence

<400> SEQUENCE: 25

cgaaagacca tatggcaggc caggcgattg c                                    31
```

```
<210> SEQ ID NO 26
<211> LENGTH: 33
<212> TYPE: DNA
<213> ORGANISM: Artificial Sequence
<220> FEATURE:
<223> OTHER INFORMATION: Synthetic sequence

<400> SEQUENCE: 26

cgcaagcttg tcgacttacg gatccttatc gtc                                  33
```

```
<210> SEQ ID NO 27
<211> LENGTH: 952
<212> TYPE: DNA
<213> ORGANISM: Artificial Sequence
<220> FEATURE:
<223> OTHER INFORMATION: Synthetic sequence

<400> SEQUENCE: 27

taatacgact cactataggg gaattgtgag cggataacaa ttcccctcta gaaataattt     60

tgtttaactt taagaaggag atatacatat ggcaggccag gcgattgcta accgcttcac    120

ttctaatatc aaaggtctga ctcaggcttc ccgtaacgct aacgacggca tttctattgc    180

gcagaccact gaaggtgcgc tgaatgaaat caacaacaac ctgcagcgtg tgcgtgagtt    240

gtctgttcag gccactaacg ggactaactc tgattccgat ctgaaatcta tccaggatga    300

aattcagcaa cgtctggaag aaatcgatcg cgtttctaat cagactcaat ttaacggtgt    360

taaagtcctg tctcaggaca accagatgaa aatccaggtt ggtgctaacg atggtgaaac    420

cattaccatc gatctgcaaa aaattgatgt gaaaagcctt ggccttgatg ggttcaatgt    480

taattccccg ggaatttccg gtggtggtgg tggaattcta gactccatgg gtacattaat    540

caatgaagac gctgccgcag ccaagaaaag taccgctaac ccactggctt caattgattc    600

tgcattgtca aaagtggacg cagttcgttc ttctctgggg gcaattcaaa accgctttga    660

ttcagccatt accaaccttg gcaatacggt aaccaatctg aactccgcgc gtagccgtat    720
```

```
cgaagatgct gactatgcaa cggaagtttc taatatgtct aaagcgcaga ttctgcagca    780

ggctggtact tccgttctgg cgcaggctaa ccaggttccg caaaacgtcc tctctttact    840

ggttccgcgg ggttctcatc atcatcatca tcatggtatg gctagcatga ctggtggaca    900

gcaaatgggt cgggatctgt acgacgatga cgataaggat ccgtaagtcg ac            952


<210> SEQ ID NO 28
<211> LENGTH: 285
<212> TYPE: PRT
<213> ORGANISM: Artificial Sequence
<220> FEATURE:
<223> OTHER INFORMATION: Synthetic sequence

<400> SEQUENCE: 28

Met Ala Gly Gln Ala Ile Ala Asn Arg Phe Thr Ser Asn Ile Lys Gly
1               5                   10                  15

Leu Thr Gln Ala Ser Arg Asn Ala Asn Asp Gly Ile Ser Ile Ala Gln
            20                  25                  30

Thr Thr Glu Gly Ala Leu Asn Glu Ile Asn Asn Asn Leu Gln Arg Val
        35                  40                  45

Arg Glu Leu Ser Val Gln Ala Thr Asn Gly Thr Asn Ser Asp Ser Asp
    50                  55                  60

Leu Lys Ser Ile Gln Asp Glu Ile Gln Gln Arg Leu Glu Glu Ile Asp
65                  70                  75                  80

Arg Val Ser Asn Gln Thr Gln Phe Asn Gly Val Lys Val Leu Ser Gln
                85                  90                  95

Asp Asn Gln Met Lys Ile Gln Val Gly Ala Asn Asp Gly Glu Thr Ile
            100                 105                 110

Thr Ile Asp Leu Gln Lys Ile Asp Val Lys Ser Leu Gly Leu Asp Gly
        115                 120                 125

Phe Asn Val Asn Ser Pro Gly Ile Ser Gly Gly Gly Gly Gly Ile Leu
    130                 135                 140

Asp Ser Met Gly Thr Leu Ile Asn Glu Asp Ala Ala Ala Ala Lys Lys
145                 150                 155                 160

Ser Thr Ala Asn Pro Leu Ala Ser Ile Asp Ser Ala Leu Ser Lys Val
                165                 170                 175

Asp Ala Val Arg Ser Ser Leu Gly Ala Ile Gln Asn Arg Phe Asp Ser
            180                 185                 190

Ala Ile Thr Asn Leu Gly Asn Thr Val Thr Asn Leu Asn Ser Ala Arg
        195                 200                 205

Ser Arg Ile Glu Asp Ala Asp Tyr Ala Thr Glu Val Ser Asn Met Ser
    210                 215                 220

Lys Ala Gln Ile Leu Gln Gln Ala Gly Thr Ser Val Leu Ala Gln Ala
225                 230                 235                 240

Asn Gln Val Pro Gln Asn Val Leu Ser Leu Leu Val Pro Arg Gly Ser
                245                 250                 255

His His His His His His Gly Met Ala Ser Met Thr Gly Gly Gln Gln
            260                 265                 270

Met Gly Arg Asp Leu Tyr Asp Asp Asp Asp Lys Asp Pro
        275                 280                 285


<210> SEQ ID NO 29
<211> LENGTH: 765
<212> TYPE: DNA
<213> ORGANISM: Artificial Sequence
<220> FEATURE:
```

<223> OTHER INFORMATION: Synthetic sequence

<400> SEQUENCE: 29

```
atgagcgggt tacggatcaa cagcgcgaaa gacgatgcgg caggccaggc gattgctaac      60
cgcttcactt ctaatatcaa aggtctgact caggcttccc gtaacgctaa cgacggcatt     120
tctattgcgc agaccactga aggtgcgctg aatgaaatca acaacaacct gcagcgtgtg     180
cgtgagttgt ctgttcaggc cactaacggg actaactctg attccgatct gaaatctatc     240
ggaccatcag gtcaggatga aattcagcaa cgtctggaag aaatcgatcg cgtttctaat     300
cagactcaat ttaacggtgt taaagtcctg tctcaggaca accagatgaa aatccaggtt     360
ggtgctaacg atggtgaaac cattaccatc gatctgcaaa aaattgatgt gaaaagcctt     420
ggccttgatg ggttcaatgt taattccccg ggaagtaccg ctaacccact ggcttcaatt     480
gattctgcat tgtcaaaagt ggacgcagtt cgttcttctc tgggggcaat tcaaaaccgc     540
tttgattcag ccattaccaa ccttggcaat acggtaacca atctgaactc cgcgcgtagc     600
cgtatcgaag atgctgacta tgcaacggaa gtttctaata tgtctaaagc gcagattctg     660
cagcaggctg gtacttccgt tctggcgcag gctaaccagg ttccgcaaaa cgtcctctct     720
ttactggttc cgcggggttc tcatcatcat catcatcatg gttaa                     765
```

<210> SEQ ID NO 30
<211> LENGTH: 254
<212> TYPE: PRT
<213> ORGANISM: Artificial Sequence
<220> FEATURE:
<223> OTHER INFORMATION: Synthetic sequence

<400> SEQUENCE: 30

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gly Pro Ser Gly Gln Asp Glu Ile Gln Gln Arg Leu Glu Glu Ile Asp
                85                  90                  95

Arg Val Ser Asn Gln Thr Gln Phe Asn Gly Val Lys Val Leu Ser Gln
            100                 105                 110

Asp Asn Gln Met Lys Ile Gln Val Gly Ala Asn Asp Gly Glu Thr Ile
        115                 120                 125

Thr Ile Asp Leu Gln Lys Ile Asp Val Lys Ser Leu Gly Leu Asp Gly
    130                 135                 140

Phe Asn Val Asn Ser Pro Gly Ser Thr Ala Asn Pro Leu Ala Ser Ile
145                 150                 155                 160

Asp Ser Ala Leu Ser Lys Val Asp Ala Val Arg Ser Ser Leu Gly Ala
                165                 170                 175

Ile Gln Asn Arg Phe Asp Ser Ala Ile Thr Asn Leu Gly Asn Thr Val
            180                 185                 190

Thr Asn Leu Asn Ser Ala Arg Ser Arg Ile Glu Asp Ala Asp Tyr Ala
        195                 200                 205
```

```
Thr Glu Val Ser Asn Met Ser Lys Ala Gln Ile Leu Gln Gln Ala Gly
    210                 215                 220

Thr Ser Val Leu Ala Gln Ala Asn Gln Val Pro Gln Asn Val Leu Ser
225                 230                 235                 240

Leu Leu Val Pro Arg Gly Ser His His His His His His Gly
                245                 250
```

<210> SEQ ID NO 31
<211> LENGTH: 32
<212> TYPE: DNA
<213> ORGANISM: Artificial Sequence
<220> FEATURE:
<223> OTHER INFORMATION: Synthetic sequence

<400> SEQUENCE: 31

```
gatatacata tgagcgggtt acggatcaac ag                                 32
```

<210> SEQ ID NO 32
<211> LENGTH: 29
<212> TYPE: DNA
<213> ORGANISM: Artificial Sequence
<220> FEATURE:
<223> OTHER INFORMATION: Synthetic sequence

<400> SEQUENCE: 32

```
agatctcccg ggaattaac attgaaccc                                      29
```

<210> SEQ ID NO 33
<211> LENGTH: 816
<212> TYPE: DNA
<213> ORGANISM: Artificial Sequence
<220> FEATURE:
<223> OTHER INFORMATION: Synthetic sequence

<400> SEQUENCE: 33

```
taatacgact cactataggg gaattgtgag cggataacaa ttcccctcta gaataatttt     60

gtttaacttt aagaaggaga tatacatatg agcgggttac ggatcaacag cgcgaaagac    120

gatgcggcag gccaggcgat tgctaaccgc ttcacttcta atatcaaagg tctgactcag    180

gcttcccgta acgctaacga cggcatttct attgcgcaga ccactgaagg tgcgctgaat    240

gaaatcaaca acaacctgca gcgtgtgcgt gagttgtctg ttcaggccac tggaccatca    300

ggtgaaattc agcaacgtct ggaagaaatc gatcgcgttt ctaatcagac tcaatttaac    360

ggtgttaaag tcctgtctca ggacaaccag atgaaaatcc aggttggtgc taacgatggt    420

gaaaccatta ccatcgatct gcaaaaaatt gatgtgaaaa gccttggcct tgatgggttc    480

aatgttaatt ccccgggaag taccgctaac ccactggctt caattgattc tgcattgtca    540

aaagtggacg cagttcgttc ttctctgggg gcaattcaaa accgctttga ttcagccatt    600

accaaccttg gcaatacggt aaccaatctg aactccgcgc gtagccgtat cgaagatgct    660

gactatgcaa cggaagtttc taatatgtct aaagcgcaga ttctgcagca ggctggtact    720

tccgttctgg cgcaggctaa ccaggttccg caaaacgtcc tctctttact ggttccgcgg    780

ggttctcatc atcatcatca tcatggttaa gtcgac                             816
```

<210> SEQ ID NO 34
<211> LENGTH: 240
<212> TYPE: PRT
<213> ORGANISM: Artificial Sequence
<220> FEATURE:
<223> OTHER INFORMATION: Synthetic sequence

<400> SEQUENCE: 34

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Gly Pro Ser Gly Glu Ile Gln Gln Arg Leu Glu Glu
65                  70                  75                  80

Ile Asp Arg Val Ser Asn Gln Thr Gln Phe Asn Gly Val Lys Val Leu
                85                  90                  95

Ser Gln Asp Asn Gln Met Lys Ile Gln Val Gly Ala Asn Asp Gly Glu
            100                 105                 110

Thr Ile Thr Ile Asp Leu Gln Lys Ile Asp Val Lys Ser Leu Gly Leu
        115                 120                 125

Asp Gly Phe Asn Val Asn Ser Pro Gly Ser Thr Ala Asn Pro Leu Ala
    130                 135                 140

Ser Ile Asp Ser Ala Leu Ser Lys Val Asp Ala Val Arg Ser Ser Leu
145                 150                 155                 160

Gly Ala Ile Gln Asn Arg Phe Asp Ser Ala Ile Thr Asn Leu Gly Asn
                165                 170                 175

Thr Val Thr Asn Leu Asn Ser Ala Arg Ser Arg Ile Glu Asp Ala Asp
            180                 185                 190

Tyr Ala Thr Glu Val Ser Asn Met Ser Lys Ala Gln Ile Leu Gln Gln
        195                 200                 205

Ala Gly Thr Ser Val Leu Ala Gln Ala Asn Gln Val Pro Gln Asn Val
    210                 215                 220

Leu Ser Leu Leu Val Pro Arg Gly Ser His His His His His His Gly
225                 230                 235                 240

<210> SEQ ID NO 35
<211> LENGTH: 275
<212> TYPE: PRT
<213> ORGANISM: Artificial Sequence
<220> FEATURE:
<223> OTHER INFORMATION: Synthetic sequence

<400> SEQUENCE: 35

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu

```
        115                 120                 125

Gln Lys Ile Asp Val Lys Ser Leu Gly Leu Asp Gly Phe Asn Val Asn
    130                 135                 140

Ser Pro Gly Ile Ser Gly Gly Gly Gly Gly Ile Leu Asp Ser Met Gly
145                 150                 155                 160

Thr Leu Ile Asn Glu Asp Ala Ala Ala Ala Lys Lys Ser Thr Ala Asn
                165                 170                 175

Pro Leu Ala Ser Ile Asp Ser Ala Leu Ser Lys Val Asp Ala Val Arg
            180                 185                 190

Ser Ser Leu Gly Ala Ile Gln Asn Arg Phe Asp Ser Ala Ile Thr Asn
        195                 200                 205

Leu Gly Asn Thr Val Thr Asn Leu Asn Ser Ala Arg Ser Arg Ile Glu
    210                 215                 220

Asp Ala Asp Tyr Ala Thr Glu Val Ser Asn Met Ser Lys Ala Gln Ile
225                 230                 235                 240

Leu Gln Gln Ala Gly Thr Ser Val Leu Ala Gln Ala Asn Gln Val Pro
                245                 250                 255

Gln Asn Val Leu Ser Leu Leu Val Pro Arg Gly Ser His His His His
            260                 265                 270

His His Gly
        275
```

```
<210> SEQ ID NO 36
<211> LENGTH: 828
<212> TYPE: DNA
<213> ORGANISM: Artificial Sequence
<220> FEATURE:
<223> OTHER INFORMATION: Synthetic sequence

<400> SEQUENCE: 36

atgagcgggt tacggatcaa cagcgcgaaa gacgatgcgg caggccaggc gattgctaac     60

cgcttcactt ctaatatcaa aggtctgact caggcttccc gtaacgctaa cgacggcatt    120

tctattgcgc agaccactga aggtgcgctg aatgaaatca acaacaacct gcagcgtgtg    180

cgtgagttgt ctgttcaggc cactaacggg actaactctg attccgatct gaaatctatc    240

caggatgaaa ttcagcaacg tctggaagaa atcgatcgcg tttctaatca gactcaattt    300

aacggtgtta aagtcctgtc tcaggacaac cagatgaaaa tccaggttgg tgctaacgat    360

ggtgaaacca ttaccatcga tctgcaaaaa attgatgtga aaagccttgg ccttgatggg    420

ttcaatgtta attccccggg aatttccggt ggtggtggtg gaattctaga ctccatgggt    480

acattaatca atgaagacgc tgccgcagcc aagaaaagta ccgctaaccc actggcttca    540

attgattctg cattgtcaaa agtggacgca gttcgttctt ctctgggggc aattcaaaac    600

cgctttgatt cagccattac caaccttggc aatacggtaa ccaatctgaa ctccgcgcgt    660

agccgtatcg aagatgctga ctatgcaacg gaagtttcta atatgtctaa agcgcagatt    720

ctgcagcagg ctggtacttc cgttctggcg caggctaacc aggttccgca aaacgtcctc    780

tctttactgg ttccgcgggg ttctcatcat catcatcatc atggttaa                 828


<210> SEQ ID NO 37
<211> LENGTH: 41
<212> TYPE: DNA
<213> ORGANISM: Artificial Sequence
<220> FEATURE:
<223> OTHER INFORMATION: Synthetic sequence

<400> SEQUENCE: 37
```

tctagacccg ggaagtaccg ctaacccact ggcttcaatt g 41

<210> SEQ ID NO 38
<211> LENGTH: 40
<212> TYPE: DNA
<213> ORGANISM: Artificial Sequence
<220> FEATURE:
<223> OTHER INFORMATION: Synthetic sequence

<400> SEQUENCE: 38
ccagtcatgt cgacttaacc atgatgatga tgatgatgag 40

<210> SEQ ID NO 39
<211> LENGTH: 55
<212> TYPE: DNA
<213> ORGANISM: Artificial Sequence
<220> FEATURE:
<223> OTHER INFORMATION: Synthetic sequence

<400> SEQUENCE: 39
ctcatcatca tcatcatcat ggttaagtcg acaagcttgc ggccgcagag ctcgc 55

<210> SEQ ID NO 40
<211> LENGTH: 846
<212> TYPE: DNA
<213> ORGANISM: Artificial Sequence
<220> FEATURE:
<223> OTHER INFORMATION: Synthetic sequence

<400> SEQUENCE: 40
taatacgact cactataggg gaattgtgag cggataacaa ttcccctcta gaataatttt 60
gtttaacttt aagaaggaga tatacatatg agcgggttac ggatcaacag cgcgaaagac 120
gatgcggcag gccaggcgat tgctaaccgc ttcacttcta atatcaaagg tctgactcag 180
gcttcccgta acgctaacga cggcatttct attgcgcaga ccactgaagg tgcgctgaat 240
gaaatcaaca acaacctgca gcgtgtgcgt gagttgtctg ttcaggccac taacgggact 300
aactctgatt ccgatctgaa atctatccag gatgaaattc agcaacgtct ggaagaaatc 360
gatcgcgttt ctaatcagac tcaatttaac ggtgttaaag tcctgtctca ggacaaccag 420
atgaaaatcc aggttggtgc taacgatggt gaaaccatta ccatcgatct gcaaaaaatt 480
gatgtgaaaa gccttggcct tgatgggttc aatgttaatt ccccgggaag taccgctaac 540
ccactggctt caattgattc tgcattgtca aaagtggacg cagttcgttc ttctctgggg 600
gcaattcaaa accgctttga ttcagccatt accaaccttg gcaatacggt aaccaatctg 660
aactccgcgc gtagccgtat cgaagatgct gactatgcaa cggaagtttc taatatgtct 720
aaagcgcaga ttctgcagca ggctggtact tccgttctgg cgcaggctaa ccaggttccg 780
caaaacgtcc tctctttact ggttccgcgg ggttctcatc atcatcatca tcatggttaa 840
gtcgac 846

<210> SEQ ID NO 41
<211> LENGTH: 753
<212> TYPE: DNA
<213> ORGANISM: Artificial Sequence
<220> FEATURE:
<223> OTHER INFORMATION: Synthetic sequence

<400> SEQUENCE: 41
atgagcgggt tacggatcaa cagcgcgaaa gacgatgcgg caggccaggc gattgctaac 60

```
cgcttcactt ctaatatcaa aggtctgact caggcttccc gtaacgctaa cgacggcatt    120

tctattgcgc agaccactga aggtgcgctg aatgaaatca acaacaacct gcagcgtgtg    180

cgtgagttgt ctgttcaggc cactaacggg actaactctg attccgatct gaaatctatc    240

caggatgaaa ttcagcaacg tctggaagaa atcgatcgcg tttctaatca gactcaattt    300

aacggtgtta aagtcctgtc tcaggacaac cagatgaaaa tccaggttgg tgctaacgat    360

ggtgaaacca ttaccatcga tctgcaaaaa attgatgtga aaagccttgg ccttgatggg    420

ttcaatgtta attccccggg aagtaccgct aacccactgg cttcaattga ttctgcattg    480

tcaaaagtgg acgcagttcg ttcttctctg gggcaattc aaaaccgctt tgattcagcc    540

attaccaacc ttggcaatac ggtaaccaat ctgaactccg cgcgtagccg tatcgaagat    600

gctgactatg caacggaagt ttctaatatg tctaaagcgc agattctgca gcaggctggt    660

acttccgttc tggcgcaggc taaccaggtt ccgcaaaacg tcctctcttt actggttccg    720

cggggttctc atcatcatca tcatcatggt taa                                 753
```

```
<210> SEQ ID NO 42
<211> LENGTH: 250
<212> TYPE: PRT
<213> ORGANISM: Artificial Sequence
<220> FEATURE:
<223> OTHER INFORMATION: Synthetic sequence

<400> SEQUENCE: 42

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240
```

```
Arg Gly Ser His His His His His His Gly
                245                 250


<210> SEQ ID NO 43
<211> LENGTH: 1005
<212> TYPE: DNA
<213> ORGANISM: Artificial Sequence
<220> FEATURE:
<223> OTHER INFORMATION: Synthetic sequence

<400> SEQUENCE: 43

atggcacaag tcattaatac aaacagcctg tcgctgttga cccagaataa cctgaacaaa     60

tctcagtcct cactgagttc cgctattgag cgtctgtcct ctggtctgcg tatcaacggc    120

gcgaaagacg atgcggcagg ccaggcgatt gctaaccgct tcacttctaa tatcaaaggt    180

ctgactcagg cttcccgtaa cgctaacgac ggcatttcta ttgcgcagac cactgaaggt    240

gcgctgaatg aaatcaacaa caacctgcag cgtgtgcgtg agttgtctgt tcaggccact    300

aacgggacta actctgattc cgatctgaaa tctatccagg atgaaattca gcaacgtctg    360

gaagaaatcg atcgcgtttc taatcagact caatttaacg gtgttaaagt cctgtctcag    420

gacaaccaga tgaaaatcca ggttggtgct aacgatggtg aaaccattac catcgatctg    480

caaaaaattg atgtgaaaag ccttggcctt gatgggttca atgttaattc cccgggaatt    540

tccggtggtg gtggtggaat tctagactcc atgggtacat taatcaatga agacgctgcc    600

gcagccaaga aaagtaccgc taacccactg gcttcaattg attctgcatt gtcaaaagtg    660

gacgcagttc gttcttctct gggggcaatt caaaaccgct ttgattcagc cattaccaac    720

cttggcaata cggtaaccaa tctgaactcc gcgcgtagcc gtatcgaaga tgctgactat    780

gcaacggaag tttctaatat gtctaaagcg cagattctgc agcaggctgg tacttccgtt    840

ctggcgcagg ctaaccaggt tccgcaaaac gtcctctctt tactggttcc gcggggttct    900

catcatcatc atcatcatgg tatggctagc atgactggtg gacagcaaat gggtcgggat    960

ctgtacgacg atgacgataa ggatccgtaa gtcgacaagc ttgcg                    1005


<210> SEQ ID NO 44
<211> LENGTH: 329
<212> TYPE: PRT
<213> ORGANISM: Artificial Sequence
<220> FEATURE:
<223> OTHER INFORMATION: Synthetic sequence

<400> SEQUENCE: 44

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Gly Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ser
                85                  90                  95

Val Gln Ala Thr Asn Gly Thr Asn Ser Asp Ser Asp Leu Lys Ser Ile
            100                 105                 110

Gln Asp Glu Ile Gln Gln Arg Leu Glu Glu Ile Asp Arg Val Ser Asn
```

```
        115                 120                 125

Gln Thr Gln Phe Asn Gly Val Lys Val Leu Ser Gln Asp Asn Gln Met
    130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Ser Pro Gly Ile Ser Gly Gly Gly Gly Gly Ile Leu Asp Ser Met Gly
            180                 185                 190

Thr Leu Ile Asn Glu Asp Ala Ala Ala Ala Lys Lys Ser Thr Ala Asn
        195                 200                 205

Pro Leu Ala Ser Ile Asp Ser Ala Leu Ser Lys Val Asp Ala Val Arg
    210                 215                 220

Ser Ser Leu Gly Ala Ile Gln Asn Arg Phe Asp Ser Ala Ile Thr Asn
225                 230                 235                 240

Leu Gly Asn Thr Val Thr Asn Leu Asn Ser Ala Arg Ser Arg Ile Glu
                245                 250                 255

Asp Ala Asp Tyr Ala Thr Glu Val Ser Asn Met Ser Lys Ala Gln Ile
            260                 265                 270

Leu Gln Gln Ala Gly Thr Ser Val Leu Ala Gln Ala Asn Gln Val Pro
        275                 280                 285

Gln Asn Val Leu Ser Leu Leu Val Pro Arg Gly Ser His His His His
    290                 295                 300

His His Gly Met Ala Ser Met Thr Gly Gly Gln Gln Met Gly Arg Asp
305                 310                 315                 320

Leu Tyr Asp Asp Asp Asp Lys Asp Pro
                325
```

<210> SEQ ID NO 45
<211> LENGTH: 36
<212> TYPE: DNA
<213> ORGANISM: Artificial Sequence
<220> FEATURE:
<223> OTHER INFORMATION: Synthetic sequence

<400> SEQUENCE: 45
ctctggtcat atgatcaaca gcgcgaaaga cgatgc 36

<210> SEQ ID NO 46
<211> LENGTH: 46
<212> TYPE: DNA
<213> ORGANISM: Artificial Sequence
<220> FEATURE:
<223> OTHER INFORMATION: Synthetic sequence

<400> SEQUENCE: 46
tctagagtcg actattaagc cataccatga tgatgatgat gatgag 46

<210> SEQ ID NO 47
<211> LENGTH: 918
<212> TYPE: DNA
<213> ORGANISM: Artificial Sequence
<220> FEATURE:
<223> OTHER INFORMATION: Synthetic sequence

<400> SEQUENCE: 47
taatacgact cactataggg gaattgtgag cggataacaa ttcccctcta gaaataattt 60
tgtttaactt taagaaggag atatacatat gatcaacagc gcgaaagacg atgcggcagg 120

```
ccaggcgatt gctaaccgct tcacttctaa tatcaaaggt ctgactcagg cttcccgtaa    180

cgctaacgac ggcatttcta ttgcgcagac cactgaaggt gcgctgaatg aaatcaacaa    240

caacctgcag cgtgtgcgtg agttgtctgt tcaggccact aacgggacta actctgattc    300

cgatctgaaa tctatccagg atgaaattca gcaacgtctg gaagaaatcg atcgcgtttc    360

taatcagact caatttaacg gtgttaaagt cctgtctcag gacaaccaga tgaaaatcca    420

ggttggtgct aacgatggtg aaaccattac catcgatctg caaaaaattg atgtgaaaag    480

ccttggcctt gatgggttca atgttaattc cccgggaatt tccggtggtg gtggtggaat    540

tctagactcc atgggtacat taatcaatga agacgctgcc gcagccaaga aaagtaccgc    600

taacccactg gcttcaattg attctgcatt gtcaaaagtg gacgcagttc gttcttctct    660

gggggcaatt caaaaccgct ttgattcagc cattaccaac cttggcaata cggtaaccaa    720

tctgaactcc gcgcgtagcc gtatcgaaga tgctgactat gcaacggaag tttctaatat    780

gtctaaagcg cagattctgc agcaggctgg tacttccgtt ctggcgcagg ctaaccaggt    840

tccgcaaaac gtcctctctt tactggttcc gcggggttct catcatcatc atcatcatgg    900

tatggcttaa tagtcgac                                                  918
```

```
<210> SEQ ID NO 48
<211> LENGTH: 273
<212> TYPE: PRT
<213> ORGANISM: Artificial Sequence
<220> FEATURE:
<223> OTHER INFORMATION: Synthetic sequence

<400> SEQUENCE: 48

Met Ile Asn Ser Ala Lys Asp Asp Ala Ala Gly Gln Ala Ile Ala Asn
1               5                   10                  15

Arg Phe Thr Ser Asn Ile Lys Gly Leu Thr Gln Ala Ser Arg Asn Ala
            20                  25                  30

Asn Asp Gly Ile Ser Ile Ala Gln Thr Thr Glu Gly Ala Leu Asn Glu
        35                  40                  45

Ile Asn Asn Asn Leu Gln Arg Val Arg Glu Leu Ser Val Gln Ala Thr
    50                  55                  60

Asn Gly Thr Asn Ser Asp Ser Asp Leu Lys Ser Ile Gln Asp Glu Ile
65                  70                  75                  80

Gln Gln Arg Leu Glu Glu Ile Asp Arg Val Ser Asn Gln Thr Gln Phe
                85                  90                  95

Asn Gly Val Lys Val Leu Ser Gln Asp Asn Gln Met Lys Ile Gln Val
            100                 105                 110

Gly Ala Asn Asp Gly Glu Thr Ile Thr Ile Asp Leu Gln Lys Ile Asp
        115                 120                 125

Val Lys Ser Leu Gly Leu Asp Gly Phe Asn Val Asn Ser Pro Gly Ile
    130                 135                 140

Ser Gly Gly Gly Gly Gly Ile Leu Asp Ser Met Gly Thr Leu Ile Asn
145                 150                 155                 160

Glu Asp Ala Ala Ala Ala Lys Lys Ser Thr Ala Asn Pro Leu Ala Ser
                165                 170                 175

Ile Asp Ser Ala Leu Ser Lys Val Asp Ala Val Arg Ser Ser Leu Gly
            180                 185                 190

Ala Ile Gln Asn Arg Phe Asp Ser Ala Ile Thr Asn Leu Gly Asn Thr
        195                 200                 205

Val Thr Asn Leu Asn Ser Ala Arg Ser Arg Ile Glu Asp Ala Asp Tyr
    210                 215                 220
```

```
Ala Thr Glu Val Ser Asn Met Ser Lys Ala Gln Ile Leu Gln Gln Ala
225                 230                 235                 240

Gly Thr Ser Val Leu Ala Gln Ala Asn Gln Val Pro Gln Asn Val Leu
                245                 250                 255

Ser Leu Leu Val Pro Arg Gly Ser His His His His His His Gly Met
            260                 265                 270

Ala


<210> SEQ ID NO 49
<211> LENGTH: 333
<212> TYPE: PRT
<213> ORGANISM: Artificial Sequence
<220> FEATURE:
<223> OTHER INFORMATION: Synthetic sequence

<400> SEQUENCE: 49

Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Met Ala Gln Val Ile Asn Thr Asn Ser Leu Ser
        35                  40                  45

Leu Leu Thr Gln Asn Asn Leu Asn Lys Ser Gln Ser Ser Leu Ser Ser
    50                  55                  60

Ala Ile Glu Arg Leu Ser Ser Gly Leu Arg Ile Asn Ser Ala Lys Asp
65                  70                  75                  80

Asp Ala Ala Gly Gln Ala Ile Ala Asn Arg Phe Thr Ser Asn Ile Lys
                85                  90                  95

Gly Leu Thr Gln Ala Ser Arg Asn Ala Asn Asp Gly Ile Ser Ile Ala
            100                 105                 110

Gln Thr Thr Glu Gly Ala Leu Asn Glu Ile Asn Asn Asn Leu Gln Arg
        115                 120                 125

Val Arg Glu Leu Ser Val Gln Ala Thr Asn Gly Thr Asn Ser Asp Ser
    130                 135                 140

Asp Leu Lys Ser Ile Gln Asp Glu Ile Gln Gln Arg Leu Glu Glu Ile
145                 150                 155                 160

Asp Arg Val Ser Asn Gln Thr Gln Phe Asn Gly Val Lys Val Leu Ser
                165                 170                 175

Gln Asp Asn Gln Met Lys Ile Gln Val Gly Ala Asn Asp Gly Glu Thr
            180                 185                 190

Ile Thr Ile Asp Leu Gln Lys Ile Asp Val Lys Ser Leu Gly Leu Asp
        195                 200                 205

Gly Phe Asn Val Asn Ser Pro Gly Ile Ser Gly Gly Gly Gly Gly Ile
    210                 215                 220

Leu Asp Ser Met Gly Thr Leu Ile Asn Glu Asp Ala Ala Ala Ala Lys
225                 230                 235                 240

Lys Ser Thr Ala Asn Pro Leu Ala Ser Ile Asp Ser Ala Leu Ser Lys
                245                 250                 255

Val Asp Ala Val Arg Ser Ser Leu Gly Ala Ile Gln Asn Arg Phe Asp
            260                 265                 270

Ser Ala Ile Thr Asn Leu Gly Asn Thr Val Thr Asn Leu Asn Ser Ala
        275                 280                 285

Arg Ser Arg Ile Glu Asp Ala Asp Tyr Ala Thr Glu Val Ser Asn Met
    290                 295                 300
```

```
Ser Lys Ala Gln Ile Leu Gln Gln Ala Gly Thr Ser Val Leu Ala Gln
305                 310                 315                 320

Ala Asn Gln Val Pro Gln Asn Val Leu Ser Leu Leu Arg
                325                 330


<210> SEQ ID NO 50
<211> LENGTH: 1002
<212> TYPE: DNA
<213> ORGANISM: Artificial Sequence
<220> FEATURE:
<223> OTHER INFORMATION: Synthetic sequence

<400> SEQUENCE: 50

atgcggggtt ctcatcatca tcatcatcat ggtatggcta gcatgactgg tggacagcaa      60

atgggtcggg atctgtacga cctggttccg cgcggtagcg cgaaggatcc gatggcacaa     120

gtcattaata caaacagcct gtcgctgttg acccagaata acctgaacaa atctcagtcc     180

tcactgagtt ccgctattga gcgtctgtcc tctggtctgc gtatcaacag cgcgaaagac     240

gatgcggcag gccaggcgat tgctaaccgc ttcacttcta atatcaaagg tctgactcag     300

gcttcccgta acgctaacga cggcatttct attgcgcaga ccactgaagg tgcgctgaat     360

gaaatcaaca acaacctgca gcgtgtgcgt gagttgtctg ttcaggccac taacgggact     420

aactctgatt ccgatctgaa atctatccag gatgaaattc agcaacgtct ggaagaaatc     480

gatcgcgttt ctaatcagac tcaatttaac ggtgttaaag tcctgtctca ggacaaccag     540

atgaaaatcc aggttggtgc taacgatggt gaaaccatta ccatcgatct gcaaaaaatt     600

gatgtgaaaa gccttggcct tgatgggttc aatgttaatt ccccgggaat ttccggtggt     660

ggtggtggaa ttctagactc catgggtaca ttaatcaatg aagacgctgc cgcagccaag     720

aaaagtaccg ctaacccact ggcttcaatt gattctgcat tgtcaaaagt ggacgcagtt     780

cgttcttctc tgggggcaat tcaaaaccgt tttgattcag ccattaccaa ccttggcaat     840

acggtaacca atctgaactc cgcgcgtagc cgtatcgaag atgctgacta tgcaacggaa     900

gtttctaata tgtctaaagc gcagattctg cagcaggctg gtacttccgt tctggcgcag     960

gctaaccagg ttccgcaaaa cgtcctctct ttactgcgtt aa                      1002


<210> SEQ ID NO 51
<211> LENGTH: 42
<212> TYPE: DNA
<213> ORGANISM: Artificial Sequence
<220> FEATURE:
<223> OTHER INFORMATION: Synthetic sequence

<400> SEQUENCE: 51

ggcaattcaa aaccgttttg attaagccat taccaacctt gg                        42


<210> SEQ ID NO 52
<211> LENGTH: 42
<212> TYPE: DNA
<213> ORGANISM: Artificial Sequence
<220> FEATURE:
<223> OTHER INFORMATION: Synthetic sequence

<400> SEQUENCE: 52

ccaaggttgg taatggctta atcaaaacgg ttttgaattg cc                        42


<210> SEQ ID NO 53
<211> LENGTH: 906
<212> TYPE: DNA
<213> ORGANISM: Artificial Sequence
```

<220> FEATURE:
<223> OTHER INFORMATION: Synthetic sequence

<400> SEQUENCE: 53
taatacgact cactataggg gaattgtgag cggataacaa ttcccctcta gaataatttt 60
gtttaacttt aagaaggaga tatacatatg cggggttctc atcatcatca tcatcatggt 120
atggctagca tgactggtgg acagcaaatg ggtcgggatc tgtacgacct ggttccgcgc 180
ggtagcgcga aggatccgat ggcacaagtc attaatacaa acagcctgtc gctgttgacc 240
cagaataacc tgaacaaatc tcagtcctca ctgagttccg ctattgagcg tctgtcctct 300
ggtctgcgta tcaacagcgc gaaagacgat gcggcaggcc aggcgattgc taaccgcttc 360
acttctaata tcaaaggtct gactcaggct tcccgtaacg ctaacgacgg catttctatt 420
gcgcagacca ctgaaggtgc gctgaatgaa atcaacaaca acctgcagcg tgtgcgtgag 480
ttgtctgttc aggccactaa cgggactaac tctgattccg atctgaaatc tatccaggat 540
gaaattcagc aacgtctgga agaaatcgat cgcgtttcta atcagactca atttaacggt 600
gttaaagtcc tgtctcagga caaccagatg aaaatccagg ttggtgctaa cgatggtgaa 660
accattacca tcgatctgca aaaaattgat gtgaaaagcc ttggccttga tgggttcaat 720
gttaattccc cgggaatttc cggtggtggt ggtggaattc tagactccat gggtacatta 780
atcaatgaag acgctgccgc agccaagaaa agtaccgcta acccactggc ttcaattgat 840
tctgcattgt caaaagtgga cgcagttcgt tcttctctgg gggcaattca aaaccgtttt 900
gattaa 906

<210> SEQ ID NO 54
<211> LENGTH: 272
<212> TYPE: PRT
<213> ORGANISM: Artificial Sequence
<220> FEATURE:
<223> OTHER INFORMATION: Synthetic sequence

<400> SEQUENCE: 54

Met Arg Gly Ser His His His His His His Gly Met Ala Ser Met Thr
1 5 10 15

Gly Gly Gln Gln Met Gly Arg Asp Leu Tyr Asp Leu Val Pro Arg Gly
20 25 30

Ser Ala Lys Asp Pro Met Ala Gln Val Ile Asn Thr Asn Ser Leu Ser
35 40 45

Leu Leu Thr Gln Asn Asn Leu Asn Lys Ser Gln Ser Ser Leu Ser Ser
50 55 60

Ala Ile Glu Arg Leu Ser Ser Gly Leu Arg Ile Asn Ser Ala Lys Asp
65 70 75 80

Asp Ala Ala Gly Gln Ala Ile Ala Asn Arg Phe Thr Ser Asn Ile Lys
85 90 95

Gly Leu Thr Gln Ala Ser Arg Asn Ala Asn Asp Gly Ile Ser Ile Ala
100 105 110

Gln Thr Thr Glu Gly Ala Leu Asn Glu Ile Asn Asn Asn Leu Gln Arg
115 120 125

Val Arg Glu Leu Ser Val Gln Ala Thr Asn Gly Thr Asn Ser Asp Ser
130 135 140

Asp Leu Lys Ser Ile Gln Asp Glu Ile Gln Gln Arg Leu Glu Glu Ile
145 150 155 160

Asp Arg Val Ser Asn Gln Thr Gln Phe Asn Gly Val Lys Val Leu Ser
165 170 175

```
Gln Asp Asn Gln Met Lys Ile Gln Val Gly Ala Asn Asp Gly Glu Thr
            180                 185                 190

Ile Thr Ile Asp Leu Gln Lys Ile Asp Val Lys Ser Leu Gly Leu Asp
        195                 200                 205

Gly Phe Asn Val Asn Ser Pro Gly Ile Ser Gly Gly Gly Gly Gly Ile
    210                 215                 220

Leu Asp Ser Met Gly Thr Leu Ile Asn Glu Asp Ala Ala Ala Ala Lys
225                 230                 235                 240

Lys Ser Thr Ala Asn Pro Leu Ala Ser Ile Asp Ser Ala Leu Ser Lys
                245                 250                 255

Val Asp Ala Val Arg Ser Ser Leu Gly Ala Ile Gln Asn Arg Phe Asp
            260                 265                 270


<210> SEQ ID NO 55
<211> LENGTH: 45
<212> TYPE: DNA
<213> ORGANISM: Artificial Sequence
<220> FEATURE:
<223> OTHER INFORMATION: Synthetic sequence

<400> SEQUENCE: 55

caatctgaac tccgcgcgtt gacgtatcta agatgctgac tatgc                   45


<210> SEQ ID NO 56
<211> LENGTH: 45
<212> TYPE: DNA
<213> ORGANISM: Artificial Sequence
<220> FEATURE:
<223> OTHER INFORMATION: Synthetic sequence

<400> SEQUENCE: 56

gcatagtcag catcttagat acgtcaacgc gcggagttca gattg                   45


<210> SEQ ID NO 57
<211> LENGTH: 966
<212> TYPE: DNA
<213> ORGANISM: Artificial Sequence
<220> FEATURE:
<223> OTHER INFORMATION: Synthetic sequence

<400> SEQUENCE: 57

taatacgact cactataggg gaattgtgag cggataacaa ttcccctcta gaataatttt     60

gtttaacttt aagaaggaga tatacatatg cggggttctc atcatcatca tcatcatggt    120

atggctagca tgactggtgg acagcaaatg ggtcgggatc tgtacgacct ggttccgcgc    180

ggtagcgcga aggatccgat ggcacaagtc attaatacaa acagcctgtc gctgttgacc    240

cagaataacc tgaacaaatc tcagtcctca ctgagttccg ctattgagcg tctgtcctct    300

ggtctgcgta tcaacagcgc gaaagacgat gcggcaggcc aggcgattgc taaccgcttc    360

acttctaata tcaaaggtct gactcaggct tcccgtaacg ctaacgacgg catttctatt    420

gcgcagacca ctgaaggtgc gctgaatgaa atcaacaaca acctgcagcg tgtgcgtgag    480

ttgtctgttc aggccactaa cgggactaac tctgattccg atctgaaatc tatccaggat    540

gaaattcagc aacgtctgga agaaatcgat cgcgtttcta atcagactca atttaacggt    600

gttaaagtcc tgtctcagga caaccagatg aaaatccagg ttggtgctaa cgatggtgaa    660

accattacca tcgatctgca aaaaattgat gtgaaaagcc ttggccttga tgggttcaat    720

gttaattccc cgggaatttc cggtggtggt ggtggaattc tagactccat gggtacatta    780
```

```
atcaatgaag acgctgccgc agccaagaaa agtaccgcta acccactggc ttcaattgat    840

tctgcattgt caaaagtgga cgcagttcgt tcttctctgg gggcaattca aaaccgtttt    900

gattcagcca ttaccaacct tggcaatacg gtaaccaatc tgaactccgc gcgttgacgt    960

atctaa                                                               966


<210> SEQ ID NO 58
<211> LENGTH: 289
<212> TYPE: PRT
<213> ORGANISM: Artificial Sequence
<220> FEATURE:
<223> OTHER INFORMATION: Synthetic sequence

<400> SEQUENCE: 58

Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Met Ala Gln Val Ile Asn Thr Asn Ser Leu Ser
        35                  40                  45

Leu Leu Thr Gln Asn Asn Leu Asn Lys Ser Gln Ser Ser Leu Ser Ser
    50                  55                  60

Ala Ile Glu Arg Leu Ser Ser Gly Leu Arg Ile Asn Ser Ala Lys Asp
65                  70                  75                  80

Asp Ala Ala Gly Gln Ala Ile Ala Asn Arg Phe Thr Ser Asn Ile Lys
                85                  90                  95

Gly Leu Thr Gln Ala Ser Arg Asn Ala Asn Asp Gly Ile Ser Ile Ala
            100                 105                 110

Gln Thr Thr Glu Gly Ala Leu Asn Glu Ile Asn Asn Asn Leu Gln Arg
        115                 120                 125

Val Arg Glu Leu Ser Val Gln Ala Thr Asn Gly Thr Asn Ser Asp Ser
    130                 135                 140

Asp Leu Lys Ser Ile Gln Asp Glu Ile Gln Gln Arg Leu Glu Glu Ile
145                 150                 155                 160

Asp Arg Val Ser Asn Gln Thr Gln Phe Asn Gly Val Lys Val Leu Ser
                165                 170                 175

Gln Asp Asn Gln Met Lys Ile Gln Val Gly Ala Asn Asp Gly Glu Thr
            180                 185                 190

Ile Thr Ile Asp Leu Gln Lys Ile Asp Val Lys Ser Leu Gly Leu Asp
        195                 200                 205

Gly Phe Asn Val Asn Ser Pro Gly Ile Ser Gly Gly Gly Gly Gly Ile
    210                 215                 220

Leu Asp Ser Met Gly Thr Leu Ile Asn Glu Asp Ala Ala Ala Ala Lys
225                 230                 235                 240

Lys Ser Thr Ala Asn Pro Leu Ala Ser Ile Asp Ser Ala Leu Ser Lys
                245                 250                 255

Val Asp Ala Val Arg Ser Ser Leu Gly Ala Ile Gln Asn Arg Phe Asp
            260                 265                 270

Ser Ala Ile Thr Asn Leu Gly Asn Thr Val Thr Asn Leu Asn Ser Ala
        275                 280                 285

Arg


<210> SEQ ID NO 59
<211> LENGTH: 48
<212> TYPE: DNA
<213> ORGANISM: Artificial Sequence
```

<220> FEATURE:
<223> OTHER INFORMATION: Synthetic sequence

<400> SEQUENCE: 59
cgtagccgta tcgaagatgc ttaataggca acggaagttt ctaatatg 48

<210> SEQ ID NO 60
<211> LENGTH: 48
<212> TYPE: DNA
<213> ORGANISM: Artificial Sequence
<220> FEATURE:
<223> OTHER INFORMATION: Synthetic sequence

<400> SEQUENCE: 60
catattagaa acttccgttg cctattaagc atcttcgata cggctacg 48

<210> SEQ ID NO 61
<211> LENGTH: 978
<212> TYPE: DNA
<213> ORGANISM: Artificial Sequence
<220> FEATURE:
<223> OTHER INFORMATION: Synthetic sequence

<400> SEQUENCE: 61
taatacgact cactataggg gaattgtgag cggataacaa ttcccctcta gaataatttt 60
gtttaacttt aagaaggaga tatacatatg cggggttctc atcatcatca tcatcatggt 120
atggctagca tgactggtgg acagcaaatg ggtcgggatc tgtacgacct ggttccgcgc 180
ggtagcgcga aggatccgat ggcacaagtc attaatacaa acagcctgtc gctgttgacc 240
cagaataacc tgaacaaatc tcagtcctca ctgagttccg ctattgagcg tctgtcctct 300
ggtctgcgta tcaacagcgc gaaagacgat gcggcaggcc aggcgattgc taaccgcttc 360
acttctaata tcaaaggtct gactcaggct tcccgtaacg ctaacgacgg catttctatt 420
gcgcagacca ctgaaggtgc gctgaatgaa atcaacaaca acctgcagcg tgtgcgtgag 480
ttgtctgttc aggccactaa cgggactaac tctgattccg atctgaaatc tatccaggat 540
gaaattcagc aacgtctgga agaaatcgat cgcgtttcta atcagactca atttaacggt 600
gttaaagtcc tgtctcagga caaccagatg aaaatccagg ttggtgctaa cgatggtgaa 660
accattacca tcgatctgca aaaaattgat gtgaaaagcc ttggccttga tgggttcaat 720
gttaattccc cgggaatttc cggtggtggt ggtggaattc tagactccat gggtacatta 780
atcaatgaag acgctgccgc agccaagaaa agtaccgcta acccactggc ttcaattgat 840
tctgcattgt caaaagtgga cgcagttcgt tcttctctgg gggcaattca aaaccgtttt 900
gattcagcca ttaccaacct tggcaatacg gtaaccaatc tgaactccgc gcgtagccgt 960
atcgaagatg cttaatag 978

<210> SEQ ID NO 62
<211> LENGTH: 295
<212> TYPE: PRT
<213> ORGANISM: Artificial Sequence
<220> FEATURE:
<223> OTHER INFORMATION: Synthetic sequence

<400> SEQUENCE: 62

Met Arg Gly Ser His His His His His His Gly Met Ala Ser Met Thr
1 5 10 15

Gly Gly Gln Gln Met Gly Arg Asp Leu Tyr Asp Leu Val Pro Arg Gly
20 25 30

```
Ser Ala Lys Asp Pro Met Ala Gln Val Ile Asn Thr Asn Ser Leu Ser
        35                  40                  45

Leu Leu Thr Gln Asn Asn Leu Asn Lys Ser Gln Ser Ser Leu Ser Ser
    50                  55                  60

Ala Ile Glu Arg Leu Ser Ser Gly Leu Arg Ile Asn Ser Ala Lys Asp
65                  70                  75                  80

Asp Ala Ala Gly Gln Ala Ile Ala Asn Arg Phe Thr Ser Asn Ile Lys
                85                  90                  95

Gly Leu Thr Gln Ala Ser Arg Asn Ala Asn Asp Gly Ile Ser Ile Ala
            100                 105                 110

Gln Thr Thr Glu Gly Ala Leu Asn Glu Ile Asn Asn Asn Leu Gln Arg
        115                 120                 125

Val Arg Glu Leu Ser Val Gln Ala Thr Asn Gly Thr Asn Ser Asp Ser
    130                 135                 140

Asp Leu Lys Ser Ile Gln Asp Glu Ile Gln Gln Arg Leu Glu Glu Ile
145                 150                 155                 160

Asp Arg Val Ser Asn Gln Thr Gln Phe Asn Gly Val Lys Val Leu Ser
                165                 170                 175

Gln Asp Asn Gln Met Lys Ile Gln Val Gly Ala Asn Asp Gly Glu Thr
            180                 185                 190

Ile Thr Ile Asp Leu Gln Lys Ile Asp Val Lys Ser Leu Gly Leu Asp
        195                 200                 205

Gly Phe Asn Val Asn Ser Pro Gly Ile Ser Gly Gly Gly Gly Gly Ile
    210                 215                 220

Leu Asp Ser Met Gly Thr Leu Ile Asn Glu Asp Ala Ala Ala Ala Lys
225                 230                 235                 240

Lys Ser Thr Ala Asn Pro Leu Ala Ser Ile Asp Ser Ala Leu Ser Lys
                245                 250                 255

Val Asp Ala Val Arg Ser Ser Leu Gly Ala Ile Gln Asn Arg Phe Asp
            260                 265                 270

Ser Ala Ile Thr Asn Leu Gly Asn Thr Val Thr Asn Leu Asn Ser Ala
        275                 280                 285

Arg Ser Arg Ile Glu Asp Ala
    290                 295
```

<210> SEQ ID NO 63
<211> LENGTH: 990
<212> TYPE: DNA
<213> ORGANISM: Artificial Sequence
<220> FEATURE:
<223> OTHER INFORMATION: Synthetic sequence

<400> SEQUENCE: 63

```
atgcggggtt ctcatcatca tcatcatcat ggtatggcta gcatgactgg tggacagcaa     60

atgggtcggg atctgtacga cgatgacgat aaggatccga tggcacaagt cattaataca    120

aacagcctgt cgctgttgac ccagaataac ctgaacaaat ctcagtcctc actgagttcc    180

gctattgagc gtctgtcctc tggtctgcgt atcaacagcg cgaaagacga tgcggcaggc    240

caggcgattg ctaaccgctt cacttctaat atcaaaggtc tgactcaggc ttcccgtaac    300

gctaacgacg gcatttctat tgcgcagacc actgaaggtg cgctgaatga aatcaacaac    360

aacctgcagc gtgtgcgtga gttgtctgtt caggccacta acgggactaa ctctgattcc    420

gatctgaaat ctatccagga tgaaattcag caacgtctgg aagaaatcga tcgcgtttct    480

aatcagactc aatttaacgg tgttaaagtc ctgtctcagg acaaccagat gaaaatccag    540
```

```
gttggtgcta acgatggtga aaccattacc atcgatctgc aaaaaattga tgtgaaaagc    600

cttggccttg atgggttcaa tgttaattcc ccgggaattt ccggtggtgg tggtggaatt    660

ctagactcca tgggtacatt aatcaatgaa gacgctgccg cagccaagaa aagtaccgct    720

aacccactgg cttcaattga ttctgcattg tcaaaagtgg acgcagttcg ttcttctctg    780

ggggcaattc aaaaccgttt tgattcagcc attaccaacc ttggcaatac ggtaaccaat    840

ctgaactccg cgcgtagccg tatcgaagat gctgactatg caacggaagt ttctaatatg    900

tctaaagcgc agattctgca gcaggctggt acttccgttc tggcgcaggc taaccaggtt    960

ccgcaaaacg tcctctcttt actgcgttaa                                     990
```

<210> SEQ ID NO 64
<211> LENGTH: 33
<212> TYPE: DNA
<213> ORGANISM: Artificial Sequence
<220> FEATURE:
<223> OTHER INFORMATION: Synthetic sequence

<400> SEQUENCE: 64

```
cgataaggat catatggcac aagtcattaa tac                                  33
```

<210> SEQ ID NO 65
<211> LENGTH: 78
<212> TYPE: DNA
<213> ORGANISM: Artificial Sequence
<220> FEATURE:
<223> OTHER INFORMATION: Synthetic sequence

<400> SEQUENCE: 65

```
agatctgtcg acttaaccat gatgatgatg atgatgagaa ccccgcggaa ccagtgcata     60

gtcagcatct tcgatacg                                                   78
```

<210> SEQ ID NO 66
<211> LENGTH: 918
<212> TYPE: DNA
<213> ORGANISM: Artificial Sequence
<220> FEATURE:
<223> OTHER INFORMATION: Synthetic sequence

<400> SEQUENCE: 66

```
taatacgact cactataggg gaattgtgag cggataacaa ttcccctcta gaataatttt     60

gtttaacttt aagaaggaga tatacatatg gcacaagtca ttaatacaaa cagcctgtcg    120

ctgttgaccc agaataacct gaacaaatct cagtcctcac tgagttccgc tattgagcgt    180

ctgtcctctg gtctgcgtat caacagcgcg aaagacgatg cggcaggcca ggcgattgct    240

aaccgcttca cttctaatat caaaggtctg actcaggctt cccgtaacgc taacgacggc    300

atttctattg cgcagaccac tgaaggtgcg ctgaatgaaa tcaacaacaa cctgcagcgt    360

gtgcgtgagt tgtctgttca ggccactaac gggactaact ctgattccga tctgaaatct    420

atccaggatg aaattcagca acgtctggaa gaaatcgatc gcgtttctaa tcagactcaa    480

tttaacggtg ttaaagtcct gtctcaggac aaccagatga aaatccaggt tggtgctaac    540

gatggtgaaa ccattaccat cgatctgcaa aaaattgatg tgaaaagcct tggccttgat    600

gggttcaatg ttaattcccc gggaatttcc ggtggtggtg gtggaattct agactccatg    660

ggtacattaa tcaatgaaga cgctgccgca gccaagaaaa gtaccgctaa cccactggct    720

tcaattgatt ctgcattgtc aaaagtggac gcagttcgtt cttctctggg ggcaattcaa    780

aaccgttttg attcagccat taccaacctt ggcaatacgg taaccaatct gaactccgcg    840
```

cgtagccgta tcgaagatgc tgactatgca ctggttccgc ggggttctca tcatcatcat 900
catcatggtt aagtcgac 918

<210> SEQ ID NO 67
<211> LENGTH: 274
<212> TYPE: PRT
<213> ORGANISM: Artificial Sequence
<220> FEATURE:
<223> OTHER INFORMATION: Synthetic sequence

<400> SEQUENCE: 67

Met Ala Gln Val Ile Asn Thr Asn Ser Leu Ser Leu Leu Thr Gln Asn
1 5 10 15

Asn Leu Asn Lys Ser Gln Ser Ser Leu Ser Ser Ala Ile Glu Arg Leu
20 25 30

Ser Ser Gly Leu Arg Ile Asn Ser Ala Lys Asp Asp Ala Ala Gly Gln
35 40 45

Ala Ile Ala Asn Arg Phe Thr Ser Asn Ile Lys Gly Leu Thr Gln Ala
50 55 60

Ser Arg Asn Ala Asn Asp Gly Ile Ser Ile Ala Gln Thr Thr Glu Gly
65 70 75 80

Ala Leu Asn Glu Ile Asn Asn Asn Leu Gln Arg Val Arg Glu Leu Ser
85 90 95

Val Gln Ala Thr Asn Gly Thr Asn Ser Asp Ser Asp Leu Lys Ser Ile
100 105 110

Gln Asp Glu Ile Gln Gln Arg Leu Glu Glu Ile Asp Arg Val Ser Asn
115 120 125

Gln Thr Gln Phe Asn Gly Val Lys Val Leu Ser Gln Asp Asn Gln Met
130 135 140

Lys Ile Gln Val Gly Ala Asn Asp Gly Glu Thr Ile Thr Ile Asp Leu
145 150 155 160

Gln Lys Ile Asp Val Lys Ser Leu Gly Leu Asp Gly Phe Asn Val Asn
165 170 175

Ser Pro Gly Ile Ser Gly Gly Gly Gly Gly Ile Leu Asp Ser Met Gly
180 185 190

Thr Leu Ile Asn Glu Asp Ala Ala Ala Ala Lys Lys Ser Thr Ala Asn
195 200 205

Pro Leu Ala Ser Ile Asp Ser Ala Leu Ser Lys Val Asp Ala Val Arg
210 215 220

Ser Ser Leu Gly Ala Ile Gln Asn Arg Phe Asp Ser Ala Ile Thr Asn
225 230 235 240

Leu Gly Asn Thr Val Thr Asn Leu Asn Ser Ala Arg Ser Arg Ile Glu
245 250 255

Asp Ala Asp Tyr Ala Leu Val Pro Arg Gly Ser His His His His His
260 265 270

His Gly

<210> SEQ ID NO 68
<211> LENGTH: 40
<212> TYPE: DNA
<213> ORGANISM: Artificial Sequence
<220> FEATURE:
<223> OTHER INFORMATION: Synthetic sequence

<400> SEQUENCE: 68
agatctccgc ggaaccagac cagcctgctg cagaatctgc 40

<210> SEQ ID NO 69
<211> LENGTH: 795
<212> TYPE: DNA
<213> ORGANISM: Artificial Sequence
<220> FEATURE:
<223> OTHER INFORMATION: Synthetic sequence

<400> SEQUENCE: 69

```
taatacgact cactataggg gaattgtgag cggataacaa ttcccctcta gaataatttt     60
gtttaacttt aagaaggaga tatacatatg agcgggttac ggatcaacag cgcgaaagac    120
gatgcggcag gccaggcgat tgctaaccgc ttcacttcta atatcaaagg tctgactcag    180
gcttcccgta acgctaacga cggcatttct attgcgcaga ccactgaagg tgcgctgaat    240
gaaatcaaca acaacctgca gcgtgtgcgt gagttgtctg ttcaggccac taacgggact    300
aactctgatt ccgatctgaa atctatccag gatgaaattc agcaacgtct ggaagaaatc    360
gatcgcgttt ctaatcagac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaaccttg gcaatacggt aaccaatctg    660
aactccgcgc gtagccgtat cgaagatgct gactatgcaa cggaagtttc taatatgtct    720
aaagcgcaga ttctgcagca ggctggtctg gttccgcggg gttctcatca tcatcatcat    780
catggttaag tcgac                                                     795
```

<210> SEQ ID NO 70
<211> LENGTH: 702
<212> TYPE: DNA
<213> ORGANISM: Artificial Sequence
<220> FEATURE:
<223> OTHER INFORMATION: Synthetic sequence

<400> SEQUENCE: 70

```
atgagcgggt tacggatcaa cagcgcgaaa gacgatgcgg caggccaggc gattgctaac     60
cgcttcactt ctaatatcaa aggtctgact caggcttccc gtaacgctaa cgacggcatt    120
tctattgcgc agaccactga aggtgcgctg aatgaaatca acaacaacct gcagcgtgtg    180
cgtgagttgt ctgttcaggc cactaacggg actaactctg attccgatct gaaatctatc    240
caggatgaaa ttcagcaacg tctggaagaa atcgatcgcg tttctaatca gactcaattt    300
aacggtgtta aagtcctgtc tcaggacaac cagatgaaaa tccaggttgg tgctaacgat    360
ggtgaaacca ttaccatcga tctgcaaaaa attgatgtga aaagccttgg ccttgatggg    420
ttcaatgtta attccccggg aagtaccgct aacccactgg cttcaattga ttctgcattg    480
tcaaaagtgg acgcagttcg ttcttctctg gggcaattc aaaaccgctt tgattcagcc    540
attaccaacc ttggcaatac ggtaaccaat ctgaactccg cgcgtagccg tatcgaagat    600
gctgactatg caacggaagt ttctaatatg tctaaagcgc agattctgca gcaggctggt    660
ctggttccgc ggggttctca tcatcatcat catcatggtt aa                       702
```

<210> SEQ ID NO 71
<211> LENGTH: 233
<212> TYPE: PRT
<213> ORGANISM: Artificial Sequence
<220> FEATURE:

<223> OTHER INFORMATION: Synthetic sequence

<400> SEQUENCE: 71

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Leu Val Pro Arg
    210                 215                 220

Gly Ser His His His His His His Gly
225                 230
```

<210> SEQ ID NO 72
<211> LENGTH: 120
<212> TYPE: DNA
<213> ORGANISM: Artificial Sequence
<220> FEATURE:
<223> OTHER INFORMATION: Synthetic sequence

<400> SEQUENCE: 72

```
aacccactgg cttcaattga ttctgcattg tcaaaagtgg acgcagttcg ttcttctctg     60

ggggcaattc aaaaccgttt tgattcagcc attaccgccc ttggcaatac ggtaaccaat    120
```

<210> SEQ ID NO 73
<211> LENGTH: 40
<212> TYPE: PRT
<213> ORGANISM: Artificial Sequence
<220> FEATURE:
<223> OTHER INFORMATION: Synthetic sequence

<400> SEQUENCE: 73

```
Asn Pro Leu Ala Ser Ile Asp Ser Ala Leu Ser Lys Val Asp Ala Val
1               5                   10                  15

Arg Ser Ser Leu Gly Ala Ile Gln Asn Arg Phe Asp Ser Ala Ile Thr
            20                  25                  30
```

```
Ala Leu Gly Asn Thr Val Thr Asn
        35                  40


<210> SEQ ID NO 74
<211> LENGTH: 46
<212> TYPE: DNA
<213> ORGANISM: Artificial Sequence
<220> FEATURE:
<223> OTHER INFORMATION: Synthetic sequence

<400> SEQUENCE: 74

gttcgttctt ctctgggggc aattgattca gccattaccg cccttg                  46


<210> SEQ ID NO 75
<211> LENGTH: 46
<212> TYPE: DNA
<213> ORGANISM: Artificial Sequence
<220> FEATURE:
<223> OTHER INFORMATION: Synthetic sequence

<400> SEQUENCE: 75

caagggcggt aatggctgaa tcaattgccc ccagagaaga acgaac                  46


<210> SEQ ID NO 76
<211> LENGTH: 783
<212> TYPE: DNA
<213> ORGANISM: Artificial Sequence
<220> FEATURE:
<223> OTHER INFORMATION: Synthetic sequence

<400> SEQUENCE: 76

taatacgact cactataggg gaattgtgag cggataacaa ttcccctcta gaataatttt     60

gtttaacttt aagaaggaga tatacatatg agcgggttac ggatcaacag cgcgaaagac    120

gatgcggcag gccaggcgat tgctaaccgc ttcacttcta atatcaaagg tctgactcag    180

gcttcccgta acgctaacga cggcatttct attgcgcaga ccactgaagg tgcgctgaat    240

gaaatcaaca acaacctgca gcgtgtgcgt gagttgtctg ttcaggccac taacgggact    300

aactctgatt ccgatctgaa atctatccag gatgaaattc agcaacgtct ggaagaaatc    360

gatcgcgttt ctaatcagac tcaatttaac ggtgttaaag tcctgtctca ggacaaccag    420

atgaaaatcc aggttggtgc taacgatggt gaaaccatta ccatcgatct gcaaaaaatt    480

gatgtgaaaa gccttggcct tgatgggttc aatgttaatt ccccgggaag taccgctaac    540

ccactggctt caattgattc tgcattgtca aaagtggacg cagttcgttc ttctctgggg    600

gcaattgatt cagccattac cgcccttggc aatacggtaa ccaatctgaa ctccgcgcgt    660

agccgtatcg aagatgctga ctatgcaacg gaagtttcta atatgtctaa agcgcagatt    720

ctgcagcagg ctggtctggt tccgcggggt tctcatcatc atcatcatca tggttaagtc    780

gac                                                                  783


<210> SEQ ID NO 77
<211> LENGTH: 229
<212> TYPE: PRT
<213> ORGANISM: Artificial Sequence
<220> FEATURE:
<223> OTHER INFORMATION: Synthetic sequence

<400> SEQUENCE: 77

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
```

```
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Asp Ser Ala
                165                 170                 175

Ile Thr Ala Leu Gly Asn Thr Val Thr Asn Leu Asn Ser Ala Arg Ser
            180                 185                 190

Arg Ile Glu Asp Ala Asp Tyr Ala Thr Glu Val Ser Asn Met Ser Lys
        195                 200                 205

Ala Gln Ile Leu Gln Gln Ala Gly Leu Val Pro Arg Gly Ser His His
    210                 215                 220

His His His His Gly
225
```

```
<210> SEQ ID NO 78
<211> LENGTH: 654
<212> TYPE: DNA
<213> ORGANISM: Artificial Sequence
<220> FEATURE:
<223> OTHER INFORMATION: Synthetic sequence

<400> SEQUENCE: 78

atgagcgggt tacggatcaa cagcgcgaaa gacgatgcgg caggccaggc gattgctaac     60

cgcttcactt ctaatatcaa aggtctgact caggcttccc gtaacgctaa cgacggcatt    120

tctattgcgc agaccactga aggtgcgctg aatgaaatca acaacaacct gcagcgtgtg    180

cgtgagttgt ctgttcaggc cactaacggg actaactctg attccgatct gaaatctatc    240

caggatgaaa ttcagcaacg tctggaagaa atcgatcgcg tttctaatca gactcaattt    300

aacggtgtta aagtcctgtc tcaggacaac cagatgaaaa tccaggttgg tgctaacgat    360

ggtgaaacca ttaccatcga tctgcaaaaa attgatgtga aaagccttgg ccttgatggg    420

ttcaatgtta attccccggg aagtaccgct aacccactgg cttcaattga ttctgcattg    480

tcaaaagtgg acgcagttcg ttcttctctg ggggcaattc aaaaccgctt tgattcagcc    540

attaccaacc ttggcaatac ggtaaccaat ctgaactccg cgcgtagccg tatcgaagat    600

gctgactatg cactggttcc gcggggttct catcatcatc atcatcatgg ttaa          654

<210> SEQ ID NO 79
<211> LENGTH: 217
<212> TYPE: PRT
<213> ORGANISM: Artificial Sequence
<220> FEATURE:
```

<223> OTHER INFORMATION: Synthetic sequence

<400> SEQUENCE: 79

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Leu Val Pro Arg
        195                 200                 205

Gly Ser His His His His His His Gly
    210                 215
```

<210> SEQ ID NO 80
<211> LENGTH: 714
<212> TYPE: DNA
<213> ORGANISM: Artificial Sequence
<220> FEATURE:
<223> OTHER INFORMATION: Synthetic sequence

<400> SEQUENCE: 80

```
atgagtaaag gagaagaact tttcactgga gttgtcccaa ttcttgttga attagatggt     60

gatgttaatg ggcacaaatt ttctgtcagt ggagagggtg aaggtgatgc aacatacgga    120

aaacttaccc ttaaatttat ttgcactact ggaaaactac ctgttccatg gccaacactt    180

gtcactactc tgacgtatgg tgttcaatgc ttttcccgtt atccggatca tatgaaacgg    240

catgactttt tcaagagtgc catgcccgaa ggttatgtac aggaacgcac tatatctttc    300

aaagatgacg ggaactacaa gacgcgtgct gaagtcaagt ttgaaggtga tacccttgtt    360

aatcgtatcg agttaaaagg tattgatttt aaagaagatg gaaacattct cggacacaaa    420

ctcgagtaca actataactc acacaatgta tacatcacgg cagacaaaca aaagaatgga    480

atcaaagcta acttcaaaat tcgccacaac attgaagatg gatccgttca actagcagac    540

cattatcaac aaaatactcc aattggcgat ggccctgtcc ttttaccaga caaccattac    600

ctgtcgacac aatctgccct ttgaaagat cccaacgaaa agcgtgacca catggtcctt     660

cttgagtttg taactgctgc tgggattaca catggcatgg atgaactata caaa          714
```

<210> SEQ ID NO 81
<211> LENGTH: 238
<212> TYPE: PRT
<213> ORGANISM: Artificial Sequence
<220> FEATURE:
<223> OTHER INFORMATION: Synthetic sequence

<400> SEQUENCE: 81

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Leu
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 82
<211> LENGTH: 717
<212> TYPE: DNA
<213> ORGANISM: Artificial Sequence
<220> FEATURE:
<223> OTHER INFORMATION: Synthetic sequence

<400> SEQUENCE: 82

```
atgagtaaag gagaagaact tttcactgga gttgtcccaa ttcttgttga attagatggt      60

gatgttaatg ggcacaaatt ttctgtcagt ggagagggtg aaggtgatgc aacatacgga     120

aaacttaccc ttaaatttat ttgcactact ggaaaactac ctgttccatg gccaacactt     180

gtcactactc tgacgtatgg tgttcaatgc ttttcccgtt atccggatca catgaaacgg     240

catgactttt tcaagagtgc catgcccgaa ggttatgtac aggaacgcac tatatctttc     300

aaagatgacg ggaactacaa gacgcgtgct gaagtcaagt ttgaaggtga tacccttgtt     360

aatcgtatcg agttaaaagg tattgatttt aaagaagatg gaaacattct cggacacaaa     420
```

ctcgagtaca actataactc acacaatgta tacatcacgg cagacaaaca aaagaatgga 480
atcaaagcta acttcaaaat tcgccacaac attgaagatg gatccgttca actagcagac 540
cattatcaac aaaatactcc aattggcgat ggccctgtcc ttttaccaga caaccattac 600
ctgtcgacac aatctgccct ttgaaagat cccaacgaaa agcgtgacca catggtcctt 660
cttgagtttg taactgctgc tgggattaca catggcatgg atgaactata caaataa 717

<210> SEQ ID NO 83
<211> LENGTH: 54
<212> TYPE: DNA
<213> ORGANISM: Artificial Sequence
<220> FEATURE:
<223> OTHER INFORMATION: Synthetic sequence

<400> SEQUENCE: 83
tctagacggc cgatctcagg taagaatgga atcaaagcta acttcaaaat tcgc 54

<210> SEQ ID NO 84
<211> LENGTH: 20
<212> TYPE: PRT
<213> ORGANISM: Artificial Sequence
<220> FEATURE:
<223> OTHER INFORMATION: Synthetic sequence

<400> SEQUENCE: 84

Asn Val Tyr Ile Pro Ile Ser Gly Lys Asn Gly Ile Lys Ala Asn Phe
1 5 10 15

Lys Ile Arg His
20

<210> SEQ ID NO 85
<211> LENGTH: 45
<212> TYPE: DNA
<213> ORGANISM: Artificial Sequence
<220> FEATURE:
<223> OTHER INFORMATION: Synthetic sequence

<400> SEQUENCE: 85
agatctccgc ggtttgtata gttcatccat gccatgtgta atccc 45

<210> SEQ ID NO 86
<211> LENGTH: 1005
<212> TYPE: DNA
<213> ORGANISM: Artificial Sequence
<220> FEATURE:
<223> OTHER INFORMATION: Synthetic sequence

<400> SEQUENCE: 86
taatacgact cactataggg gaattgtgag cggataacaa ttcccctcta gaataatttt 60
gtttaacttt aagaaggaga tatacatatg agcgggttac ggatcaacag cgcgaaagac 120
gatgcggcag gccaggcgat tgctaaccgc ttcacttcta atatcaaagg tctgactcag 180
gcttcccgta acgctaacga cggcatttct attgcgcaga ccactgaagg tgcgctgaat 240
gaaatcaaca acaacctgca gcgtgtgcgt gagttgtctg ttcaggccac taacgggact 300
aactctgatt ccgatctgaa atctatccag gatgaaattc agcaacgtct ggaagaaatc 360
gatcgcgttt ctaatcagac tcaatttaac ggtgttaaag tcctgtctca ggacaaccag 420
atgaaaatcc aggttggtgc taacgatggt gaaaccatta ccatcgatct gcaaaaaatt 480
gatgtgaaaa gccttggcct tgatgggttc aatgttaatt ccccgggaag taccgctaac 540

```
ccactggctt caattgattc tgcattgtca aaagtggacg cagttcgttc ttctctgggg    600

gcaattcaaa accgctttga ttcagccatt accaaccttg gcaatacggt aaccaatctg    660

aactccgcgc gtagccgtat cgaagatgct gactatgcac tggttccgcc gatctcaggt    720

aagaatggaa tcaaagctaa cttcaaaatt cgccacaaca ttgaagatgg atccgttcaa    780

ctagcagacc attatcaaca aaatactcca attggcgatg gccctgtcct tttaccagac    840

aaccattacc tgtcgacaca atctgccctt ttgaaagatc ccaacgaaaa gcgtgaccac    900

atggtccttc ttgagtttgt aactgctgct gggattacac atggcatgga tgaactatac    960

aaaccgcggg gttctcatca tcatcatcat catggttaag tcgac                   1005


<210> SEQ ID NO 87
<211> LENGTH: 912
<212> TYPE: DNA
<213> ORGANISM: Artificial Sequence
<220> FEATURE:
<223> OTHER INFORMATION: Synthetic sequence

<400> SEQUENCE: 87

atgagcgggt tacggatcaa cagcgcgaaa gacgatgcgg caggccaggc gattgctaac     60

cgcttcactt ctaatatcaa aggtctgact caggcttccc gtaacgctaa cgacggcatt    120

tctattgcgc agaccactga aggtgcgctg aatgaaatca acaacaacct gcagcgtgtg    180

cgtgagttgt ctgttcaggc cactaacggg actaactctg attccgatct gaaatctatc    240

caggatgaaa ttcagcaacg tctggaagaa atcgatcgcg tttctaatca gactcaattt    300

aacggtgtta aagtcctgtc tcaggacaac cagatgaaaa tccaggttgg tgctaacgat    360

ggtgaaacca ttaccatcga tctgcaaaaa attgatgtga aaagccttgg ccttgatggg    420

ttcaatgtta attccccggg aagtaccgct aacccactgg cttcaattga ttctgcattg    480

tcaaaagtgg acgcagttcg ttcttctctg gggcaattc aaaaccgctt tgattcagcc    540

attaccaacc ttggcaatac ggtaaccaat ctgaactccg cgcgtagccg tatcgaagat    600

gctgactatg cactggttcc gccgatctca ggtaagaatg gaatcaaagc taacttcaaa    660

attcgccaca acattgaaga tggatccgtt caactagcag accattatca acaaaatact    720

ccaattggcg atggccctgt ccttttacca gacaaccatt acctgtcgac acaatctgcc    780

cttttgaaag atcccaacga aaagcgtgac cacatggtcc ttcttgagtt tgtaactgct    840

gctgggatta cacatggcat ggatgaacta tacaaaccgc ggggttctca tcatcatcat    900

catcatggtt aa                                                        912


<210> SEQ ID NO 88
<211> LENGTH: 303
<212> TYPE: PRT
<213> ORGANISM: Artificial Sequence
<220> FEATURE:
<223> OTHER INFORMATION: Synthetic sequence

<400> SEQUENCE: 88

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60
```

```
Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Leu Val Pro Pro
        195                 200                 205

Ile Ser Gly Lys Asn Gly Ile Lys Ala Asn Phe Lys Ile Arg His Asn
    210                 215                 220

Ile Glu Asp Gly Ser Val Gln Leu Ala Asp His Tyr Gln Gln Asn Thr
225                 230                 235                 240

Pro Ile Gly Asp Gly Pro Val Leu Leu Pro Asp Asn His Tyr Leu Ser
                245                 250                 255

Thr Gln Ser Ala Leu Leu Lys Asp Pro Asn Glu Lys Arg Asp His Met
            260                 265                 270

Val Leu Leu Glu Phe Val Thr Ala Ala Gly Ile Thr His Gly Met Asp
        275                 280                 285

Glu Leu Tyr Lys Pro Arg Gly Ser His His His His His His Gly
    290                 295                 300
```

<210> SEQ ID NO 89
<211> LENGTH: 585
<212> TYPE: DNA
<213> ORGANISM: Artificial Sequence
<220> FEATURE:
<223> OTHER INFORMATION: Synthetic sequence

<400> SEQUENCE: 89

```
atgagtaccg ctaacccact ggcttcaatt gattctgcat tgtcaaaagt ggacgcagtt      60

cgttcttctc tgggggcaat tcaaaaccgc tttgattcag ccattaccaa ccttggcaat     120

acggtaacca atctgaactc cgcgcgtagc cgtatcgaag atgctgacta tgcatccccg     180

ggaagcgggt tacggatcaa cagcgcgaaa gacgatgcgg caggccaggc gattgctaac     240

cgcttcactt ctaatatcaa aggtctgact caggcttccc gtaacgctaa cgacggcatt     300

tctattgcgc agaccactga aggtgcgctg aatgaaatca acaacaacct gcagcgtgtg     360

cgtgagttgt ctgttcaggc cactaacggg actaactctg attccgatct gaaatctatc     420

caggatgaaa ttcagcaacg tctggaagaa atcgatcgcg tttctaatca gactcaattt     480

aacggtgtta aagtcctgtc tcaggacaac cagatgaaaa tccaggttgg tgctaacgat     540

ggtctggttc cgcggggttc tcatcatcat catcatcatg gttaa                     585
```

<210> SEQ ID NO 90
<211> LENGTH: 194

<212> TYPE: PRT
<213> ORGANISM: Artificial Sequence
<220> FEATURE:
<223> OTHER INFORMATION: Synthetic sequence

<400> SEQUENCE: 90

```
Met Ser Thr Ala Asn Pro Leu Ala Ser Ile Asp Ser Ala Leu Ser Lys
1               5                   10                  15

Val Asp Ala Val Arg Ser Ser Leu Gly Ala Ile Gln Asn Arg Phe Asp
            20                  25                  30

Ser Ala Ile Thr Asn Leu Gly Asn Thr Val Thr Asn Leu Asn Ser Ala
        35                  40                  45

Arg Ser Arg Ile Glu Asp Ala Asp Tyr Ala Ser Pro Gly Ser Gly Leu
    50                  55                  60

Arg Ile Asn Ser Ala Lys Asp Asp Ala Ala Gly Gln Ala Ile Ala Asn
65                  70                  75                  80

Arg Phe Thr Ser Asn Ile Lys Gly Leu Thr Gln Ala Ser Arg Asn Ala
                85                  90                  95

Asn Asp Gly Ile Ser Ile Ala Gln Thr Thr Glu Gly Ala Leu Asn Glu
            100                 105                 110

Ile Asn Asn Asn Leu Gln Arg Val Arg Glu Leu Ser Val Gln Ala Thr
        115                 120                 125

Asn Gly Thr Asn Ser Asp Ser Asp Leu Lys Ser Ile Gln Asp Glu Ile
    130                 135                 140

Gln Gln Arg Leu Glu Glu Ile Asp Arg Val Ser Asn Gln Thr Gln Phe
145                 150                 155                 160

Asn Gly Val Lys Val Leu Ser Gln Asp Asn Gln Met Lys Ile Gln Val
                165                 170                 175

Gly Ala Asn Asp Gly Leu Val Pro Arg Gly Ser His His His His His
            180                 185                 190

His Gly
```

<210> SEQ ID NO 91
<211> LENGTH: 678
<212> TYPE: DNA
<213> ORGANISM: Artificial Sequence
<220> FEATURE:
<223> OTHER INFORMATION: Synthetic sequence

<400> SEQUENCE: 91

```
taatacgact cactataggg gaattgtgag cggataacaa ttcccctcta gaataatttt     60

gtttaacttt aagaaggaga tatacatatg agtaccgcta acccactggc ttcaattgat    120

tctgcattgt caaaagtgga cgcagttcgt tcttctctgg gggcaattca aaaccgcttt    180

gattcagcca ttaccaacct tggcaatacg gtaaccaatc tgaactccgc gcgtagccgt    240

atcgaagatg ctgactatgc atccccggga agcgggttac ggatcaacag cgcgaaagac    300

gatgcggcag gccaggcgat tgctaaccgc ttcacttcta atatcaaagg tctgactcag    360

gcttcccgta acgctaacga cggcatttct attgcgcaga ccactgaagg tgcgctgaat    420

gaaatcaaca acaacctgca gcgtgtgcgt gagttgtctg ttcaggccac taacgggact    480

aactctgatt ccgatctgaa atctatccag gatgaaattc agcaacgtct ggaagaaatc    540

gatcgcgttt ctaatcagac tcaatttaac ggtgttaaag tcctgtctca ggacaaccag    600

atgaaaatcc aggttggtgc taacgatggt ctggttccgc ggggttctca tcatcatcat    660

catcatggtt aagtcgac                                                  678
```

<210> SEQ ID NO 92
<211> LENGTH: 40
<212> TYPE: DNA
<213> ORGANISM: Artificial Sequence
<220> FEATURE:
<223> OTHER INFORMATION: Synthetic sequence

<400> SEQUENCE: 92
tctagacata tgagtaccgc taacccactg gcttcaattg 40

<210> SEQ ID NO 93
<211> LENGTH: 38
<212> TYPE: DNA
<213> ORGANISM: Artificial Sequence
<220> FEATURE:
<223> OTHER INFORMATION: Synthetic sequence

<400> SEQUENCE: 93
gcttcccggg gatgcatagt cagcatcttc gatacggc 38

<210> SEQ ID NO 94
<211> LENGTH: 34
<212> TYPE: DNA
<213> ORGANISM: Artificial Sequence
<220> FEATURE:
<223> OTHER INFORMATION: Synthetic sequence

<400> SEQUENCE: 94
gcatccccgg gaagcgggtt acggatcaac agcg 34

<210> SEQ ID NO 95
<211> LENGTH: 50
<212> TYPE: DNA
<213> ORGANISM: Artificial Sequence
<220> FEATURE:
<223> OTHER INFORMATION: Synthetic sequence

<400> SEQUENCE: 95
agatctccgc ggaaccagac catcgttagc accaacctgg attttcatct 50

<210> SEQ ID NO 96
<211> LENGTH: 654
<212> TYPE: DNA
<213> ORGANISM: Artificial Sequence
<220> FEATURE:
<223> OTHER INFORMATION: Synthetic sequence

<400> SEQUENCE: 96
atgagtaccg ctaacccact ggcttcaatt gattctgcat tgtcaaaagt ggacgcagtt 60
cgttcttctc tgggggcaat tcaaaaccgc tttgattcag ccattaccaa ccttggcaat 120
acggtaacca atctgaactc cgcgcgtagc cgtatcgaag atgctgacta tgcatccccg 180
ggaagcgggt tacggatcaa cagcgcgaaa gacgatgcgg caggccaggc gattgctaac 240
cgcttcactt ctaatatcaa aggtctgact caggcttccc gtaacgctaa cgacggcatt 300
tctattgcgc agaccactga aggtgcgctg aatgaaatca acaacaacct gcagcgtgtg 360
cgtgagttgt ctgttcaggc cactaacggg actaactctg attccgatct gaaatctatc 420
caggatgaaa ttcagcaacg tctggaagaa atcgatcgcg tttctaatca gactcaattt 480
aacggtgtta aagtcctgtc tcaggacaac cagatgaaaa tccaggttgg tgctaacgat 540
ggtgaaacca ttaccatcga tctgcaaaaa attgatgtga aaagccttgg ccttgatggg 600
ttcaatgtta atctggttcc gcggggttct catcatcatc atcatcatgg ttaa 654

<210> SEQ ID NO 97
<211> LENGTH: 217
<212> TYPE: PRT
<213> ORGANISM: Artificial Sequence
<220> FEATURE:
<223> OTHER INFORMATION: Synthetic sequence

<400> SEQUENCE: 97

```
Met Ser Thr Ala Asn Pro Leu Ala Ser Ile Asp Ser Ala Leu Ser Lys
1               5                   10                  15

Val Asp Ala Val Arg Ser Ser Leu Gly Ala Ile Gln Asn Arg Phe Asp
            20                  25                  30

Ser Ala Ile Thr Asn Leu Gly Asn Thr Val Thr Asn Leu Asn Ser Ala
        35                  40                  45

Arg Ser Arg Ile Glu Asp Ala Asp Tyr Ala Ser Pro Gly Ser Gly Leu
    50                  55                  60

Arg Ile Asn Ser Ala Lys Asp Asp Ala Ala Gly Gln Ala Ile Ala Asn
65                  70                  75                  80

Arg Phe Thr Ser Asn Ile Lys Gly Leu Thr Gln Ala Ser Arg Asn Ala
                85                  90                  95

Asn Asp Gly Ile Ser Ile Ala Gln Thr Thr Glu Gly Ala Leu Asn Glu
            100                 105                 110

Ile Asn Asn Asn Leu Gln Arg Val Arg Glu Leu Ser Val Gln Ala Thr
        115                 120                 125

Asn Gly Thr Asn Ser Asp Ser Asp Leu Lys Ser Ile Gln Asp Glu Ile
    130                 135                 140

Gln Gln Arg Leu Glu Glu Ile Asp Arg Val Ser Asn Gln Thr Gln Phe
145                 150                 155                 160

Asn Gly Val Lys Val Leu Ser Gln Asp Asn Gln Met Lys Ile Gln Val
                165                 170                 175

Gly Ala Asn Asp Gly Glu Thr Ile Thr Ile Asp Leu Gln Lys Ile Asp
            180                 185                 190

Val Lys Ser Leu Gly Leu Asp Gly Phe Asn Val Asn Leu Val Pro Arg
        195                 200                 205

Gly Ser His His His His His His Gly
    210                 215
```

<210> SEQ ID NO 98
<211> LENGTH: 747
<212> TYPE: DNA
<213> ORGANISM: Artificial Sequence
<220> FEATURE:
<223> OTHER INFORMATION: Synthetic sequence

<400> SEQUENCE: 98

```
taatacgact cactataggg gaattgtgag cggataacaa ttcccctcta gaataatttt      60

gtttaacttt aagaaggaga tatacatatg agtaccgcta acccactggc ttcaattgat     120

tctgcattgt caaaagtgga cgcagttcgt tcttctctgg gggcaattca aaaccgcttt     180

gattcagcca ttaccaacct tggcaatacg gtaaccaatc tgaactccgc gcgtagccgt     240

atcgaagatg ctgactatgc atccccggga agcgggttac ggatcaacag cgcgaaagac     300

gatgcggcag gccaggcgat tgctaaccgc ttcacttcta atatcaaagg tctgactcag     360

gcttcccgta acgctaacga cggcatttct attgcgcaga ccactgaagg tgcgctgaat     420

gaaatcaaca acaacctgca gcgtgtgcgt gagttgtctg ttcaggccac taacgggact     480
```

aactctgatt ccgatctgaa atctatccag gatgaaattc agcaacgtct ggaagaaatc 540
gatcgcgttt ctaatcagac tcaatttaac ggtgttaaag tcctgtctca ggacaaccag 600
atgaaaatcc aggttggtgc taacgatggt gaaaccatta ccatcgatct gcaaaaaatt 660
gatgtgaaaa gccttggcct tgatgggttc aatgttaatc tggttccgcg gggttctcat 720
catcatcatc atcatggtta agtcgac 747

<210> SEQ ID NO 99
<211> LENGTH: 45
<212> TYPE: DNA
<213> ORGANISM: Artificial Sequence
<220> FEATURE:
<223> OTHER INFORMATION: Synthetic sequence

<400> SEQUENCE: 99
agatctccgc ggaaccagat taacattgaa cccatcaagg ccaag 45

<210> SEQ ID NO 100
<211> LENGTH: 38
<212> TYPE: DNA
<213> ORGANISM: Artificial Sequence
<220> FEATURE:
<223> OTHER INFORMATION: Synthetic sequence

<400> SEQUENCE: 100
cccgttatcc ggatcacatg aaacggcatg actttttc 38

<210> SEQ ID NO 101
<211> LENGTH: 38
<212> TYPE: DNA
<213> ORGANISM: Artificial Sequence
<220> FEATURE:
<223> OTHER INFORMATION: Synthetic sequence

<400> SEQUENCE: 101
gaaaaagtca tgccgtttca tgtgatccgg ataacggg 38

<210> SEQ ID NO 102
<211> LENGTH: 21
<212> TYPE: DNA
<213> ORGANISM: Artificial Sequence
<220> FEATURE:
<223> OTHER INFORMATION: Synthetic sequence

<400> SEQUENCE: 102
ctgttccatg gccaacactt g 21

<210> SEQ ID NO 103
<211> LENGTH: 46
<212> TYPE: DNA
<213> ORGANISM: Artificial Sequence
<220> FEATURE:
<223> OTHER INFORMATION: Synthetic sequence

<400> SEQUENCE: 103
tctagacata tgagtaaagg agaagaactt ttcactggag ttgtcc 46

<210> SEQ ID NO 104
<211> LENGTH: 63
<212> TYPE: DNA
<213> ORGANISM: Artificial Sequence
<220> FEATURE:
<223> OTHER INFORMATION: Synthetic sequence

<400> SEQUENCE: 104

```
ggcctatgcg gccgcagtaa aggagaagaa cttttcactg gagttgtccc aattcttgtt     60

gaa                                                                    63


<210> SEQ ID NO 105
<211> LENGTH: 57
<212> TYPE: DNA
<213> ORGANISM: Artificial Sequence
<220> FEATURE:
<223> OTHER INFORMATION: Synthetic sequence

<400> SEQUENCE: 105

agatctatta atgcggcctg ataggccttg tttgtctgcc gtgatgtata cattgtg        57


<210> SEQ ID NO 106
<211> LENGTH: 18
<212> TYPE: PRT
<213> ORGANISM: Artificial Sequence
<220> FEATURE:
<223> OTHER INFORMATION: Synthetic sequence

<400> SEQUENCE: 106

Ser His Asn Val Tyr Ile Thr Ala Asp Lys Gln Gly Leu Ser Gly Arg
1               5                   10                  15

Asn Met


<210> SEQ ID NO 107
<211> LENGTH: 1494
<212> TYPE: DNA
<213> ORGANISM: Artificial Sequence
<220> FEATURE:
<223> OTHER INFORMATION: Synthetic sequence

<400> SEQUENCE: 107

taatacgact cactataggg gaattgtgag cggataacaa ttcccctcta gaataatttt     60

gtttaacttt aagaaggaga tatacatatg agtaaaggag aagaactttt cactggagtt    120

gtcccaattc ttgttgaatt agatggtgat gttaatgggc acaaattttc tgtcagtgga    180

gagggtgaag gtgatgcaac atacggaaaa cttaccctta aatttatttg cactactgga    240

aaactacctg ttccatggcc aacacttgtc actactctga cgtatggtgt tcaatgcttt    300

tcccgttatc cggatcacat gaaacggcat gactttttca agagtgccat gcccgaaggt    360

tatgtacagg aacgcactat atctttcaaa gatgacggga actacaagac gcgtgctgaa    420

gtcaagtttg aaggtgatac ccttgttaat cgtatcgagt taaaaggtat tgattttaaa    480

gaagatggaa acattctcgg acacaaactc gagtacaact ataactcaca caatgtatac    540

atcacggcag acaaacaagg cctatcaggc cgcattatga gcgggttacg gatcaacagc    600

gcgaaagacg atgcggcagg ccaggcgatt gctaaccgct tcacttctaa tatcaaaggt    660

ctgactcagg cttcccgtaa cgctaacgac ggcatttcta ttgcgcagac cactgaaggt    720

gcgctgaatg aaatcaacaa caacctgcag cgtgtgcgtg agttgtctgt tcaggccact    780

aacgggacta actctgattc cgatctgaaa tctatccagg atgaaattca gcaacgtctg    840

gaagaaatcg atcgcgtttc taatcagact caatttaacg gtgttaaagt cctgtctcag    900

gacaaccaga tgaaaatcca ggttggtgct aacgatggtg aaaccattac catcgatctg    960

caaaaaattg atgtgaaaag ccttggcctt gatgggttca atgttaattc cccgggaagt   1020

accgctaacc cactggcttc aattgattct gcattgtcaa aagtggacgc agttcgttct   1080

tctctggggg caattcaaaa ccgctttgat tcagccatta ccaaccttgg caatacggta   1140
```

```
accaatctga actccgcgcg tagccgtatc gaagatgctg actatgcact ggttccgccg   1200

atctcaggta agaatggaat caaagctaac ttcaaaattc gccacaacat tgaagatgga   1260

tccgttcaac tagcagacca ttatcaacaa aatactccaa ttggcgatgg ccctgtcctt   1320

ttaccagaca accattacct gtcgacacaa tctgcccttt tgaaagatcc caacgaaaag   1380

cgtgaccaca tggtccttct tgagtttgta actgctgctg ggattacaca tggcatggat   1440

gaactataca aaccgcgggg ttctcatcat catcatcatc atggttaagt cgac         1494
```

<210> SEQ ID NO 108
<211> LENGTH: 1401
<212> TYPE: DNA
<213> ORGANISM: Artificial Sequence
<220> FEATURE:
<223> OTHER INFORMATION: Synthetic sequence

<400> SEQUENCE: 108

```
atgagtaaag gagaagaact tttcactgga gttgtcccaa ttcttgttga attagatggt     60

gatgttaatg ggcacaaatt ttctgtcagt ggagagggtg aaggtgatgc aacatacgga    120

aaacttaccc ttaaatttat ttgcactact ggaaaactac ctgttccatg gccaacactt    180

gtcactactc tgacgtatgg tgttcaatgc ttttcccgtt atccggatca catgaaacgg    240

catgactttt tcaagagtgc catgcccgaa ggttatgtac aggaacgcac tatatctttc    300

aaagatgacg ggaactacaa gacgcgtgct gaagtcaagt ttgaaggtga tacccttgtt    360

aatcgtatcg agttaaaagg tattgatttt aaagaagatg gaaacattct cggacacaaa    420

ctcgagtaca actataactc acacaatgta tacatcacgg cagacaaaca aggcctatca    480

ggccgcatta tgagcgggtt acggatcaac agcgcgaaag acgatgcggc aggccaggcg    540

attgctaacc gcttcacttc taatatcaaa ggtctgactc aggcttcccg taacgctaac    600

gacggcattt ctattgcgca gaccactgaa ggtgcgctga atgaaatcaa caacaacctg    660

cagcgtgtgc gtgagttgtc tgttcaggcc actaacggga ctaactctga ttccgatctg    720

aaatctatcc aggatgaaat tcagcaacgt ctggaagaaa tcgatcgcgt ttctaatcag    780

actcaattta acggtgttaa agtcctgtct caggacaacc agatgaaaat ccaggttggt    840

gctaacgatg gtgaaaccat taccatcgat ctgcaaaaaa ttgatgtgaa aagccttggc    900

cttgatgggt tcaatgttaa ttccccggga agtaccgcta acccactggc ttcaattgat    960

tctgcattgt caaaagtgga cgcagttcgt tcttctctgg gggcaattca aaaccgcttt   1020

gattcagcca ttaccaacct tggcaatacg gtaaccaatc tgaactccgc gcgtagccgt   1080

atcgaagatg ctgactatgc actggttccg ccgatctcag gtaagaatgg aatcaaagct   1140

aacttcaaaa ttcgccacaa cattgaagat ggatccgttc aactagcaga ccattatcaa   1200

caaaatactc caattggcga tggccctgtc cttttaccag acaaccatta cctgtcgaca   1260

caatctgccc ttttgaaaga tcccaacgaa aagcgtgacc acatggtcct tcttgagttt   1320

gtaactgctg ctgggattac acatggcatg gatgaactat acaaaccgcg gggttctcat   1380

catcatcatc atcatggtta a                                             1401
```

<210> SEQ ID NO 109
<211> LENGTH: 466
<212> TYPE: PRT
<213> ORGANISM: Artificial Sequence
<220> FEATURE:
<223> OTHER INFORMATION: Synthetic sequence

<400> SEQUENCE: 109

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Gly Leu Ser
145                 150                 155                 160

Gly Arg Ile Met Ser Gly Leu Arg Ile Asn Ser Ala Lys Asp Asp Ala
                165                 170                 175

Ala Gly Gln Ala Ile Ala Asn Arg Phe Thr Ser Asn Ile Lys Gly Leu
            180                 185                 190

Thr Gln Ala Ser Arg Asn Ala Asn Asp Gly Ile Ser Ile Ala Gln Thr
        195                 200                 205

Thr Glu Gly Ala Leu Asn Glu Ile Asn Asn Asn Leu Gln Arg Val Arg
    210                 215                 220

Glu Leu Ser Val Gln Ala Thr Asn Gly Thr Asn Ser Asp Ser Asp Leu
225                 230                 235                 240

Lys Ser Ile Gln Asp Glu Ile Gln Gln Arg Leu Glu Glu Ile Asp Arg
                245                 250                 255

Val Ser Asn Gln Thr Gln Phe Asn Gly Val Lys Val Leu Ser Gln Asp
            260                 265                 270

Asn Gln Met Lys Ile Gln Val Gly Ala Asn Asp Gly Glu Thr Ile Thr
        275                 280                 285

Ile Asp Leu Gln Lys Ile Asp Val Lys Ser Leu Gly Leu Asp Gly Phe
    290                 295                 300

Asn Val Asn Ser Pro Gly Ser Thr Ala Asn Pro Leu Ala Ser Ile Asp
305                 310                 315                 320

Ser Ala Leu Ser Lys Val Asp Ala Val Arg Ser Ser Leu Gly Ala Ile
                325                 330                 335

Gln Asn Arg Phe Asp Ser Ala Ile Thr Asn Leu Gly Asn Thr Val Thr
            340                 345                 350

Asn Leu Asn Ser Ala Arg Ser Arg Ile Glu Asp Ala Asp Tyr Ala Leu
        355                 360                 365

Val Pro Pro Ile Ser Gly Lys Asn Gly Ile Lys Ala Asn Phe Lys Ile
    370                 375                 380

Arg His Asn Ile Glu Asp Gly Ser Val Gln Leu Ala Asp His Tyr Gln
385                 390                 395                 400

Gln Asn Thr Pro Ile Gly Asp Gly Pro Val Leu Leu Pro Asp Asn His
                405                 410                 415
```

```
Tyr Leu Ser Thr Gln Ser Ala Leu Leu Lys Asp Pro Asn Glu Lys Arg
            420                 425                 430

Asp His Met Val Leu Leu Glu Phe Val Thr Ala Ala Gly Ile Thr His
        435                 440                 445

Gly Met Asp Glu Leu Tyr Lys Pro Arg Gly Ser His His His His His
    450                 455                 460

His Gly
465
```

<210> SEQ ID NO 110
<211> LENGTH: 124
<212> TYPE: DNA
<213> ORGANISM: Artificial Sequence
<220> FEATURE:
<223> OTHER INFORMATION: Synthetic sequence

<400> SEQUENCE: 110

```
cttggccttg atgggttcaa tgttaattcc ccgggaattt ccggtggtgg tggtggaatt     60

acattaatca atgaagacgc tgccgcagcc aagaaaagta ccgctaaccc actggcttca    120

attg                                                                 124
```

<210> SEQ ID NO 111
<211> LENGTH: 41
<212> TYPE: PRT
<213> ORGANISM: Artificial Sequence
<220> FEATURE:
<223> OTHER INFORMATION: Synthetic sequence

<400> SEQUENCE: 111

```
Leu Gly Leu Asp Gly Phe Asn Val Asn Ser Pro Gly Ile Ser Gly Gly
1               5                   10                  15

Gly Gly Gly Ile Thr Leu Ile Asn Glu Asp Ala Ala Ala Ala Lys Lys
            20                  25                  30

Ser Thr Ala Asn Pro Leu Ala Ser Ile
        35                  40
```

<210> SEQ ID NO 112
<211> LENGTH: 72
<212> TYPE: DNA
<213> ORGANISM: Artificial Sequence
<220> FEATURE:
<223> OTHER INFORMATION: Synthetic sequence

<400> SEQUENCE: 112

```
agatctccgc ggaaccagta aagagaggac gttttgcgga acctggtttg catagtcagc     60

atcttcgata cg                                                         72
```

<210> SEQ ID NO 113
<211> LENGTH: 777
<212> TYPE: DNA
<213> ORGANISM: Artificial Sequence
<220> FEATURE:
<223> OTHER INFORMATION: Synthetic sequence

<400> SEQUENCE: 113

```
taatacgact cactataggg gaattgtgag cggataacaa ttcccctcta gaataatttt     60

gtttaacttt aagaaggaga tatacatatg agcgggttac ggatcaacag cgcgaaagac    120

gatgcggcag gccaggcgat tgctaaccgc ttcacttcta atatcaaagg tctgactcag    180

gcttcccgta acgctaacga cggcatttct attgcgcaga ccactgaagg tgcgctgaat    240
```

```
gaaatcaaca acaacctgca gcgtgtgcgt gagttgtctg ttcaggccac taacgggact    300

aactctgatt ccgatctgaa atctatccag gatgaaattc agcaacgtct ggaagaaatc    360

gatcgcgttt ctaatcagac tcaatttaac ggtgttaaag tcctgtctca ggacaaccag    420

atgaaaatcc aggttggtgc taacgatggt gaaaccatta ccatcgatct gcaaaaaatt    480

gatgtgaaaa gccttggcct tgatgggttc aatgttaatt ccccgggaag taccgctaac    540

ccactggctt caattgattc tgcattgtca aaagtggacg cagttcgttc ttctctgggg    600

gcaattcaaa accgttttga ttcagccatt accaaccttg gcaatacggt aaccaatctg    660

aactccgcgc gtagccgtat cgaagatgct gactatgcaa accaggttcc gcaaaacgtc    720

ctctctttac tggttccgcg gggttctcat catcatcatc atcatggtta agtcgac       777
```

<210> SEQ ID NO 114
<211> LENGTH: 684
<212> TYPE: DNA
<213> ORGANISM: Artificial Sequence
<220> FEATURE:
<223> OTHER INFORMATION: Synthetic sequence

<400> SEQUENCE: 114

```
atgagcgggt tacggatcaa cagcgcgaaa gacgatgcgg caggccaggc gattgctaac     60

cgcttcactt ctaatatcaa aggtctgact caggcttccc gtaacgctaa cgacggcatt    120

tctattgcgc agaccactga aggtgcgctg aatgaaatca acaacaacct gcagcgtgtg    180

cgtgagttgt ctgttcaggc cactaacggg actaactctg attccgatct gaaatctatc    240

caggatgaaa ttcagcaacg tctggaagaa atcgatcgcg tttctaatca gactcaattt    300

aacggtgtta aagtcctgtc tcaggacaac cagatgaaaa tccaggttgg tgctaacgat    360

ggtgaaacca ttaccatcga tctgcaaaaa attgatgtga aaagccttgg ccttgatggg    420

ttcaatgtta attccccggg aagtaccgct aacccactgg cttcaattga ttctgcattg    480

tcaaaagtgg acgcagttcg ttcttctctg ggggcaattc aaaaccgttt tgattcagcc    540

attaccaacc ttggcaatac ggtaaccaat ctgaactccg cgcgtagccg tatcgaagat    600

gctgactatg caaaccaggt tccgcaaaac gtcctctctt tactggttcc gcggggttct    660

catcatcatc atcatcatgg ttaa                                           684
```

<210> SEQ ID NO 115
<211> LENGTH: 227
<212> TYPE: PRT
<213> ORGANISM: Artificial Sequence
<220> FEATURE:
<223> OTHER INFORMATION: Synthetic sequence

<400> SEQUENCE: 115

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
```

```
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Asn Gln Val Pro
        195                 200                 205

Gln Asn Val Leu Ser Leu Leu Val Pro Arg Gly Ser His His His His
    210                 215                 220

His His Gly
225


<210> SEQ ID NO 116
<211> LENGTH: 42
<212> TYPE: DNA
<213> ORGANISM: Artificial Sequence
<220> FEATURE:
<223> OTHER INFORMATION: Synthetic sequence

<400> SEQUENCE: 116

agatctcccg gggaaccatc gttagcacca acctggattt tc                          42


<210> SEQ ID NO 117
<211> LENGTH: 777
<212> TYPE: DNA
<213> ORGANISM: Artificial Sequence
<220> FEATURE:
<223> OTHER INFORMATION: Synthetic sequence

<400> SEQUENCE: 117

taatacgact cactataggg gaattgtgag cggataacaa ttcccctcta gaataatttt       60

gtttaacttt aagaaggaga tatacatatg agcgggttac ggatcaacag cgcgaaagac      120

gatgcggcag gccaggcgat tgctaaccgc ttcacttcta atatcaaagg tctgactcag      180

gcttcccgta acgctaacga cggcatttct attgcgcaga ccactgaagg tgcgctgaat      240

gaaatcaaca acaacctgca gcgtgtgcgt gagttgtctg ttcaggccac taacgggact      300

aactctgatt ccgatctgaa atctatccag gatgaaattc agcaacgtct ggaagaaatc      360

gatcgcgttt ctaatcagac tcaatttaac ggtgttaaag tcctgtctca ggacaaccag      420

atgaaaatcc aggttggtgc taacgatggt tccccgggaa gtaccgctaa cccactggct      480

tcaattgatt ctgcattgtc aaaagtggac gcagttcgtt cttctctggg ggcaattcaa      540

aaccgctttg attcagccat taccaacctt ggcaatacgg taaccaatct gaactccgcg      600

cgtagccgta tcgaagatgc tgactatgca acggaagttt ctaatatgtc taaagcgcag      660

attctgcagc aggctggtac ttccgttctg gcgcaggcta accaggttcc gcaaaacgtc      720

ctctctttac tggttccgcg gggttctcat catcatcatc atcatggtta agtcgac          777


<210> SEQ ID NO 118
```

```
<211> LENGTH: 684
<212> TYPE: DNA
<213> ORGANISM: Artificial Sequence
<220> FEATURE:
<223> OTHER INFORMATION: Synthetic sequence

<400> SEQUENCE: 118

atgagcgggt tacggatcaa cagcgcgaaa gacgatgcgg caggccaggc gattgctaac      60

cgcttcactt ctaatatcaa aggtctgact caggcttccc gtaacgctaa cgacggcatt     120

tctattgcgc agaccactga aggtgcgctg aatgaaatca acaacaacct gcagcgtgtg     180

cgtgagttgt ctgttcaggc cactaacggg actaactctg attccgatct gaaatctatc     240

caggatgaaa ttcagcaacg tctggaagaa atcgatcgcg tttctaatca gactcaattt     300

aacggtgtta aagtcctgtc tcaggacaac cagatgaaaa tccaggttgg tgctaacgat     360

ggttccccgg gaagtaccgc taacccactg gcttcaattg attctgcatt gtcaaaagtg     420

gacgcagttc gttcttctct gggggcaatt caaaaccgct ttgattcagc cattaccaac     480

cttggcaata cggtaaccaa tctgaactcc gcgcgtagcc gtatcgaaga tgctgactat     540

gcaacggaag tttctaatat gtctaaagcg cagattctgc agcaggctgg tacttccgtt     600

ctggcgcagg ctaaccaggt tccgcaaaac gtcctctctt tactggttcc gcggggttct     660

catcatcatc atcatcatgg ttaa                                            684


<210> SEQ ID NO 119
<211> LENGTH: 227
<212> TYPE: PRT
<213> ORGANISM: Artificial Sequence
<220> FEATURE:
<223> OTHER INFORMATION: Synthetic sequence

<400> SEQUENCE: 119

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Ser Pro Gly Ser Thr Ala Asn
        115                 120                 125

Pro Leu Ala Ser Ile Asp Ser Ala Leu Ser Lys Val Asp Ala Val Arg
    130                 135                 140

Ser Ser Leu Gly Ala Ile Gln Asn Arg Phe Asp Ser Ala Ile Thr Asn
145                 150                 155                 160

Leu Gly Asn Thr Val Thr Asn Leu Asn Ser Ala Arg Ser Arg Ile Glu
                165                 170                 175

Asp Ala Asp Tyr Ala Thr Glu Val Ser Asn Met Ser Lys Ala Gln Ile
            180                 185                 190

Leu Gln Gln Ala Gly Thr Ser Val Leu Ala Gln Ala Asn Gln Val Pro
```

```
        195                 200                 205

Gln Asn Val Leu Ser Leu Leu Val Pro Arg Gly Ser His His His His
    210                 215                 220

His His Gly
225


<210> SEQ ID NO 120
<211> LENGTH: 90
<212> TYPE: DNA
<213> ORGANISM: Artificial Sequence
<220> FEATURE:
<223> OTHER INFORMATION: Synthetic sequence

<400> SEQUENCE: 120

agatctccgc ggaaccagca ggttattctg ggtcaacagc gacaggctgt ttgtattaat     60

gacttgtgca tagtcagcat cttcgatacg                                       90


<210> SEQ ID NO 121
<211> LENGTH: 795
<212> TYPE: DNA
<213> ORGANISM: Artificial Sequence
<220> FEATURE:
<223> OTHER INFORMATION: Synthetic sequence

<400> SEQUENCE: 121

taatacgact cactataggg gaattgtgag cggataacaa ttcccctcta gaaataattt     60

gtttaacttt aagaaggaga tatacatatg agcgggttac ggatcaacag cgcgaaagac    120

gatgcggcag gccaggcgat tgctaaccgc ttcacttcta atatcaaagg tctgactcag    180

gcttcccgta acgctaacga cggcatttct attgcgcaga ccactgaagg tgcgctgaat    240

gaaatcaaca acaacctgca gcgtgtgcgt gagttgtctg ttcaggccac taacgggact    300

aactctgatt ccgatctgaa atctatccag gatgaaattc agcaacgtct ggaagaaatc    360

gatcgcgttt ctaatcagac tcaatttaac ggtgttaaag tcctgtctca ggacaaccag    420

atgaaaatcc aggttggtgc taacgatggt gaaaccatta ccatcgatct gcaaaaaatt    480

gatgtgaaaa gccttggcct tgatgggttc aatgttaatt ccccgggaag taccgctaac    540

ccactggctt caattgattc tgcattgtca aaagtggacg cagttcgttc ttctctgggg    600

gcaattcaaa accgctttga ttcagccatt accaaccttg gcaatacggt aaccaatctg    660

aactccgcgc gtagccgtat cgaagatgct gactatgcac aagtcattaa tacaaacagc    720

ctgtcgctgt tgacccagaa taacctgctg gttccgcggg gttctcatca tcatcatcat    780

catggttaag tcgac                                                      795


<210> SEQ ID NO 122
<211> LENGTH: 702
<212> TYPE: DNA
<213> ORGANISM: Artificial Sequence
<220> FEATURE:
<223> OTHER INFORMATION: Synthetic sequence

<400> SEQUENCE: 122

atgagcgggt tacggatcaa cagcgcgaaa gacgatgcgg caggccaggc gattgctaac     60

cgcttcactt ctaatatcaa aggtctgact caggcttccc gtaacgctaa cgacggcatt    120

tctattgcgc agaccactga aggtgcgctg aatgaaatca acaacaacct gcagcgtgtg    180

cgtgagttgt ctgttcaggc cactaacggg actaactctg attccgatct gaaatctatc    240

caggatgaaa ttcagcaacg tctggaagaa atcgatcgcg tttctaatca gactcaattt    300
```

```
aacggtgtta aagtcctgtc tcaggacaac cagatgaaaa tccaggttgg tgctaacgat    360

ggtgaaacca ttaccatcga tctgcaaaaa attgatgtga aaagccttgg ccttgatggg    420

ttcaatgtta attccccggg aagtaccgct aacccactgg cttcaattga ttctgcattg    480

tcaaaagtgg acgcagttcg ttcttctctg ggggcaattc aaaaccgctt tgattcagcc    540

attaccaacc ttggcaatac ggtaaccaat ctgaactccg cgcgtagccg tatcgaagat    600

gctgactatg cacaagtcat taatacaaac agcctgtcgc tgttgaccca gaataacctg    660

ctggttccgc ggggttctca tcatcatcat catcatggtt aa                       702
```

<210> SEQ ID NO 123
<211> LENGTH: 233
<212> TYPE: PRT
<213> ORGANISM: Artificial Sequence
<220> FEATURE:
<223> OTHER INFORMATION: Synthetic sequence

<400> SEQUENCE: 123

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Gln Val Ile Asn
        195                 200                 205

Thr Asn Ser Leu Ser Leu Leu Thr Gln Asn Asn Leu Leu Val Pro Arg
    210                 215                 220

Gly Ser His His His His His His Gly
225                 230
```

<210> SEQ ID NO 124
<211> LENGTH: 49
<212> TYPE: DNA
<213> ORGANISM: Artificial Sequence
<220> FEATURE:
<223> OTHER INFORMATION: Synthetic sequence

<400> SEQUENCE: 124
gctgactatg caacggcagt ttctgctatg tctgcagcgc agattctgc 49

<210> SEQ ID NO 125
<211> LENGTH: 49
<212> TYPE: DNA
<213> ORGANISM: Artificial Sequence
<220> FEATURE:
<223> OTHER INFORMATION: Synthetic sequence

<400> SEQUENCE: 125
gcagaatctg cgctgcagac atagcagaaa ctgccgttgc atagtcagc 49

<210> SEQ ID NO 126
<211> LENGTH: 795
<212> TYPE: DNA
<213> ORGANISM: Artificial Sequence
<220> FEATURE:
<223> OTHER INFORMATION: Synthetic sequence

<400> SEQUENCE: 126
taatacgact cactataggg gaattgtgag cggataacaa ttcccctcta gaataatttt 60
gtttaacttt aagaaggaga tatacatatg agcgggttac ggatcaacag cgcgaaagac 120
gatgcggcag gccaggcgat tgctaaccgc ttcacttcta atatcaaagg tctgactcag 180
gcttcccgta acgctaacga cggcatttct attgcgcaga ccactgaagg tgcgctgaat 240
gaaatcaaca acaacctgca gcgtgtgcgt gagttgtctg ttcaggccac taacgggact 300
aactctgatt ccgatctgaa atctatccag gatgaaattc agcaacgtct ggaagaaatc 360
gatcgcgttt ctaatcagac tcaatttaac ggtgttaaag tcctgtctca ggacaaccag 420
atgaaaatcc aggttggtgc taacgatggt gaaaccatta ccatcgatct gcaaaaaatt 480
gatgtgaaaa gccttggcct tgatgggttc aatgttaatt ccccgggaag taccgctaac 540
ccactggctt caattgattc tgcattgtca aaagtggacg cagttcgttc ttctctgggg 600
gcaattcaaa accgctttga ttcagccatt accaaccttg gcaatacggt aaccaatctg 660
aactccgcgc gtagccgtat cgaagatgct gactatgcaa cggcagtttc tgctatgtct 720
gcagcgcaga ttctgcagca ggctggtctg gttccgcggg gttctcatca tcatcatcat 780
catggttaag tcgac 795

<210> SEQ ID NO 127
<211> LENGTH: 702
<212> TYPE: DNA
<213> ORGANISM: Artificial Sequence
<220> FEATURE:
<223> OTHER INFORMATION: Synthetic sequence

<400> SEQUENCE: 127
atgagcgggt tacggatcaa cagcgcgaaa gacgatgcgg caggccaggc gattgctaac 60
cgcttcactt ctaatatcaa aggtctgact caggcttccc gtaacgctaa cgacggcatt 120
tctattgcgc agaccactga aggtgcgctg aatgaaatca acaacaacct gcagcgtgtg 180
cgtgagttgt ctgttcaggc cactaacggg actaactctg attccgatct gaaatctatc 240
caggatgaaa ttcagcaacg tctggaagaa atcgatcgcg tttctaatca gactcaattt 300
aacggtgtta aagtcctgtc tcaggacaac cagatgaaaa tccaggttgg tgctaacgat 360
ggtgaaacca ttaccatcga tctgcaaaaa attgatgtga aaagccttgg ccttgatggg 420
ttcaatgtta attccccggg aagtaccgct aacccactgg cttcaattga ttctgcattg 480

```
tcaaaagtgg acgcagttcg ttcttctctg ggggcaattc aaaaccgctt tgattcagcc    540

attaccaacc ttggcaatac ggtaaccaat ctgaactccg cgcgtagccg tatcgaagat    600

gctgactatg caacggcagt ttctgctatg tctgcagcgc agattctgca gcaggctggt    660

ctggttccgc ggggttctca tcatcatcat catcatggtt aa                       702


<210> SEQ ID NO 128
<211> LENGTH: 233
<212> TYPE: PRT
<213> ORGANISM: Artificial Sequence
<220> FEATURE:
<223> OTHER INFORMATION: Synthetic sequence

<400> SEQUENCE: 128

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Ala Val Ser
        195                 200                 205

Ala Met Ser Ala Ala Gln Ile Leu Gln Gln Ala Gly Leu Val Pro Arg
    210                 215                 220

Gly Ser His His His His His His Gly
225                 230


<210> SEQ ID NO 129
<211> LENGTH: 54
<212> TYPE: DNA
<213> ORGANISM: Artificial Sequence
<220> FEATURE:
<223> OTHER INFORMATION: Synthetic sequence

<400> SEQUENCE: 129

gtttctaata tgtctaaagc ggcgattctg ggagcggctg gtctggttcc gcgg           54


<210> SEQ ID NO 130
<211> LENGTH: 54
<212> TYPE: DNA
```

<213> ORGANISM: Artificial Sequence
<220> FEATURE:
<223> OTHER INFORMATION: Synthetic sequence

<400> SEQUENCE: 130
ccgcggaacc agaccagccg ctcccagaat cgccgcttta gacatattag aaac 54

<210> SEQ ID NO 131
<211> LENGTH: 795
<212> TYPE: DNA
<213> ORGANISM: Artificial Sequence
<220> FEATURE:
<223> OTHER INFORMATION: Synthetic sequence

<400> SEQUENCE: 131
taatacgact cactataggg gaattgtgag cggataacaa ttcccctcta gaataatttt 60
gtttaacttt aagaaggaga tatacatatg agcgggttac ggatcaacag cgcgaaagac 120
gatgcggcag gccaggcgat tgctaaccgc ttcacttcta atatcaaagg tctgactcag 180
gcttcccgta acgctaacga cggcatttct attgcgcaga ccactgaagg tgcgctgaat 240
gaaatcaaca acaacctgca gcgtgtgcgt gagttgtctg ttcaggccac taacgggact 300
aactctgatt ccgatctgaa atctatccag gatgaaattc agcaacgtct ggaagaaatc 360
gatcgcgttt ctaatcagac tcaatttaac ggtgttaaag tcctgtctca ggacaaccag 420
atgaaaatcc aggttggtgc taacgatggt gaaaccatta ccatcgatct gcaaaaaatt 480
gatgtgaaaa gccttggcct tgatgggttc aatgttaatt ccccgggaag taccgctaac 540
ccactggctt caattgattc tgcattgtca aaagtggacg cagttcgttc ttctctgggg 600
gcaattcaaa accgctttga ttcagccatt accaaccttg gcaatacggt aaccaatctg 660
aactccgcgc gtagccgtat cgaagatgct gactatgcaa cggaagtttc taatatgtct 720
aaagcggcga ttctgggagc ggctggtctg gttccgcggg gttctcatca tcatcatcat 780
catggttaag tcgac 795

<210> SEQ ID NO 132
<211> LENGTH: 702
<212> TYPE: DNA
<213> ORGANISM: Artificial Sequence
<220> FEATURE:
<223> OTHER INFORMATION: Synthetic sequence

<400> SEQUENCE: 132
atgagcgggt tacggatcaa cagcgcgaaa gacgatgcgg caggccaggc gattgctaac 60
cgcttcactt ctaatatcaa aggtctgact caggcttccc gtaacgctaa cgacggcatt 120
tctattgcgc agaccactga aggtgcgctg aatgaaatca acaacaacct gcagcgtgtg 180
cgtgagttgt ctgttcaggc cactaacggg actaactctg attccgatct gaaatctatc 240
caggatgaaa ttcagcaacg tctggaagaa atcgatcgcg tttctaatca gactcaattt 300
aacggtgtta aagtcctgtc tcaggacaac cagatgaaaa tccaggttgg tgctaacgat 360
ggtgaaacca ttaccatcga tctgcaaaaa attgatgtga aaagccttgg ccttgatggg 420
ttcaatgtta attccccggg aagtaccgct aacccactgg cttcaattga ttctgcattg 480
tcaaaagtgg acgcagttcg ttcttctctg ggggcaattc aaaaccgctt tgattcagcc 540
attaccaacc ttggcaatac ggtaaccaat ctgaactccg cgcgtagccg tatcgaagat 600
gctgactatg caacggaagt ttctaatatg tctaaagcgg cgattctggg agcggctggt 660
ctggttccgc ggggttctca tcatcatcat catcatggtt aa 702

<210> SEQ ID NO 133
<211> LENGTH: 233
<212> TYPE: PRT
<213> ORGANISM: Artificial Sequence
<220> FEATURE:
<223> OTHER INFORMATION: Synthetic sequence

<400> SEQUENCE: 133

Met Ser Gly Leu Arg Ile Asn Ser Ala Lys Asp Asp Ala Ala Gly Gln
1 5 10 15

Ala Ile Ala Asn Arg Phe Thr Ser Asn Ile Lys Gly Leu Thr Gln Ala
20 25 30

Ser Arg Asn Ala Asn Asp Gly Ile Ser Ile Ala Gln Thr Thr Glu Gly
35 40 45

Ala Leu Asn Glu Ile Asn Asn Asn Leu Gln Arg Val Arg Glu Leu Ser
50 55 60

Val Gln Ala Thr Asn Gly Thr Asn Ser Asp Ser Asp Leu Lys Ser Ile
65 70 75 80

Gln Asp Glu Ile Gln Gln Arg Leu Glu Glu Ile Asp Arg Val Ser Asn
85 90 95

Gln Thr Gln Phe Asn Gly Val Lys Val Leu Ser Gln Asp Asn Gln Met
100 105 110

Lys Ile Gln Val Gly Ala Asn Asp Gly Glu Thr Ile Thr Ile Asp Leu
115 120 125

Gln Lys Ile Asp Val Lys Ser Leu Gly Leu Asp Gly Phe Asn Val Asn
130 135 140

Ser Pro Gly Ser Thr Ala Asn Pro Leu Ala Ser Ile Asp Ser Ala Leu
145 150 155 160

Ser Lys Val Asp Ala Val Arg Ser Ser Leu Gly Ala Ile Gln Asn Arg
165 170 175

Phe Asp Ser Ala Ile Thr Asn Leu Gly Asn Thr Val Thr Asn Leu Asn
180 185 190

Ser Ala Arg Ser Arg Ile Glu Asp Ala Asp Tyr Ala Thr Glu Val Ser
195 200 205

Asn Met Ser Lys Ala Ala Ile Leu Gly Ala Ala Gly Leu Val Pro Arg
210 215 220

Gly Ser His His His His His His Gly
225 230

<210> SEQ ID NO 134
<211> LENGTH: 25
<212> TYPE: DNA
<213> ORGANISM: Artificial Sequence
<220> FEATURE:
<223> OTHER INFORMATION: Synthetic sequence

<400> SEQUENCE: 134
tctagaggat ccggcaggcc aggcg 25

<210> SEQ ID NO 135
<211> LENGTH: 22
<212> TYPE: DNA
<213> ORGANISM: Artificial Sequence
<220> FEATURE:
<223> OTHER INFORMATION: Synthetic sequence

<400> SEQUENCE: 135
cgcaagcttg tcgacttaac gc 22

<210> SEQ ID NO 136
<211> LENGTH: 970
<212> TYPE: DNA
<213> ORGANISM: Artificial Sequence
<220> FEATURE:
<223> OTHER INFORMATION: Synthetic sequence

<400> SEQUENCE: 136

```
taatacgact cactataggg gaattgtgag cggataacaa ttcccctcta gaataatttt     60

gtttaacttt aagaaggaga tatacatatg cggggttctc atcatcatca tcatcatggt    120

atggctagca tgactggtgg acagcaaatg ggtcgggatc tgtacgacct ggttccgcgc    180

ggtagcgcga aggatccggc aggccaggcg attgctaacc gcttcacttc taatatcaaa    240

ggtctgactc aggcttcccg taacgctaac gacggcattt ctattgcgca gaccactgaa    300

ggtgcgctga atgaaatcaa caacaacctg cagcgtgtgc gtgagttgtc tgttcaggcc    360

actaacggga ctaactctga ttccgatctg aaatctatcc aggatgaaat tcagcaacgt    420

ctggaagaaa tcgatcgcgt ttctaatcag actcaattta acggtgttaa agtcctgtct    480

caggacaacc agatgaaaat ccaggttggt gctaacgatg gtgaaaccat taccatcgat    540

ctgcaaaaaa ttgatgtgaa aagccttggc cttgatgggt tcaatgttaa ttccccggga    600

atttccggtg gtggtggtgg aattctagac tccatgggta cattaatcaa tgaagacgct    660

gccgcagcca agaaaagtac cgctaaccca ctggcttcaa ttgattctgc attgtcaaaa    720

gtggacgcag ttcgttcttc tctgggggca attcaaaacc gttttgattc agccattacc    780

aaccttggca atacggtaac caatctgaac tccgcgcgta gccgtatcga agatgctgac    840

tatgcaacgg aagtttctaa tatgtctaaa gcgcagattc tgcagcaggc tggtacttcc    900

gttctggcgc aggctaacca ggttccgcaa aacgtcctct ctttactgcg ttaagtcgac    960

aagcttgcgg                                                           970
```

<210> SEQ ID NO 137
<211> LENGTH: 288
<212> TYPE: PRT
<213> ORGANISM: Artificial Sequence
<220> FEATURE:
<223> OTHER INFORMATION: Synthetic sequence

<400> SEQUENCE: 137

```
Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Ala Gly Gln Ala Ile Ala Asn Arg Phe Thr Ser
        35                  40                  45

Asn Ile Lys Gly Leu Thr Gln Ala Ser Arg Asn Ala Asn Asp Gly Ile
    50                  55                  60

Ser Ile Ala Gln Thr Thr Glu Gly Ala Leu Asn Glu Ile Asn Asn Asn
65                  70                  75                  80

Leu Gln Arg Val Arg Glu Leu Ser Val Gln Ala Thr Asn Gly Thr Asn
                85                  90                  95

Ser Asp Ser Asp Leu Lys Ser Ile Gln Asp Glu Ile Gln Gln Arg Leu
            100                 105                 110

Glu Glu Ile Asp Arg Val Ser Asn Gln Thr Gln Phe Asn Gly Val Lys
        115                 120                 125
```

```
Val Leu Ser Gln Asp Asn Gln Met Lys Ile Gln Val Gly Ala Asn Asp
    130                 135                 140

Gly Glu Thr Ile Thr Ile Asp Leu Gln Lys Ile Asp Val Lys Ser Leu
145                 150                 155                 160

Gly Leu Asp Gly Phe Asn Val Asn Ser Pro Gly Ile Ser Gly Gly Gly
                165                 170                 175

Gly Gly Ile Leu Asp Ser Met Gly Thr Leu Ile Asn Glu Asp Ala Ala
            180                 185                 190

Ala Ala Lys Lys Ser Thr Ala Asn Pro Leu Ala Ser Ile Asp Ser Ala
        195                 200                 205

Leu Ser Lys Val Asp Ala Val Arg Ser Ser Leu Gly Ala Ile Gln Asn
    210                 215                 220

Arg Phe Asp Ser Ala Ile Thr Asn Leu Gly Asn Thr Val Thr Asn Leu
225                 230                 235                 240

Asn Ser Ala Arg Ser Arg Ile Glu Asp Ala Asp Tyr Ala Thr Glu Val
                245                 250                 255

Ser Asn Met Ser Lys Ala Gln Ile Leu Gln Gln Ala Gly Thr Ser Val
            260                 265                 270

Leu Ala Gln Ala Asn Gln Val Pro Gln Asn Val Leu Ser Leu Leu Arg
        275                 280                 285
```

<210> SEQ ID NO 138
<211> LENGTH: 1236
<212> TYPE: DNA
<213> ORGANISM: Artificial Sequence
<220> FEATURE:
<223> OTHER INFORMATION: Synthetic sequence

<400> SEQUENCE: 138

```
taatacgact cactataggg gaattgtgag cggataacaa ttcccctcta gaataatttt      60

gtttaacttt aagaaggaga tatacatatg agtaaaggag aagaactttt cactggagtt     120

gtcccaattc ttgttgaatt agatggtgat gttaatgggc acaaattttc tgtcagtgga     180

gagggtgaag gtgatgcaac atacggaaaa cttaccctta aatttatttg cactactgga     240

aaactacctg ttccatggcc aacacttgtc actactctga cgtatggtgt tcaatgcttt     300

tcccgttatc cggatcacat gaaacggcat gactttttca agagtgccat gcccgaaggt     360

tatgtacagg aacgcactat atctttcaaa gatgacggga actacaagac gcgtgctgaa     420

gtcaagtttg aaggtgatac ccttgttaat cgtatcgagt taaaaggtat tgattttaaa     480

gaagatggaa acattctcgg acacaaactc gagtacaact ataactcaca caatgtatac     540

atcacggcag acaaacaagg cctatcaggc cgcattatga gcgggttacg gatcaacagc     600

gcgaaagacg atgcggcagg ccaggcgatt gctaaccgct tcacttctaa tatcaaaggt     660

ctgactcagg cttcccgtaa cgctaacgac ggcatttcta ttgcgcagac cactgaaggt     720

gcgctgaatg aaatcaacaa caacctgcag cgtgtgcgtg agttgtctgt tcaggccact     780

aacgggacta actctgattc cgatctgaaa tctatccagg atgaaattca gcaacgtctg     840

gaagaaatcg atcgcgtttc taatcagact caatttaacg gtgttaaagt cctgtctcag     900

gacaaccaga tgaaaatcca ggttggtgct aacgatggtg aaaccattac catcgatctg     960

caaaaaattg atgtgaaaag ccttggcctt gatgggttca atgttaattc cccgggaagt    1020

accgctaacc cactggcttc aattgattct gcattgtcaa aagtggacgc agttcgttct    1080

tctctggggg caattcaaaa ccgctttgat tcagccatta ccaaccttgg caatacggta    1140

accaatctga actccgcgcg tagccgtatc gaagatgctg actatgcact ggttccgcgg    1200
```

ggttctcatc atcatcatca tcatggttaa gtcgac 1236

<210> SEQ ID NO 139
<211> LENGTH: 1143
<212> TYPE: DNA
<213> ORGANISM: Artificial Sequence
<220> FEATURE:
<223> OTHER INFORMATION: Synthetic sequence

<400> SEQUENCE: 139
atgagtaaag gagaagaact tttcactgga gttgtcccaa ttcttgttga attagatggt 60
gatgttaatg ggcacaaatt ttctgtcagt ggagagggtg aaggtgatgc aacatacgga 120
aaacttaccc ttaaatttat ttgcactact ggaaaactac ctgttccatg gccaacactt 180
gtcactactc tgacgtatgg tgttcaatgc ttttcccgtt atccggatca catgaaacgg 240
catgactttt tcaagagtgc catgcccgaa ggttatgtac aggaacgcac tatatctttc 300
aaagatgacg ggaactacaa gacgcgtgct gaagtcaagt ttgaaggtga tacccttgtt 360
aatcgtatcg agttaaaagg tattgatttt aaagaagatg gaaacattct cggacacaaa 420
ctcgagtaca actataactc acacaatgta tacatcacgg cagacaaaca aggcctatca 480
ggccgcatta tgagcgggtt acggatcaac agcgcgaaag acgatgcggc aggccaggcg 540
attgctaacc gcttcacttc taatatcaaa ggtctgactc aggcttcccg taacgctaac 600
gacggcattt ctattgcgca gaccactgaa ggtgcgctga atgaaatcaa caacaacctg 660
cagcgtgtgc gtgagttgtc tgttcaggcc actaacggga ctaactctga ttccgatctg 720
aaatctatcc aggatgaaat tcagcaacgt ctggaagaaa tcgatcgcgt ttctaatcag 780
actcaattta acggtgttaa agtcctgtct caggacaacc agatgaaaat ccaggttggt 840
gctaacgatg gtgaaaccat taccatcgat ctgcaaaaaa ttgatgtgaa aagccttggc 900
cttgatgggt tcaatgttaa ttccccggga agtaccgcta acccactggc ttcaattgat 960
tctgcattgt caaaagtgga cgcagttcgt tcttctctgg gggcaattca aaaccgcttt 1020
gattcagcca ttaccaacct tggcaatacg gtaaccaatc tgaactccgc gcgtagccgt 1080
atcgaagatg ctgactatgc actggttccg cggggttctc atcatcatca tcatcatggt 1140
taa 1143

<210> SEQ ID NO 140
<211> LENGTH: 380
<212> TYPE: PRT
<213> ORGANISM: Artificial Sequence
<220> FEATURE:
<223> OTHER INFORMATION: Synthetic sequence

<400> SEQUENCE: 140

Met Ser Lys Gly Glu Glu Leu Phe Thr Gly Val Val Pro Ile Leu Val
1 5 10 15

Glu Leu Asp Gly Asp Val Asn Gly His Lys Phe Ser Val Ser Gly Glu
20 25 30

Gly Glu Gly Asp Ala Thr Tyr Gly Lys Leu Thr Leu Lys Phe Ile Cys
35 40 45

Thr Thr Gly Lys Leu Pro Val Pro Trp Pro Thr Leu Val Thr Thr Leu
50 55 60

Thr Tyr Gly Val Gln Cys Phe Ser Arg Tyr Pro Asp His Met Lys Arg
65 70 75 80

His Asp Phe Phe Lys Ser Ala Met Pro Glu Gly Tyr Val Gln Glu Arg

```
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Gly Leu Ser
145                 150                 155                 160

Gly Arg Ile Met Ser Gly Leu Arg Ile Asn Ser Ala Lys Asp Asp Ala
                165                 170                 175

Ala Gly Gln Ala Ile Ala Asn Arg Phe Thr Ser Asn Ile Lys Gly Leu
            180                 185                 190

Thr Gln Ala Ser Arg Asn Ala Asn Asp Gly Ile Ser Ile Ala Gln Thr
        195                 200                 205

Thr Glu Gly Ala Leu Asn Glu Ile Asn Asn Asn Leu Gln Arg Val Arg
    210                 215                 220

Glu Leu Ser Val Gln Ala Thr Asn Gly Thr Asn Ser Asp Ser Asp Leu
225                 230                 235                 240

Lys Ser Ile Gln Asp Glu Ile Gln Gln Arg Leu Glu Glu Ile Asp Arg
                245                 250                 255

Val Ser Asn Gln Thr Gln Phe Asn Gly Val Lys Val Leu Ser Gln Asp
            260                 265                 270

Asn Gln Met Lys Ile Gln Val Gly Ala Asn Asp Gly Glu Thr Ile Thr
        275                 280                 285

Ile Asp Leu Gln Lys Ile Asp Val Lys Ser Leu Gly Leu Asp Gly Phe
    290                 295                 300

Asn Val Asn Ser Pro Gly Ser Thr Ala Asn Pro Leu Ala Ser Ile Asp
305                 310                 315                 320

Ser Ala Leu Ser Lys Val Asp Ala Val Arg Ser Ser Leu Gly Ala Ile
                325                 330                 335

Gln Asn Arg Phe Asp Ser Ala Ile Thr Asn Leu Gly Asn Thr Val Thr
            340                 345                 350

Asn Leu Asn Ser Ala Arg Ser Arg Ile Glu Asp Ala Asp Tyr Ala Leu
        355                 360                 365

Val Pro Arg Gly Ser His His His His His His Gly
    370                 375                 380


<210> SEQ ID NO 141
<211> LENGTH: 36
<212> TYPE: DNA
<213> ORGANISM: Artificial Sequence
<220> FEATURE:
<223> OTHER INFORMATION: Synthetic sequence

<400> SEQUENCE: 141

tctagaggat ccgtctggtc tgcgtatcaa cagcgc                              36


<210> SEQ ID NO 142
<211> LENGTH: 996
<212> TYPE: DNA
<213> ORGANISM: Artificial Sequence
<220> FEATURE:
<223> OTHER INFORMATION: Synthetic sequence

<400> SEQUENCE: 142

taatacgact cactataggg gaattgtgag cggataacaa ttcccctcta gaataatttt     60
```

```
gtttaacttt aagaaggaga tatacatatg cggggttctc atcatcatca tcatcatggt    120
atggctagca tgactggtgg acagcaaatg ggtcgggatc tgtacgacct ggttccgcgc    180
ggtagcgcga aggatccgtc tggtctgcgt atcaacagcg cgaaagacga tgcggcaggc    240
caggcgattg ctaaccgctt cacttctaat atcaaaggtc tgactcaggc ttcccgtaac    300
gctaacgacg gcatttctat tgcgcagacc actgaaggtg cgctgaatga aatcaacaac    360
aacctgcagc gtgtgcgtga gttgtctgtt caggccacta acgggactaa ctctgattcc    420
gatctgaaat ctatccagga tgaaattcag caacgtctgg aagaaatcga tcgcgtttct    480
aatcagactc aatttaacgg tgttaaagtc ctgtctcagg acaaccagat gaaaatccag    540
gttggtgcta acgatggtga aaccattacc atcgatctgc aaaaaattga tgtgaaaagc    600
cttggccttg atgggttcaa tgttaattcc ccgggaattt ccggtggtgg tggtggaatt    660
ctagactcca tgggtacatt aatcaatgaa gacgctgccg cagccaagaa aagtaccgct    720
aacccactgg cttcaattga ttctgcattg tcaaaagtgg acgcagttcg ttcttctctg    780
ggggcaattc aaaaccgttt tgattcagcc attaccaacc ttggcaatac ggtaaccaat    840
ctgaactccg cgcgtagccg tatcgaagat gctgactatg caacggaagt ttctaatatg    900
tctaaagcgc agattctgca gcaggctggt acttccgttc tggcgcaggc taaccaggtt    960
ccgcaaaacg tcctctcttt actgcgttaa gtcgac                              996
```

<210> SEQ ID NO 143
<211> LENGTH: 903
<212> TYPE: DNA
<213> ORGANISM: Artificial Sequence
<220> FEATURE:
<223> OTHER INFORMATION: Synthetic sequence

<400> SEQUENCE: 143

```
atgcggggtt ctcatcatca tcatcatcat ggtatggcta gcatgactgg tggacagcaa     60
atgggtcggg atctgtacga cctggttccg cgcggtagcg cgaaggatcc gtctggtctg    120
cgtatcaaca gcgcgaaaga cgatgcggca ggccaggcga ttgctaaccg cttcacttct    180
aatatcaaag gtctgactca ggcttcccgt aacgctaacg acggcatttc tattgcgcag    240
accactgaag gtgcgctgaa tgaaatcaac aacaacctgc agcgtgtgcg tgagttgtct    300
gttcaggcca ctaacgggac taactctgat tccgatctga aatctatcca ggatgaaatt    360
cagcaacgtc tggaagaaat cgatcgcgtt tctaatcaga ctcaatttaa cggtgttaaa    420
gtcctgtctc aggacaacca gatgaaaatc caggttggtg ctaacgatgg tgaaaccatt    480
accatcgatc tgcaaaaaat tgatgtgaaa agccttggcc ttgatgggtt caatgttaat    540
tccccgggaa tttccggtgg tggtggtgga attctagact ccatgggtac attaatcaat    600
gaagacgctg ccgcagccaa gaaaagtacc gctaacccac tggcttcaat tgattctgca    660
ttgtcaaaag tggacgcagt tcgttcttct ctgggggcaa ttcaaaaccg ttttgattca    720
gccattacca accttggcaa tacggtaacc aatctgaact ccgcgcgtag ccgtatcgaa    780
gatgctgact atgcaacgga agtttctaat atgtctaaag cgcagattct gcagcaggct    840
ggtacttccg ttctggcgca ggctaaccag gttccgcaaa acgtcctctc tttactgcgt    900
taa                                                                  903
```

<210> SEQ ID NO 144
<211> LENGTH: 300
<212> TYPE: PRT

```
<213> ORGANISM: Artificial Sequence
<220> FEATURE:
<223> OTHER INFORMATION: Synthetic sequence

<400> SEQUENCE: 144

Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Ser Gly Leu Arg Ile Asn Ser Ala Lys Asp Asp
        35                  40                  45

Ala Ala Gly Gln Ala Ile Ala Asn Arg Phe Thr Ser Asn Ile Lys Gly
    50                  55                  60

Leu Thr Gln Ala Ser Arg Asn Ala Asn Asp Gly Ile Ser Ile Ala Gln
65                  70                  75                  80

Thr Thr Glu Gly Ala Leu Asn Glu Ile Asn Asn Asn Leu Gln Arg Val
                85                  90                  95

Arg Glu Leu Ser Val Gln Ala Thr Asn Gly Thr Asn Ser Asp Ser Asp
            100                 105                 110

Leu Lys Ser Ile Gln Asp Glu Ile Gln Gln Arg Leu Glu Glu Ile Asp
        115                 120                 125

Arg Val Ser Asn Gln Thr Gln Phe Asn Gly Val Lys Val Leu Ser Gln
    130                 135                 140

Asp Asn Gln Met Lys Ile Gln Val Gly Ala Asn Asp Gly Glu Thr Ile
145                 150                 155                 160

Thr Ile Asp Leu Gln Lys Ile Asp Val Lys Ser Leu Gly Leu Asp Gly
                165                 170                 175

Phe Asn Val Asn Ser Pro Gly Ile Ser Gly Gly Gly Gly Gly Ile Leu
            180                 185                 190

Asp Ser Met Gly Thr Leu Ile Asn Glu Asp Ala Ala Ala Ala Lys Lys
        195                 200                 205

Ser Thr Ala Asn Pro Leu Ala Ser Ile Asp Ser Ala Leu Ser Lys Val
    210                 215                 220

Asp Ala Val Arg Ser Ser Leu Gly Ala Ile Gln Asn Arg Phe Asp Ser
225                 230                 235                 240

Ala Ile Thr Asn Leu Gly Asn Thr Val Thr Asn Leu Asn Ser Ala Arg
                245                 250                 255

Ser Arg Ile Glu Asp Ala Asp Tyr Ala Thr Glu Val Ser Asn Met Ser
            260                 265                 270

Lys Ala Gln Ile Leu Gln Gln Ala Gly Thr Ser Val Leu Ala Gln Ala
        275                 280                 285

Asn Gln Val Pro Gln Asn Val Leu Ser Leu Leu Arg
    290                 295                 300


<210> SEQ ID NO 145
<211> LENGTH: 44
<212> TYPE: DNA
<213> ORGANISM: Artificial Sequence
<220> FEATURE:
<223> OTHER INFORMATION: Synthetic sequence

<400> SEQUENCE: 145

agatctccgc ggaaccagtg catagtcagc atcttcgata cggc                    44


<210> SEQ ID NO 146
<211> LENGTH: 747
<212> TYPE: DNA
```

<213> ORGANISM: Artificial Sequence
<220> FEATURE:
<223> OTHER INFORMATION: Synthetic sequence

<400> SEQUENCE: 146

```
taatacgact cactataggg gaattgtgag cggataacaa ttcccctcta gaataatttt     60

gtttaacttt aagaaggaga tatacatatg agcgggttac ggatcaacag cgcgaaagac    120

gatgcggcag gccaggcgat tgctaaccgc ttcacttcta atatcaaagg tctgactcag    180

gcttcccgta acgctaacga cggcatttct attgcgcaga ccactgaagg tgcgctgaat    240

gaaatcaaca acaacctgca gcgtgtgcgt gagttgtctg ttcaggccac taacgggact    300

aactctgatt ccgatctgaa atctatccag gatgaaattc agcaacgtct ggaagaaatc    360

gatcgcgttt ctaatcagac tcaatttaac ggtgttaaag tcctgtctca ggacaaccag    420

atgaaaatcc aggttggtgc taacgatggt gaaaccatta ccatcgatct gcaaaaaatt    480

gatgtgaaaa gccttggcct tgatgggttc aatgttaatt ccccgggaag taccgctaac    540

ccactggctt caattgattc tgcattgtca aaagtggacg cagttcgttc ttctctgggg    600

gcaattcaaa accgctttga ttcagccatt accaaccttg gcaatacggt aaccaatctg    660

aactccgcgc gtagccgtat cgaagatgct gactatgcac tggttccgcg gggttctcat    720

catcatcatc atcatggtta agtcgac                                         747
```

<210> SEQ ID NO 147
<211> LENGTH: 654
<212> TYPE: DNA
<213> ORGANISM: Artificial Sequence
<220> FEATURE:
<223> OTHER INFORMATION: Synthetic sequence

<400> SEQUENCE: 147

```
atgagcgggt tacggatcaa cagcgcgaaa gacgatgcgg caggccaggc gattgctaac     60

cgcttcactt ctaatatcaa aggtctgact caggcttccc gtaacgctaa cgacggcatt    120

tctattgcgc agaccactga aggtgcgctg aatgaaatca acaacaacct gcagcgtgtg    180

cgtgagttgt ctgttcaggc cactaacggg actaactctg attccgatct gaaatctatc    240

caggatgaaa ttcagcaacg tctggaagaa atcgatcgcg tttctaatca gactcaattt    300

aacggtgtta aagtcctgtc tcaggacaac cagatgaaaa tccaggttgg tgctaacgat    360

ggtgaaacca ttaccatcga tctgcaaaaa attgatgtga aaagccttgg ccttgatggg    420

ttcaatgtta attccccggg aagtaccgct aacccactgg cttcaattga ttctgcattg    480

tcaaaagtgg acgcagttcg ttcttctctg ggggcaattc aaaaccgctt tgattcagcc    540

attaccaacc ttggcaatac ggtaaccaat ctgaactccg cgcgtagccg tatcgaagat    600

gctgactatg cactggttcc gcggggttct catcatcatc atcatcatgg ttaa          654
```

<210> SEQ ID NO 148
<211> LENGTH: 217
<212> TYPE: PRT
<213> ORGANISM: Artificial Sequence
<220> FEATURE:
<223> OTHER INFORMATION: Synthetic sequence

<400> SEQUENCE: 148

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30
```

```
Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Leu Val Pro Arg
        195                 200                 205

Gly Ser His His His His His His Gly
    210                 215
```

<210> SEQ ID NO 149
<211> LENGTH: 753
<212> TYPE: DNA
<213> ORGANISM: Artificial Sequence
<220> FEATURE:
<223> OTHER INFORMATION: Synthetic sequence

<400> SEQUENCE: 149

```
atgagcgggt tacggatcaa cagcgcgaaa gacgatgcgg caggccaggc gattgctaac      60

cgcttcactt ctaatatcaa aggtctgact caggcttccc gtaacgctgc agacggcatt     120

tctattgcgc agaccactga aggtgcgctg aatgaaatca acaacaacct gcagcgtgtg     180

cgtgagttgt ctgttcaggc cactgccggg gctaacgctg atgccgctct gaaagctatc     240

caggctgaaa ttcagcaacg tctggaagaa atcgatcgcg tttctcagca gactcaagct     300

gccgctgtta aagtcctgtc tcaggacaac gcaatggcaa tccaggttgg tgctaacgat     360

ggtgccgcta ttaccatcga tctgcaaaaa attgatgtga aaagccttgg ccttgatggg     420

ttcaatgtta attccccggg aagtaccgct aacccactgg cttcaattga ttctgcattg     480

tcaaaagtgg acgcagttcg ttcttctctg gggcaattc aaaaccgctt tgattcagcc      540

attaccaacc ttggcaatac ggtaaccaat ctgaactccg cgcgtagccg tatcgaagat     600

gctgactatg caacggaagt ttctcaaatg tctaaagcgc agattctgca gcaggctggt     660

acttccgttc tggcgcaggc taaccaggtt ccgcaaaacg tcctctcttt actggttccg     720

cggggttctc atcatcatca tcatcatggt taa                                 753
```

<210> SEQ ID NO 150
<211> LENGTH: 250
<212> TYPE: PRT
<213> ORGANISM: Artificial Sequence
<220> FEATURE:

<223> OTHER INFORMATION: Synthetic sequence

<400> SEQUENCE: 150

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Ala Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Ala Gly Ala Asn Ala Asp Ala Ala Leu Lys Ala Ile
65                  70                  75                  80

Gln Ala Glu Ile Gln Gln Arg Leu Glu Glu Ile Asp Arg Val Ser Gln
                85                  90                  95

Gln Thr Gln Ala Ala Ala Val Lys Val Leu Ser Gln Asp Asn Ala Met
            100                 105                 110

Ala Ile Gln Val Gly Ala Asn Asp Gly Ala Ala Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Gln Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250
```

<210> SEQ ID NO 151
<211> LENGTH: 846
<212> TYPE: DNA
<213> ORGANISM: Artificial Sequence
<220> FEATURE:
<223> OTHER INFORMATION: Synthetic sequence

<400> SEQUENCE: 151

```
taatacgact cactataggg gaattgtgag cggataacaa ttcccctcta gaataatttt      60

gtttaacttt aagaaggaga tatacatatg agcgggttac ggatcaacag cgcgaaagac     120

gatgcggcag gccaggcgat tgctaaccgc ttcacttcta atatcaaagg tctgactcag     180

gcttcccgta acgctgcaga cggcatttct attgcgcaga ccactgaagg tgcgctgaat     240

gaaatcaaca acaacctgca gcgtgtgcgt gagttgtctg ttcaggccac tgccggggct     300

aacgctgatg ccgctctgaa agctatccag gctgaaattc agcaacgtct ggaagaaatc     360

gatcgcgttt ctcagcagac tcaagctgcc gctgttaaag tcctgtctca ggacaacgca     420

atggcaatcc aggttggtgc taacgatggt gccgctatta ccatcgatct gcaaaaaatt     480

gatgtgaaaa gccttggcct tgatgggttc aatgttaatt ccccgggaag taccgctaac     540
```

```
ccactggctt caattgattc tgcattgtca aaagtggacg cagttcgttc ttctctgggg    600

gcaattcaaa accgctttga ttcagccatt accaaccttg gcaatacggt aaccaatctg    660

aactccgcgc gtagccgtat cgaagatgct gactatgcaa cggaagtttc tcaaatgtct    720

aaagcgcaga ttctgcagca ggctggtact tccgttctgg cgcaggctaa ccaggttccg    780

caaaacgtcc tctctttact ggttccgcgg ggttctcatc atcatcatca tcatggttaa    840

gtcgac                                                               846
```

<210> SEQ ID NO 152
<211> LENGTH: 795
<212> TYPE: DNA
<213> ORGANISM: Artificial Sequence
<220> FEATURE:
<223> OTHER INFORMATION: Synthetic sequence

<400> SEQUENCE: 152

```
taatacgact cactataggg gaattgtgag cggataacaa ttcccctcta gaaataatttt    60

gtttaacttt aagaaggaga tatacatatg agcgggttac ggatcaacag cgcgaaagac    120

gatgcggcag gccaggcgat tgctaaccgc ttcacttcta atatcaaagg tctgactcag    180

gcttcccgta acgctgcaga cggcatttct attgcgcaga ccactgaagg tgcgctgaat    240

gaaatcaaca acaacctgca gcgtgtgcgt gagttgtctg ttcaggccac tgccggggct    300

aacgctgatg ccgctctgaa agctatccag gctgaaattc agcaacgtct ggaagaaatc    360

gatcgcgttt ctcagcagac tcaagctgcc gctgttaaag tcctgtctca ggacaacgca    420

atggcaatcc aggttggtgc taacgatggt gccgctatta ccatcgatct gcaaaaaatt    480

gatgtgaaaa gccttggcct tgatgggttc aatgttaatt ccccgggaag taccgctaac    540

ccactggctt caattgattc tgcattgtca aaagtggacg cagttcgttc ttctctgggg    600

gcaattcaaa accgctttga ttcagccatt accaaccttg gcaatacggt aaccaatctg    660

aactccgcgc gtagccgtat cgaagatgct gactatgcaa cggaagtttc tcaaatgtct    720

aaagcgcaga ttctgcagca ggctggtctg gttccgcggg gttctcatca tcatcatcat    780

catggttaag tcgac                                                     795
```

<210> SEQ ID NO 153
<211> LENGTH: 702
<212> TYPE: DNA
<213> ORGANISM: Artificial Sequence
<220> FEATURE:
<223> OTHER INFORMATION: Synthetic sequence

<400> SEQUENCE: 153

```
atgagcgggt tacggatcaa cagcgcgaaa gacgatgcgg caggccaggc gattgctaac    60

cgcttcactt ctaatatcaa aggtctgact caggcttccc gtaacgctgc agacggcatt    120

tctattgcgc agaccactga aggtgcgctg aatgaaatca acaacaacct gcagcgtgtg    180

cgtgagttgt ctgttcaggc cactgccggg gctaacgctg atgccgctct gaaagctatc    240

caggctgaaa ttcagcaacg tctggaagaa atcgatcgcg tttctcagca gactcaagct    300

gccgctgtta aagtcctgtc tcaggacaac gcaatggcaa tccaggttgg tgctaacgat    360

ggtgccgcta ttaccatcga tctgcaaaaa attgatgtga aaagccttgg ccttgatggg    420

ttcaatgtta attccccggg aagtaccgct aacccactgg cttcaattga ttctgcattg    480

tcaaaagtgg acgcagttcg ttcttctctg gggcaattc aaaaccgctt tgattcagcc    540
```

attaccaacc ttggcaatac ggtaaccaat ctgaactccg cgcgtagccg tatcgaagat 600
gctgactatg caacggaagt ttctcaaatg tctaaagcgc agattctgca gcaggctggt 660
ctggttccgc ggggttctca tcatcatcat catcatggtt aa 702

<210> SEQ ID NO 154
<211> LENGTH: 233
<212> TYPE: PRT
<213> ORGANISM: Artificial Sequence
<220> FEATURE:
<223> OTHER INFORMATION: Synthetic sequence

<400> SEQUENCE: 154

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Ala Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Ala Gly Ala Asn Ala Asp Ala Ala Leu Lys Ala Ile
65                  70                  75                  80

Gln Ala Glu Ile Gln Gln Arg Leu Glu Glu Ile Asp Arg Val Ser Gln
                85                  90                  95

Gln Thr Gln Ala Ala Ala Val Lys Val Leu Ser Gln Asp Asn Ala Met
            100                 105                 110

Ala Ile Gln Val Gly Ala Asn Asp Gly Ala Ala Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Gln Met Ser Lys Ala Gln Ile Leu Gln Gln Ala Gly Leu Val Pro Arg
    210                 215                 220

Gly Ser His His His His His His Gly
225                 230
```

<210> SEQ ID NO 155
<211> LENGTH: 990
<212> TYPE: DNA
<213> ORGANISM: Artificial Sequence
<220> FEATURE:
<223> OTHER INFORMATION: Synthetic sequence

<400> SEQUENCE: 155
atgcggggtt ctcatcatca tcatcatcat ggtatggcta gcatgactgg tggacagcaa 60
atgggtcggg atctgtacga cgatgacgat aaggatccga tggcacaagt cattaataca 120
aacagcctgt cgctgttgac ccagaataac ctgcagaaat ctcagtcctc actgagttcc 180
gctattgagc gtctgtcctc tggtctgcgt atcaacagcg cgaaagacga tgcggcaggc 240

```
caggcgattg ctaaccgctt cacttctaat atcaaaggtc tgactcaggc ttcccgtaac    300

gctaacgacg gcatttctat tgcgcagacc actgaaggtg cgctgaatga aatcaacaac    360

aacctgcagc gtgtgcgtga gttgtctgtt caggccactc aagggactaa ctctgattcc    420

gatctgaaat ctatccagga tgaaattcag caacgtctgg aagaaatcga tcgcgtttct    480

cagcagactc aatttaacgg tgttaaagtc ctgtctcagg acaaccagat gaaaatccag    540

gttggtgcta acgatggtga aaccattacc atcgatctgc aaaaaattga tgtgaaaagc    600

cttggccttg atgggttcaa tgttaattcc ccgggaattt ccggtggtgg tggtggaatt    660

ctagactcca tgggtacatt aatcaatgaa gacgctgccg cagccaagaa aagtaccgct    720

aacccactgg cttcaattga ttctgcattg tcaaaagtgg acgcagttcg ttcttctctg    780

ggggcaattc aaaaccgttt tgattcagcc attaccaacc ttggcaatac ggtaaccaat    840

ctgaactccg cgcgtagccg tatcgaagat gctgactatg caacggaagt ttctcaaatg    900

tctaaagcgc agattctgca gcaggctggt acttccgttc tggcgcaggc taaccaggtt    960

ccgcaaaacg tcctctcttt actgcgttaa                                     990
```

<210> SEQ ID NO 156
<211> LENGTH: 180
<212> TYPE: DNA
<213> ORGANISM: Artificial Sequence
<220> FEATURE:
<223> OTHER INFORMATION: Synthetic sequence

<400> SEQUENCE: 156

```
aacccactgg cttcaattga ttctgcattg tcaaaagtgg acgcagttcg ttcttctctg     60

ggggcaattc aaaaccgttt tgattcagcc attaccgccc ttggcgctac ggtaaccgct    120

ctggcctccg cgcgtagcgc tatcgaagat gctgactatg caacggaagt ttctcaaatg    180
```

<210> SEQ ID NO 157
<211> LENGTH: 60
<212> TYPE: PRT
<213> ORGANISM: Artificial Sequence
<220> FEATURE:
<223> OTHER INFORMATION: Synthetic sequence

<400> SEQUENCE: 157

```
Asn Pro Leu Ala Ser Ile Asp Ser Ala Leu Ser Lys Val Asp Ala Val
1               5                   10                  15

Arg Ser Ser Leu Gly Ala Ile Gln Asn Arg Phe Asp Ser Ala Ile Thr
            20                  25                  30

Ala Leu Gly Ala Thr Val Thr Ala Leu Ala Ser Ala Arg Ser Ala Ile
        35                  40                  45

Glu Asp Ala Asp Tyr Ala Thr Glu Val Ser Asn Met
    50                  55                  60
```

<210> SEQ ID NO 158
<211> LENGTH: 50
<212> TYPE: DNA
<213> ORGANISM: Artificial Sequence
<220> FEATURE:
<223> OTHER INFORMATION: Synthetic sequence

<400> SEQUENCE: 158

```
gcagttcgtt cttctctggg ggcaattgat tcagccatta ccgcccttgg                50
```

<210> SEQ ID NO 159
<211> LENGTH: 50

```
<212> TYPE: DNA
<213> ORGANISM: Artificial Sequence
<220> FEATURE:
<223> OTHER INFORMATION: Synthetic sequence

<400> SEQUENCE: 159

ccaagggcgg taatggctga atcaattgcc cccagagaag aacgaactgc              50


<210> SEQ ID NO 160
<211> LENGTH: 1066
<212> TYPE: DNA
<213> ORGANISM: Artificial Sequence
<220> FEATURE:
<223> OTHER INFORMATION: Synthetic sequence

<400> SEQUENCE: 160

taatacgact cactataggg gaattgtgag cggataacaa ttcccctcta gaaataattt     60

tgtttaactt taagaaggag atatacatat gcggggttct catcatcatc atcatcatgg    120

tatggctagc atgactggtg gacagcaaat gggtcgggat ctgtacgacg atgacgataa    180

ggatccgatg gcacaagtca ttaatacaaa cagcctgtcg ctgttgaccc agaataacct    240

gaacaaatct cagtcctcac tgagttccgc tattgagcgt ctgtcctctg gtctgcgtat    300

caacagcgcg aaagacgatg cggcaggcca ggcgattgct aaccgcttca cttctaatat    360

caaaggtctg actcaggctt cccgtaacgc taacgacggc atttctattg cgcagaccac    420

tgaaggtgcg ctgaatgaaa tcaacaacaa cctgcagcgt gtgcgtgagt tgtctgttca    480

ggccactaac gggactaact ctgattccga tctgaaatct atccaggatg aaattcagca    540

acgtctggaa gaaatcgatc gcgtttctaa tcagactcaa tttaacggtg ttaaagtcct    600

gtctcaggac aaccagatga aaatccaggt tggtgctaac gatggtgaaa ccattaccat    660

cgatctgcaa aaaattgatg tgaaaagcct tggccttgat gggttcaatg ttaattcccc    720

gggaatttcc ggtggtggtg gtggaattct agactccatg ggtacattaa tcaatgaaga    780

cgctgccgca gccaagaaaa gtaccgctaa cccactggct tcaattgatt ctgcattgtc    840

aaaagtggac gcagttcgtt cttctctggg ggcaattgat tcagccatta ccgcccttgg    900

cgctacggta accgctctgg cctccgcggc tagccgtatc gaagatgctg actatgcaac    960

ggaagtttct aatatgtcta aagcgcagat tctgcagcag gctggtactt ccgttctggc   1020

gcaggctaac caggttccgc aaaacgtcct ctctttactg cgttaa                  1066


<210> SEQ ID NO 161
<211> LENGTH: 325
<212> TYPE: PRT
<213> ORGANISM: Artificial Sequence
<220> FEATURE:
<223> OTHER INFORMATION: Synthetic sequence

<400> SEQUENCE: 161

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80
```

```
Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Asp Val Lys Ser Leu Gly Leu Asp Gly Phe Asn Val
        195                 200                 205

Asn Ser Pro Gly Ile Ser Gly Gly Gly Gly Gly Ile Leu Asp Ser Met
    210                 215                 220

Gly Thr Leu Ile Asn Glu Asp Ala Ala Ala Ala Lys Lys Ser Thr Ala
225                 230                 235                 240

Asn Pro Leu Ala Ser Ile Asp Ser Ala Leu Ser Lys Val Asp Ala Val
                245                 250                 255

Arg Ser Ser Leu Gly Ala Ile Asp Ser Ala Ile Thr Ala Leu Gly Ala
            260                 265                 270

Thr Val Thr Ala Leu Ala Ser Ala Ala Ser Arg Ile Glu Asp Ala Asp
        275                 280                 285

Tyr Ala Thr Glu Val Ser Asn Met Ser Lys Ala Gln Ile Leu Gln Gln
    290                 295                 300

Ala Gly Thr Ser Val Leu Ala Gln Ala Asn Gln Val Pro Gln Asn Val
305                 310                 315                 320

Leu Ser Leu Leu Arg
                325
```

<210> SEQ ID NO 162
<211> LENGTH: 180
<212> TYPE: DNA
<213> ORGANISM: Artificial Sequence
<220> FEATURE:
<223> OTHER INFORMATION: Synthetic sequence

<400> SEQUENCE: 162

```
aacccactgg cttcaattga ttctgcattg tcaaaagtgg acgcagttcg ttcttctctg     60

ggggcaattg caaaggcttt tgattcagcc attaccgccc ttggcgctac ggtaaccgct    120

ctggcctccg cgcgtagcgc tatcgaagat gctgactatg caacggaagt ttctcaaatg    180
```

<210> SEQ ID NO 163
<211> LENGTH: 60
<212> TYPE: PRT
<213> ORGANISM: Artificial Sequence
<220> FEATURE:
<223> OTHER INFORMATION: Synthetic sequence

<400> SEQUENCE: 163

```
Asn Pro Leu Ala Ser Ile Asp Ser Ala Leu Ser Lys Val Asp Ala Val
1               5                   10                  15

Arg Ser Ser Leu Gly Ala Ile Ala Lys Ala Phe Asp Ser Ala Ile Thr
```

```
            20                  25                  30

Ala Leu Gly Ala Thr Val Thr Ala Leu Ala Ser Ala Arg Ser Ala Ile
        35                  40                  45

Glu Asp Ala Asp Tyr Ala Thr Glu Val Ser Asn Met
    50                  55                  60


<210> SEQ ID NO 164
<211> LENGTH: 50
<212> TYPE: DNA
<213> ORGANISM: Artificial Sequence
<220> FEATURE:
<223> OTHER INFORMATION: Synthetic sequence

<400> SEQUENCE: 164

cgttcttctc tgggggcaat tgcaaaggct tttgattcag ccattaccgc                50


<210> SEQ ID NO 165
<211> LENGTH: 50
<212> TYPE: DNA
<213> ORGANISM: Artificial Sequence
<220> FEATURE:
<223> OTHER INFORMATION: Synthetic sequence

<400> SEQUENCE: 165

gcggtaatgg ctgaatcaaa agcctttgca attgccccca gagaagaacg                50


<210> SEQ ID NO 166
<211> LENGTH: 1078
<212> TYPE: DNA
<213> ORGANISM: Artificial Sequence
<220> FEATURE:
<223> OTHER INFORMATION: Synthetic sequence

<400> SEQUENCE: 166

taatacgact cactataggg gaattgtgag cggataacaa ttcccctcta gaaataattt      60

tgtttaactt taagaaggag atatacatat gcggggttct catcatcatc atcatcatgg     120

tatggctagc atgactggtg gacagcaaat gggtcgggat ctgtacgacg atgacgataa     180

ggatccgatg gcacaagtca ttaatacaaa cagcctgtcg ctgttgaccc agaataacct     240

gaacaaatct cagtcctcac tgagttccgc tattgagcgt ctgtcctctg gtctgcgtat     300

caacagcgcg aaagacgatg cggcaggcca ggcgattgct aaccgcttca cttctaatat     360

caaaggtctg actcaggctt cccgtaacgc taacgacggc atttctattg cgcagaccac     420

tgaaggtgcg ctgaatgaaa tcaacaacaa cctgcagcgt gtgcgtgagt tgtctgttca     480

ggccactaac gggactaact ctgattccga tctgaaatct atccaggatg aaattcagca     540

acgtctggaa gaaatcgatc gcgtttctaa tcagactcaa tttaacggtg ttaaagtcct     600

gtctcaggac aaccagatga aaatccaggt tggtgctaac gatggtgaaa ccattaccat     660

cgatctgcaa aaaattgatg tgaaaagcct tggccttgat gggttcaatg ttaattcccc     720

gggaatttcc ggtggtggtg gtggaattct agactccatg ggtacattaa tcaatgaaga     780

cgctgccgca gccaagaaaa gtaccgctaa cccactggct tcaattgatt ctgcattgtc     840

aaaagtggac gcagttcgtt cttctctggg ggcaattgca aaggcttttg attcagccat     900

taccgccctt ggcgctacgg taaccgctct ggcctccgcg gctagccgta tcgaagatgc     960

tgactatgca acggaagttt ctaatatgtc taaagcgcag attctgcagc aggctggtac    1020

ttccgttctg gcgcaggcta accaggttcc gcaaaacgtc ctctctttac tgcgttaa      1078
```

<210> SEQ ID NO 167
<211> LENGTH: 329
<212> TYPE: PRT
<213> ORGANISM: Artificial Sequence
<220> FEATURE:
<223> OTHER INFORMATION: Synthetic sequence

<400> SEQUENCE: 167

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Asp Val Lys Ser Leu Gly Leu Asp Gly Phe Asn Val
        195                 200                 205

Asn Ser Pro Gly Ile Ser Gly Gly Gly Gly Gly Ile Leu Asp Ser Met
    210                 215                 220

Gly Thr Leu Ile Asn Glu Asp Ala Ala Ala Ala Lys Lys Ser Thr Ala
225                 230                 235                 240

Asn Pro Leu Ala Ser Ile Asp Ser Ala Leu Ser Lys Val Asp Ala Val
                245                 250                 255

Arg Ser Ser Leu Gly Ala Ile Ala Lys Ala Phe Asp Ser Ala Ile Thr
            260                 265                 270

Ala Leu Gly Ala Thr Val Thr Ala Leu Ala Ser Ala Ala Ser Arg Ile
        275                 280                 285

Glu Asp Ala Asp Tyr Ala Thr Glu Val Ser Asn Met Ser Lys Ala Gln
    290                 295                 300

Ile Leu Gln Gln Ala Gly Thr Ser Val Leu Ala Gln Ala Asn Gln Val
305                 310                 315                 320

Pro Gln Asn Val Leu Ser Leu Leu Arg
                325
```

<210> SEQ ID NO 168
<211> LENGTH: 903
<212> TYPE: DNA
<213> ORGANISM: Artificial Sequence
<220> FEATURE:
<223> OTHER INFORMATION: Synthetic sequence

<400> SEQUENCE: 168

```
atgcggggtt ctcatcatca tcatcatcat ggtatggcta gcatgactgg tggacagcaa     60

atgggtcggg atctgtacga cctggttccg cgcggtagcg cgaaggatcc gtctggtctg    120

cgtatcaaca gcgcgaaaga cgatgcggca ggccaggcga ttgctaaccg cttcacttct    180

aatatcaaag gtctgactca ggcttcccgt aacgctgcag acggcatttc tattgcgcag    240

accactgaag gtgcgctgaa tgaaatcaac aacaacctgc agcgtgtgcg tgagttgtct    300

gttcaggcca ctaacgggac taactctgat tccgatctga aatctatcca ggatgaaatt    360

cagcaacgtc tggaagaaat cgatcgcgtt tctaatcaga ctcaagctaa cggtgttaaa    420

gtcctgtctc aggacaacgc aatgaaaatc caggttggtg ctaacgatgg tgccgctatt    480

accatcgatc tgcaaaaaat tgatgtgaaa agccttggcc ttgatgggtt caatgttaat    540

tccccgggaa tttccggtgg tggtggtgga attctagact ccatgggtac attaatcaat    600

gaagacgctg ccgcagccaa gaaaagtacc gctaacccac tggcttcaat tgattctgca    660

ttgtcaaaag tggacgcagt tcgttcttct ctgggggcaa ttcaagctcg ttttgccgcg    720

gccattgcta accttggcaa tacggtaacc aatctgaact ccgcgcgtag ccgtatcgaa    780

gatgctgact atgcaacgga agtttctaat atgtctaaag cgcagattct gcagcaggct    840

ggtacttccg ttctggcgca ggctaaccag gttccgcaaa acgtcctctc tttactgcgt    900

taa                                                                  903
```

<210> SEQ ID NO 169
<211> LENGTH: 300
<212> TYPE: PRT
<213> ORGANISM: Artificial Sequence
<220> FEATURE:
<223> OTHER INFORMATION: Synthetic sequence

<400> SEQUENCE: 169

```
Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Ser Gly Leu Arg Ile Asn Ser Ala Lys Asp Asp
        35                  40                  45

Ala Ala Gly Gln Ala Ile Ala Asn Arg Phe Thr Ser Asn Ile Lys Gly
    50                  55                  60

Leu Thr Gln Ala Ser Arg Asn Ala Ala Asp Gly Ile Ser Ile Ala Gln
65                  70                  75                  80

Thr Thr Glu Gly Ala Leu Asn Glu Ile Asn Asn Asn Leu Gln Arg Val
                85                  90                  95

Arg Glu Leu Ser Val Gln Ala Thr Asn Gly Thr Asn Ser Asp Ser Asp
            100                 105                 110

Leu Lys Ser Ile Gln Asp Glu Ile Gln Gln Arg Leu Glu Glu Ile Asp
        115                 120                 125

Arg Val Ser Asn Gln Thr Gln Ala Asn Gly Val Lys Val Leu Ser Gln
    130                 135                 140

Asp Asn Ala Met Lys Ile Gln Val Gly Ala Asn Asp Gly Ala Ala Ile
145                 150                 155                 160

Thr Ile Asp Leu Gln Lys Ile Asp Val Lys Ser Leu Gly Leu Asp Gly
                165                 170                 175

Phe Asn Val Asn Ser Pro Gly Ile Ser Gly Gly Gly Gly Gly Ile Leu
```

```
            180                 185                 190

Asp Ser Met Gly Thr Leu Ile Asn Glu Asp Ala Ala Ala Ala Lys Lys
        195                 200                 205

Ser Thr Ala Asn Pro Leu Ala Ser Ile Asp Ser Ala Leu Ser Lys Val
    210                 215                 220

Asp Ala Val Arg Ser Ser Leu Gly Ala Ile Gln Ala Arg Phe Ala Ala
225                 230                 235                 240

Ala Ile Ala Asn Leu Gly Asn Thr Val Thr Asn Leu Asn Ser Ala Arg
                245                 250                 255

Ser Arg Ile Glu Asp Ala Asp Tyr Ala Thr Glu Val Ser Asn Met Ser
            260                 265                 270

Lys Ala Gln Ile Leu Gln Gln Ala Gly Thr Ser Val Leu Ala Gln Ala
        275                 280                 285

Asn Gln Val Pro Gln Asn Val Leu Ser Leu Leu Arg
    290                 295                 300


<210> SEQ ID NO 170
<211> LENGTH: 996
<212> TYPE: DNA
<213> ORGANISM: Artificial Sequence
<220> FEATURE:
<223> OTHER INFORMATION: Synthetic sequence

<400> SEQUENCE: 170

taatacgact cactataggg gaattgtgag cggataacaa ttcccctcta gaataatttt      60

gtttaacttt aagaaggaga tatacatatg cggggttctc atcatcatca tcatcatggt     120

atggctagca tgactggtgg acagcaaatg ggtcgggatc tgtacgacct ggttccgcgc     180

ggtagcgcga aggatccgtc tggtctgcgt atcaacagcg cgaaagacga tgcggcaggc     240

caggcgattg ctaaccgctt cacttctaat atcaaaggtc tgactcaggc ttcccgtaac     300

gctgcagacg gcatttctat tgcgcagacc actgaaggtg cgctgaatga aatcaacaac     360

aacctgcagc gtgtgcgtga gttgtctgtt caggccacta acgggactaa ctctgattcc     420

gatctgaaat ctatccagga tgaaattcag caacgtctgg aagaaatcga tcgcgtttct     480

aatcagactc aagctaacgg tgttaaagtc ctgtctcagg acaacgcaat gaaaatccag     540

gttggtgcta acgatggtgc cgctattacc atcgatctgc aaaaaattga tgtgaaaagc     600

cttggccttg atgggttcaa tgttaattcc ccgggaattt ccggtggtgg tggtggaatt     660

ctagactcca tgggtacatt aatcaatgaa gacgctgccg cagccaagaa aagtaccgct     720

aacccactgg cttcaattga ttctgcattg tcaaaagtgg acgcagttcg ttcttctctg     780

ggggcaattc aagctcgttt tgccgcggcc attgctaacc ttggcaatac ggtaaccaat     840

ctgaactccg cgcgtagccg tatcgaagat gctgactatg caacggaagt ttctaatatg     900

tctaaagcgc agattctgca gcaggctggt acttccgttc tggcgcaggc taaccaggtt     960

ccgcaaaacg tcctctcttt actgcgttaa gtcgac                                996


<210> SEQ ID NO 171
<211> LENGTH: 79
<212> TYPE: DNA
<213> ORGANISM: Artificial Sequence
<220> FEATURE:
<223> OTHER INFORMATION: Synthetic sequence

<400> SEQUENCE: 171

agatctgtcg acttaaccat gatgatgatg atgatgagaa ccccgcggaa ccagtaaaga      60
```

```
gaggacgttt tgcggaacc                                                 79


<210> SEQ ID NO 172
<211> LENGTH: 846
<212> TYPE: DNA
<213> ORGANISM: Artificial Sequence
<220> FEATURE:
<223> OTHER INFORMATION: Synthetic sequence

<400> SEQUENCE: 172

taatacgact cactataggg gaattgtgag cggataacaa ttcccctcta gaataatttt     60

gtttaacttt aagaaggaga tatacatatg agcgggttac ggatcaacag cgcgaaagac    120

gatgcggcag gccaggcgat tgctaaccgc ttcacttcta atatcaaagg tctgactcag    180

gcttcccgta acgctaacga cggcatttct attgcgcaga ccactgaagg tgcgctgaat    240

gaaatcaaca acaacctgca gcgtgtgcgt gagttgtctg ttcaggccac taacgggact    300

aactctgatt ccgatctgaa atctatccag gatgaaattc agcaacgtct ggaagaaatc    360

gatcgcgttt ctaatcagac tcaatttaac ggtgttaaag tcctgtctca ggacaaccag    420

atgaaaatcc aggttggtgc taacgatggt gaaaccatta ccatcgatct gcaaaaaatt    480

gatgtgaaaa gccttggcct tgatgggttc aatgttaatt ccccgggaag taccgctaac    540

ccactggctt caattgattc tgcattgtca aaagtggacg cagttcgttc ttctctgggg    600

gcaattcaag ctcgttttgc cgcggccatt gctaaccttg gcaatacggt aaccaatctg    660

aactccgcgc gtagccgtat cgaagatgct gactatgcaa cggaagtttc taatatgtct    720

aaagcgcaga ttctgcagca ggctggtact tccgttctgg cgcaggctaa ccaggttccg    780

caaaacgtcc tctctttact ggttccgcgg ggttctcatc atcatcatca tcatggttaa    840

gtcgac                                                               846


<210> SEQ ID NO 173
<211> LENGTH: 250
<212> TYPE: PRT
<213> ORGANISM: Artificial Sequence
<220> FEATURE:
<223> OTHER INFORMATION: Synthetic sequence

<400> SEQUENCE: 173

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140
```

```
Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Ala Arg
                165                 170                 175

Phe Ala Ala Ala Ile Ala Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250


<210> SEQ ID NO 174
<211> LENGTH: 47
<212> TYPE: DNA
<213> ORGANISM: Artificial Sequence
<220> FEATURE:
<223> OTHER INFORMATION: Synthetic sequence

<400> SEQUENCE: 174

agatctcata tgagcgggtt acggatcaac agcgcgaaag acgatgc                 47


<210> SEQ ID NO 175
<211> LENGTH: 846
<212> TYPE: DNA
<213> ORGANISM: Artificial Sequence
<220> FEATURE:
<223> OTHER INFORMATION: Synthetic sequence

<400> SEQUENCE: 175

taatacgact cactataggg gaattgtgag cggataacaa ttcccctcta gaataatttt      60

gtttaacttt aagaaggaga tatacatatg agcgggttac ggatcaacag cgcgaaagac     120

gatgcggcag gccaggcgat tgctaaccgc ttcacttcta atatcaaagg tctgactcag     180

gcttcccgta acgctgcaga cggcatttct attgcgcaga ccactgaagg tgcgctgaat     240

gaaatcaaca acaacctgca gcgtgtgcgt gagttgtctg ttcaggccac taacgggact     300

aactctgatt ccgatctgaa atctatccag gatgaaattc agcaacgtct ggaagaaatc     360

gatcgcgttt ctaatcagac tcaagctaac ggtgttaaag tcctgtctca ggacaacgca     420

atgaaaatcc aggttggtgc taacgatggt gccgctatta ccatcgatct gcaaaaaatt     480

gatgtgaaaa gccttggcct tgatgggttc aatgttaatt ccccgggaag taccgctaac     540

ccactggctt caattgattc tgcattgtca aaagtggacg cagttcgttc ttctctgggg     600

gcaattcaaa accgctttga ttcagccatt accaaccttg gcaatacggt aaccaatctg     660

aactccgcgc gtagccgtat cgaagatgct gactatgcaa cggaagtttc taatatgtct     720

aaagcgcaga ttctgcagca ggctggtact tccgttctgg cgcaggctaa ccaggttccg     780

caaaacgtcc tctctttact ggttccgcgg ggttctcatc atcatcatca tcatggttaa     840

gtcgac                                                                846


<210> SEQ ID NO 176
<211> LENGTH: 250
<212> TYPE: PRT
<213> ORGANISM: Artificial Sequence
<220> FEATURE:
```

```
<223> OTHER INFORMATION: Synthetic sequence

<400> SEQUENCE: 176

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Ala Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Ala Asn Gly Val Lys Val Leu Ser Gln Asp Asn Ala Met
            100                 105                 110

Lys Ile Gln Val Gly Ala Asn Asp Gly Ala Ala Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250


<210> SEQ ID NO 177
<211> LENGTH: 270
<212> TYPE: DNA
<213> ORGANISM: Artificial Sequence
<220> FEATURE:
<223> OTHER INFORMATION: Synthetic sequence

<400> SEQUENCE: 177

aacccactgg cttcaattga ttctgcattg tcaaaagtgg acgcagttcg ttcttctctg      60

ggggcaattc aaaaccgttt tgattcagcc attaccaacc ttggcaatac ggtaaccaat     120

ctgaactccg cgcgtagccg tatcgaagat gctgactatg caacggaagt ttctcaaatg     180

tctaaagcgc agattctgca gcaggctggt acttccgttc tggcgcaggc taaccaggtt     240

ccgcaaaacg tcctctcttt actgcgttaa                                      270


<210> SEQ ID NO 178
<211> LENGTH: 60
<212> TYPE: DNA
<213> ORGANISM: Artificial Sequence
<220> FEATURE:
<223> OTHER INFORMATION: Synthetic sequence
```

<400> SEQUENCE: 178
attaccaacc ttggcaatac ggtaaccaat ctgaactccg cgcgtagccg tatcgaagat 60

<210> SEQ ID NO 179
<211> LENGTH: 20
<212> TYPE: PRT
<213> ORGANISM: Artificial Sequence
<220> FEATURE:
<223> OTHER INFORMATION: Synthetic sequence

<400> SEQUENCE: 179

Ile Thr Asn Leu Gly Asn Thr Val Thr Asn Leu Asn Ser Ala Arg Ser
1 5 10 15

Arg Ile Glu Asp
20

<210> SEQ ID NO 180
<211> LENGTH: 46
<212> TYPE: DNA
<213> ORGANISM: Artificial Sequence
<220> FEATURE:
<223> OTHER INFORMATION: Synthetic sequence

<400> SEQUENCE: 180
ccttggcaat acggtaaccg ctctggcctc cgcgcgtagc cgtatc 46

<210> SEQ ID NO 181
<211> LENGTH: 46
<212> TYPE: DNA
<213> ORGANISM: Artificial Sequence
<220> FEATURE:
<223> OTHER INFORMATION: Synthetic sequence

<400> SEQUENCE: 181
gatacggcta cgcgcggagg ccagagcggt taccgtattg ccaagg 46

<210> SEQ ID NO 182
<211> LENGTH: 60
<212> TYPE: DNA
<213> ORGANISM: Artificial Sequence
<220> FEATURE:
<223> OTHER INFORMATION: Synthetic sequence

<400> SEQUENCE: 182
acggtaaccg ctctggcctc cgcgcgtagc cgtatcgaag atgctgacta tgcaacggaa 60

<210> SEQ ID NO 183
<211> LENGTH: 20
<212> TYPE: PRT
<213> ORGANISM: Artificial Sequence
<220> FEATURE:
<223> OTHER INFORMATION: Synthetic sequence

<400> SEQUENCE: 183

Thr Val Thr Ala Leu Ala Ser Ala Arg Ser Arg Ile Glu Asp Ala Asp
1 5 10 15

Tyr Ala Thr Glu
20

<210> SEQ ID NO 184
<211> LENGTH: 34
<212> TYPE: DNA
<213> ORGANISM: Artificial Sequence
<220> FEATURE:

<223> OTHER INFORMATION: Synthetic sequence

<400> SEQUENCE: 184
gctctggcct ccgcggctag ccgtatcgaa gatg 34

<210> SEQ ID NO 185
<211> LENGTH: 34
<212> TYPE: DNA
<213> ORGANISM: Artificial Sequence
<220> FEATURE:
<223> OTHER INFORMATION: Synthetic sequence

<400> SEQUENCE: 185
catcttcgat acggctagcc gcggaggcca gagc 34

<210> SEQ ID NO 186
<211> LENGTH: 60
<212> TYPE: DNA
<213> ORGANISM: Artificial Sequence
<220> FEATURE:
<223> OTHER INFORMATION: Synthetic sequence

<400> SEQUENCE: 186
caaaaccgtt ttgattcagc cattaccaac cttggcaata cggtaaccgc tctggcctcc 60

<210> SEQ ID NO 187
<211> LENGTH: 20
<212> TYPE: PRT
<213> ORGANISM: Artificial Sequence
<220> FEATURE:
<223> OTHER INFORMATION: Synthetic sequence

<400> SEQUENCE: 187

Gln Asn Arg Phe Asp Ser Ala Ile Thr Asn Leu Gly Asn Thr Val Thr
1 5 10 15

Ala Leu Ala Ser
20

<210> SEQ ID NO 188
<211> LENGTH: 48
<212> TYPE: DNA
<213> ORGANISM: Artificial Sequence
<220> FEATURE:
<223> OTHER INFORMATION: Synthetic sequence

<400> SEQUENCE: 188
gttttgattc agccattacc gcccttggcg ctacggtaac cgctctgg 48

<210> SEQ ID NO 189
<211> LENGTH: 48
<212> TYPE: DNA
<213> ORGANISM: Artificial Sequence
<220> FEATURE:
<223> OTHER INFORMATION: Synthetic sequence

<400> SEQUENCE: 189
ccagagcggt taccgtagcg ccaagggcgg taatggctga atcaaaac 48

<210> SEQ ID NO 190
<211> LENGTH: 39
<212> TYPE: DNA
<213> ORGANISM: Artificial Sequence
<220> FEATURE:
<223> OTHER INFORMATION: Synthetic sequence

<400> SEQUENCE: 190
caacagcgcg aaagccgatg cgggaggcca ggcgattgc 39

<210> SEQ ID NO 191
<211> LENGTH: 39
<212> TYPE: DNA
<213> ORGANISM: Artificial Sequence
<220> FEATURE:
<223> OTHER INFORMATION: Synthetic sequence

<400> SEQUENCE: 191
gcaatcgcct ggcctcccgc atcggctttc gcgctgttg 39

<210> SEQ ID NO 192
<211> LENGTH: 846
<212> TYPE: DNA
<213> ORGANISM: Artificial Sequence
<220> FEATURE:
<223> OTHER INFORMATION: Synthetic sequence

<400> SEQUENCE: 192
taatacgact cactataggg gaattgtgag cggataacaa ttcccctcta gaataatttt 60
gtttaacttt aagaaggaga tatacatatg agcgggttac ggatcaacag cgcgaaagcc 120
gatgcgggag gccaggcgat tgctaaccgc ttcacttcta atatcaaagg tctgactcag 180
gcttcccgta acgctaacga cggcatttct attgcgcaga ccactgaagg tgcgctgaat 240
gaaatcaaca acaacctgca gcgtgtgcgt gagttgtctg ttcaggccac taacgggact 300
aactctgatt ccgatctgaa atctatccag gatgaaattc agcaacgtct ggaagaaatc 360
gatcgcgttt ctaatcagac tcaatttaac ggtgttaaag tcctgtctca ggacaaccag 420
atgaaaatcc aggttggtgc taacgatggt gaaaccatta ccatcgatct gcaaaaaatt 480
gatgtgaaaa gccttggcct tgatgggttc aatgttaatt ccccgggaag taccgctaac 540
ccactggctt caattgattc tgcattgtca aaagtggacg cagttcgttc ttctctgggg 600
gcaattcaaa accgctttga ttcagccatt accaaccttg gcaatacggt aaccaatctg 660
aactccgcgc gtagccgtat cgaagatgct gactatgcaa cggaagtttc taatatgtct 720
aaagcgcaga ttctgcagca ggctggtact tccgttctgg cgcaggctaa ccaggttccg 780
caaaacgtcc tctctttact ggttccgcgg ggttctcatc atcatcatca tcatggttaa 840
gtcgac 846

<210> SEQ ID NO 193
<211> LENGTH: 250
<212> TYPE: PRT
<213> ORGANISM: Artificial Sequence
<220> FEATURE:
<223> OTHER INFORMATION: Synthetic sequence

<400> SEQUENCE: 193

Met Ser Gly Leu Arg Ile Asn Ser Ala Lys Ala Asp Ala Gly Gly Gln
1 5 10 15

Ala Ile Ala Asn Arg Phe Thr Ser Asn Ile Lys Gly Leu Thr Gln Ala
20 25 30

Ser Arg Asn Ala Asn Asp Gly Ile Ser Ile Ala Gln Thr Thr Glu Gly
35 40 45

Ala Leu Asn Glu Ile Asn Asn Asn Leu Gln Arg Val Arg Glu Leu Ser
50 55 60

Val Gln Ala Thr Asn Gly Thr Asn Ser Asp Ser Asp Leu Lys Ser Ile
65 70 75 80

```
Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250
```

<210> SEQ ID NO 194
<211> LENGTH: 43
<212> TYPE: DNA
<213> ORGANISM: Artificial Sequence
<220> FEATURE:
<223> OTHER INFORMATION: Synthetic sequence

<400> SEQUENCE: 194

```
gtctgttcag gccactgccg gggctaactc tgattccgat ctg                   43
```

<210> SEQ ID NO 195
<211> LENGTH: 43
<212> TYPE: DNA
<213> ORGANISM: Artificial Sequence
<220> FEATURE:
<223> OTHER INFORMATION: Synthetic sequence

<400> SEQUENCE: 195

```
cagatcggaa tcagagttag ccccggcagt ggcctgaaca gac                   43
```

<210> SEQ ID NO 196
<211> LENGTH: 846
<212> TYPE: DNA
<213> ORGANISM: Artificial Sequence
<220> FEATURE:
<223> OTHER INFORMATION: Synthetic sequence

<400> SEQUENCE: 196

```
taatacgact cactataggg gaattgtgag cggataacaa ttcccctcta gaataatttt     60

gtttaacttt aagaaggaga tatacatatg agcgggttac ggatcaacag cgcgaaagac    120

gatgcggcag gccaggcgat tgctaaccgc ttcacttcta atatcaaagg tctgactcag    180

gcttcccgta acgctaacga cggcatttct attgcgcaga ccactgaagg tgcgctgaat    240

gaaatcaaca acaacctgca gcgtgtgcgt gagttgtctg ttcaggccac tgccggggct    300

aactctgatt ccgatctgaa atctatccag gatgaaattc agcaacgtct ggaagaaatc    360
```

```
gatcgcgttt ctaatcagac tcaatttaac ggtgttaaag tcctgtctca ggacaaccag    420

atgaaaatcc aggttggtgc taacgatggt gaaaccatta ccatcgatct gcaaaaaatt    480

gatgtgaaaa gccttggcct tgatgggttc aatgttaatt ccccgggaag taccgctaac    540

ccactggctt caattgattc tgcattgtca aaagtggacg cagttcgttc ttctctgggg    600

gcaattcaaa accgctttga ttcagccatt accaaccttg gcaatacggt aaccaatctg    660

aactccgcgc gtagccgtat cgaagatgct gactatgcaa cggaagtttc taatatgtct    720

aaagcgcaga ttctgcagca ggctggtact tccgttctgg cgcaggctaa ccaggttccg    780

caaaacgtcc tctctttact ggttccgcgg ggttctcatc atcatcatca tcatggttaa    840

gtcgac                                                               846
```

```
<210> SEQ ID NO 197
<211> LENGTH: 250
<212> TYPE: PRT
<213> ORGANISM: Artificial Sequence
<220> FEATURE:
<223> OTHER INFORMATION: Synthetic sequence

<400> SEQUENCE: 197

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Ala Gly Ala Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250

<210> SEQ ID NO 198
```

<211> LENGTH: 45
<212> TYPE: DNA
<213> ORGANISM: Artificial Sequence
<220> FEATURE:
<223> OTHER INFORMATION: Synthetic sequence

<400> SEQUENCE: 198
ctgattccga tctgaaagct atccaggctg aaattcagca acgtc 45

<210> SEQ ID NO 199
<211> LENGTH: 45
<212> TYPE: DNA
<213> ORGANISM: Artificial Sequence
<220> FEATURE:
<223> OTHER INFORMATION: Synthetic sequence

<400> SEQUENCE: 199
gacgttgctg aatttcagcc tggatagctt tcagatcgga atcag 45

<210> SEQ ID NO 200
<211> LENGTH: 846
<212> TYPE: DNA
<213> ORGANISM: Artificial Sequence
<220> FEATURE:
<223> OTHER INFORMATION: Synthetic sequence

<400> SEQUENCE: 200
taatacgact cactataggg gaattgtgag cggataacaa ttcccctcta gaataatttt 60
gtttaacttt aagaaggaga tatacatatg agcgggttac ggatcaacag cgcgaaagac 120
gatgcggcag gccaggcgat tgctaaccgc ttcacttcta atatcaaagg tctgactcag 180
gcttcccgta acgctaacga cggcatttct attgcgcaga ccactgaagg tgcgctgaat 240
gaaatcaaca acaacctgca gcgtgtgcgt gagttgtctg ttcaggccac tgccggggct 300
aactctgatt ccgatctgaa agctatccag gctgaaattc agcaacgtct ggaagaaatc 360
gatcgcgttt ctaatcagac tcaatttaac ggtgttaaag tcctgtctca ggacaaccag 420
atgaaaatcc aggttggtgc taacgatggt gaaaccatta ccatcgatct gcaaaaaatt 480
gatgtgaaaa gccttggcct tgatgggttc aatgttaatt ccccgggaag taccgctaac 540
ccactggctt caattgattc tgcattgtca aaagtggacg cagttcgttc ttctctgggg 600
gcaattcaaa accgctttga ttcagccatt accaaccttg gcaatacggt aaccaatctg 660
aactccgcgc gtagccgtat cgaagatgct gactatgcaa cggaagtttc taatatgtct 720
aaagcgcaga ttctgcagca ggctggtact tccgttctgg cgcaggctaa ccaggttccg 780
caaaacgtcc tctctttact ggttccgcgg ggttctcatc atcatcatca tcatggttaa 840
gtcgac 846

<210> SEQ ID NO 201
<211> LENGTH: 753
<212> TYPE: DNA
<213> ORGANISM: Artificial Sequence
<220> FEATURE:
<223> OTHER INFORMATION: Synthetic sequence

<400> SEQUENCE: 201
atgagcgggt tacggatcaa cagcgcgaaa gacgatgcgg caggccaggc gattgctaac 60
cgcttcactt ctaatatcaa aggtctgact caggcttccc gtaacgctaa cgacggcatt 120
tctattgcgc agaccactga aggtgcgctg aatgaaatca acaacaacct gcagcgtgtg 180
cgtgagttgt ctgttcaggc cactgccggg gctaactctg attccgatct gaaagctatc 240

```
caggctgaaa ttcagcaacg tctggaagaa atcgatcgcg tttctaatca gactcaattt    300

aacggtgtta aagtcctgtc tcaggacaac cagatgaaaa tccaggttgg tgctaacgat    360

ggtgaaacca ttaccatcga tctgcaaaaa attgatgtga aaagccttgg ccttgatggg    420

ttcaatgtta attccccggg aagtaccgct aacccactgg cttcaattga ttctgcattg    480

tcaaaagtgg acgcagttcg ttcttctctg gggcaattc aaaaccgctt tgattcagcc    540

attaccaacc ttggcaatac ggtaaccaat ctgaactccg cgcgtagccg tatcgaagat    600

gctgactatg caacggaagt ttctaatatg tctaaagcgc agattctgca gcaggctggt    660

acttccgttc tggcgcaggc taaccaggtt ccgcaaaacg tcctctcttt actggttccg    720

cggggttctc atcatcatca tcatcatggt taa                                 753
```

<210> SEQ ID NO 202
<211> LENGTH: 250
<212> TYPE: PRT
<213> ORGANISM: Artificial Sequence
<220> FEATURE:
<223> OTHER INFORMATION: Synthetic sequence

<400> SEQUENCE: 202

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Ala Gly Ala Asn Ser Asp Ser Asp Leu Lys Ala Ile
65                  70                  75                  80

Gln Ala Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250
```

<210> SEQ ID NO 203

<211> LENGTH: 45
<212> TYPE: DNA
<213> ORGANISM: Artificial Sequence
<220> FEATURE:
<223> OTHER INFORMATION: Synthetic sequence

<400> SEQUENCE: 203
gccactaacg ggactaacgc tgatgccgct ctgaaatcta tccag 45

<210> SEQ ID NO 204
<211> LENGTH: 45
<212> TYPE: DNA
<213> ORGANISM: Artificial Sequence
<220> FEATURE:
<223> OTHER INFORMATION: Synthetic sequence

<400> SEQUENCE: 204
ctggatagat ttcagagcgg catcagcgtt agtcccgtta gtggc 45

<210> SEQ ID NO 205
<211> LENGTH: 846
<212> TYPE: DNA
<213> ORGANISM: Artificial Sequence
<220> FEATURE:
<223> OTHER INFORMATION: Synthetic sequence

<400> SEQUENCE: 205
taatacgact cactataggg gaattgtgag cggataacaa ttcccctcta gaataatttt 60
gtttaacttt aagaaggaga tatacatatg agcgggttac ggatcaacag cgcgaaagac 120
gatgcggcag gccaggcgat tgctaaccgc ttcacttcta atatcaaagg tctgactcag 180
gcttcccgta acgctaacga cggcatttct attgcgcaga ccactgaagg tgcgctgaat 240
gaaatcaaca acaacctgca gcgtgtgcgt gagttgtctg ttcaggccac taacgggact 300
aacgctgatg ccgctctgaa atctatccag gatgaaattc agcaacgtct ggaagaaatc 360
gatcgcgttt ctaatcagac tcaatttaac ggtgttaaag tcctgtctca ggacaaccag 420
atgaaaatcc aggttggtgc taacgatggt gaaaccatta ccatcgatct gcaaaaaatt 480
gatgtgaaaa gccttggcct tgatgggttc aatgttaatt ccccgggaag taccgctaac 540
ccactggctt caattgattc tgcattgtca aaagtggacg cagttcgttc ttctctgggg 600
gcaattcaaa accgctttga ttcagccatt accaaccttg gcaatacggt aaccaatctg 660
aactccgcgc gtagccgtat cgaagatgct gactatgcaa cggaagtttc taatatgtct 720
aaagcgcaga ttctgcagca ggctggtact tccgttctgg cgcaggctaa ccaggttccg 780
caaaacgtcc tctctttact ggttccgcgg ggttctcatc atcatcatca tcatggttaa 840
gtcgac 846

<210> SEQ ID NO 206
<211> LENGTH: 250
<212> TYPE: PRT
<213> ORGANISM: Artificial Sequence
<220> FEATURE:
<223> OTHER INFORMATION: Synthetic sequence

<400> SEQUENCE: 206

Met Ser Gly Leu Arg Ile Asn Ser Ala Lys Asp Asp Ala Ala Gly Gln
1 5 10 15

Ala Ile Ala Asn Arg Phe Thr Ser Asn Ile Lys Gly Leu Thr Gln Ala
20 25 30

Ser Arg Asn Ala Asn Asp Gly Ile Ser Ile Ala Gln Thr Thr Glu Gly

```
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ala Asp Ala Ala Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250
```

<210> SEQ ID NO 207
<211> LENGTH: 45
<212> TYPE: DNA
<213> ORGANISM: Artificial Sequence
<220> FEATURE:
<223> OTHER INFORMATION: Synthetic sequence

<400> SEQUENCE: 207

```
gccactgccg gggctaacgc tgatgccgct ctgaaagcta tccag                 45
```

<210> SEQ ID NO 208
<211> LENGTH: 45
<212> TYPE: DNA
<213> ORGANISM: Artificial Sequence
<220> FEATURE:
<223> OTHER INFORMATION: Synthetic sequence

<400> SEQUENCE: 208

```
ctggatagct ttcagagcgg catcagcgtt agccccggca gtggc                 45
```

<210> SEQ ID NO 209
<211> LENGTH: 846
<212> TYPE: DNA
<213> ORGANISM: Artificial Sequence
<220> FEATURE:
<223> OTHER INFORMATION: Synthetic sequence

<400> SEQUENCE: 209

```
taatacgact cactataggg gaattgtgag cggataacaa ttcccctcta gaataatttt     60

gtttaacttt aagaaggaga tatacatatg agcgggttac ggatcaacag cgcgaaagac    120
```

```
gatgcggcag gccaggcgat tgctaaccgc ttcacttcta atatcaaagg tctgactcag    180

gcttcccgta acgctaacga cggcatttct attgcgcaga ccactgaagg tgcgctgaat    240

gaaatcaaca acaacctgca gcgtgtgcgt gagttgtctg ttcaggccac tgccggggct    300

aacgctgatg ccgctctgaa agctatccag gctgaaattc agcaacgtct ggaagaaatc    360

gatcgcgttt ctaatcagac tcaatttaac ggtgttaaag tcctgtctca ggacaaccag    420

atgaaaatcc aggttggtgc taacgatggt gaaaccatta ccatcgatct gcaaaaaatt    480

gatgtgaaaa gccttggcct tgatgggttc aatgttaatt ccccgggaag taccgctaac    540

ccactggctt caattgattc tgcattgtca aaagtggacg cagttcgttc ttctctgggg    600

gcaattcaaa accgctttga ttcagccatt accaaccttg gcaatacggt aaccaatctg    660

aactccgcgc gtagccgtat cgaagatgct gactatgcaa cggaagtttc taatatgtct    720

aaagcgcaga ttctgcagca ggctggtact tccgttctgg cgcaggctaa ccaggttccg    780

caaaacgtcc tctctttact ggttccgcgg ggttctcatc atcatcatca tcatggttaa    840

gtcgac                                                               846
```

```
<210> SEQ ID NO 210
<211> LENGTH: 250
<212> TYPE: PRT
<213> ORGANISM: Artificial Sequence
<220> FEATURE:
<223> OTHER INFORMATION: Synthetic sequence

<400> SEQUENCE: 210

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Ala Gly Ala Asn Ala Asp Ala Ala Leu Lys Ala Ile
65                  70                  75                  80

Gln Ala Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
```

```
225                 230                 235                 240

Arg Gly Ser His His His His His His Gly
                245                 250


<210> SEQ ID NO 211
<211> LENGTH: 846
<212> TYPE: DNA
<213> ORGANISM: Artificial Sequence
<220> FEATURE:
<223> OTHER INFORMATION: Synthetic sequence

<400> SEQUENCE: 211

taatacgact cactataggg gaattgtgag cggataacaa ttcccctcta gaataatttt      60

gtttaacttt aagaaggaga tatacatatg agcgggttac ggatcaacag cgcgaaagac     120

gatgcggcag gccaggcgat tgctaaccgc ttcacttcta atatcaaagg tctgactcag     180

gcttcccgta acgctaacga cggcatttct attgcgcaga ccactgaagg tgcgctgaat     240

gaaatcaaca acaacctgca gcgtgtgcgt gagttgtctg ttcaggccac taacgggact     300

aactctgatt ccgatctgaa agctatccag gctgaaattc agcaacgtct ggaagaaatc     360

gatcgcgttt ctaatcagac tcaatttaac ggtgttaaag tcctgtctca ggacaaccag     420

atgaaaatcc aggttggtgc taacgatggt gaaaccatta ccatcgatct gcaaaaaatt     480

gatgtgaaaa gccttggcct tgatgggttc aatgttaatt ccccgggaag taccgctaac     540

ccactggctt caattgattc tgcattgtca aaagtggacg cagttcgttc ttctctgggg     600

gcaattcaaa accgctttga ttcagccatt accaaccttg gcaatacggt aaccaatctg     660

aactccgcgc gtagccgtat cgaagatgct gactatgcaa cggaagtttc taatatgtct     720

aaagcgcaga ttctgcagca ggctggtact tccgttctgg cgcaggctaa ccaggttccg     780

caaaacgtcc tctctttact ggttccgcgg ggttctcatc atcatcatca tcatggttaa     840

gtcgac                                                                846


<210> SEQ ID NO 212
<211> LENGTH: 250
<212> TYPE: PRT
<213> ORGANISM: Artificial Sequence
<220> FEATURE:
<223> OTHER INFORMATION: Synthetic sequence

<400> SEQUENCE: 212

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ala Ile
65                  70                  75                  80

Gln Ala Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125
```

```
Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250


<210> SEQ ID NO 213
<211> LENGTH: 45
<212> TYPE: DNA
<213> ORGANISM: Artificial Sequence
<220> FEATURE:
<223> OTHER INFORMATION: Synthetic sequence

<400> SEQUENCE: 213

ctatccagga tgaaattcag gcacgtctgg cagaaatcga tcgcg                        45


<210> SEQ ID NO 214
<211> LENGTH: 45
<212> TYPE: DNA
<213> ORGANISM: Artificial Sequence
<220> FEATURE:
<223> OTHER INFORMATION: Synthetic sequence

<400> SEQUENCE: 214

cgcgatcgat ttctgccaga cgtgcctgaa tttcatcctg gatag                        45


<210> SEQ ID NO 215
<211> LENGTH: 846
<212> TYPE: DNA
<213> ORGANISM: Artificial Sequence
<220> FEATURE:
<223> OTHER INFORMATION: Synthetic sequence

<400> SEQUENCE: 215

taatacgact cactataggg gaattgtgag cggataacaa ttcccctcta gaaataattt      60

gtttaacttt aagaaggaga tatacatatg agcgggttac ggatcaacag cgcgaaagac     120

gatgcggcag gccaggcgat tgctaaccgc ttcacttcta atatcaaagg tctgactcag     180

gcttcccgta acgctaacga cggcatttct attgcgcaga ccactgaagg tgcgctgaat     240

gaaatcaaca acaacctgca gcgtgtgcgt gagttgtctg ttcaggccac taacgggact     300

aactctgatt ccgatctgaa atctatccag gatgaaattc aggcacgtct ggcagaaatc     360

gatcgcgttt ctaatcagac tcaatttaac ggtgttaaag tcctgtctca ggacaaccag     420

atgaaaatcc aggttggtgc taacgatggt gaaaccatta ccatcgatct gcaaaaaatt     480

gatgtgaaaa gccttggcct tgatgggttc aatgttaatt ccccgggaag taccgctaac     540

ccactggctt caattgattc tgcattgtca aaagtggacg cagttcgttc ttctctgggg     600

gcaattcaaa accgctttga ttcagccatt accaaccttg gcaatacggt aaccaatctg     660
```

```
aactccgcgc gtagccgtat cgaagatgct gactatgcaa cggaagtttc taatatgtct    720

aaagcgcaga ttctgcagca ggctggtact tccgttctgg cgcaggctaa ccaggttccg    780

caaaacgtcc tctctttact ggttccgcgg ggttctcatc atcatcatca tcatggttaa    840

gtcgac                                                               846


<210> SEQ ID NO 216
<211> LENGTH: 250
<212> TYPE: PRT
<213> ORGANISM: Artificial Sequence
<220> FEATURE:
<223> OTHER INFORMATION: Synthetic sequence

<400> SEQUENCE: 216

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Ala Arg Leu Ala Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250


<210> SEQ ID NO 217
<211> LENGTH: 59
<212> TYPE: DNA
<213> ORGANISM: Artificial Sequence
<220> FEATURE:
<223> OTHER INFORMATION: Synthetic sequence

<400> SEQUENCE: 217

ggaagaaatc gatgccgttt ctgctgcgac tcaatttaac ggtgttaaag tcctgtctc      59
```

<210> SEQ ID NO 218
<211> LENGTH: 59
<212> TYPE: DNA
<213> ORGANISM: Artificial Sequence
<220> FEATURE:
<223> OTHER INFORMATION: Synthetic sequence

<400> SEQUENCE: 218
gagacaggac tttaacaccg ttaaattgag tcgcagcaga aacggcatcg atttcttcc 59

<210> SEQ ID NO 219
<211> LENGTH: 846
<212> TYPE: DNA
<213> ORGANISM: Artificial Sequence
<220> FEATURE:
<223> OTHER INFORMATION: Synthetic sequence

<400> SEQUENCE: 219
taatacgact cactataggg gaattgtgag cggataacaa ttcccctcta gaataatttt 60
gtttaacttt aagaaggaga tatacatatg agcgggttac ggatcaacag cgcgaaagac 120
gatgcggcag gccaggcgat tgctaaccgc ttcacttcta atatcaaagg tctgactcag 180
gcttcccgta acgctaacga cggcatttct attgcgcaga ccactgaagg tgcgctgaat 240
gaaatcaaca acaacctgca gcgtgtgcgt gagttgtctg ttcaggccac taacgggact 300
aactctgatt ccgatctgaa atctatccag gatgaaattc agcaacgtct ggaagaaatc 360
gatgccgttt ctgctgcgac tcaatttaac ggtgttaaag tcctgtctca ggacaaccag 420
atgaaaatcc aggttggtgc taacgatggt gaaaccatta ccatcgatct gcaaaaaatt 480
gatgtgaaaa gccttggcct tgatgggttc aatgttaatt ccccgggaag taccgctaac 540
ccactggctt caattgattc tgcattgtca aaagtggacg cagttcgttc ttctctgggg 600
gcaattcaaa accgctttga ttcagccatt accaaccttg gcaatacggt aaccaatctg 660
aactccgcgc gtagccgtat cgaagatgct gactatgcaa cggaagtttc taatatgtct 720
aaagcgcaga ttctgcagca ggctggtact tccgttctgg cgcaggctaa ccaggttccg 780
caaaacgtcc tctctttact ggttccgcgg ggttctcatc atcatcatca tcatggttaa 840
gtcgac 846

<210> SEQ ID NO 220
<211> LENGTH: 250
<212> TYPE: PRT
<213> ORGANISM: Artificial Sequence
<220> FEATURE:
<223> OTHER INFORMATION: Synthetic sequence

<400> SEQUENCE: 220

Met Ser Gly Leu Arg Ile Asn Ser Ala Lys Asp Asp Ala Ala Gly Gln
1 5 10 15

Ala Ile Ala Asn Arg Phe Thr Ser Asn Ile Lys Gly Leu Thr Gln Ala
20 25 30

Ser Arg Asn Ala Asn Asp Gly Ile Ser Ile Ala Gln Thr Thr Glu Gly
35 40 45

Ala Leu Asn Glu Ile Asn Asn Asn Leu Gln Arg Val Arg Glu Leu Ser
50 55 60

Val Gln Ala Thr Asn Gly Thr Asn Ser Asp Ser Asp Leu Lys Ser Ile
65 70 75 80

Gln Asp Glu Ile Gln Gln Arg Leu Glu Glu Ile Asp Ala Val Ser Ala
85 90 95

```
Ala Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250
```

<210> SEQ ID NO 221
<211> LENGTH: 53
<212> TYPE: DNA
<213> ORGANISM: Artificial Sequence
<220> FEATURE:
<223> OTHER INFORMATION: Synthetic sequence

<400> SEQUENCE: 221

```
cagcaacgtc tggaagaaat cgatgccgtt tctaatcaga ctcaatttaa cgg           53
```

<210> SEQ ID NO 222
<211> LENGTH: 53
<212> TYPE: DNA
<213> ORGANISM: Artificial Sequence
<220> FEATURE:
<223> OTHER INFORMATION: Synthetic sequence

<400> SEQUENCE: 222

```
ccgttaaatt gagtctgatt agaaacggca tcgatttctt ccagacgttg ctg           53
```

<210> SEQ ID NO 223
<211> LENGTH: 753
<212> TYPE: DNA
<213> ORGANISM: Artificial Sequence
<220> FEATURE:
<223> OTHER INFORMATION: Synthetic sequence

<400> SEQUENCE: 223

```
atgagcgggt tacggatcaa cagcgcgaaa gacgatgcgg caggccaggc gattgctaac     60

cgcttcactt ctaatatcaa aggtctgact caggcttccc gtaacgctaa cgacggcatt    120

tctattgcgc agaccactga aggtgcgctg aatgaaatca acaacaacct gcagcgtgtg    180

cgtgagttgt ctgttcaggc cactaacggg actaactctg attccgatct gaaatctatc    240

caggatgaaa ttcagcaacg tctggaagaa atcgatgccg tttctaatca gactcaattt    300

aacggtgtta aagtcctgtc tcaggacaac cagatgaaaa tccaggttgg tgctaacgat    360

ggtgaaacca ttaccatcga tctgcaaaaa attgatgtga aaagccttgg ccttgatggg    420
```

```
ttcaatgtta attccccggg aagtaccgct aacccactgg cttcaattga ttctgcattg    480

tcaaaagtgg acgcagttcg ttcttctctg gggcaattc aaaaccgctt tgattcagcc     540

attaccaacc ttggcaatac ggtaaccaat ctgaactccg cgcgtagccg tatcgaagat    600

gctgactatg caacggaagt ttctaatatg tctaaagcgc agattctgca gcaggctggt    660

acttccgttc tggcgcaggc taaccaggtt ccgcaaaacg tcctctcttt actggttccg    720

cggggttctc atcatcatca tcatcatggt taa                                 753
```

<210> SEQ ID NO 224
<211> LENGTH: 846
<212> TYPE: DNA
<213> ORGANISM: Artificial Sequence
<220> FEATURE:
<223> OTHER INFORMATION: Synthetic sequence

<400> SEQUENCE: 224

```
taatacgact cactataggg gaattgtgag cggataacaa ttcccctcta gaataatttt     60

gtttaacttt aagaaggaga tatacatatg agcgggttac ggatcaacag cgcgaaagac    120

gatgcggcag gccaggcgat tgctaaccgc ttcacttcta atatcaaagg tctgactcag    180

gcttcccgta acgctaacga cggcatttct attgcgcaga ccactgaagg tgcgctgaat    240

gaaatcaaca acaacctgca gcgtgtgcgt gagttgtctg ttcaggccac taacgggact    300

aactctgatt ccgatctgaa atctatccag gatgaaattc agcaacgtct ggaagaaatc    360

gatgccgttt ctaatcagac tcaatttaac ggtgttaaag tcctgtctca ggacaaccag    420

atgaaaatcc aggttggtgc taacgatggt gaaaccatta ccatcgatct gcaaaaaatt    480

gatgtgaaaa gccttggcct tgatgggttc aatgttaatt ccccgggaag taccgctaac    540

ccactggctt caattgattc tgcattgtca aaagtggacg cagttcgttc ttctctgggg    600

gcaattcaaa accgctttga ttcagccatt accaaccttg gcaatacggt aaccaatctg    660

aactccgcgc gtagccgtat cgaagatgct gactatgcaa cggaagtttc taatatgtct    720

aaagcgcaga ttctgcagca ggctggtact tccgttctgg cgcaggctaa ccaggttccg    780

caaaacgtcc tctctttact ggttccgcgg ggttctcatc atcatcatca tcatggttaa    840

gtcgac                                                               846
```

<210> SEQ ID NO 225
<211> LENGTH: 250
<212> TYPE: PRT
<213> ORGANISM: Artificial Sequence
<220> FEATURE:
<223> OTHER INFORMATION: Synthetic sequence

<400> SEQUENCE: 225

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Ala Val Ser Asn
                85                  90                  95
```

```
Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250


<210> SEQ ID NO 226
<211> LENGTH: 53
<212> TYPE: DNA
<213> ORGANISM: Artificial Sequence
<220> FEATURE:
<223> OTHER INFORMATION: Synthetic sequence

<400> SEQUENCE: 226

cgtttctaat cagactcaat ttgccgctgt taaagtcctg tctcaggaca acc           53


<210> SEQ ID NO 227
<211> LENGTH: 53
<212> TYPE: DNA
<213> ORGANISM: Artificial Sequence
<220> FEATURE:
<223> OTHER INFORMATION: Synthetic sequence

<400> SEQUENCE: 227

ggttgtcctg agacaggact ttaacagcgg caaattgagt ctgattagaa acg           53


<210> SEQ ID NO 228
<211> LENGTH: 846
<212> TYPE: DNA
<213> ORGANISM: Artificial Sequence
<220> FEATURE:
<223> OTHER INFORMATION: Synthetic sequence

<400> SEQUENCE: 228

taatacgact cactataggg gaattgtgag cggataacaa ttcccctcta gaataatttt     60

gtttaacttt aagaaggaga tatacatatg agcgggttac ggatcaacag cgcgaaagac    120

gatgcggcag gccaggcgat tgctaaccgc ttcacttcta atatcaaagg tctgactcag    180

gcttcccgta acgctaacga cggcatttct attgcgcaga ccactgaagg tgcgctgaat    240

gaaatcaaca acaacctgca gcgtgtgcgt gagttgtctg ttcaggccac taacgggact    300

aactctgatt ccgatctgaa atctatccag gatgaaattc agcaacgtct ggaagaaatc    360

gatcgcgttt ctaatcagac tcaatttgcc gctgttaaag tcctgtctca ggacaaccag    420
```

```
atgaaaatcc aggttggtgc taacgatggt gaaaccatta ccatcgatct gcaaaaaatt    480

gatgtgaaaa gccttggcct tgatgggttc aatgttaatt ccccgggaag taccgctaac    540

ccactggctt caattgattc tgcattgtca aaagtggacg cagttcgttc ttctctgggg    600

gcaattcaaa accgctttga ttcagccatt accaaccttg gcaatacggt aaccaatctg    660

aactccgcgc gtagccgtat cgaagatgct gactatgcaa cggaagtttc taatatgtct    720

aaagcgcaga ttctgcagca ggctggtact tccgttctgg cgcaggctaa ccaggttccg    780

caaaacgtcc tctctttact ggttccgcgg ggttctcatc atcatcatca tcatggttaa    840

gtcgac                                                               846
```

<210> SEQ ID NO 229
<211> LENGTH: 250
<212> TYPE: PRT
<213> ORGANISM: Artificial Sequence
<220> FEATURE:
<223> OTHER INFORMATION: Synthetic sequence

<400> SEQUENCE: 229

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Ala Ala Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250
```

<210> SEQ ID NO 230
<211> LENGTH: 52
<212> TYPE: DNA
<213> ORGANISM: Artificial Sequence
<220> FEATURE:
<223> OTHER INFORMATION: Synthetic sequence

<400> SEQUENCE: 230
gttaaagtcc tgtctcagga caacgcgatg gcaatccagg ttggtgctaa cg 52

<210> SEQ ID NO 231
<211> LENGTH: 52
<212> TYPE: DNA
<213> ORGANISM: Artificial Sequence
<220> FEATURE:
<223> OTHER INFORMATION: Synthetic sequence

<400> SEQUENCE: 231
cgttagcacc aacctggatt gccatcgcgt tgtcctgaga caggacttta ac 52

<210> SEQ ID NO 232
<211> LENGTH: 846
<212> TYPE: DNA
<213> ORGANISM: Artificial Sequence
<220> FEATURE:
<223> OTHER INFORMATION: Synthetic sequence

<400> SEQUENCE: 232
taatacgact cactataggg gaattgtgag cggataacaa ttcccctcta gaataatttt 60
gtttaacttt aagaaggaga tatacatatg agcgggttac ggatcaacag cgcgaaagac 120
gatgcggcag gccaggcgat tgctaaccgc ttcacttcta atatcaaagg tctgactcag 180
gcttcccgta acgctaacga cggcatttct attgcgcaga ccactgaagg tgcgctgaat 240
gaaatcaaca acaacctgca gcgtgtgcgt gagttgtctg ttcaggccac taacgggact 300
aactctgatt ccgatctgaa atctatccag gatgaaattc agcaacgtct ggaagaaatc 360
gatcgcgttt ctaatcagac tcaatttaac ggtgttaaag tcctgtctca ggacaacgcg 420
atggcaatcc aggttggtgc taacgatggt gaaaccatta ccatcgatct gcaaaaaatt 480
gatgtgaaaa gccttggcct tgatgggttc aatgttaatt ccccgggaag taccgctaac 540
ccactggctt caattgattc tgcattgtca aaagtggacg cagttcgttc ttctctgggg 600
gcaattcaaa accgctttga ttcagccatt accaaccttg gcaatacggt aaccaatctg 660
aactccgcgc gtagccgtat cgaagatgct gactatgcaa cggaagtttc taatatgtct 720
aaagcgcaga ttctgcagca ggctggtact tccgttctgg cgcaggctaa ccaggttccg 780
caaaacgtcc tctctttact ggttccgcgg ggttctcatc atcatcatca tcatggttaa 840
gtcgac 846

<210> SEQ ID NO 233
<211> LENGTH: 250
<212> TYPE: PRT
<213> ORGANISM: Artificial Sequence
<220> FEATURE:
<223> OTHER INFORMATION: Synthetic sequence

<400> SEQUENCE: 233

Met Ser Gly Leu Arg Ile Asn Ser Ala Lys Asp Asp Ala Ala Gly Gln
1 5 10 15

Ala Ile Ala Asn Arg Phe Thr Ser Asn Ile Lys Gly Leu Thr Gln Ala
20 25 30

Ser Arg Asn Ala Asn Asp Gly Ile Ser Ile Ala Gln Thr Thr Glu Gly
35 40 45

Ala Leu Asn Glu Ile Asn Asn Asn Leu Gln Arg Val Arg Glu Leu Ser

```
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Ala Met
            100                 105                 110

Ala Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250
```

<210> SEQ ID NO 234
<211> LENGTH: 53
<212> TYPE: DNA
<213> ORGANISM: Artificial Sequence
<220> FEATURE:
<223> OTHER INFORMATION: Synthetic sequence

<400> SEQUENCE: 234

```
gatgaaaatc caggttggtg ctagcgctgc tgaaaccatt accatcgatc tgc           53
```

<210> SEQ ID NO 235
<211> LENGTH: 53
<212> TYPE: DNA
<213> ORGANISM: Artificial Sequence
<220> FEATURE:
<223> OTHER INFORMATION: Synthetic sequence

<400> SEQUENCE: 235

```
gcagatcgat ggtaatggtt tcagcagcgc tagcaccaac ctggattttc atc           53
```

<210> SEQ ID NO 236
<211> LENGTH: 846
<212> TYPE: DNA
<213> ORGANISM: Artificial Sequence
<220> FEATURE:
<223> OTHER INFORMATION: Synthetic sequence

<400> SEQUENCE: 236

```
taatacgact cactataggg gaattgtgag cggataacaa ttcccctcta gaataatttt     60

gtttaacttt aagaaggaga tatacatatg agcgggttac ggatcaacag cgcgaaagac    120

gatgcggcag gccaggcgat tgctaaccgc ttcacttcta atatcaaagg tctgactcag    180

gcttcccgta acgctaacga cggcatttct attgcgcaga ccactgaagg tgcgctgaat    240
```

```
gaaatcaaca acaacctgca gcgtgtgcgt gagttgtctg ttcaggccac taacgggact    300

aactctgatt ccgatctgaa atctatccag gatgaaattc agcaacgtct ggaagaaatc    360

gatcgcgttt ctaatcagac tcaatttaac ggtgttaaag tcctgtctca ggacaaccag    420

atgaaaatcc aggttggtgc tagcgctgct gaaaccatta ccatcgatct gcaaaaaatt    480

gatgtgaaaa gccttggcct tgatgggttc aatgttaatt ccccgggaag taccgctaac    540

ccactggctt caattgattc tgcattgtca aaagtggacg cagttcgttc ttctctgggg    600

gcaattcaaa accgctttga ttcagccatt accaaccttg gcaatacggt aaccaatctg    660

aactccgcgc gtagccgtat cgaagatgct gactatgcaa cggaagtttc taatatgtct    720

aaagcgcaga ttctgcagca ggctggtact tccgttctgg cgcaggctaa ccaggttccg    780

caaaacgtcc tctctttact ggttccgcgg ggttctcatc atcatcatca tcatggttaa    840

gtcgac                                                               846
```

<210> SEQ ID NO 237
<211> LENGTH: 250
<212> TYPE: PRT
<213> ORGANISM: Artificial Sequence
<220> FEATURE:
<223> OTHER INFORMATION: Synthetic sequence

<400> SEQUENCE: 237

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Ser Ala Ala Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
```

245 250

<210> SEQ ID NO 238
<211> LENGTH: 56
<212> TYPE: DNA
<213> ORGANISM: Artificial Sequence
<220> FEATURE:
<223> OTHER INFORMATION: Synthetic sequence

<400> SEQUENCE: 238
gccgtatcga agatgctgac gctggagcgg aagttgctaa tatgtctaaa gcgcag 56

<210> SEQ ID NO 239
<211> LENGTH: 56
<212> TYPE: DNA
<213> ORGANISM: Artificial Sequence
<220> FEATURE:
<223> OTHER INFORMATION: Synthetic sequence

<400> SEQUENCE: 239
ctgcgcttta gacatattag caacttccgc tccagcgtca gcatcttcga tacggc 56

<210> SEQ ID NO 240
<211> LENGTH: 846
<212> TYPE: DNA
<213> ORGANISM: Artificial Sequence
<220> FEATURE:
<223> OTHER INFORMATION: Synthetic sequence

<400> SEQUENCE: 240
taatacgact cactataggg gaattgtgag cggataacaa ttcccctcta gaataatttt 60
gtttaacttt aagaaggaga tatacatatg agcgggttac ggatcaacag cgcgaaagac 120
gatgcggcag gccaggcgat tgctaaccgc ttcacttcta atatcaaagg tctgactcag 180 gcttccccgta acgctaacga cggcatttct attgcgcaga ccactgaagg tgcgctgaat 240
gaaatcaaca acaacctgca gcgtgtgcgt gagttgtctg ttcaggccac taacgggact 300
aactctgatt ccgatctgaa atctatccag gatgaaattc agcaacgtct ggaagaaatc 360
gatcgcgttt ctaatcagac tcaatttaac ggtgttaaag tcctgtctca ggacaaccag 420
atgaaaatcc aggttggtgc taacgatggt gaaaccatta ccatcgatct gcaaaaaatt 480
gatgtgaaaa gccttggcct tgatgggttc aatgttaatt ccccgggaag taccgctaac 540
ccactggctt caattgattc tgcattgtca aaagtggacg cagttcgttc ttctctgggg 600
gcaattcaaa accgctttga ttcagccatt accaaccttg gcaatacggt aaccaatctg 660
aactccgcgc gtagccgtat cgaagatgct gacgctggag cggaagttgc taatatgtct 720
aaagcgcaga ttctgcagca ggctggtact tccgttctgg cgcaggctaa ccaggttccg 780
caaaacgtcc tctctttact ggttccgcgg ggttctcatc atcatcatca tcatggttaa 840
gtcgac 846

<210> SEQ ID NO 241
<211> LENGTH: 250
<212> TYPE: PRT
<213> ORGANISM: Artificial Sequence
<220> FEATURE:
<223> OTHER INFORMATION: Synthetic sequence

<400> SEQUENCE: 241

Met Ser Gly Leu Arg Ile Asn Ser Ala Lys Asp Asp Ala Ala Gly Gln
1 5 10 15

```
Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Ala Gly Ala Glu Val Ala
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250


<210> SEQ ID NO 242
<211> LENGTH: 3
<212> TYPE: PRT
<213> ORGANISM: Artificial Sequence
<220> FEATURE:
<223> OTHER INFORMATION: Synthetic sequence

<400> SEQUENCE: 242

Ser Pro Gly
1


<210> SEQ ID NO 243
<211> LENGTH: 293
<212> TYPE: PRT
<213> ORGANISM: Artificial Sequence
<220> FEATURE:
<223> OTHER INFORMATION: Synthetic sequence

<400> SEQUENCE: 243

Met Gly His His His His His His Ser Gly Met Glu Glu Phe Asn Met
1               5                   10                  15

Arg Ile Asn Thr Asn Val Ala Ala Met Asn Thr Tyr Ser Arg Leu Thr
            20                  25                  30

Ala Ala Asn Thr Ala Lys Ser Asn Ser Leu Ala Lys Leu Ser Ser Gly
        35                  40                  45

Leu Arg Ile Asn Lys Ala Gly Asp Asp Ala Ala Gly Leu Ala Ile Ser
    50                  55                  60
```

Glu Lys Met Lys Ser Gln Ile Gly Gly Leu Thr Gln Ala Lys Arg Asn
65 70 75 80

Ala Gln Asp Gly Ile Ser Leu Val Gln Thr Ala Glu Gly Ala Leu Asn
85 90 95

Glu Thr His Ser Ile Leu Glu Arg Met Arg Asp Leu Ala Val Gln Gly
100 105 110

Ser Asn Gly Thr Leu Thr Ser Ser Asp Arg Gly Ser Ile Asn Lys Glu
115 120 125

Leu Lys Ala Leu His Gln Glu Leu Thr Arg Ile Ser Asn Thr Thr Glu
130 135 140

Phe Asn Thr Gln Lys Leu Phe Ser Gln Thr Lys Gln Lys Ser Val Thr
145 150 155 160

Phe Thr Phe Gln Ile Gly Ala Asn Ala Gly Gln Thr Leu Ser Val Ala
165 170 175

Ile Thr Ala Met Ser Gly Glu Ala Leu Leu Val Ser Thr Asp Ala Lys
180 185 190

Phe Ser Leu Asn Ala Ala Gly Thr Asn Ala Gly Ala Met Ile Lys Ser
195 200 205

Ile Asp Ala Ala Ile Ala Lys Val Ser Asp Gln Arg Ala Asp Leu Gly
210 215 220

Ala Val Gln Asn Arg Leu Glu His Thr Ile Asn Asn Leu Thr Ala Thr
225 230 235 240

Asn Glu Asn Leu Ser Asp Ala Asn Ser Arg Ile Arg Asp Val Asp Met
245 250 255

Ala Glu Glu Met Met Thr Phe Thr Lys Ser Asn Ile Leu Ser Gln Ala
260 265 270

Ala Thr Ser Met Leu Ala Gln Ala Asn Ala Met Pro Asn Ser Val Leu
275 280 285

Asn Leu Leu Gln Gly
290

<210> SEQ ID NO 244
<211> LENGTH: 280
<212> TYPE: PRT
<213> ORGANISM: Artificial Sequence
<220> FEATURE:
<223> OTHER INFORMATION: Synthetic sequence

<400> SEQUENCE: 244

Met Gly His His His His His His Ser Gly Met Arg Ile Asn His Asn
1 5 10 15

Ile Ser Ala Leu Asn Ala Trp Arg Asn Ile Asp Gln Thr Gln Tyr Ser
20 25 30

Met Ser Lys Thr Leu Glu Arg Leu Ser Ser Gly Leu Arg Ile Asn Arg
35 40 45

Ala Gly Asp Asp Ala Ala Gly Leu Ala Ile Ser Glu Lys Met Arg Gly
50 55 60

Gln Ile Lys Gly Leu Asn Met Ala Ile Lys Asn Ala Gln Asp Ala Ile
65 70 75 80

Ser Leu Ile Gln Thr Ala Glu Gly Ala Leu Thr Glu Val His Ser Ile
85 90 95

Leu Gln Arg Met Arg Glu Leu Ala Val Gln Ala Ala Ser Asp Thr Asn
100 105 110

Thr Asn Val Asp Arg Glu Gln Ile Gln Lys Glu Ile Asp Gln Leu Arg
115 120 125

```
Glu Glu Ile Asp Arg Ile Ala Arg Thr Thr Glu Phe Asn Thr Lys Lys
    130                 135                 140

Leu Leu Asp Gly Lys Leu Glu Gly Phe Arg Ser Gln Val Asp Ala Lys
145                 150                 155                 160

Val Val Thr Gly Gly Asn Ile Asn Val Gln Leu Gly Thr Val Ser Ser
                165                 170                 175

Lys Ala Val Glu Gly Thr Tyr Val Ile Glu Val Gly Ala Ala Glu Arg
            180                 185                 190

Ala Ile Met Val Val Asp Ala Ala Ile His Arg Val Ser Thr Ala Arg
        195                 200                 205

Ala Ala Leu Gly Ala Ile Gln Asn Arg Leu Glu His Thr Ile Ser Asn
    210                 215                 220

Leu Gly Val Ala Ala Glu Asn Leu Thr Ala Ala Glu Ser Arg Ile Arg
225                 230                 235                 240

Asp Ala Asp Met Ala Lys Glu Met Met Glu Phe Thr Lys Gln Gln Ile
                245                 250                 255

Leu Leu Gln Ser Ser Met Ala Met Leu Ala Gln Ser Asn Thr Leu Pro
            260                 265                 270

Gln Asn Val Leu Gln Leu Met Arg
        275                 280


<210> SEQ ID NO 245
<211> LENGTH: 168
<212> TYPE: PRT
<213> ORGANISM: Artificial Sequence
<220> FEATURE:
<223> OTHER INFORMATION: Synthetic sequence

<400> SEQUENCE: 245

Met Gly His His His His His His Ser Gly Leu Asn Met Ala Ile Lys
1               5                   10                  15

Asn Ala Gln Asp Ala Ile Ser Leu Ile Gln Thr Ala Glu Gly Ala Leu
            20                  25                  30

Thr Glu Val His Ser Ile Leu Gln Arg Met Arg Glu Leu Ala Val Gln
        35                  40                  45

Ala Ala Ser Asp Thr Asn Thr Asn Val Asp Arg Glu Gln Ile Gln Lys
    50                  55                  60

Glu Ile Asp Gln Leu Arg Glu Glu Ile Asp Arg Ile Ala Arg Thr Thr
65                  70                  75                  80

Glu Phe Asn Thr Lys Lys Leu Leu Asp Gly Lys Leu Glu Gly Phe Arg
                85                  90                  95

Ser Gln Val Asp Ala Lys Val Val Thr Gly Gly Asn Ile Asn Val Gln
            100                 105                 110

Leu Gly Thr Val Ser Ser Lys Ala Val Glu Gly Thr Tyr Val Ile Glu
        115                 120                 125

Val Gly Ala Ala Glu Arg Ala Ile Met Val Val Asp Ala Ala Ile His
    130                 135                 140

Arg Val Ser Thr Ala Arg Ala Ala Leu Gly Ala Ile Gln Asn Arg Leu
145                 150                 155                 160

Glu His Thr Ile Ser Asn Leu Gly
                165


<210> SEQ ID NO 246
<211> LENGTH: 285
<212> TYPE: PRT
<213> ORGANISM: Artificial Sequence
```

<220> FEATURE:
<223> OTHER INFORMATION: Synthetic sequence

<400> SEQUENCE: 246

```
Met Gly His His His His His His Ser Gly Met Ser Leu Arg Ile Asn
1               5                   10                  15

Asn Asn Ile Glu Ala Leu Asn Ala Trp Arg Ala Leu Asn Ser Thr Ser
            20                  25                  30

Asn Ala Leu Gln Lys Ser Met Glu Lys Leu Ser Ser Gly Leu Arg Ile
        35                  40                  45

Asn Arg Ala Gly Asp Asp Ala Ala Gly Leu Ala Ile Ser Glu Lys Leu
    50                  55                  60

Arg Ala Gln Ile Arg Gly Leu Asn Gln Ala Ile Arg Asn Ala Gln Asp
65                  70                  75                  80

Gly Ile Ser Leu Ile Gln Thr Ala Glu Gly Gly Leu Ser Glu Ile Gln
                85                  90                  95

Asn Ile Leu Gln Arg Met Arg Glu Leu Gly Val Gln Ala Ala Asn Gly
            100                 105                 110

Thr Leu Asn Asn Gln Asp Ile Ser Ala Ile Thr Thr Glu Leu Asn Gln
        115                 120                 125

Leu Phe Asn Glu Ile Asp Arg Ile Ala Gly Ala Thr Glu Phe Asn Thr
    130                 135                 140

Lys Asn Leu Leu Ala Val Ser Thr Gly Leu Val Val Thr Leu Gln Val
145                 150                 155                 160

Gly Ala Asn Ala Gly Gln Val Ile Ala Phe Thr Ile Asp Asn Ala Gly
                165                 170                 175

Thr Ala Ser Leu Gly Leu Ser Ser Ala Asp Leu Ala Ile Asn Asp Asn
            180                 185                 190

Ala Ser Ala Ser Ala Phe Ile Ser Lys Val Asp Ser Ala Leu Gln Lys
        195                 200                 205

Val Ser Thr Tyr Arg Ala Asn Leu Gly Ser Ile Gln Asn Arg Leu Glu
    210                 215                 220

His Thr Ile Ala Asn Leu Gly Ile Ala Ser Glu Asn Leu Ser Ala Ser
225                 230                 235                 240

Glu Ser Arg Ile Arg Asp Val Asp Met Ala Ala Glu Met Met Asn Phe
                245                 250                 255

Thr Lys Asn Gln Ile Leu Gln Gln Ala Gly Val Ala Ile Leu Ala Gln
            260                 265                 270

Ala Asn Gln Ala Pro Gln Ala Val Leu Gln Leu Leu Arg
        275                 280                 285
```

<210> SEQ ID NO 247
<211> LENGTH: 171
<212> TYPE: PRT
<213> ORGANISM: Artificial Sequence
<220> FEATURE:
<223> OTHER INFORMATION: Synthetic sequence

<400> SEQUENCE: 247

```
Met Gly His His His His His His Ser Gly Leu Asn Gln Ala Ile Arg
1               5                   10                  15

Asn Ala Gln Asp Gly Ile Ser Leu Ile Gln Thr Ala Glu Gly Gly Leu
            20                  25                  30

Ser Glu Ile Gln Asn Ile Leu Gln Arg Met Arg Glu Leu Gly Val Gln
        35                  40                  45

Ala Ala Asn Gly Thr Leu Asn Asn Gln Asp Ile Ser Ala Ile Thr Thr
```

```
    50                  55                  60

Glu Leu Asn Gln Leu Phe Asn Glu Ile Asp Arg Ile Ala Gly Ala Thr
65                  70                  75                  80

Glu Phe Asn Thr Lys Asn Leu Leu Ala Val Ser Thr Gly Leu Val Val
                85                  90                  95

Thr Leu Gln Val Gly Ala Asn Ala Gly Gln Val Ile Ala Phe Thr Ile
            100                 105                 110

Asp Asn Ala Gly Thr Ala Ser Leu Gly Leu Ser Ser Ala Asp Leu Ala
        115                 120                 125

Ile Asn Asp Asn Ala Ser Ala Ser Ala Phe Ile Ser Lys Val Asp Ser
    130                 135                 140

Ala Leu Gln Lys Val Ser Thr Tyr Arg Ala Asn Leu Gly Ser Ile Gln
145                 150                 155                 160

Asn Arg Leu Glu His Thr Ile Ala Asn Leu Gly
                165                 170


<210> SEQ ID NO 248
<211> LENGTH: 146
<212> TYPE: PRT
<213> ORGANISM: Artificial Sequence
<220> FEATURE:
<223> OTHER INFORMATION: Synthetic sequence

<400> SEQUENCE: 248

Met Gly His His His His His His Ser Gly Leu Asn Gln Ala Ile Arg
1               5                   10                  15

Asn Ala Gln Asp Gly Ile Ser Leu Ile Gln Thr Ala Glu Gly Gly Leu
            20                  25                  30

Ser Glu Ile Gln Asn Ile Leu Gln Arg Met Arg Glu Leu Gly Val Gln
        35                  40                  45

Ala Ala Asn Gly Thr Leu Asn Asn Gln Asp Ile Ser Ala Ile Thr Thr
    50                  55                  60

Glu Leu Asn Gln Leu Phe Asn Glu Ile Asp Arg Ile Ala Gly Ala Thr
65                  70                  75                  80

Glu Phe Asn Thr Lys Asn Leu Leu Ala Ala Gly Thr Ala Ser Leu Gly
                85                  90                  95

Leu Ser Ser Ala Asp Leu Ala Ile Asn Asp Asn Ala Ser Ala Ser Ala
            100                 105                 110

Phe Ile Ser Lys Val Asp Ser Ala Leu Gln Lys Val Ser Thr Tyr Arg
        115                 120                 125

Ala Asn Leu Gly Ser Ile Gln Asn Arg Leu Glu His Thr Ile Ala Asn
    130                 135                 140

Leu Gly
145


<210> SEQ ID NO 249
<211> LENGTH: 116
<212> TYPE: PRT
<213> ORGANISM: Artificial Sequence
<220> FEATURE:
<223> OTHER INFORMATION: Synthetic sequence

<400> SEQUENCE: 249

Met Gly His His His His His His Ser Ala Ser Ala Phe Ile Ser Lys
1               5                   10                  15

Val Asp Ser Ala Leu Gln Lys Val Ser Thr Tyr Arg Ala Asn Leu Gly
            20                  25                  30
```

```
Ser Ile Gln Asn Arg Leu Glu His Thr Ile Ala Asn Leu Gly Pro Asp
        35                  40                  45

Gly Leu Asn Gln Ala Ile Arg Asn Ala Gln Asp Gly Ile Ser Leu Ile
    50                  55                  60

Gln Thr Ala Glu Gly Gly Leu Ser Glu Ile Gln Asn Ile Leu Gln Arg
65                  70                  75                  80

Met Arg Glu Leu Gly Val Gln Ala Ala Asn Gly Thr Leu Asn Asn Gln
                85                  90                  95

Asp Ile Ser Ala Ile Thr Thr Glu Leu Asn Gln Leu Phe Asn Glu Ile
            100                 105                 110

Asp Arg Ile Ala
        115


<210> SEQ ID NO 250
<211> LENGTH: 103
<212> TYPE: PRT
<213> ORGANISM: Artificial Sequence
<220> FEATURE:
<223> OTHER INFORMATION: Synthetic sequence

<400> SEQUENCE: 250

Met Gly His His His His His His Ser Asn Asn Gln Asp Ile Ser Ala
1               5                   10                  15

Ile Thr Thr Glu Leu Asn Gln Leu Phe Asn Glu Ile Asp Arg Ile Ala
            20                  25                  30

Gly Ala Thr Gly Ser Gly Gly Leu Ser Glu Ile Gln Asn Ile Leu Gln
        35                  40                  45

Arg Met Arg Glu Leu Gly Val Gln Ala Ala Asn Gly Thr Leu Asn Gly
    50                  55                  60

Gly Ser Ala Ser Ala Phe Ile Ser Lys Val Asp Ser Ala Leu Gln Lys
65                  70                  75                  80

Val Ser Thr Tyr Arg Ala Asn Leu Gly Ser Ile Gln Asn Arg Leu Glu
                85                  90                  95

His Thr Ile Ala Asn Leu Gly
            100


<210> SEQ ID NO 251
<211> LENGTH: 170
<212> TYPE: PRT
<213> ORGANISM: Artificial Sequence
<220> FEATURE:
<223> OTHER INFORMATION: Synthetic sequence

<400> SEQUENCE: 251

Met Gly His His His His His His Ser Gly Leu Ala Gln Ala Ser Arg
1               5                   10                  15

Asn Ala Gln Asp Ala Ile Ser Ile Ala Gln Thr Ala Glu Gly Ala Leu
            20                  25                  30

Asp Glu Thr Gln Ser Ile Leu Gln Arg Val Arg Glu Leu Gly Val Gln
        35                  40                  45

Gly Ala Asn Gly Thr Leu Thr Ala Asp Asp Ile Asn Ala Leu Gln Ala
    50                  55                  60

Glu Val Asp Gln Leu Ile Ala Glu Ile Asp Arg Ile Ala Gly Ala Thr
65                  70                  75                  80

Glu Phe Asn Thr Gln Asn Leu Leu Asp Gly Ser Phe Thr Thr Lys Ala
                85                  90                  95

Phe Gln Val Gly Ala Asn Ser Gly Gln Asn Met Thr Leu Thr Ile Gly
            100                 105                 110
```

```
Lys Met Asp Thr Thr Thr Leu Gly Leu Ser Ser Ala Asp Leu Ala Ile
        115                 120                 125

Asn Asp Asn Ala Phe Ala Asn Gly Ala Ile Ser Thr Val Asp Ser Ala
    130                 135                 140

Leu Gln Lys Val Ser Ala Glu Arg Ala Lys Leu Gly Ala Ile Gln Asn
145                 150                 155                 160

Arg Leu Glu His Thr Ile Ala Asn Leu Gly
                165                 170
```

<210> SEQ ID NO 252
<211> LENGTH: 170
<212> TYPE: PRT
<213> ORGANISM: Artificial Sequence
<220> FEATURE:
<223> OTHER INFORMATION: Synthetic sequence

<400> SEQUENCE: 252

```
Met Gly His His His His His His Ser Gly Leu Ala Gln Ala Ser Arg
1               5                   10                  15

Gln Ala Gln Asp Ala Ile Ser Ile Ala Gln Thr Ala Glu Gly Ala Leu
            20                  25                  30

Asp Glu Thr Gln Ser Ile Leu Gln Arg Val Arg Glu Leu Gly Val Gln
        35                  40                  45

Gly Ala Asp Gly Thr Leu Thr Ala Asp Asp Ile Asp Ala Leu Gln Ala
    50                  55                  60

Glu Val Asp Gln Leu Ile Ala Glu Ile Asp Arg Ile Ala Gly Ala Thr
65                  70                  75                  80

Glu Phe Ala Thr Gln Lys Leu Leu Asp Gly Ser Phe Thr Thr Lys Ala
                85                  90                  95

Phe Gln Val Gly Ala Ala Ser Gly Gln Asp Val Thr Leu Thr Ile Gly
            100                 105                 110

Lys Val Asp Thr Thr Thr Leu Gly Leu Ser Ser Ala Asp Leu Ala Ile
        115                 120                 125

Asp Ser Ala Ala Phe Ala Asp Gly Ala Ile Ser Thr Val Asp Ser Ala
    130                 135                 140

Leu Gln Lys Val Ser Ala Glu Arg Ala Lys Leu Gly Ala Ile Gln Asn
145                 150                 155                 160

Arg Leu Glu His Thr Ile Ala Gln Leu Gly
                165                 170
```

<210> SEQ ID NO 253
<211> LENGTH: 174
<212> TYPE: PRT
<213> ORGANISM: Artificial Sequence
<220> FEATURE:
<223> OTHER INFORMATION: Synthetic peptide accession number Q53970

<400> SEQUENCE: 253

```
Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
```

65 70 75 80

Ala Leu Asn Glu Ile Asn Asn Asn Leu Gln Arg Val Arg Glu Leu Ser
85 90 95

Val Gln Ala Thr Asn Gly Thr Asn Ser Asp Ser Asp Leu Lys Ser Ile
100 105 110

Gln Asp Glu Ile Gln Gln Arg Leu Glu Glu Ile Asp Arg Val Ser Asn
115 120 125

Gln Thr Gln Phe Asn Gly Val Lys Val Leu Ser Gln Asp Asn Gln Met
130 135 140

Lys Ile Gln Val Gly Ala Asn Asp Gly Glu Thr Ile Thr Ile Asp Leu
145 150 155 160

Gln Lys Ile Asp Val Lys Ser Leu Gly Leu Asp Gly Phe Asn
165 170

<210> SEQ ID NO 254
<211> LENGTH: 189
<212> TYPE: PRT
<213> ORGANISM: Artificial Sequence
<220> FEATURE:
<223> OTHER INFORMATION: Synthetic peptide accession number P72151

<400> SEQUENCE: 254

Met Ala Leu Thr Val Asn Thr Asn Ile Ala Ser Leu Asn Thr Gln Arg
1 5 10 15

Asn Leu Asn Ala Ser Ser Asn Asp Leu Asn Thr Ser Leu Gln Arg Leu
20 25 30

Thr Thr Gly Tyr Arg Ile Asn Ser Ala Lys Asp Asp Ala Ala Gly Leu
35 40 45

Gln Ile Ser Asn Arg Leu Ser Asn Gln Ile Ser Gly Leu Asn Val Ala
50 55 60

Thr Arg Asn Ala Asn Asp Gly Ile Ser Leu Ala Gln Thr Ala Glu Gly
65 70 75 80

Ala Leu Gln Gln Ser Thr Asn Ile Leu Gln Arg Ile Arg Asp Leu Ala
85 90 95

Leu Gln Ser Ala Asn Gly Ser Asn Ser Asp Ala Asp Arg Ala Ala Leu
100 105 110

Gln Lys Glu Val Ala Ala Gln Gln Ala Glu Leu Thr Arg Ile Ser Asp
115 120 125

Thr Thr Thr Phe Gly Gly Arg Lys Leu Leu Asp Gly Ser Phe Gly Thr
130 135 140

Thr Ser Phe Gln Val Gly Ser Asn Ala Tyr Glu Thr Ile Asp Ile Ser
145 150 155 160

Leu Gln Asn Ala Ser Ala Ser Ala Ile Gly Ser Tyr Gln Val Gly Ser
165 170 175

Asn Gly Ala Gly Thr Val Ala Ser Val Ala Gly Thr Ala
180 185

<210> SEQ ID NO 255
<211> LENGTH: 179
<212> TYPE: PRT
<213> ORGANISM: Artificial Sequence
<220> FEATURE:
<223> OTHER INFORMATION: Synthetic peptide accession number Q5X5M6

<400> SEQUENCE: 255

Met Ala Gln Val Ile Asn Thr Asn Val Ala Ser Leu Thr Ala Gln Arg
1 5 10 15

```
Asn Leu Gly Val Ser Gly Asn Met Met Gln Thr Ser Ile Gln Arg Leu
            20                  25                  30

Ser Ser Gly Leu Arg Ile Asn Ser Ala Lys Asp Asp Ala Ala Gly Leu
        35                  40                  45

Ala Ile Ser Gln Arg Met Thr Ala Gln Ile Arg Gly Met Asn Gln Ala
    50                  55                  60

Val Arg Asn Ala Asn Asp Gly Ile Ser Leu Ala Gln Val Ala Glu Gly
65                  70                  75                  80

Ala Met Gln Glu Thr Thr Asn Ile Leu Gln Arg Met Arg Glu Leu Ser
                85                  90                  95

Val Gln Ala Ala Asn Ser Thr Asn Asn Ser Ser Asp Arg Ala Ser Ile
            100                 105                 110

Gln Ser Glu Ile Ser Gln Leu Lys Ser Glu Leu Glu Arg Ile Ala Gln
        115                 120                 125

Asn Thr Glu Phe Asn Gly Gln Arg Ile Leu Asp Gly Ser Phe Ser Gly
    130                 135                 140

Ala Ser Phe Gln Val Gly Ala Asn Ser Asn Gln Thr Ile Asn Phe Ser
145                 150                 155                 160

Ile Gly Ser Ile Lys Ala Ser Ser Ile Gly Gly Ile Ala Thr Ala Thr
                165                 170                 175

Gly Thr Glu


<210> SEQ ID NO 256
<211> LENGTH: 174
<212> TYPE: PRT
<213> ORGANISM: Artificial Sequence
<220> FEATURE:
<223> OTHER INFORMATION: Synthetic peptide accession number Q6VMV6

<400> SEQUENCE: 256

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Val Ala Gln Thr Thr Glu Gly
65                  70                  75                  80

Ala Leu Asn Glu Ile Asn Asn Asn Leu Gln Arg Val Arg Glu Leu Thr
                85                  90                  95

Val Gln Ala Thr Asn Gly Thr Asn Ser Asp Ser Asp Leu Ser Ser Ile
            100                 105                 110

Gln Ala Glu Ile Thr Gln Arg Leu Glu Glu Ile Asp Arg Val Ser Glu
        115                 120                 125

Gln Thr Gln Phe Asn Gly Val Lys Val Leu Ala Glu Asn Asn Glu Met
    130                 135                 140

Lys Ile Gln Val Gly Ala Asn Asp Gly Glu Thr Ile Thr Ile Asn Leu
145                 150                 155                 160

Ala Lys Ile Asp Ala Lys Thr Leu Gly Leu Asp Gly Phe Asn
                165                 170


<210> SEQ ID NO 257
<211> LENGTH: 173
<212> TYPE: PRT
```

```
<213> ORGANISM: Artificial Sequence
<220> FEATURE:
<223> OTHER INFORMATION: Synthetic peptide accession number P13713

<400> SEQUENCE: 257

Met Ala Gln Val Ile Asn Thr Asn Ser Leu Ser Leu Met Ala Gln Asn
1               5                   10                  15

Asn Leu Asn Lys Ser Gln Ser Ser Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ser Asn Arg Phe Thr Ala Asn Ile Lys Gly Leu Thr Gln Ala
    50                  55                  60

Ser Arg Asn Ala Asn Asp Gly Ile Ser Leu Ala Gln Thr Thr Glu Gly
65                  70                  75                  80

Ala Leu Asn Glu Val Asn Asp Asn Leu Gln Asn Ile Arg Arg Leu Thr
                85                  90                  95

Val Gln Ala Gln Asn Gly Ser Asn Ser Thr Ser Asp Leu Lys Ser Ile
            100                 105                 110

Gln Asp Glu Ile Thr Gln Arg Leu Ser Glu Ile Asn Arg Ile Ser Glu
        115                 120                 125

Gln Thr Asp Phe Asn Gly Val Lys Val Leu Ser Ser Asp Gln Lys Leu
    130                 135                 140

Thr Ile Gln Val Gly Ala Asn Asp Gly Glu Thr Thr Asp Ile Asp Leu
145                 150                 155                 160

Lys Lys Ile Asp Ala Lys Gln Leu Gly Met Asp Thr Phe
                165                 170


<210> SEQ ID NO 258
<211> LENGTH: 168
<212> TYPE: PRT
<213> ORGANISM: Artificial Sequence
<220> FEATURE:
<223> OTHER INFORMATION: Synthetic peptide accession number Q93RK8

<400> SEQUENCE: 258

Met Arg Ile Asn His Asn Ile Ala Ala Leu Asn Thr Ser Arg Gln Leu
1               5                   10                  15

Asn Ala Gly Ser Asn Ser Ala Ala Lys Asn Met Glu Lys Leu Ser Ser
            20                  25                  30

Gly Leu Arg Ile Asn Arg Ala Gly Asp Asp Ala Ala Gly Leu Ala Ile
        35                  40                  45

Ser Glu Lys Met Arg Ser Gln Ile Arg Gly Leu Asp Met Ala Ser Lys
    50                  55                  60

Asn Ala Gln Asp Gly Ile Ser Leu Ile Gln Thr Ser Glu Gly Ala Leu
65                  70                  75                  80

Asn Glu Thr His Ser Ile Leu Gln Arg Met Ser Glu Leu Ala Thr Gln
                85                  90                  95

Ala Ala Asn Asp Thr Asn Thr Asp Ser Asp Arg Ser Glu Leu Gln Lys
            100                 105                 110

Glu Met Asp Gln Leu Ala Ser Glu Val Thr Arg Ile Ser Thr Asp Thr
        115                 120                 125

Glu Phe Asn Thr Lys Lys Leu Leu Asp Gly Thr Ala Gln Asn Leu Thr
    130                 135                 140

Phe Gln Ile Gly Ala Asn Glu Gly Gln Thr Met Ser Leu Ser Ile Asn
145                 150                 155                 160
```

```
Lys Met Asp Ser Glu Ser Leu Lys
                165


<210> SEQ ID NO 259
<211> LENGTH: 192
<212> TYPE: PRT
<213> ORGANISM: Artificial Sequence
<220> FEATURE:
<223> OTHER INFORMATION: Synthetic peptide accession number Q02551

<400> SEQUENCE: 259

Met Lys Val Asn Thr Asn Ile Ile Ser Leu Lys Thr Gln Glu Tyr Leu
1               5                   10                  15

Arg Lys Asn Asn Glu Gly Met Thr Gln Ala Gln Arg Arg Leu Ala Ser
            20                  25                  30

Gly Lys Arg Ile Asn Ser Ser Leu Asp Asp Ala Ala Gly Leu Ala Val
        35                  40                  45

Val Thr Arg Met Asn Val Lys Ser Thr Gly Leu Asp Ala Ala Ser Lys
    50                  55                  60

Asn Ser Ser Met Gly Ile Asp Leu Leu Gln Thr Ala Asp Ser Ala Leu
65                  70                  75                  80

Ser Ser Met Ser Ser Ile Leu Gln Arg Met Arg Gln Leu Ala Val Gln
                85                  90                  95

Ser Ser Asn Gly Ser Phe Ser Asp Glu Asp Arg Lys Gln Tyr Thr Ala
            100                 105                 110

Glu Phe Gly Ser Leu Ile Lys Glu Leu Asp His Val Ala Asp Thr Thr
        115                 120                 125

Asn Tyr Asn Asn Ile Lys Leu Leu Asp Gln Thr Ala Thr Gly Ala Ala
    130                 135                 140

Thr Gln Val Ser Ile Gln Ala Ser Asp Lys Ala Asn Asp Leu Ile Asn
145                 150                 155                 160

Ile Asp Leu Phe Asn Ala Lys Gly Leu Ser Ala Gly Thr Ile Thr Leu
                165                 170                 175

Gly Ser Gly Ser Thr Val Ala Gly Tyr Ser Ala Leu Ser Val Ala Asp
            180                 185                 190


<210> SEQ ID NO 260
<211> LENGTH: 174
<212> TYPE: PRT
<213> ORGANISM: Artificial Sequence
<220> FEATURE:
<223> OTHER INFORMATION: Synthetic peptide accession number Q09012

<400> SEQUENCE: 260

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Val Ala Gln Thr Thr Glu Gly
65                  70                  75                  80

Ala Leu Ser Glu Ile Asn Asn Asn Leu Gln Arg Ile Arg Glu Leu Ser
                85                  90                  95

Val Gln Ala Thr Asn Gly Thr Asn Ser Asp Ser Asp Leu Asn Ser Ile
            100                 105                 110
```

```
Gln Asp Glu Ile Thr Gln Arg Leu Ser Glu Ile Asp Arg Val Ser Asn
        115                 120                 125

Gln Thr Gln Phe Asn Gly Val Lys Val Leu Ala Ser Asp Gln Thr Met
    130                 135                 140

Lys Ile Gln Val Gly Ala Asn Asp Gly Glu Thr Ile Glu Ile Ala Leu
145                 150                 155                 160

Asp Lys Ile Asp Ala Lys Thr Leu Gly Leu Asp Asn Phe Ser
                165                 170


<210> SEQ ID NO 261
<211> LENGTH: 174
<212> TYPE: PRT
<213> ORGANISM: Artificial Sequence
<220> FEATURE:
<223> OTHER INFORMATION: Synthetic peptide accession number Q8GNT8

<400> SEQUENCE: 261

Met Ala Gln Val Ile Asn Thr Asn Ser Leu Ser Leu Met Ala Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ser Asn Arg Phe Thr Ala Asn Ile Asn Gly Leu Thr Gln Ala
    50                  55                  60

Ser Arg Asn Ala Asn Asp Gly Ile Ser Leu Ala Gln Thr Thr Glu Gly
65                  70                  75                  80

Ala Leu Asn Glu Val Asn Asp Asn Leu Gln Asn Ile Arg Arg Leu Thr
                85                  90                  95

Val Gln Ala Gln Asn Gly Ser Asn Ser Ser Ser Asp Leu Gln Ser Ile
            100                 105                 110

Gln Asp Glu Ile Thr Gln Arg Leu Ser Glu Ile Asp Arg Ile Ser Gln
        115                 120                 125

Gln Thr Asp Phe Asn Gly Val Lys Val Leu Ser Lys Asp Gln Lys Leu
    130                 135                 140

Thr Ile Gln Val Gly Ala Asn Asp Gly Glu Thr Ile Asp Ile Asp Leu
145                 150                 155                 160

Lys Asn Ile Asn Ala Gln Ser Leu Gly Leu Asp Lys Phe Asn
                165                 170


<210> SEQ ID NO 262
<211> LENGTH: 186
<212> TYPE: PRT
<213> ORGANISM: Artificial Sequence
<220> FEATURE:
<223> OTHER INFORMATION: Synthetic peptide accession number Q9FAE7

<400> SEQUENCE: 262

Met Ala Ser Thr Ile Asn Thr Asn Val Ser Ser Leu Thr Ala Gln Arg
1               5                   10                  15

Asn Leu Ser Leu Ser Gln Ser Ser Leu Asn Thr Ser Ile Gln Arg Leu
            20                  25                  30

Ser Ser Gly Leu Arg Ile Asn Ser Ala Lys Asp Asp Ala Ala Gly Leu
        35                  40                  45

Ala Ile Ser Glu Arg Phe Thr Ser Gln Ile Arg Gly Leu Asn Gln Ala
    50                  55                  60

Val Arg Asn Ala Asn Asp Gly Ile Ser Leu Ala Gln Thr Ala Glu Gly
```

```
65                  70                  75                  80

Ala Leu Lys Ser Thr Gly Asp Ile Leu Gln Arg Val Arg Glu Leu Ala
                85                  90                  95

Val Gln Ser Ala Asn Ala Thr Asn Ser Ser Gly Asp Arg Lys Ala Ile
            100                 105                 110

Gln Ala Glu Val Gly Gln Leu Leu Ser Glu Met Asp Arg Ile Ala Gly
        115                 120                 125

Asn Thr Glu Phe Asn Gly Gln Lys Leu Leu Asp Gly Ser Phe Gly Ser
    130                 135                 140

Ala Thr Phe Gln Val Gly Ala Asn Ala Asn Gln Thr Ile Thr Ala Thr
145                 150                 155                 160

Thr Gly Asn Phe Arg Thr Asn Asn Tyr Gly Ala Gln Leu Thr Ala Ser
                165                 170                 175

Ala Ser Gly Ala Ala Thr Ser Gly Ala Ser
            180                 185


<210> SEQ ID NO 263
<211> LENGTH: 173
<212> TYPE: PRT
<213> ORGANISM: Artificial Sequence
<220> FEATURE:
<223> OTHER INFORMATION: Synthetic peptide accession number Q8ZF76

<400> SEQUENCE: 263

Met Ala Val Ile Asn Thr Asn Ser Leu Ser Leu Leu Thr Gln Asn Asn
1               5                   10                  15

Leu Asn Lys Ser Gln Ser Ser Leu Gly Thr Ala Ile Glu Arg Leu Ser
            20                  25                  30

Ser Gly Leu Arg Ile Asn Ser Ala Lys Asp Asp Ala Ala Gly Gln Ala
        35                  40                  45

Ile Ala Asn Arg Phe Thr Ser Asn Ile Lys Gly Leu Thr Gln Ala Ala
    50                  55                  60

Arg Asn Ala Asn Asp Gly Ile Ser Ile Ala Gln Thr Thr Glu Gly Ser
65                  70                  75                  80

Leu Asn Glu Ile Asn Asn Asn Leu Gln Arg Val Arg Glu Leu Thr Val
                85                  90                  95

Gln Ala Gln Asn Gly Ser Asn Ser Ser Ser Asp Leu Asp Ser Ile Gln
            100                 105                 110

Asp Glu Ile Ser Leu Arg Leu Ala Glu Ile Asp Arg Val Ser Asp Gln
        115                 120                 125

Thr Gln Phe Asn Gly Lys Lys Val Leu Ala Glu Asn Thr Thr Met Ser
    130                 135                 140

Ile Gln Val Gly Ala Asn Asp Gly Glu Thr Ile Asp Ile Asn Leu Gln
145                 150                 155                 160

Lys Ile Asp Ser Lys Ser Leu Gly Leu Gly Ser Tyr Ser
                165                 170


<210> SEQ ID NO 264
<211> LENGTH: 174
<212> TYPE: PRT
<213> ORGANISM: Artificial Sequence
<220> FEATURE:
<223> OTHER INFORMATION: Synthetic peptide accession number Q7N5J4

<400> SEQUENCE: 264

Met Ala Gln Val Ile Asn Thr Asn Ser Leu Ser Leu Leu Thr Gln Asn
1               5                   10                  15
```

```
Asn Leu Asn Arg Ser Gln Gly Thr Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Arg Gly Leu Thr Gln Ala
    50                  55                  60

Ala Arg Asn Ala Asn Asp Gly Ile Ser Ile Ala Gln Thr Thr Glu Gly
65                  70                  75                  80

Ala Leu Asn Glu Ile Asn Thr Asn Leu Gln Arg Ile Arg Glu Leu Thr
                85                  90                  95

Val Gln Ser Gln Asn Gly Ser Asn Ser Glu Ser Asp Ile Lys Ser Ile
            100                 105                 110

Gln Glu Glu Val Thr Gln Arg Leu Lys Glu Ile Asp Arg Ile Ser Glu
        115                 120                 125

Gln Thr Gln Phe Asn Gly Val Arg Val Leu Arg Glu Asp Ser Lys Met
    130                 135                 140

Thr Ile Gln Val Gly Ala Asn Asp Asn Glu Val Ile Asp Ile Asp Leu
145                 150                 155                 160

Lys Lys Ile Asp Lys Glu Ala Leu Asn Leu Gly Lys Phe Thr
                165                 170
```

<210> SEQ ID NO 265
<211> LENGTH: 189
<212> TYPE: PRT
<213> ORGANISM: Artificial Sequence
<220> FEATURE:
<223> OTHER INFORMATION: Synthetic peptide accession number O33578

<400> SEQUENCE: 265

```
Met Thr Thr Ile Asn Thr Asn Ile Gly Ala Ile Ala Ala Gln Ala Asn
1               5                   10                  15

Met Thr Lys Val Asn Asp Gln Phe Asn Thr Ala Met Thr Arg Leu Ser
            20                  25                  30

Thr Gly Leu Arg Ile Asn Ala Ala Lys Asp Asp Ala Ala Gly Met Ala
        35                  40                  45

Ile Gly Glu Lys Met Thr Ala Gln Val Met Gly Leu Asn Gln Ala Ile
    50                  55                  60

Arg Asn Ala Gln Asp Gly Lys Asn Leu Val Asp Thr Thr Glu Gly Ala
65                  70                  75                  80

His Val Glu Val Ser Ser Met Leu Gln Arg Leu Arg Glu Leu Ala Val
                85                  90                  95

Gln Ser Ser Asn Asp Thr Asn Thr Ala Ala Asp Arg Gly Ser Leu Ala
            100                 105                 110

Ala Glu Gly Lys Gln Leu Ile Ala Glu Ile Asn Arg Val Ala Glu Ser
        115                 120                 125

Thr Thr Phe Asn Gly Met Lys Val Leu Asp Gly Ser Phe Thr Gly Lys
    130                 135                 140

Gln Leu Gln Ile Gly Ala Asp Ser Gly Gln Thr Met Ala Ile Asn Val
145                 150                 155                 160

Asp Ser Ala Ala Ala Thr Asp Ile Gly Ala His Lys Ile Ser Ser Ala
                165                 170                 175

Ser Thr Val Val Ala Asp Ala Ala Leu Thr Asp Thr Thr
            180                 185
```

<210> SEQ ID NO 266
<211> LENGTH: 175

```
<212> TYPE: PRT
<213> ORGANISM: Artificial Sequence
<220> FEATURE:
<223> OTHER INFORMATION: Synthetic peptide accession number Q56826

<400> SEQUENCE: 266

Met Ala Ser Val Ile Asn Thr Asn Asp Ser Ala Leu Leu Ala Gln Asn
1               5                   10                  15

Asn Leu Thr Lys Ser Lys Gly Ile Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Lys Gly Leu Thr Gln Ala
    50                  55                  60

Ala Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Ile Arg Glu Leu Thr
                85                  90                  95

Val Gln Ser Glu Asn Gly Ser Asn Ser Lys Ser Asp Leu Asp Ser Ile
            100                 105                 110

Gln Lys Glu Val Thr Gln Arg Leu Glu Glu Ile Asp Arg Ile Ser Thr
        115                 120                 125

Gln Thr Gln Phe Asn Gly Ile Lys Val Leu Asn Gly Asp Val Thr Glu
    130                 135                 140

Met Lys Ile Gln Val Gly Ala Asn Asp Asn Glu Thr Ile Gly Ile Lys
145                 150                 155                 160

Leu Gly Lys Ile Asn Ser Glu Lys Leu Asn Leu Lys Glu Phe Ser
                165                 170                 175


<210> SEQ ID NO 267
<211> LENGTH: 175
<212> TYPE: PRT
<213> ORGANISM: Artificial Sequence
<220> FEATURE:
<223> OTHER INFORMATION: Synthetic peptide accession number P42273

<400> SEQUENCE: 267

Met Ala Gln Val Ile Asn Thr Asn Tyr Leu Ser Leu Val Thr Gln Asn
1               5                   10                  15

Asn Leu Asn Arg Ser Gln Ser Ala Leu Gly Asn Ala Ile Glu Arg Leu
            20                  25                  30

Ser Ser Gly Met Arg Ile Asn Ser Ala Lys Asp Asp Ala Ala Gly Gln
        35                  40                  45

Ala Ile Ala Asn Arg Phe Thr Ser Asn Ile Asn Gly Leu Thr Gln Ala
    50                  55                  60

Ser Arg Asn Ala Asn Asp Gly Ile Ser Val Ser Gln Thr Thr Glu Gly
65                  70                  75                  80

Ala Leu Asn Glu Ile Asn Asn Asn Leu Gln Arg Ile Arg Glu Leu Thr
                85                  90                  95

Val Gln Ala Lys Asn Gly Thr Asn Ser Asn Ser Asp Ile Asn Ser Ile
            100                 105                 110

Gln Asn Glu Val Asn Gln Arg Leu Asp Glu Ile Asn Arg Val Ser Glu
        115                 120                 125

Gln Thr Gln Phe Asn Gly Val Lys Val Leu Ser Gly Glu Lys Ser Lys
    130                 135                 140

Met Thr Ile Gln Val Gly Thr Asn Asp Asn Glu Val Ile Glu Phe Asn
145                 150                 155                 160
```

```
Leu Asp Lys Ile Asp Asn Asp Thr Leu Gly Val Ala Ser Asp Lys
                165                 170                 175


<210> SEQ ID NO 268
<211> LENGTH: 200
<212> TYPE: PRT
<213> ORGANISM: Artificial Sequence
<220> FEATURE:
<223> OTHER INFORMATION: Synthetic peptide accession number O31059

<400> SEQUENCE: 268

Met Val Val Gln His Asn Met Gln Ala Ala Asn Ala Ser Arg Met Leu
1               5                   10                  15

Gly Ile Thr Thr Gly Asp Gln Ser Lys Ser Thr Glu Lys Leu Ser Ser
            20                  25                  30

Gly Phe Lys Ile Asn Arg Ala Ala Asp Asp Ala Ala Gly Leu Ser Ile
        35                  40                  45

Ser Glu Lys Met Arg Lys Gln Ile Arg Gly Leu Asp Gln Ala Ser Thr
    50                  55                  60

Asn Ala Ser Asp Gly Ile Ser Ala Val Gln Thr Ala Glu Gly Ala Leu
65                  70                  75                  80

Thr Glu Val His Ser Met Leu Gln Arg Met Asn Glu Leu Ala Val Gln
                85                  90                  95

Ala Ala Asn Gly Thr Asn Ser Glu Ser Asp Arg Ser Ser Ile Gln Asp
            100                 105                 110

Glu Ile Asn Gln Leu Thr Thr Glu Ile Asp Arg Val Ala Glu Thr Thr
        115                 120                 125

Lys Phe Asn Glu Thr Tyr Leu Leu Lys Gly Gly Asn Gly Asp Arg Thr
    130                 135                 140

Val Arg Val Tyr Ala His Asp Ala Gly Leu Val Gly Ser Leu Ser Gln
145                 150                 155                 160

Asn Thr Thr Lys Ala Thr Phe Gln Met Arg Lys Leu Glu Ile Gly Asp
                165                 170                 175

Ser Tyr Thr Ile Gly Gly Thr Thr Tyr Lys Ile Gly Ala Glu Thr Val
            180                 185                 190

Lys Glu Ala Met Thr Ala Leu Lys
        195                 200


<210> SEQ ID NO 269
<211> LENGTH: 177
<212> TYPE: PRT
<213> ORGANISM: Artificial Sequence
<220> FEATURE:
<223> OTHER INFORMATION: Synthetic peptide accession number Q7VZC2

<400> SEQUENCE: 269

Met Ala Ala Val Ile Asn Thr Asn Tyr Leu Ser Leu Val Ala Gln Asn
1               5                   10                  15

Asn Leu Asn Lys Ser Gln Ser Ala Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Lys Gly Leu Thr Gln Ala
    50                  55                  60

Ala Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Ile Arg Glu Leu Thr
```

```
                85                  90                  95

Val Gln Ala Ser Asn Gly Thr Asn Ser Ala Ser Asp Ile Asp Ser Ile
            100                 105                 110

Gln Gln Glu Val Asn Gln Arg Leu Glu Glu Ile Asn Arg Ile Ala Glu
        115                 120                 125

Gln Thr Asp Phe Asn Gly Ile Lys Val Leu Lys Ser Asn Ala Thr Asp
    130                 135                 140

Met Thr Leu Ser Ile Gln Val Gly Ala Lys Asp Asn Glu Thr Ile Asp
145                 150                 155                 160

Ile Lys Ile Asp Arg Asn Ser Asn Trp Asn Leu Tyr Asp Ala Val Gly
                165                 170                 175

Thr


<210> SEQ ID NO 270
<211> LENGTH: 167
<212> TYPE: PRT
<213> ORGANISM: Artificial Sequence
<220> FEATURE:
<223> OTHER INFORMATION: Synthetic peptide accession number Q9F4A4

<400> SEQUENCE: 270

Met Ile Ile Asn His Asn Met Asn Ala Leu Asn Ala His Arg Asn Met
1               5                   10                  15

Met Gly Asn Ile Ala Thr Ala Gly Lys Ser Met Glu Lys Leu Ser Ser
            20                  25                  30

Gly Leu Arg Ile Asn Arg Ala Gly Asp Asp Ala Ala Gly Leu Ala Ile
        35                  40                  45

Ser Glu Lys Met Arg Gly Gln Ile Arg Gly Leu Asp Gln Ala Ser Arg
    50                  55                  60

Asn Ala Gln Asp Gly Ile Ser Leu Ile Gln Thr Ala Glu Gly Ala Leu
65                  70                  75                  80

Ala Glu Thr His Ser Ile Leu Gln Arg Met Arg Glu Leu Ser Val Gln
                85                  90                  95

Ser Ala Asn Asp Thr Asn Val Ala Val Asp Arg Thr Ala Ile Gln Asp
            100                 105                 110

Glu Ile Asn Ser Leu Thr Glu Glu Ile Asn Arg Ile Ser Gly Asp Thr
        115                 120                 125

Glu Phe Asn Thr Gln Lys Leu Leu Asp Gly Gly Phe Lys Gly Glu Phe
    130                 135                 140

Gln Ile Gly Ala Asn Ser Asn Gln Thr Val Lys Leu Asp Ile Gly Asn
145                 150                 155                 160

Met Ser Ala Ala Ser Leu Gly
                165


<210> SEQ ID NO 271
<211> LENGTH: 178
<212> TYPE: PRT
<213> ORGANISM: Artificial Sequence
<220> FEATURE:
<223> OTHER INFORMATION: Synthetic peptide accession number Q8P9C4

<400> SEQUENCE: 271

Met Ala Gln Val Ile Asn Thr Asn Val Met Ser Leu Asn Ala Gln Arg
1               5                   10                  15

Asn Leu Asn Thr Asn Ser Ser Ser Met Ala Leu Ser Ile Gln Gln Leu
            20                  25                  30

Ser Ser Gly Lys Arg Ile Thr Ser Ala Ser Val Asp Ala Ala Gly Leu
```

```
        35                  40                  45

Ala Ile Ser Glu Arg Phe Thr Thr Gln Ile Arg Gly Leu Asp Val Ala
    50                  55                  60

Ser Arg Asn Ala Asn Asp Gly Ile Ser Leu Ala Gln Thr Ala Glu Gly
65                  70                  75                  80

Ala Met Val Glu Ile Gly Asn Asn Leu Gln Arg Ile Arg Glu Leu Ser
                85                  90                  95

Val Gln Ser Ala Asn Ala Thr Asn Ser Ala Thr Asp Arg Glu Ala Leu
            100                 105                 110

Asn Ser Glu Val Lys Gln Leu Thr Ser Glu Ile Asp Arg Val Ala Asn
        115                 120                 125

Gln Thr Ser Phe Asn Gly Thr Lys Leu Leu Asn Gly Asp Phe Ser Gly
    130                 135                 140

Ala Leu Phe Gln Val Gly Ala Asp Ala Gly Gln Thr Ile Gly Ile Asn
145                 150                 155                 160

Ser Ile Val Asp Ala Asn Val Asp Ser Leu Gly Lys Ala Asn Phe Ala
                165                 170                 175

Ala Ser


<210> SEQ ID NO 272
<211> LENGTH: 161
<212> TYPE: PRT
<213> ORGANISM: Artificial Sequence
<220> FEATURE:
<223> OTHER INFORMATION: Synthetic peptide accession number Q82UA3

<400> SEQUENCE: 272

Met Pro Gln Val Ile Asn Thr Asn Ile Ala Ser Leu Asn Ala Gln Arg
1               5                   10                  15

Asn Leu Asn Val Ser Gln Asn Ser Leu Ser Thr Ala Leu Gln Arg Leu
            20                  25                  30

Ser Ser Gly Leu Arg Ile Asn Ser Ala Lys Asp Asp Ala Ala Gly Leu
        35                  40                  45

Ala Ile Ser Glu Arg Met Thr Ser Gln Ile Arg Gly Met Asn Gln Ala
    50                  55                  60

Ala Arg Asn Ala Asn Asp Gly Ile Ser Leu Ala Gln Thr Ala Glu Gly
65                  70                  75                  80

Ala Leu Val Glu Ile Gly Asn Asn Leu Gln Arg Ile Arg Glu Leu Ala
                85                  90                  95

Val Gln Ser Ala Asn Ala Thr Asn Ser Glu Asp Asp Arg Glu Ala Leu
            100                 105                 110

Gln Lys Glu Val Thr Gln Leu Ile Asp Glu Ile Gln Arg Val Gly Glu
        115                 120                 125

Gln Thr Ser Phe Asn Gly Thr Lys Leu Leu Asp Gly Ser Phe Ala Ser
    130                 135                 140

Gln Ile Phe Gln Val Gly Ala Asn Glu Gly Glu Thr Ile Asp Phe Thr
145                 150                 155                 160

Asp


<210> SEQ ID NO 273
<211> LENGTH: 178
<212> TYPE: PRT
<213> ORGANISM: Artificial Sequence
<220> FEATURE:
<223> OTHER INFORMATION: Synthetic peptide accession number Q84IC5

<400> SEQUENCE: 273
```

```
Gly Phe Arg Ile Asn Thr Asn Gly Ala Ser Leu Asn Ala Gln Val Asn
1               5                   10                  15

Ala Gly Leu Asn Ser Arg Asn Leu Asp Ser Ser Leu Ala Arg Leu Ser
            20                  25                  30

Ser Gly Leu Arg Ile Asn Ser Ala Ala Asp Asp Ala Ser Gly Leu Ala
        35                  40                  45

Ile Ala Asp Ser Leu Lys Thr Gln Ala Asn Ser Leu Gly Gln Ala Ile
    50                  55                  60

Asn Asn Ala Asn Asp Ala Asn Ser Met Leu Gln Ile Ala Asp Lys Ala
65                  70                  75                  80

Met Asp Glu Gln Leu Lys Ile Leu Asp Thr Ile Lys Val Lys Ala Thr
                85                  90                  95

Gln Ala Ala Gln Asp Gly Gln Thr Ala Lys Thr Arg Ala Met Ile Gln
            100                 105                 110

Gly Glu Ile Asn Lys Leu Met Glu Glu Leu Asp Asn Ile Ala Asn Thr
        115                 120                 125

Thr Thr Tyr Asn Gly Lys Gln Leu Leu Ser Gly Ser Phe Ser Asn Ala
    130                 135                 140

Gln Phe Gln Ile Gly Asp Lys Ala Asn Gln Thr Val Asn Ala Thr Ile
145                 150                 155                 160

Gly Ser Thr Asn Ser Ala Lys Val Gly Gln Thr Arg Phe Glu Thr Gly
                165                 170                 175

Ala Val


<210> SEQ ID NO 274
<211> LENGTH: 88
<212> TYPE: PRT
<213> ORGANISM: Artificial Sequence
<220> FEATURE:
<223> OTHER INFORMATION: Synthetic polypeptide accession number Q53970

<400> SEQUENCE: 274

Pro Leu Ala Ser Ile Asp Ser Ala Leu Ser Lys Val Asp Ala Val Arg
1               5                   10                  15

Ser Ser Leu Gly Ala Ile Gln Asn Arg Phe Asp Ser Ala Ile Thr Asn
            20                  25                  30

Leu Gly Asn Thr Val Thr Asn Leu Asn Ser Ala Arg Ser Arg Ile Glu
        35                  40                  45

Asp Ala Asp Tyr Ala Thr Glu Val Ser Asn Met Ser Lys Ala Gln Ile
    50                  55                  60

Leu Gln Gln Ala Gly Thr Ser Val Leu Ala Gln Ala Asn Gln Val Pro
65                  70                  75                  80

Gln Asn Val Leu Ser Leu Leu Arg
                85


<210> SEQ ID NO 275
<211> LENGTH: 88
<212> TYPE: PRT
<213> ORGANISM: Artificial Sequence
<220> FEATURE:
<223> OTHER INFORMATION: Synthetic peptide accession number P72151

<400> SEQUENCE: 275

Ala Ile Ala Val Val Asp Asn Ala Leu Ala Ala Ile Asp Ala Gln Arg
1               5                   10                  15

Ala Asp Leu Gly Ala Val Gln Asn Arg Phe Lys Asn Thr Ile Asp Asn
            20                  25                  30
```

```
Leu Thr Asn Ile Ser Glu Asn Ala Thr Asn Ala Arg Ser Arg Ile Lys
        35                  40                  45

Asp Thr Asp Phe Ala Ala Glu Thr Ala Ala Leu Ser Lys Asn Gln Val
    50                  55                  60

Leu Gln Gln Ala Gly Thr Ala Ile Leu Ala Gln Ala Asn Gln Leu Pro
65                  70                  75                  80

Gln Ala Val Leu Ser Leu Leu Arg
                85
```

```
<210> SEQ ID NO 276
<211> LENGTH: 89
<212> TYPE: PRT
<213> ORGANISM: Artificial Sequence
<220> FEATURE:
<223> OTHER INFORMATION: Synthetic peptide accession number Q5X5M6

<400> SEQUENCE: 276

Ala Ile Lys Arg Ile Asp Ala Ala Leu Asn Ser Val Asn Ser Asn Arg
1               5                   10                  15

Ala Asn Met Gly Ala Leu Gln Asn Arg Phe Glu Ser Thr Ile Ala Asn
            20                  25                  30

Leu Gln Asn Val Ser Asp Asn Leu Ser Ala Ala Arg Ser Arg Ile Gln
        35                  40                  45

Asp Ala Asp Tyr Ala Ala Glu Met Ala Ser Leu Thr Lys Asn Gln Ile
    50                  55                  60

Leu Gln Gln Ala Gly Thr Ala Met Leu Ala Gln Ala Asn Ser Leu Pro
65                  70                  75                  80

Gln Ser Val Leu Ser Leu Leu Gly Arg
                85
```

```
<210> SEQ ID NO 277
<211> LENGTH: 89
<212> TYPE: PRT
<213> ORGANISM: Artificial Sequence
<220> FEATURE:
<223> OTHER INFORMATION: Synthetic peptide accession number Q6VMV6

<400> SEQUENCE: 277

Pro Leu Glu Thr Ile Asp Lys Ala Leu Ala Lys Val Asp Asn Leu Arg
1               5                   10                  15

Ser Asp Leu Gly Ala Val Gln Asn Arg Phe Asp Ser Ala Ile Thr Asn
            20                  25                  30

Leu Gly Asn Thr Val Asn Asn Leu Ser Ser Ala Arg Ser Arg Ile Arg
        35                  40                  45

Asp Ala Asp Tyr Ala Thr Glu Val Ser Asn Met Ser Arg Ala Gln Ile
    50                  55                  60

Leu Gln Gln Ala Gly Thr Ser Val Leu Ala Gln Ala Asn Gln Thr Thr
65                  70                  75                  80

Gln Asn Val Leu Ser Leu Leu Gln Gly
                85
```

```
<210> SEQ ID NO 278
<211> LENGTH: 88
<212> TYPE: PRT
<213> ORGANISM: Artificial Sequence
<220> FEATURE:
<223> OTHER INFORMATION: Synthetic peptide accession number P13713

<400> SEQUENCE: 278
```

```
Pro Leu Ala Thr Leu Asp Lys Ala Leu Ala Gln Val Asp Gly Leu Arg
1               5                   10                  15

Ser Ser Leu Gly Ala Val Gln Asn Arg Phe Asp Ser Val Ile Asn Asn
            20                  25                  30

Leu Asn Ser Thr Val Asn Asn Leu Ser Ala Ser Gln Ser Arg Ile Gln
        35                  40                  45

Asp Ala Asp Tyr Ala Thr Glu Val Ser Asn Met Ser Arg Ala Asn Ile
    50                  55                  60

Leu Gln Gln Ala Gly Thr Ser Val Leu Ala Gln Ala Asn Gln Ser Thr
65                  70                  75                  80

Gln Asn Val Leu Ser Leu Leu Arg
                85


<210> SEQ ID NO 279
<211> LENGTH: 89
<212> TYPE: PRT
<213> ORGANISM: Artificial Sequence
<220> FEATURE:
<223> OTHER INFORMATION: Synthetic peptide accession number Q93RK8
<220> FEATURE:
<221> NAME/KEY: misc_feature
<222> LOCATION: (6)..(6)
<223> OTHER INFORMATION: Xaa can be any naturally occurring amino acid

<400> SEQUENCE: 279

Ala Leu Thr Thr Ile Xaa Thr Ala Ile Asp Thr Val Ser Ser Glu Arg
1               5                   10                  15

Ala Lys Leu Gly Ala Val Gln Asn Arg Leu Glu His Thr Ile Asn Asn
            20                  25                  30

Leu Gly Thr Ser Ser Glu Asn Leu Thr Ser Ala Asx Ser Arg Ile Arg
        35                  40                  45

Asp Val Asp Met Ala Ser Glu Met Met Glu Tyr Thr Lys Asn Asn Ile
    50                  55                  60

Leu Thr Gln Ala Ser Gln Ala Met Leu Ala Gln Ala Asn Gln Gln Pro
65                  70                  75                  80

Gln Gln Val Leu Gln Leu Leu Lys Gly
                85


<210> SEQ ID NO 280
<211> LENGTH: 90
<212> TYPE: PRT
<213> ORGANISM: Artificial Sequence
<220> FEATURE:
<223> OTHER INFORMATION: Synthetic peptide accession number Q02551

<400> SEQUENCE: 280

Val Ile Gly Leu Ala Asp Ala Ala Leu Thr Lys Ile Met Lys Gln Arg
1               5                   10                  15

Ala Asp Met Gly Ala Tyr Tyr Asn Arg Leu Glu Tyr Thr Ala Lys Gly
            20                  25                  30

Leu Met Gly Ala Tyr Glu Asn Met Gln Ala Ser Glu Ser Arg Ile Arg
        35                  40                  45

Asp Ala Asp Met Ala Glu Glu Val Val Ser Leu Thr Thr Lys Gln Ile
    50                  55                  60

Leu Val Gln Ser Gly Thr Ala Met Leu Ala Gln Ala Asn Met Lys Pro
65                  70                  75                  80

Asn Ser Val Leu Lys Leu Leu Gln Gln Ile
                85                  90
```

<210> SEQ ID NO 281
<211> LENGTH: 88
<212> TYPE: PRT
<213> ORGANISM: Artificial Sequence
<220> FEATURE:
<223> OTHER INFORMATION: Synthetic peptide accession number Q09012

<400> SEQUENCE: 281

```
Pro Leu Ser Lys Leu Asp Glu Ala Leu Ala Lys Val Asp Lys Leu Arg
1               5                   10                  15

Ser Ser Leu Gly Ala Val Gln Asn Arg Phe Asp Ser Ala Ile Thr Asn
            20                  25                  30

Leu Gly Asn Thr Val Asn Asp Leu Ser Ser Ala Arg Ser Arg Ile Glu
        35                  40                  45

Asp Ala Asp Tyr Ala Thr Glu Val Ser Asn Met Ser Arg Ala Gln Ile
    50                  55                  60

Leu Gln Gln Ala Gly Thr Ser Val Leu Ala Gln Ala Asn Gln Thr Thr
65                  70                  75                  80

Gln Asn Val Leu Ser Leu Leu Arg
                85
```

<210> SEQ ID NO 282
<211> LENGTH: 88
<212> TYPE: PRT
<213> ORGANISM: Artificial Sequence
<220> FEATURE:
<223> OTHER INFORMATION: Synthetic peptide accession number Q8GNT8

<400> SEQUENCE: 282

```
Pro Leu Ala Thr Leu Asp Lys Ala Leu Ser Gln Val Asp Ile Leu Arg
1               5                   10                  15

Ser Gly Leu Gly Ala Val Gln Asn Arg Phe Asp Ser Val Ile Asn Asn
            20                  25                  30

Leu Asn Ser Thr Val Asn Asn Leu Ser Ala Ser Arg Ser Arg Ile Gln
        35                  40                  45

Asp Ala Asp Tyr Ala Thr Glu Val Ser Asn Met Ser Arg Ala Gln Ile
    50                  55                  60

Leu Gln Gln Ala Gly Thr Ser Val Leu Ala Gln Ala Asn Gln Ser Thr
65                  70                  75                  80

Gln Asn Val Leu Ser Leu Leu Arg
                85
```

<210> SEQ ID NO 283
<211> LENGTH: 88
<212> TYPE: PRT
<213> ORGANISM: Artificial Sequence
<220> FEATURE:
<223> OTHER INFORMATION: Synthetic peptide accession number Q9FAE7

<400> SEQUENCE: 283

```
Ala Leu Lys Ile Ile Asp Ala Ala Leu Ser Ala Val Asn Gln Gln Arg
1               5                   10                  15

Ala Ser Phe Gly Ala Leu Gln Ser Arg Phe Glu Thr Thr Val Asn Asn
            20                  25                  30

Leu Gln Ser Thr Ser Glu Asn Met Ser Ala Ser Arg Ser Arg Ile Gln
        35                  40                  45

Asp Ala Asp Phe Ala Ala Glu Thr Ala Asn Leu Ser Arg Ser Gln Ile
    50                  55                  60

Leu Gln Gln Ala Gly Thr Ala Met Val Ala Gln Ala Asn Gln Leu Pro
65                  70                  75                  80
```

```
Gln Gly Val Leu Ser Leu Leu Lys
                85


<210> SEQ ID NO 284
<211> LENGTH: 88
<212> TYPE: PRT
<213> ORGANISM: Artificial Sequence
<220> FEATURE:
<223> OTHER INFORMATION: Synthetic peptide accession number Q8ZF76

<400> SEQUENCE: 284

Pro Leu Glu Thr Leu Asp Asp Ala Ile Lys Gln Val Asp Gly Leu Arg
1               5                   10                  15

Ser Ser Leu Gly Ala Val Gln Asn Arg Phe Glu Ser Ala Val Thr Asn
            20                  25                  30

Leu Asn Asn Thr Val Thr Asn Leu Thr Ser Ala Arg Ser Arg Ile Glu
        35                  40                  45

Asp Ala Asp Tyr Ala Thr Glu Val Ser Asn Met Ser Arg Ala Gln Ile
    50                  55                  60

Leu Gln Gln Ala Gly Thr Ser Val Leu Ser Gln Ala Asn Gln Val Pro
65                  70                  75                  80

Gln Thr Val Leu Ser Leu Leu Asn
                85


<210> SEQ ID NO 285
<211> LENGTH: 88
<212> TYPE: PRT
<213> ORGANISM: Artificial Sequence
<220> FEATURE:
<223> OTHER INFORMATION: Synthetic peptide accession number Q7N5J4

<400> SEQUENCE: 285

Pro Leu Glu Thr Leu Asp Ser Ala Leu Ala Gln Val Asp Ser Leu Arg
1               5                   10                  15

Ser Ser Leu Gly Ala Ile Gln Asn Arg Leu Glu Ser Thr Val Asn Asn
            20                  25                  30

Leu Asn Asn Thr Val Asn Asn Leu Ser Ala Ala Arg Ser Arg Ile Glu
        35                  40                  45

Asp Ala Asp Tyr Ala Thr Glu Val Ser Asn Met Ser Arg Gly Gln Ile
    50                  55                  60

Leu Gln Gln Ala Gly Thr Ala Val Leu Ala Gln Ala Met Gln Val Pro
65                  70                  75                  80

Gln Asn Val Met Ser Leu Leu Arg
                85


<210> SEQ ID NO 286
<211> LENGTH: 89
<212> TYPE: PRT
<213> ORGANISM: Artificial Sequence
<220> FEATURE:
<223> OTHER INFORMATION: Synthetic peptide accession number O33578

<400> SEQUENCE: 286

Ala Ile Gly Val Ile Asp Val Ala Leu Ser Lys Ile Ser Gln Ser Arg
1               5                   10                  15

Ser Glu Leu Gly Ala Val Ser Asn Arg Leu Asp Ser Thr Ile Ser Asn
            20                  25                  30

Leu Thr Asn Ile Ser Thr Ser Val Gln Ala Ala Lys Ser Gln Val Met
        35                  40                  45
```

```
Asp Ala Asp Phe Ala Ala Glu Ser Thr Asn Leu Ala Arg Ser Gln Ile
    50                  55                  60

Leu Ser Gln Ala Ser Thr Ala Met Leu Ala Gln Ala Asn Ser Ser Lys
65                  70                  75                  80

Gln Asn Val Leu Ser Leu Leu Arg Gly
                85


<210> SEQ ID NO 287
<211> LENGTH: 88
<212> TYPE: PRT
<213> ORGANISM: Artificial Sequence
<220> FEATURE:
<223> OTHER INFORMATION: Synthetic peptide accession number Q56826

<400> SEQUENCE: 287

Pro Leu Asp Thr Leu Asp Lys Ala Leu Ala Gln Val Asp Asp Asn Arg
1               5                   10                  15

Ser Ser Leu Gly Ala Val Gln Asn Arg Leu Glu Ser Thr Val Asn Asn
            20                  25                  30

Leu Asn Asn Thr Val Asn Asn Leu Ser Ala Ala Arg Ser Arg Ile Glu
        35                  40                  45

Asp Ala Asp Tyr Ala Val Glu Val Ser Asn Met Ser Arg Gly Gln Ile
    50                  55                  60

Leu Gln Gln Ala Gly Thr Ser Val Leu Ala Gln Ala Asn Gln Val Pro
65                  70                  75                  80

Gln Thr Val Leu Ser Leu Leu Arg
                85


<210> SEQ ID NO 288
<211> LENGTH: 88
<212> TYPE: PRT
<213> ORGANISM: Artificial Sequence
<220> FEATURE:
<223> OTHER INFORMATION: Synthetic peptide accession number P42273

<400> SEQUENCE: 288

Ala Leu Ala Thr Leu Asp Asn Ala Ile Ser Lys Val Asp Glu Ser Arg
1               5                   10                  15

Ser Lys Leu Gly Ala Ile Gln Asn Arg Phe Gln Ser Thr Ile Asn Asn
            20                  25                  30

Leu Asn Asn Thr Val Asn Asn Leu Ser Ala Ser Arg Ser Arg Ile Leu
        35                  40                  45

Asp Ala Asp Tyr Ala Thr Glu Val Ser Asn Met Ser Lys Asn Gln Ile
    50                  55                  60

Leu Gln Gln Ala Gly Thr Ala Val Leu Ala Gln Ala Asn Gln Val Pro
65                  70                  75                  80

Gln Thr Val Leu Ser Leu Leu Arg
                85


<210> SEQ ID NO 289
<211> LENGTH: 88
<212> TYPE: PRT
<213> ORGANISM: Artificial Sequence
<220> FEATURE:
<223> OTHER INFORMATION: Synthetic peptide accession number O31059

<400> SEQUENCE: 289

Ala Ile Asp Ala Ile Ser Asp Ala Leu Ala Lys Val Ser Ala Gln Arg
1               5                   10                  15

Ser Ala Leu Gly Ser Ile Gln Asn Arg Leu Glu His Ser Ile Ala Asn
```

```
            20                  25                  30

Leu Asp Asn Val Val Glu Asn Thr Asn Ala Ala Glu Ser Arg Ile Arg
        35                  40                  45

Asp Thr Asp Met Ala Asp Glu Met Val Thr Tyr Ser Lys Asn Asn Ile
    50                  55                  60

Leu Met Gln Ala Gly Gln Ser Met Leu Ala Gln Ala Asn Gln Ala Thr
65                  70                  75                  80

Gln Gly Val Leu Ser Ile Leu Gln
                85


<210> SEQ ID NO 290
<211> LENGTH: 88
<212> TYPE: PRT
<213> ORGANISM: Artificial Sequence
<220> FEATURE:
<223> OTHER INFORMATION: Synthetic peptide accession number Q7VZC2

<400> SEQUENCE: 290

Ala Leu Ser Lys Leu Asp Asp Ala Met Lys Ala Val Asp Glu Gln Arg
1               5                   10                  15

Ser Ser Leu Gly Ala Ile Gln Asn Arg Phe Glu Ser Thr Val Ala Asn
            20                  25                  30

Leu Asn Asn Thr Ile Thr Asn Leu Ser Ala Ala Arg Ser Arg Ile Glu
        35                  40                  45

Asp Ser Asp Tyr Ala Thr Glu Val Ser Asn Met Thr Lys Asn Gln Ile
    50                  55                  60

Leu Gln Gln Ala Gly Thr Ser Val Leu Ala Gln Ala Asn Gln Val Pro
65                  70                  75                  80

Gln Asn Val Leu Ser Leu Leu Arg
                85


<210> SEQ ID NO 291
<211> LENGTH: 88
<212> TYPE: PRT
<213> ORGANISM: Artificial Sequence
<220> FEATURE:
<223> OTHER INFORMATION: Synthetic peptide accession number Q9F4A4

<400> SEQUENCE: 291

Ser Ile Lys Thr Ile Asn Ser Ala Ile Glu Gln Val Ser Thr Gln Arg
1               5                   10                  15

Ser Lys Leu Gly Ala Val Gln Asn Arg Leu Glu His Thr Ile Asn Asn
            20                  25                  30

Leu Asn Thr Ser Ser Glu Asn Leu Thr Ala Ala Glu Ser Arg Val Arg
        35                  40                  45

Asp Val Asp Met Ala Lys Glu Met Met Ala Phe Ser Lys Asn Asn Ile
    50                  55                  60

Leu Ser Gln Ala Ala Gln Ala Met Leu Gly Gln Ala Asn Gln Gln Pro
65                  70                  75                  80

Gln Gly Val Leu Gln Leu Leu Arg
                85


<210> SEQ ID NO 292
<211> LENGTH: 88
<212> TYPE: PRT
<213> ORGANISM: Artificial Sequence
<220> FEATURE:
<223> OTHER INFORMATION: Synthetic peptide accession number Q8P9C4

<400> SEQUENCE: 292
```

```
Ala Leu Glu Ile Val Asp Lys Ala Leu Thr Ser Val Asn Ser Ser Arg
1               5                   10                  15

Ala Asp Met Gly Ala Val Gln Asn Arg Phe Thr Ser Thr Leu Ala Asn
            20                  25                  30

Leu Ala Ala Thr Ser Glu Asn Leu Thr Ala Ser Arg Ser Arg Ile Ala
        35                  40                  45

Asp Thr Asp Tyr Ala Lys Thr Thr Ala Glu Leu Thr Arg Thr Gln Ile
    50                  55                  60

Leu Gln Gln Ala Gly Thr Ala Met Leu Ala Gln Ala Lys Ser Val Pro
65                  70                  75                  80

Gln Asn Val Leu Ser Leu Leu Gln
                85


<210> SEQ ID NO 293
<211> LENGTH: 84
<212> TYPE: PRT
<213> ORGANISM: Artificial Sequence
<220> FEATURE:
<223> OTHER INFORMATION: Synthetic peptide accession number Q82UA3

<400> SEQUENCE: 293

Ile Asp Asp Ala Leu Lys Ile Val Asn Ser Thr Arg Ala Asp Leu Gly
1               5                   10                  15

Ala Ile Gln Asn Arg Phe Ser Ser Ala Ile Ala Asn Leu Gln Thr Ser
            20                  25                  30

Ala Glu Asn Leu Ser Ala Ser Arg Ser Arg Ile Gln Asp Ala Asp Phe
        35                  40                  45

Ala Ala Glu Thr Ala Ala Leu Thr Arg Ala Gln Ile Leu Gln Gln Ala
    50                  55                  60

Gly Val Ala Met Leu Ser Gln Ala Asn Ala Leu Pro Asn Asn Val Leu
65                  70                  75                  80

Ser Leu Leu Arg


<210> SEQ ID NO 294
<211> LENGTH: 89
<212> TYPE: PRT
<213> ORGANISM: Artificial Sequence
<220> FEATURE:
<223> OTHER INFORMATION: Synthetic peptide accession number Q84IC5

<400> SEQUENCE: 294

Val Met Asp Ile Ala Asp Thr Ala Ile Ala Asn Leu Asp Thr Ile Arg
1               5                   10                  15

Ala Asn Ile Gly Ala Thr Gln Asn Gln Ile Thr Ser Thr Ile Asn Asn
            20                  25                  30

Ile Ser Val Thr Gln Val Asn Val Lys Ala Ala Glu Ser Gln Ile Arg
        35                  40                  45

Asp Val Asp Phe Ala Ser Glu Lys Ser Ala Asn Tyr Ser Lys Ala Asn
    50                  55                  60

Ile Leu Ala Gln Ser Gly Ser Tyr Ala Met Ala Gln Ala Asn Ala Ala
65                  70                  75                  80

Ser Gln Asn Val Leu Arg Leu Leu Gln
                85
```

FLAGELLIN-BASED AGENTS AND USES INCLUDING EFFECTIVE VACCINATION

CROSS-REFERENCE TO RELATED APPLICATIONS

This application is a continuation application of U.S. application Ser. No. 15/500,133, filed on Jan. 30, 2017 (now U.S. Pat. No. 10,336,793), which is a national stage entry of International Patent Application No. PCT/US2015/042887, filed Jul. 30, 2015, which claims the benefit of U.S. Provisional Patent Application No. 62/031,116, filed Jul. 30, 2014; 62/110,744, filed Feb. 2, 2015; and 62/117,366, filed Feb. 17, 2015 the entire contents of which are herein incorporated by reference.

FIELD OF THE INVENTION

The present invention relates to, inter alia, new compositions and methods for vaccination, including adjuvants comprising flagellin-based agents.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: CLE019PC SequenceListing.txt; date recorded: Jul. 24, 2015; file size: 261 KB).

BACKGROUND

Vaccines are one of the most effective preventative health tools available against infectious diseases, cancers, and allergies. Vaccination aims to generate a strong immune response to the administrated antigen and provide long-term protection against a disorder. Often, however, an antigen alone is insufficient to stimulate protective immunity.

Vaccine adjuvants are compounds that enhance the specific immune responses against antigens in vaccines. Currently, several hundred natural and synthetic compounds are known to have adjuvant activity but only alum salts and AS04 are licensed for use in humans in the United States. This limited list of adjuvants is insufficient for meeting the functional needs of effective vaccination. For example, although alum is able to induce a good $T_{H2}$ response, it has little capacity to stimulate cellular ($T_{H1}$) immune responses which are so important for protection against many pathogens.

Accordingly, there remains a need for improved vaccines and/or adjuvants that can effectively stimulate a subject's immune response.

SUMMARY OF THE INVENTION

Accordingly, in some aspects, the present invention provides for improved vaccines and/or adjuvants.

In some aspects, the present invention provides a vaccine composition, comprising an adjuvant comprising a flagellin-based agent, such as, for example, CBLB502 (a/k/a entolimod) as well as any of the flagellin-based agents or derivatives described herein (e.g. Table 1), and an aluminum gel or salt and an antigen and, optionally, an additional adjuvant. In some aspects, the present invention provides an adjuvant composition, comprising an adjuvant comprising a flagellin-based agent, including CBLB502 as well as any of the flagellin-based agents or derivatives described herein (e.g. Table 1), and an aluminum gel or salt. In various embodiments, the vaccine described herein causes an improvement in adjuvant properties relative to a vaccine comprising the antigen and the aluminum gel or salt alone. In various embodiments, the vaccine and/or adjuvant described herein causes a broader, more diverse, more robust and longer lasting immunostimulatory effect than the vaccine comprising the antigen and the aluminum gel or salt alone and/or the adjuvant comprising the aluminum gel or salt alone. In various embodiments, the vaccine and/or adjuvant described herein causes immunostimulation of one or more of $T_{H1}$ and $T_{H2}$-mediated immune response (e.g. both of $T_{H1}$ and $T_{H2}$-mediated immune response) and/or the vaccine and/or adjuvant described herein causes immunostimulation of $T_{H1}$-mediated immune response at levels greater than a vaccine comprising the antigen and the aluminum gel or salt alone and/or the adjuvant comprising the aluminum gel or salt alone.

In some embodiments, the flagellin-based agent may be a flagellin molecule or flagellin-based agent, or variants thereof that has TLR5 agonist activity. The flagellin-based agent may comprise one or more of the sequences of Table 1 (SEQ ID Nos.: 1-252), or variants thereof that have TLR5 agonist activity and can include a variant of *Salmonella dublin* wild type flagellin (SEQ ID No: 1), CBLB502 (SEQ ID NO: 2) or variants thereof (including closely-related variants such as S33ML (SEQ ID NO: 35), CBLB502-485CT (CBLB533, SEQ ID NO: 71), and CBLB502-S33MX (SEQ ID NO: 150)) and more distantly related variants such as flagellin derivatives from a thermophilic microorganism or flagellin derivatives from a microorganism well-tolerated by human (e.g. SEQ ID NOs: 243-252). In some embodiments, the aluminum gel or salt is selected from aluminum hydroxide, aluminum phosphate, and potassium aluminum sulfate, and ALHYDROGEL.

In various embodiments, the present vaccine composition is part of the following vaccines (e.g. the antigens of these vaccines may be used as the antigen of the present vaccines): DTP (diphtheria-tetanus-pertussis vaccine), DTaP (diphtheria-tetanus-acellular pertussis vaccine), Hib (*Haemophilus influenzae* type b) conjugate vaccines, Pneumococcal conjugate vaccine, Hepatitis A vaccines, Poliomyelitis vaccines, Yellow fever vaccines, Hepatitis B vaccines, combination DTaP, Tdap, Hib, Human Papillomavirus (HPV) vaccine, Anthrax vaccine, and Rabies vaccine.

In various embodiments, the vaccine described herein is formed, in part, by mixing the flagellin-based agent and aluminum gel or salt to form a stable complex, the ratio (w/w) of flagellin-based agent to aluminum gel or salt being about 1:500 or less (e.g. about 1:500, or about 1:600, or about 1:700, or about 1:800, or about 1:900, or about 1:1000, or about 1:2000, or about 1:5000). In some embodiments, the flagellin-based agent and aluminum gel or salt are mixed in a ratio that is substantially below a loading capacity of the aluminum gel or salt. In some embodiments, the flagellin-based agent and antigen are adsorbed to the aluminum gel or salt.

In another aspect, the present invention provides a method of vaccinating a subject against a disorder, comprising administering an effective amount of a vaccine comprising an adjuvant comprising a flagellin-based agent and an aluminum gel or salt and an antigen associated with the disorder. In another aspect, the present invention provides a method of immunostimulating a subject in advance of or concurrent with vaccination, comprising administering an effective amount of an adjuvant comprising a flagellin-based agent and an aluminum gel or salt, wherein both $T_{H1}$ and $T_{H2}$-mediated immune responses are immunostimulated. In various embodiments the disorder is selected from infectious diseases, cancer, allergy, and autoimmune diseases (by way of example, diphtheria, tetanus, pertussis, influenza, pneumonia, hepatitis A, hepatitis B, polio, yellow fever, Human Papillomavirus (HPV) infection, various cancers, anthrax, rabies, Japanese Encephalitis, meningitis, measles, mumps, rubella, gastroenteritis, smallpox, typhoid fever, varicella (chickenpox), rotavirus, and shingles).

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

BRIEF DESCRIPTION OF THE FIGURES

FIGS. 1A and 1B show the 13 conserved amino acids of flagellin that may be important for TLR5 activity. FIGS. 1A and 1B show a comparison of amino acid sequences of the conserved amino (FIG. 1A) and carboxy (FIG. 1B) terminus from 21 species of bacteria. The 13 conserved amino acids important for TLR5 activity are indicated by the letter "C" at the bottom of each column. The amino acid sequences are identified by their accession numbers from TrEMBL (first letter=Q) or Swiss-Prot (first letter=P). With respect to FIG. 1A, SEQ ID Nos: 253-273 correspond to the sequences listed on the figure from top to bottom, respectively. With respect to FIG. 1B. SEQ ID Nos: 274-294 correspond to the sequences listed on the figure from top to bottom, respectively.

FIG. 11 shows immunopotentiating effects of a 502 adjuvant. Anti-MA IgG (μg/ml) response (panel A) and anti-502 antibody response (panel B) by ELISA to TT-SMA vaccine in the presence and absence of alum or entolimod (a varying range from 0 to 20 μg) in pooled sera collected at week 2,4 and 6 post initial vaccination is shown. Data represent the levels of antibody in the pooled samples from each group (n=5/group).

DETAILED DESCRIPTION OF THE INVENTION

Figure 2:
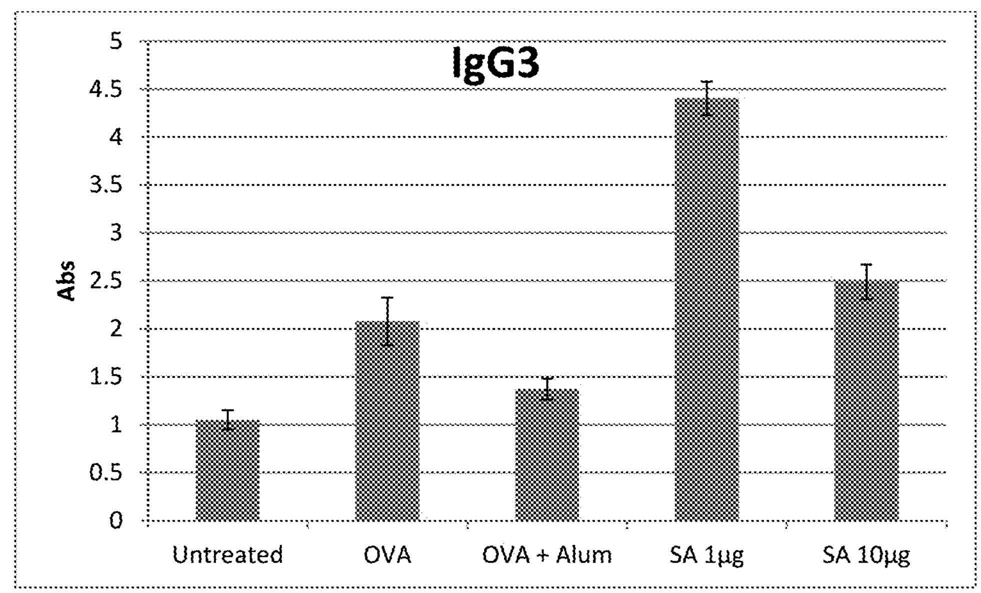
FIG. 2 shows ELISA data for the average response of five mouse treatment groups at the time point of 1 week post-boost. Panel A is total IgG, Panel B is IgG1, Panel C is IgG2a, Panel D is IgG2b and Panel E is IgG3. Groups 1-5 are defined in TABLE B (Example 2): Group 1 is also called "Untreated;" Group 2 is also called "OVA," Groups 3 is also called "OVA+Alum," Group 4 is also called "SA 1 μg," and Group 5 is also called "SA 10 μg."

The present invention is also based, in part, on the surprising discovery that flagellin-based agents, including CBLB502 and any of the flagellin-based agents (e.g. agents comprising the sequences of Table 1, including MX-33) described herein, can be mixed with aluminum gels or salts (and, optionally antigens), in ratios well-below the loading/adsorbing capacity of the aluminum gel or salt (e.g. 1:500), and cause a broader, more diverse, more robust and longer lasting immunostimulatory effect than the vaccine comprising the antigen and the aluminum gel or salt alone and/or the adjuvant comprising the aluminum gel or salt alone. The inventors have also surprisingly discovered that the immunostimulatory effect can influence both the $T_{H1}$ and $T_{H2}$-mediated arms of an immune response. The inventors have also surprisingly discovered that low amounts of flagellin-based agents, including CBLB502 and any of the flagellin-based agents (e.g. agents comprising the sequences of Table 1, including MX-33) relative to antigen are effective for immunostimulation.

In one aspect, the invention provides a vaccine composition, comprising an adjuvant comprising a flagellin-based agent and an aluminum gel or salt and an antigen and, optionally, an additional adjuvant. In one aspect, the invention provides an adjuvant comprising a flagellin-based agent and an aluminum gel or salt.

In some embodiments, the described vaccine causes an improvement in adjuvant properties relative to a vaccine comprising the antigen and the aluminum gel or salt alone. In various embodiments, the vaccine and/or adjuvant described herein causes a broader, more diverse, more robust and longer lasting immunostimulatory effect than the vaccine comprising the antigen and the aluminum gel or salt alone (or as compared to the vaccine comprising the antigen and flagellin-based agent alone) and/or the adjuvant comprising the aluminum gel or salt alone (or as compared to the adjuvant comprising the flagellin-based agent alone).

In some embodiments, the described vaccine and/or described adjuvant causes immunostimulation of one or more of $T_{H1}$ and $T_{H2}$-mediated immune response. In some embodiments, the described vaccine and/or described adjuvant causes immunostimulation of both of $T_{H1}$ and $T_{H2}$-mediated immune response. In some embodiments, the described vaccine and/or described adjuvant causes immunostimulation of $T_{H1}$-mediated immune response at levels greater than a vaccine comprising the antigen and the aluminum gel or salt alone or an adjuvant comprising the aluminum gel or salt alone.

$T_{H1}$-mediated immune response (or "Type 1 response") largely involves interaction with macrophages and CD8+ T cells and may be linked to interferon-γ, TNF-β, interleukin-2, and interleukin-10 production. The $T_{H1}$-mediated immune response promotes cellular immune system and maximizes the killing efficacy of the macrophages and the proliferation of cytotoxic $CD8^+$ T cells. The $T_{H1}$-mediated immune response also promotes the production of opsonizing antibodies (e.g. IgG, IgM and IgA). The Type 1 cytokine IFN-γ increases the production of interleukin-12 by dendritic cells and macrophages, and via positive feedback, IL-12 stimulates the production of IFN-γ in helper T cells, thereby promoting the $T_{H1}$ profile. Interferon-γ also inhibits the production of cytokines such as interleukin-4, a cytokine associated with the Type 2 response, and thus it also acts to preserve its own response.

$T_{H2}$-mediated immune response (or "Type 2 response") largely involves interaction with B-cells, eosinophils, and mast cells and may be linked to interleukin-4, interleukin-5, interleukin-6, interleukin-9, interleukin-10, and interleukin-13. $T_{H2}$-mediated immune response promotes humoral immune system and may stimulate B-cells into proliferation, induce B-cell antibody class switching, and increase neutralizing antibody production (e.g. IgG, IgM and IgA as well as IgE antibodies). Other functions of the Type 2 response include promoting its own profile using two different cytokines. Interleukin-4 acts on helper T cells to promote the production of $T_{H2}$ cytokines (including itself; it is autoregulatory), while interleukin-10 (IL-10) inhibits a variety of cytokines including interleukin-2 and IFN-γ in helper T cells and IL-12 in dendritic cells and macrophages. The combined action of these two cytokines suggests that once the T cell has decided to produce these cytokines, that decision is preserved (and also encourages other T cells to do the same).

The division is medically relevant to, inter alia and without wishing to be bound by theory, the fact that alum adjuvants are only effective at inducing a $T_{H2}$-mediated response and not a $T_{H1}$_mediated response (see, e.g., Smith Korsholm, et al. Immunology. January 2010; 129(1): 75-86, the contents of which are hereby incorporated by reference in their entirety).

In various embodiments, the stimulation of $T_{H1}$ and $T_{H2}$-mediated immune responses may be measured by assays known in the art, including a number of antibody surrogate assays (e.g. ELISA and the like). For instance, without wishing to be bound by theory, IgG1 is associated with a $T_{H2}$-like response, while a $T_{H1}$ response is associated with the induction of IgG2a, IgG2b, and IgG3 antibodies.

In some embodiments, the described vaccine and/or described adjuvant causes an increase in titer of one or more of IgG1, IgG2a, IgG2b, and IgG3 antibodies (e.g. relative to the adjuvant comprising the aluminum gel or salt or flagellin-based agent alone, or relative to the vaccine comprising the antigen and the aluminum gel or salt alone (or flagellin-based agent) alone)). In some embodiments, the described vaccine and/or described adjuvant causes a relative increase in the titer of all of IgG1, IgG2a, IgG2b, and IgG3 antibodies. In some embodiments, the described vaccine and/or described adjuvant causes a relative increase in the titer of more IgG3 antibodies than the described vaccine and/or described adjuvant in the absence of a flagellin-based agent (or the described vaccine and/or described adjuvant in the absence of an aluminum gel or salt alone).

Accordingly, in some embodiments, the described vaccine and/or described adjuvant causes a diversified immune response. For example, in some embodiments, the total IgG generated by the described vaccines and/or adjuvants is greater than the described vaccines and/or adjuvants without the flagellin-based agent.

In some embodiments, the flagellin-based agent may be a flagellin molecule or flagellin-related polypeptide, or variants thereof that have TLR5 agonist activity. The flagellin-based agent may be from various sources, including a variety of Gram-positive and Gram-negative bacterial species. In some embodiments, the flagellin-based agents may have an amino acid sequence that is derived from any of the flagellins from bacterial species that are depicted in, for example, FIG. 7 of U.S. Patent Publication No. 2003/0044429, the contents of which are incorporated herein by reference in their entirety. The flagellin-based agent may have nucleotide sequences related to those encoding the flagellin polypeptides listed in, for example, FIG. 7 of U.S. 2003/0044429, which are publicly available at sources including the NCBI Genbank database.

The flagellin-based agent may be the major component of bacterial flagellum. The flagellin-based agents may be composed of one, or two, or three, or four, or five, or six, or seven domains or fragments thereof (see, e.g., FIG. 10 of U.S. Pat. No. 8,324,163, the contents of which are incorporated herein by reference in their entirety). The domains may be selected from ND0, ND1, ND2, D3, CD2, CD1, and CD0. Domains 0 (D0), 1 (D1), and 2 (D2) may be discontinuous and may be formed when residues in the amino terminus and carboxy terminus are juxtaposed by the formation of a hairpin structure. The amino and carboxy terminus comprising the D1 and D2 domains may be most conserved, whereas the middle hypervariable domain (D3) may be highly variable. The non-conserved D3 domain may be on the surface of the flagellar filament and may contain the major antigenic epitopes. The potent proinflammatory activity of flagellin may reside in the highly conserved N and CD1 and D2 regions.

The flagellin-based agents may be from a species of *Salmonella*, representative examples of which are *S. typhimurium* and *S. dublin* (encoded by GenBank Accession Number M84972). The flagellin related-polypeptide may be a fragment, variant, analog, homolog, or derivative of wild type flagellin (SEQ ID NO: 1), or combination thereof. A fragment, variant, analog, homolog, or derivative of flagellin may be obtained by rational-based design based on the domain structure of flagellin and the conserved structure recognized by TLR5.

The flagellin-based agent may be related to a flagellin polypeptide from any Gram-positive or Gram-negative bacterial species including, but not limited to, the flagellin polypeptides disclosed in U.S. Pat. Pub. 2003/0044429, the contents of which are incorporated herein, and the flagellin peptides corresponding to the Accession numbers listed in the BLAST results shown in FIG. 7 (panels A-F) of U.S. Patent Pub. 2003/0044429, or variants thereof.

In some embodiments, the flagellin-based agent comprises or consists of any of the polypeptides or nucleic acids encoding said polypeptides listed in Table 1. In some embodiments, the flagellin-based agent is encoded by the nucleotide sequences listed in Table 1. In a further embodiment, the flagellin-based agent comprises the polypeptides listed in Table 1. In some embodiments, the flagellin-based agent comprises one or more of SEQ ID NOs.: 1-252. In some embodiments, the flagellin-based agent comprises a flexible linker. In a further embodiment, the flexible linker comprises SEQ ID NO: 16. In yet a further embodiment, the flexible linker comprises SEQ ID NO: 242.

In some embodiments, the flagellin-based agent is a variant of SEQ ID NO: 1. In various embodiments, the flagellin-based agent is not SEQ ID NO: 1.

In some embodiments, the flagellin-based agent comprises or consists of CBLB502 (SEQ ID NO: 2) or is a variant of CBLB502 (SEQ ID NO: 2). In various embodiments, CBLB502 provides the advantage of, inter alia, removal of epitopes that generate neutralizing anti-flagellin antibodies and therefore allow for the surprising adjuvant properties seen here in combination with alum.

In some embodiments, the flagellin-based agent comprises mutations in epitopes recognized by neutralizing anti-CBLB502 antibodies. The flagellin-based agent may comprise one or more mutations in the epitopes recognized by neutralizing anti-CBLB502 antibodies which inhibit or abrogate the ability of the antibodies to neutralize the composition. In yet a further embodiment, the flagellin-based agent comprises a truncation and mutations in one or more epitopes. In a further embodiment, the mutations comprise replacement of the epitope residues with alanine. In a further embodiment, the mutated epitopes comprise one or more of the following residues: E153, S444, T154, N440, Q142, F131, D443, N68, T447, S110, Q117, R124, D113, E120, N127, and Q128.

The flagellin-based agent may comprise insertions, deletions, transposon insertions, and changes to any one of the D0, D1, D2, and the variable D3 domains. The D3 domain may be substituted in part, or in whole, with a hinge or linker polypeptide that allows the D1 and D2 domains to properly fold such that the variant stimulates TLR5 activity.

In some embodiments, the flagellin-based agent may be a minimal functional core of a flagellin, for example, deleting residues relative to the already shortened CBLB502 molecule. In some embodiments, the flagellin-based agent has altered amino acid identity relative to wild type, including deletions, additions and substitutions, that provide for improved activity. In some embodiments, the flagellin-based agent is derived from CBLB502 (SEQ ID NO: 2). In some embodiments, the flagellin-based agent comprises a truncation in one or more domains. In a further embodiment, the flagellin-based agent comprises a deletion in an N-terminal domain. In yet a further embodiment, the flagellin-based agent comprises a deletion in the ND0 domain. In yet a further embodiment, the flagellin-based agent comprises a deletion of the entire ND0 domain. In a further embodiment, the flagellin-based agent comprises a deletion in a C-terminal domain. In yet another embodiment, the flagellin-based agent comprises a deletion in the CD0 domain. In yet another embodiment, the flagellin-based agent retains amino acids 470-485 of the CD0 domain. In yet a further embodiment, the flagellin-based agent is CBLB502-S33 (SEQ ID NO: 17).

The flagellin-based agent may comprise at least 10, 11, 12, or 13 of the 13 conserved amino acids shown in FIG. 1A and FIG. 1B (positions 89, 90, 91, 95, 98, 101, 115, 422, 423, 426, 431, 436 and 452). The flagellin may be at least 30-99% identical to amino acids 1-174 and 418-505 of SEQ ID NO: 1.

In some embodiments, the flagellin-based agent comprises a tag. In yet a further embodiment, the tag is attached to the N-terminus of the flagellin-based agent. In yet another embodiment, the tag is attached to the C-terminus of the flagellin-based agent.

In some embodiments, the flagellin-based agent comprises a flexible linker. In a further embodiment, the flexible linker comprises SEQ ID NO: 16. In yet a further embodiment, the flexible linker comprises SEQ ID NO:242.

In various embodiments, the flagellin-based agent is one or more of the flagellin related composition derived from SEQ ID NO: 2. In various embodiments, the flagellin-based agent is one or more of CBLB502-S33ML (SEQ ID NO: 35), CBLB502-485CT (CBLB533, SEQ ID NO: 71), and CBLB502-S33MX (SEQ ID NO: 150).

In various embodiments, the flagellin-based agent is a flagellin derivative from a thermophilic microorganism. In various embodiments, the flagellin-based agent is a flagellin derivative from a microorganism well-tolerated by human. In some embodiments, the flagellin-based agent is one or more of SEQ ID NOs: 243-252.

In some embodiments, a variant includes molecules that have TLR5 agonist activity. In some embodiments, a variant includes molecules comprising an amino acid sequence having at least about 70% (e.g. about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 1 or SEQ ID NO: 2.

In some embodiments, the flagellin-based agent comprises or consists of any of the polypeptides or nucleic acids encoding said polypeptides listed in Table 1. In some embodiments, the flagellin-based agent is encoded by the nucleotide sequences listed in Table 1. In a further embodiment, the flagellin-based agent comprises one or more of the polypeptides listed in Table 1. In some embodiments, the flagellin-based agent comprises or consists of polypeptides encoded by either SEQ ID NOs: 69 or 70. In some embodiments, the flagellin-based agent comprises or consists of the polypeptides of SEQ ID NO: 71, "CBLB543". In some embodiments, the flagellin-based agent comprises or consists of polypeptides encoded by either SEQ ID NOs: 149 or 151. In some embodiments, the flagellin-based agent comprises or consists of the polypeptides of SEQ ID NO: 150, "CBLB533".

TABLE 1

| Illustrative Flagellin-Based Agents | | | | |
|---|---|---|---|---|
| SEQ ID | Construct Name | DNA/PRT | Species | Sequence |
| 0001 | Wild type | PRT | *Salmonella dublin* | MAQVINTNSLSLLTQNNLNKSQSSLSSAIERLSSGLRINSAKDDAAGQAIANRFTSNIKGLTQASRN ANDGISIAQTTEGALNEINNNLQRVRELSVQATNGTNSDSDLKSIQDEIQQRLEEIDRVSNQTQFN GVKVLSQDNQMKIQVGANDGETITIDLQKIDVKSLGLDGFNVNGPKEATVGDLKSSFKNVTGYDTY AAGADKYRVDINSGAVVTDAAAPDKVYVNAANGQLTTDDAENNTAVDLFKTTKSTAGTAEAKAIA GAIKGGKEGDTFDYKGVTFTIDTKTGDDGNGKVSTTINGEKVTLTVADIATGAADVNAATLQSSKN VYTSVVNGQFTFDDKTKNESAKLSDLEANNAVKGESKITVNGAEYTANATGDKITLAGKTMFIDKT ASGVSTLINEDAAAAKKSTANPLASIDSALSKVDAVRSSLGAIQNRFDSAITNLGNTVTNLNSARSRI EDADYATEVSNMSKAQILQQAGTSVLAQANQVPQNVLSLLR |
| 0002 | CBLB502 | PRT | Artificial Sequence | MRGSHHHHHHGMASMTGGQQMGRDLYDDDDKDPMAQVINTNSLSLLTQNNLNKSQSSLSSAIE RLSSGLRINSAKDDAAGQAIANRFTSNIKGLTQASRNANDGISIAQTTEGALNEINNNLQRVRELSV QATNGTNSDSDLKSIQDEIQQRLEEIDRVSNQTQFNGVKVLSQDNQMKIQVGANDGETITIDLQKI DVKSLGLDGFNVNSPGISGGGGGILDSMGTLINEDAAAAKKSTANPLASIDSALSKVDAVRSSLGAI QNRFDSAITNLGNTVTNLNSARSRIEDADYATEVSNMSKAQILQQAGTSVLAQANQVPQNVLSLL R |
| 0003 | T7 Promoter (forward) | DNA | Artificial Sequence | TAATACGACTCACTATAGGGG |
| 0004 | FliC AA74-80 (forward) | DNA | Artificial Sequence | ATTGCGCAGACCACTGAAGG |
| 0005 | Thrombin cleavage site | PRT | Artificial Sequence | LVPRGS |
| 0006 | Enterokinase cleavage site | | Artificial Sequence | DDDDK |
| 0007 | NS (N-terminal spoke region; Ser32-Ala44) | PRT | Artificial Sequence | SSGLRINSAKDDA |
| 0008 | CS (C-terminal spoke region; Glu464 to Ala469) | PRT | Artificial Sequence | EDADYA |
| 0009 | linker | PRT | Artificial Sequence | AASAGAGQGGGGSG |
| 0010 | linker | PRT | Artificial Sequence | EGKSSGSGSESKST |
| 0011 | linker | PRT | Artificial Sequence | GGGRTSSSAASAGAGQGGGGSG |
| 0012 | linker | PRT | Artificial Sequence | GPSG |

TABLE 1-continued

| Illustrative Flagellin-Based Agents | | | | |
|---|---|---|---|---|
| SEQ ID | Construct Name | DNA/ PRT | Species | Sequence |
| 0013 | linker | PRT | Artificial Sequence | GSAGSAAGSGEF |
| 0014 | linker | PRT | Artificial Sequence | GSPG |
| 0015 | linker | PRT | Artificial Sequence | KESGSVSSEQLAQFRSLD |
| 0016 | linker | PRT | Artificial Sequence | SPGISGGGGGILDSMG |
| 0017 | Mutant 33-485 Mutant S33 | PRT | Artificial Sequence | MRGSHHHHHHGMASMTGGQQMGRDLYDLVPRGSAKDPSGLRINSAKDDAAGQAIANRFTSNIK GLTQASRNANDGISIAQTTEGALNEINNNLQRVRELSVQATNGTNSDSDLKSIQDEIQQRLEEIDRV SNQTQFNGVKVLSQDNQMKIQVGANDGETITIDLQKIDVKSLGLDGFNVNSPGISGGGGGILDSM GTLINEDAAAAKKSTANPLASIDSALSKVDAVRSSLGAIQNRFDSAITNLGNTVTNLNSARSRIEDA DYATEVSNMSKAQILQQAGTSVLAQANQVPQNVLSLLR |
| 0018 | Mutant 33-485 Forward Primer CBLB485 | DNA | Artificial Sequence | GCAGATTCTGCAGCAGGCTGGTTGATAATCTGGCGCAGGCTAACCAGG |
| 0019 | Mutant 33-485 502 template sequence | DNA | Artificial Sequence | TCTAAAGCGCAGATTCTGCAGCAGGCTGGTACTTCCGTTCTGGCGCAGGCTAACCAGGTT |
| 0020 | Mutant 33-485 Reverse Primer CBLB485 | DNA | Artificial Sequence | CCTGGTTAGCCTGCGCCAGATTATCAACCAGCCTGCTGCAGAATCTGC |
| 0021 | Mutant 33-485 DNA sequence of 485 Mutant (T7 Promoter to Stop) | DNA | Artificial Sequence | TAATACGACTCACTATAGGGGAATTGTGAGCGGATAACAATTCCCCTCTAGAATAATTTTGTTT AACTTTAAGAAGGAGATATACATATGCGGGGTTCTCATCATCATCATCATCATGGTATGGCTA GCATGACTGGTGGACAGCAAATGGGTCGGGATCTGTACGACCTGGTTCCGCGCGGTAGCGC GAAGGATCCGTCTGGTCTGCGTATCAACAGCGCGAAAGACGATGCGGCAGGCCAGGCGATT GCTAACCGCTTCACTTCTAATATCAAAGGTCTGACTCAGGCTTCCCGTAACGCTAACGACGGC ATTTCTATTGCGCAGACCACTGAAGGTGCGCTGAATGAAATCAACAACAACCTGCAGCGTGT GCGTGAGTTGTCTGTTCAGGCCACTAACGGGACTAACTCTGATTCCGATCTGAAATCTATCCA GGATGAAATTCAGCAACGTCTGGAAGAAATCGATCGCGTTTCTAATCAGACTCAATTTAACGG TGTTAAAGTCCTGTCTCAGGACAACCAGATGAAAATCCAGGTTGGTGCTAACGATGGTGAAAC CATTACCATCGATCTGCAAAAAATTGATGTGAAAAGCCTTGGCCTTGATGGGTTCAATGTTAAT TCCCCGGGAATTTCCGGTGGTGGTGGTGGAATTCTAGACTCCATGGGTACATTAATCAATGAA GACGCTGCCGCAGCCAAGAAAAGTACCGCTAACCCACTGGCTTCAATTGATTCTGCATTGTC AAAAGTGGACGCAGTTCGTTCTTCTCTGGGGGCAATTCAAAACCGTTTTGATTCAGCCATTAC CAACCTTGGCAATACGGTAACCAATCTGAACTCCGCGCGTAGCCGTATCGAAGATGCTGACT ATGCAACGGAAGTTTCTAATATGTCTAAAGCGCAGATTCTGCAGCAGGCTGGTTGATAA |
| 0022 | Mutant 33-485 Expressed Mutant 33-485 | PRT | Artificial Sequence | MRGSHHHHHHGMASMTGGQQMGRDLYDLVPRGSAKDPSGLRINSAKDDAAGQAIANRFTSNIK GLTQASRNANDGISIAQTTEGALNEINNNLQRVRELSVQATNGTNSDSDLKSIQDEIQQRLEEIDRV SNQTQFNGVKVLSQDNQMKIQVGANDGETITIDLQKIDVKSLGLDGFNVNSPGISGGGGGILDSM GTLINEDAAAAKKSTANPLASIDSALSKVDAVRSSLGAIQNRFDSAITNLGNTVTNLNSARSRIEDA DYATEVSNMSKAQILQQAG |

TABLE 1-continued

| Illustrative Flagellin-Based Agents | | | | |
|---|---|---|---|---|
| SEQ ID | Construct Name | DNA/ PRT | Species | Sequence |
| 0023 | Mutant 45CT Mutant 506T | PRT | Artificial Sequence | MAQVINTNSLSLLTQNNLNKSQSSLSSAIERLSSGLRINSAKDDAAGQAIANRFTSNIKGLTQASRN ANDGISIAQTTEGALNEINNNLQRVRELSVQATNGTNSDSDLKSIQDEIQQRLEEIDRVSNQTQFN GVKVLSQDNQMKIQVGANDGETITIDLQKIDVKSLGLDGFNVNSPGISGGGGGILDSMGTLINEDA AAAKKSTANPLASIDSALSKVDAVRSSLGAIQNRFDSAITNLGNTVTNLNSARSRIEDADYATEVSN MSKAQILQQAGTSVLAQANQVPQNVLSLLVPRGSHHHHHHGMASMTGGQQMGRDLYDDDDKD P |
| 0024 | Mutant 45CT Mutant 506T | DNA | Artificial Sequence | ATGGCACAAGTCATTAATACAAACAGCCTGTCGCTGTTGACCCAGAATAACCTGAACAAATCT CAGTCCTCACTGAGTTCCGCTATTGAGCGTCTGTCCTCTGGTCTGCGTATCAACAGCGCGAA AGACGATGCGGCAGGCCAGGCGATTGCTAACCGCTTCACTTCTAATATCAAAGGTCTGACTC AGGCTTCCCGTAACGCTAACGACGGCATTTCTATTGCGCAGACCACTGAAGGTGCGCTGAAT GAAATCAACAACAACCTGCAGCGTGTGCGTGAGTTGTCTGTTCAGGCCACTAACGGGACTAA CTCTGATTCCGATCTGAAATCTATCCAGGATGAAATTCAGCAACGTCTGGAAGAAATCGATCG CGTTTCTAATCAGACTCAATTTAACGGTGTTAAAGTCCTGTCTCAGGACAACCAGATGAAAATC CAGGTTGGTGCTAACGATGGTGAAACCATTACCATCGATCTGCAAAAAATTGATGTGAAAAGC CTTGGCCTTGATGGGTTCAATGTTAATTCCCCGGGAATTTCCGGTGGTGGTGGTGGAATTCTA GACTCCATGGGTACATTAATCAATGAAGACGCTGCCGCAGCCAAGAAAAGTACCGCTAACCC ACTGGCTTCAATTGATTCTGCATTGTCAAAAGTGGACGCAGTTCGTTCTTCTCTGGGGGCAAT TCAAAACCGTTTTGATTCAGCCATTACCAACCTTGGCAATACGGTAACCAATCTGAACTCCGC GCGTAGCCGTATCGAAGATGCTGACTATGCAACGGAAGTTTCTAATATGTCTAAAGCGCAGAT TCTGCAGCAGGCTGGTACTTCCGTTCTGGCGCAGGCTAACCAGGTTCCGCAAAACGTCCTCT CTTTACTGGTTCCGCGGGGTTCTCATCATCATCATCATCATGGTATGGCTAGCATGACTGGTG GACAGCAAATGGGTCGGGATCTGTACGACGATGACGATAAGGATCCGTAAGTCGACAAGCTT GCG |
| 0025 | Mutant 45CT Forward F45CT | DNA | Artificial Sequence | CGAAAGACCATATGGCAGGCCAGGCGATTGC |
| 0026 | Mutant 45CT Reverse R45CT | DNA | Artificial Sequence | CGCAAGCTTGTCGACTTACGGATCCTTATCGTC |
| 0027 | Mutant 45CT Sequence of 45CT construct | DNA | Artificial Sequence | TAATACGACTCACTATAGGGGAATTGTGAGCGGATAACAATTCCCCTCTAGAAATAATTTTGTT TAACTTTAAGAAGGAGATATACATATGGCAGGCCAGGCGATTGCTAACCGCTTCACTTCTAAT ATCAAAGGTCTGACTCAGGCTTCCCGTAACGCTAACGACGGCATTTCTATTGCGCAGACCACT GAAGGTGCGCTGAATGAAATCAACAACAACCTGCAGCGTGTGCGTGAGTTGTCTGTTCAGGC CACTAACGGGACTAACTCTGATTCCGATCTGAAATCTATCCAGGATGAAATTCAGCAACGTCT GGAAGAAATCGATCGCGTTTCTAATCAGACTCAATTTAACGGTGTTAAAGTCCTGTCTCAGGA CAACCAGATGAAAATCCAGGTTGGTGCTAACGATGGTGAAACCATTACCATCGATCTGCAAAA AATTGATGTGAAAAGCCTTGGCCTTGATGGGTTCAATGTTAATTCCCCGGGAATTTCCGGTGG TGGTGGTGGAATTCTAGACTCCATGGGTACATTAATCAATGAAGACGCTGCCGCAGCCAAGA AAAGTACCGCTAACCCACTGGCTTCAATTGATTCTGCATTGTCAAAAGTGGACGCAGTTCGTT CTTCTCTGGGGGCAATTCAAAACCGCTTTGATTCAGCCATTACCAACCTTGGCAATACGGTAA CCAATCTGAACTCCGCGCGTAGCCGTATCGAAGATGCTGACTATGCAACGGAAGTTTCTAATA TGTCTAAAGCGCAGATTCTGCAGCAGGCTGGTACTTCCGTTCTGGCGCAGGCTAACCAGGTT CCGCAAAACGTCCTCTCTTTACTGGTTCCGCGGGGTTCTCATCATCATCATCATCATGGTATG GCTAGCATGACTGGTGGACAGCAAATGGGTCGGGATCTGTACGACGATGACGATAAGGATCC GTAAGTCGAC |

TABLE 1-continued

Illustrative Flagellin-Based Agents

| SEQ ID | Construct Name | DNA/ PRT | Species | Sequence |
|---|---|---|---|---|
| 0028 | Mutant 45CT Expressed Mutant 45CT | PRT | Artificial Sequence | MAGQAIANRFTSNIKGLTQASRNANDGISIAQTTEGALNEINNNLQRVRELSVQATNGTNSDSDLK SIQDEIQQRLEEIDRVSNQTQFNGVKVLSQDNQMKIQVGANDGETITIDLQKIDVKSLGLDGFNVNS PGISGGGGGILDSMGTLINEDAAAAKKSTANPLASIDSALSKVDAVRSSLGAIQNRFDSAITNLGNT VTNLNSARSRIEDADYATEVSNMSKAQILQQAGTSVLAQANQVPQNVLSLLVPRGSHHHHHHGM ASMTGGQQMGRDLYDDDDKDP |
| 0029 | Mutant 33GP5 Expressed Mutant 33ML | DNA | Artificial Sequence | ATGAGCGGGTTACGGATCAACAGCGCGAAAGACGATGCGGCAGGCCAGGCGATTGCTAACC GCTTCACTTCTAATATCAAAGGTCTGACTCAGGCTTCCCGTAACGCTAACGACGGCATTTCTA TTGCGCAGACCACTGAAGGTGCGCTGAATGAAATCAACAACAACCTGCAGCGTGTGCGTGAG TTGTCTGTTCAGGCCACTAACGGGACTAACTCTGATTCCGATCTGAAATCTATCGGACCATCA GGTCAGGATGAAATTCAGCAACGTCTGGAAGAAATCGATCGCGTTTCTAATCAGACTCAATTT AACGGTGTTAAAGTCCTGTCTCAGGACAACCAGATGAAAATCCAGGTTGGTGCTAACGATGG TGAAACCATTACCATCGATCTGCAAAAAATTGATGTGAAAAGCCTTGGCCTTGATGGGTTCAA TGTTAATTCCCCGGGAAGTACCGCTAACCCACTGGCTTCAATTGATTCTGCATTGTCAAAAGT GGACGCAGTTCGTTCTTCTCTGGGGGCAATTCAAAACCGCTTTGATTCAGCCATTACCAACCT TGGCAATACGGTAACCAATCTGAACTCCGCGCGTAGCCGTATCGAAGATGCTGACTATGCAA CGGAAGTTTCTAATATGTCTAAAGCGCAGATTCTGCAGCAGGCTGGTACTTCCGTTCTGGCG CAGGCTAACCAGGTTCCGCAAAACGTCCTCTCTTTACTGGTTCCGCGGGGTTCTCATCATCAT CATCATCATGGTTAA |
| 0030 | Mutant 33GPS Expressed Mutant 33ML | PRT | Artificial Sequence | MSGLRINSAKDDAAGQAIANRFTSNIKGLTQASRNANDGISIAQTTEGALNEINNNLQRVRELSVQ ATNGTNSDSDLKSIGPSGQDEIQQRLEEIDRVSNQTQFNGVKVLSQDNQMKIQVGANDGETITIDL QKIDVKSLGLDGFNVNSPGSTANPLASIDSALSKVDAVRSSLGAIQNRFDSAITNLGNTVTNLNSAR SRIEDADYATEVSNMSKAQILQQAGTSVLAQANQVPQNVLSLLVPRGSHHHHHHG |
| 0031 | Mutant 33GP5 Forward primer FSY3CT | DNA | Artificial Sequence | GATATACATATGAGCGGGTTACGGATCAACAG |
| 0032 | Mutant 33GP5 Reverse primer RMIMxN | DNA | Artificial Sequence | AGATCTCCCGGGGAATTAACATTGAACCC |
| 0033 | Mutant 33GP5 DNA sequence of mutant 33GP5 | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG TAACGCTAACGACGGCATTTCTATTGCGCAGACCACTGAAGGTGCGCTGAATGAAATCAACAA CAACCTGCAGCGTGTGCGTGAGTTGTCTGTTCAGGCCACTGGACCATCAGGTGAAATTCAGC AACGTCTGGAAGAAATCGATCGCGTTTCTAATCAGACTCAATTTAACGGTGTTAAAGTCCTGT CTCAGGACAACCAGATGAAAATCCAGGTTGGTGCTAACGATGGTGAAACCATTACCATCGATC TGCAAAAAATTGATGTGAAAAGCCTTGGCCTTGATGGGTTCAATGTTAATTCCCCGGGAAGTA CCGCTAACCCACTGGCTTCAATTGATTCTGCATTGTCAAAAGTGGACGCAGTTCGTTCTTCTC TGGGGGCAATTCAAAACCGCTTTGATTCAGCCATTACCAACCTTGGCAATACGGTAACCAATC TGAACTCCGCGCGTAGCCGTATCGAAGATGCTGACTATGCAACGGAAGTTTCTAATATGTCTA AAGCGCAGATTCTGCAGCAGGCTGGTACTTCCGTTCTGGCGCAGGCTAACCAGGTTCCGCAA AACGTCCTCTCTTTACTGGTTCCGCGGGGTTCTCATCATCATCATCATCATGGTTAAGTCGAC |
| 0034 | Mutant 33GP5 Expressed Mutant | PRT | Artificial Sequence | MSGLRINSAKDDAAGQAIANRFTSNIKGLTQASRNANDGISIAQTTEGALNEINNNLQRVRELSVQ ATGPSGEIQQRLEEIDRVSNQTQFNGVKVLSQDNQMKIQVGANDGETITIDLQKIDVKSLGLDGFN |

TABLE 1-continued

Illustrative Flagellin-Based Agents

| SEQ ID | Construct Name | DNA/ PRT | Species | Sequence |
|---|---|---|---|---|
| | 33GP5 | | | VNSPGSTANLPLASIDSALSKVDAVRSSLGAIQNRFDSAITNGNTVTNLNSARSRIEDADYATEVSN<br>MSKAQILQQAGTSVLAQANQVPQNVLSLLVPRGSHHHHHHG |
| 0035 | Mutant 33ML<br>Mutant 33CT (Fixed A) | PRT | Artificial Sequence | MSGLRINSAKDDAAGQAIANRFTSNIKGLTQASRNANDGISIAQTTEGALNEINNNLQRVRELSVQ<br>ATNGTNSDSDLKSIQDEIQQRLEEIDRVSNQTQFNGVKVLSQDNQMKIQVGANDGETITIDLQKIDV<br>KSLGLDGFNVNSPGISGGGGGILDSMGTLINEDAAAAKKSTANPLASIDSALSKVDAVRSSLGAIQ<br>NRFDSAITNLGNTVTNLNSARSRIEDADYATEVSNMSKAQILQQAGTSVLAQANQVPQNVLSLLVP<br>RGSHHHHHHG |
| 0036 | Mutant 33ML<br>Mutant 33CT (Fixed A) | DNA | Artificial Sequence | ATGAGCGGGTTACGGATCAACAGCGCGAAAGACGATGCGGCAGGCCAGGCGATTGCTAACC<br>GCTTCACTTCTAATATCAAAGGTCTGACTCAGGCTTCCCGTAACGCTAACGACGGCATTTCTA<br>TTGCGCAGACCACTGAAGGTGCGCTGAATGAAATCAACAACAACCTGCAGCGTGTGCGTGAG<br>TTGTCTGTTCAGGCCACTAACGGGACTAACTCTGATTCCGATCTGAAATCTATCCAGGATGAA<br>ATTCAGCAACGTCTGGAAGAAATCGATCGCGTTTCTAATCAGACTCAATTTAACGGTGTTAAA<br>GTCCTGTCTCAGGACAACCAGATGAAAATCCAGGTTGGTGCTAACGATGGTGAAACCATTAC<br>CATCGATCTGCAAAAAATTGATGTGAAAAGCCTTGGCCTTGATGGGTTCAATGTTAATTCCCC<br>GGGAATTTCCGGTGGTGGTGGTGGAATTCTAGACTCCATGGGTACATTAATCAATGAAGACG<br>CTGCCGCAGCCAAGAAAAGTACCGCTAACCCACTGGCTTCAATTGATTCTGCATTGTCAAAAG<br>TGGACGCAGTTCGTTCTTCTCTGGGGGCAATTCAAAACCGCTTTGATTCAGCCATTACCAACC<br>TTGGCAATACGGTAACCAATCTGAACTCCGCGCGTAGCCGTATCGAAGATGCTGACTATGCA<br>ACGGAAGTTTCTAATATGTCTAAAGCGCAGATTCTGCAGCAGGCTGGTACTTCCGTTCTGGCG<br>CAGGCTAACCAGGTTCCGCAAAACGTCCTCTCTTTACTGGTTCCGCGGGGTTCTCATCATCAT<br>CATCATCATGGTTAA |
| 0037 | Mutant 33ML<br>Forward primer F502ML | DNA | Artificial Sequence | TCTAGACCCGGGAAGTACCGCTAACCCACTGGCTTCAATTG |
| 0038 | Mutant 33ML<br>Reverse primer R33CT | DNA | Artificial Sequence | CCAGTCATGTCGACTTAACCATGATGATGATGATGATGAG |
| 0039 | Mutant 33ML<br>502 template sequence | DNA | Artificial Sequence | CTCATCATCATCATCATCATGGTTAAGTCGACAAGCTTGCGGCCGCAGAGCTCGC |
| 0040 | Mutant 33ML<br>33ML construct | DNA | Artificial Sequence | TAATACGACTCACTATAGGGGAATTGTGAGCGGATAACAATTCCCCTCTAGAATAATTTTGTTT<br>AACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCG<br>TAACGCTAACGACGGCATTTCTATTGCGCAGACCACTGAAGGTGCGCTGAATGAAATCAACAA<br>CAACCTGCAGCGTGTGCGTGAGTTGTCTGTTCAGGCCACTAACGGGACTAACTCTGATTCCG<br>ATCTGAAATCTATCCAGGATGAAATTCAGCAACGTCTGGAAGAAATCGATCGCGTTTCTAATC<br>AGACTCAATTTAACGGTGTTAAAGTCCTGTCTCAGGACAACCAGATGAAAATCCAGGTTGGTG<br>CTAACGATGGTGAAACCATTACCATCGATCTGCAAAAAATTGATGTGAAAAGCCTTGGCCTTG<br>ATGGGTTCAATGTTAATTCCCCGGGAAGTACCGCTAACCCACTGGCTTCAATTGATTCTGCAT<br>TGTCAAAAGTGGACGCAGTTCGTTCTTCTCTGGGGGCAATTCAAAACCGCTTTGATTCAGCCA<br>TTACCAACCTTGGCAATACGGTAACCAATCTGAACTCCGCGCGTAGCCGTATCGAAGATGCT<br>GACTATGCAACGGAAGTTTCTAATATGTCTAAAGCGCAGATTCTGCAGCAGGCTGGTACTTCC<br>GTTCTGGCGCAGGCTAACCAGGTTCCGCAAAACGTCCTCTCTTTACTGGTTCCGCGGGGTTC<br>TCATCATCATCATCATCATGGTTAAGTCGAC |

TABLE 1-continued

| SEQ ID | Construct Name | DNA/ PRT | Species | Sequence |
|---|---|---|---|---|
| Illustrative Flagellin-Based Agents | | | | |
| 0041 | Mutant 33ML Expressed Mutant 33ML | DNA | Artificial Sequence | ATGAGCGGGTTACGGATCAACAGCGCGAAAGACGATGCGGCAGGCCAGGCGATTGCTAACC GCTTCACTTCTAATATCAAAGGTCTGACTCAGGCTTCCCGTAACGCTAACGACGGCATTTCTA TTGCGCAGACCACTGAAGGTGCGCTGAATGAAATCAACAACAACCTGCAGCGTGTGCGTGAG TTGTCTGTTCAGGCCACTAACGGGACTAACTCTGATTCCGATCTGAAATCTATCCAGGATGAA ATTCAGCAACGTCTGGAAGAAATCGATCGCGTTTCTAATCAGACTCAATTTAACGGTGTTAAA GTCCTGTCTCAGGACAACCAGATGAAAATCCAGGTTGGTGCTAACGATGGTGAAACCATTAC CATCGATCTGCAAAAAATTGATGTGAAAAGCCTTGGCCTTGATGGGTTCAATGTTAATTCCCC GGGAAGTACCGCTAACCCACTGGCTTCAATTGATTCTGCATTGTCAAAAGTGGACGCAGTTC GTTCTTCTCTGGGGGCAATTCAAAACCGCTTTGATTCAGCCATTACCAACCTTGGCAATACGG TAACCAATCTGAACTCCGCGCGTAGCCGTATCGAAGATGCTGACTATGCAACGGAAGTTTCTA ATATGTCTAAAGCGCAGATTCTGCAGCAGGCTGGTACTTCCGTTCTGGCGCAGGCTAACCAG GTTCCGCAAAACGTCCTCTCTTTACTGGTTCCGCGGGGTTCTCATCATCATCATCATCATGGT TAA |
| 0042 | Mutant 33ML Mutant 33ML | PRT | Artificial Sequence | MSGLRINSAKDDAAGQAIANRFTSNIKGLTQASRNANDGISIAQTTEGALNEINNNLQRVRELSVQ ATNGTNSDSDLKSIQDEIQQRLEEIDRVSNQTQFNGVKVLSQDNQMKIQVGANDGETITIDLQKIDV KSLGLDGFNVNSPGSTANPLASIDSALSKVDAVRSSLGAIQNRFDSAITNLGNTVTNLNSARSRIED ADYATEVSNMSKAQILQQAGTSVLAQANQVPQNVLSLLVPRGSHHHHHHG |
| 0043 | Mutant 37CT delta ND0 mutant based on CBLB506T | DNA | Artificial Sequence | ATGGCACAAGTCATTAATACAAACAGCCTGTCGCTGTTGACCCAGAATAACCTGAACAAATCT CAGTCCTCACTGAGTTCCGCTATTGAGCGTCTGTCCTCTGGTCTGCGTATCAACGGCGCGAA AGACGATGCGGCAGGCCAGGCGATTGCTAACCGCTTCACTTCTAATATCAAAGGTCTGACTC AGGCTTCCCGTAACGCTAACGACGGCATTTCTATTGCGCAGACCACTGAAGGTGCGCTGAAT GAAATCAACAACAACCTGCAGCGTGTGCGTGAGTTGTCTGTTCAGGCCACTAACGGGACTAA CTCTGATTCCGATCTGAAATCTATCCAGGATGAAATTCAGCAACGTCTGGAAGAAATCGATCG CGTTTCTAATCAGACTCAATTTAACGGTGTTAAAGTCCTGTCTCAGGACAACCAGATGAAAATC CAGGTTGGTGCTAACGATGGTGAAACCATTACCATCGATCTGCAAAAAATTGATGTGAAAAGC CTTGGCCTTGATGGGTTCAATGTTAATTCCCCGGGAATTTCCGGTGGTGGTGGTGGAATTCTA GACTCCATGGGTACATTAATCAATGAAGACGCTGCCGCAGCCAAGAAAAGTACCGCTAACCC ACTGGCTTCAATTGATTCTGCATTGTCAAAAGTGGACGCAGTTCGTTCTTCTCTGGGGGCAAT TCAAAACCGCTTTGATTCAGCCATTACCAACCTTGGCAATACGGTAACCAATCTGAACTCCGC GCGTAGCCGTATCGAAGATGCTGACTATGCAACGGAAGTTTCTAATATGTCTAAAGCGCAGAT TCTGCAGCAGGCTGGTACTTCCGTTCTGGCGCAGGCTAACCAGGTTCCGCAAAACGTCCTCT CTTTACTGGTTCCGCGGGGTTCTCATCATCATCATCATCATGGTATGGCTAGCATGACTGGTG GACAGCAAATGGGTCGGGATCTGTACGACGATGACGATAAGGATCCGTAAGTCGACAAGCTT GCG |
| 0044 | Mutant 37CT delta ND0 mutant based on CBLB506T | PRT | Artificial Sequence | MAQVINTNSLSLLTQNNLNKSQSSLSSAIERLSSGLRINGAKDDAAGQAIANRFTSNIKGLTQASRN ANDGISIAQTTEGALNEINNNLQRVRELSVQATNGTNSDSDLKSIQDEIQQRLEEIDRVSNQTQFN GVKVLSQDNQMKIQVGANDGETITIDLQKIDVKSLGLDGFNVNSPGISGGGGGILDSMGTLINEDA AAAKKSTANPLASIDSALSKVDAVRSSLGAIQNRFDSAITNLGNTVTNLNSARSRIEDADYATEVSN MSKAQILQQAGTSVLAQANQVPQNVLSLLVPRGSHHHHHHGMASMTGGQQMGRDLYDDDDKD P |
| 0045 | Mutant 37CT Forward F37CT | DNA | Artificial Sequence | CTCTGGTCATATGATCAACAGCGCGAAAGACGATGC |

TABLE 1-continued

Illustrative Flagellin-Based Agents

| SEQ ID | Construct Name | DNA/ PRT | Species | Sequence |
|---|---|---|---|---|
| 0046 | Mutant 370T Reverse R37CT | DNA | Artificial Sequence | TCTAGAGTCGACTATTAAGCCATACCATGATGATGATGATGATGAG |
| 0047 | Mutant 37CT 37CT construct | DNA | Artificial Sequence | TAATACGACTCACTATAGGGGAATTGTGAGCGGATAACAATTCCCCTCTAGAAATAATTTTGTT<br>TAACTTTAAGAAGGAGATATACATATGATCAACAGCGCGAAAGACGATGCGGCAGGCCAGGC<br>GATTGCTAACCGCTTCACTTCTAATATCAAAGGTCTGACTCAGGCTTCCCGTAACGCTAACGA<br>CGGCATTTCTATTGCGCAGACCACTGAAGGTGCGCTGAATGAAATCAACAACAACCTGCAGC<br>GTGTGCGTGAGTTGTCTGTTCAGGCCACTAACGGGACTAACTCTGATTCCGATCTGAAATCTA<br>TCCAGGATGAAATTCAGCAACGTCTGGAAGAAATCGATCGCGTTTCTAATCAGACTCAATTTA<br>ACGGTGTTAAAGTCCTGTCTCAGGACAACCAGATGAAAATCCAGGTTGGTGCTAACGATGGT<br>GAAACCATTACCATCGATCTGCAAAAAATTGATGTGAAAAGCCTTGGCCTTGATGGGTTCAAT<br>GTTAATTCCCCGGGAATTTCCGGTGGTGGTGGTGGAATTCTAGACTCCATGGGTACATTAATC<br>AATGAAGACGCTGCCGCAGCCAAGAAAAGTACCGCTAACCCACTGGCTTCAATTGATTCTGC<br>ATTGTCAAAAGTGGACGCAGTTCGTTCTTCTCTGGGGGCAATTCAAAACCGCTTTGATTCAGC<br>CATTACCAACCTTGGCAATACGGTAACCAATCTGAACTCCGCGCGTAGCCGTATCGAAGATG<br>CTGACTATGCAACGGAAGTTTCTAATATGTCTAAAGCGCAGATTCTGCAGCAGGCTGGTACTT<br>CCGTTCTGGCGCAGGCTAACCAGGTTCCGCAAAACGTCCTCTCTTTACTGGTTCCGCGGGGT<br>TCTCATCATCATCATCATCATGGTATGGCTTAATAGTCGAC |
| 0048 | Mutant 37CT Mutant 37CT | PRT | Artificial Sequence | MINSAKDDAAGQAIANRFTSNIKGLTQASRNANDGISIAQTTEGALNEINNNLQRVRELSVQATNG<br>TNSDSDLKSIQDEIQQRLEEIDRVSNQTQFNGVKVLSQDNQMKIQVGANDGETITIDLQKIDVKSLG<br>LDGFNVNSPGISGGGGGILDSMGTLINEDAAAAKKSTANPLASIDSALSKVDAVRSSLGAIQNRFD<br>SAITNLGNTVTNLNSARSRIEDADYATEVSNMSKAQILQQAGTSVLAQANQVPQNVLSLLVPRGSH<br>HHHHHGMA |
| 0049 | Mutant 445 502-SY1 | PRT | Artificial Sequence | MRGSHHHHHHGMASMTGGQQMGRDLYDLVPRGSAKDPMAQVINTNSLSLLTQNNLNKSQSSLS<br>SAIERLSSGLRINSAKDDAAGQAIANRFTSNIKGLTQASRNANDGISIAQTTEGALNEINNNLQRVR<br>ELSVQATNGTNSDSDLKSIQDEIQQRLEEIDRVSNQTQFNGVKVLSQDNQMKIQVGANDGETITID<br>LQKIDVKSLGLDGFNVNSPGISGGGGGILDSMGTLINEDAAAAKKSTANPLASIDSALSKVDAVRSS<br>LGAIQNRFDSAITNLGNTVTNLNSARSRIEDADYATEVSNMSKAQILQQAGTSVLAQANQVPQNVL<br>SLLR |
| 0050 | Mutant 445 502-SY1 | DNA | Artificial Sequence | ATGCGGGGTTCTCATCATCATCATCATCATGGTATGGCTAGCATGACTGGTGGACAGCAAATG<br>GGTCGGGATCTGTACGACCTGGTTCCGCGCGGTAGCGCGAAGGATCCGATGGCACAAGTCA<br>TTAATACAAACAGCCTGTCGCTGTTGACCCAGAATAACCTGAACAAATCTCAGTCCTCACTGA<br>GTTCCGCTATTGAGCGTCTGTCCTCTGGTCTGCGTATCAACAGCGCGAAAGACGATGCGGCA<br>GGCCAGGCGATTGCTAACCGCTTCACTTCTAATATCAAAGGTCTGACTCAGGCTTCCCGTAAC<br>GCTAACGACGGCATTTCTATTGCGCAGACCACTGAAGGTGCGCTGAATGAAATCAACAACAA<br>CCTGCAGCGTGTGCGTGAGTTGTCTGTTCAGGCCACTAACGGGACTAACTCTGATTCCGATC<br>TGAAATCTATCCAGGATGAAATTCAGCAACGTCTGGAAGAAATCGATCGCGTTTCTAATCAGA<br>CTCAATTTAACGGTGTTAAAGTCCTGTCTCAGGACAACCAGATGAAAATCCAGGTTGGTGCTA<br>ACGATGGTGAAACCATTACCATCGATCTGCAAAAAATTGATGTGAAAAGCCTTGGCCTTGATG<br>GGTTCAATGTTAATTCCCCGGGAATTTCCGGTGGTGGTGGTGGAATTCTAGACTCCATGGGT<br>ACATTAATCAATGAAGACGCTGCCGCAGCCAAGAAAAGTACCGCTAACCCACTGGCTTCAATT<br>GATTCTGCATTGTCAAAAGTGGACGCAGTTCGTTCTTCTCTGGGGGCAATTCAAAACCGTTTT<br>GATTCAGCCATTACCAACCTTGGCAATACGGTAACCAATCTGAACTCCGCGCGTAGCCGTATC<br>GAAGATGCTGACTATGCAACGGAAGTTTCTAATATGTCTAAAGCGCAGATTCTGCAGCAGGCT<br>GGTACTTCCGTTCTGGCGCAGGCTAACCAGGTTCCGCAAAACGTCCTCTCTTTACTGCGTTAA |

TABLE 1-continued

Illustrative Flagellin-Based Agents

| SEQ ID | Construct Name | DNA/ PRT | Species | Sequence |
|---|---|---|---|---|
| 0051 | Mutant 445 Forward Primer CBLB445 | DNA | Artificial Sequence | GGCAATTCAAAACCGTTTTGATTAAGCCATTACCAACCTTGG |
| 0052 | Mutant 445 Reverse Primer CBLB445 | DNA | Artificial Sequence | CCAAGGTTGGTAATGGCTTAATCAAAACGGTTTTGAATTGCC |
| 0053 | Mutant 445 mutant 445 | DNA | Artificial Sequence | TAATACGACTCACTATAGGGGAATTGTGAGCGGATAACAATTCCCCTCTAGAATAATTTTGTTT AACTTTAAGAAGGAGATATACATATGCGGGGTTCTCATCATCATCATCATCATGGTATGGCTA GCATGACTGGTGGACAGCAAATGGGTCGGGATCTGTACGACCTGGTTCCGCGCGGTAGCGC GAAGGATCCGATGGCACAAGTCATTAATACAAACAGCCTGTCGCTGTTGACCCAGAATAACCT GAACAAATCTCAGTCCTCACTGAGTTCCGCTATTGAGCGTCTGTCCTCTGGTCTGCGTATCAA CAGCGCGAAAGACGATGCGGCAGGCCAGGCGATTGCTAACCGCTTCACTTCTAATATCAAAG GTCTGACTCAGGCTTCCCGTAACGCTAACGACGGCATTTCTATTGCGCAGACCACTGAAGGT GCGCTGAATGAAATCAACAACAACCTGCAGCGTGTGCGTGAGTTGTCTGTTCAGGCCACTAA CGGGACTAACTCTGATTCCGATCTGAAATCTATCCAGGATGAAATTCAGCAACGTCTGGAAGA AATCGATCGCGTTTCTAATCAGACTCAATTTAACGGTGTTAAAGTCCTGTCTCAGGACAACCA GATGAAAATCCAGGTTGGTGCTAACGATGGTGAAACCATTACCATCGATCTGCAAAAAATTGA TGTGAAAAGCCTTGGCCTTGATGGGTTCAATGTTAATTCCCCGGGAATTTCCGGTGGTGGTG GTGGAATTCTAGACTCCATGGGTACATTAATCAATGAAGACGCTGCCGCAGCCAAGAAAAGTA CCGCTAACCCACTGGCTTCAATTGATTCTGCATTGTCAAAAGTGGACGCAGTTCGTTCTTCTC TGGGGGCAATTCAAAACCGTTTTGATTAA |
| 0054 | Mutant 445 mutant 445 | PRT | Artificial Sequence | MRGSHHHHHHGMASMTGGQQMGRDLYDLVPRGSAKDPMAQVINTNSLSLLTQNNLNKSQSSLS SAIERLSSGLRINSAKDDAAGQAIANRFTSNIKGLTQASRNANDGISIAQTTEGALNEINNNLQRVR ELSVQATNGTNSDSDLKSIQDEIQQRLEEIDRVSNQTQFNGVKVLSQDNQMKIQVGANDGETITID LQKIDVKSLGLDGFNVNSPGISGGGGGILDSMGTLINEDAAAKKSTANPLASIDSALSKVDAVRSS LGAIQNRFD |
| 0055 | Mutant 461 Forward Primer CBLB461 | DNA | Artificial Sequence | CAATCTGAACTCCGCGCGTTGACGTATCTAAGATGCTGACTATGC |
| 0056 | Mutant 461 Reverse Primer CBLB461 | DNA | Artificial Sequence | GCATAGTCAGCATCTTAGATACGTCAACGCGCGGAGTTCAGATTG |
| 0057 | Mutant 461 Mutant 461 | DNA | Artificial Sequence | TAATACGACTCACTATAGGGGAATTGTGAGCGGATAACAATTCCCCTCTAGAATAATTTTGTTT AACTTTAAGAAGGAGATATACATATGCGGGGTTCTCATCATCATCATCATCATGGTATGGCTA GCATGACTGGTGGACAGCAAATGGGTCGGGATCTGTACGACCTGGTTCCGCGCGGTAGCGC GAAGGATCCGATGGCACAAGTCATTAATACAAACAGCCTGTCGCTGTTGACCCAGAATAACCT GAACAAATCTCAGTCCTCACTGAGTTCCGCTATTGAGCGTCTGTCCTCTGGTCTGCGTATCAA CAGCGCGAAAGACGATGCGGCAGGCCAGGCGATTGCTAACCGCTTCACTTCTAATATCAAAG GTCTGACTCAGGCTTCCCGTAACGCTAACGACGGCATTTCTATTGCGCAGACCACTGAAGGT GCGCTGAATGAAATCAACAACAACCTGCAGCGTGTGCGTGAGTTGTCTGTTCAGGCCACTAA CGGGACTAACTCTGATTCCGATCTGAAATCTATCCAGGATGAAATTCAGCAACGTCTGGAAGA |

TABLE 1-continued

| Illustrative Flagellin-Based Agents | | | | |
|---|---|---|---|---|
| SEQ ID | Construct Name | DNA/ PRT | Species | Sequence |
| | | | | AATCGATCGCGTTTCTAATCAGACTCAATTTAACGGTGTTAAAGTCCTGTCTCAGGACAACCA<br>GATGAAAATCCAGGTTGGTGCTAACGATGGTGAAACCATTACCATCGATCTGCAAAAAATTGA<br>TGTGAAAAGCCTTGGCCTTGATGGGTTCAATGTTAATTCCCCGGGAATTTCCGGTGGTGGTG<br>GTGGAATTCTAGACTCCATGGGTACATTAATCAATGAAGACGCTGCCGCAGCCAAGAAAAGTA<br>CCGCTAACCCACTGGCTTCAATTGATTCTGCATTGTCAAAAGTGGACGCAGTTCGTTCTTCTC<br>TGGGGGCAATTCAAAACCGTTTTGATTCAGCCATTACCAACCTTGGCAATACGGTAACCAATC<br>TGAACTCCGCGCGTTGACGTATCTAA |
| 0058 | Mutant 461<br>Mutant 461 | PRT | Artificial Sequence | MRGSHHHHHHGMASMTGGQQMGRDLYDLVPRGSAKDPMAQVINTNSLSLLTQNNLNKSQSSLS<br>SAIERLSSGLRINSAKDDAAGQAIANRFTSNIKGLTQASRNANDGISIAQTTEGALNEINNNLQRVR<br>ELSVQATNGTNSDSDLKSIQDEIQQRLEEIDRVSNQTQFNGVKVLSQDNQMKIQVGANDGETITID<br>LQKIDVKSLGLDGFNVNSPGISGGGGGILDSMGTLINEDAAAAKKSTANPLASIDSALSKVDAVRSS<br>LGAIQNRFDSAITNLGNTVTNLNSAR |
| 0059 | Mutant 467<br>Forward Primer<br>CBLB467 | DNA | Artificial Sequence | CGTAGCCGTATCGAAGATGCTTAATAGGCAACGGAAGTTTCTAATATG |
| 0060 | Mutant 467<br>Reverse Primer<br>CBLB467 | DNA | Artificial Sequence | CATATTAGAAACTTCCGTTGCCTATTAAGCATCTTCGATACGGCTACG |
| 0061 | Mutant 467<br>Mutant 467 | DNA | Artificial Sequence | TAATACGACTCACTATAGGGGAATTGTGAGCGGATAACAATTCCCCTCTAGAATAATTTTGTTT<br>AACTTTAAGAAGGAGATATACATATGCGGGGTTCTCATCATCATCATCATCATGGTATGGCTA<br>GCATGACTGGTGGACAGCAAATGGGTCGGGATCTGTACGACCTGGTTCCGCGCGGTAGCGC<br>GAAGGATCCGATGGCACAAGTCATTAATACAAACAGCCTGTCGCTGTTGACCCAGAATAACCT<br>GAACAAATCTCAGTCCTCACTGAGTTCCGCTATTGAGCGTCTGTCCTCTGGTCTGCGTATCAA<br>CAGCGCGAAAGACGATGCGGCAGGCCAGGCGATTGCTAACCGCTTCACTTCTAATATCAAAG<br>GTCTGACTCAGGCTTCCCGTAACGCTAACGACGGCATTTCTATTGCGCAGACCACTGAAGGT<br>GCGCTGAATGAAATCAACAACAACCTGCAGCGTGTGCGTGAGTTGTCTGTTCAGGCCACTAA<br>CGGGACTAACTCTGATTCCGATCTGAAATCTATCCAGGATGAAATTCAGCAACGTCTGGAAGA<br>AATCGATCGCGTTTCTAATCAGACTCAATTTAACGGTGTTAAAGTCCTGTCTCAGGACAACCA<br>GATGAAAATCCAGGTTGGTGCTAACGATGGTGAAACCATTACCATCGATCTGCAAAAAATTGA<br>TGTGAAAAGCCTTGGCCTTGATGGGTTCAATGTTAATTCCCCGGGAATTTCCGGTGGTGGTG<br>GTGGAATTCTAGACTCCATGGGTACATTAATCAATGAAGACGCTGCCGCAGCCAAGAAAAGTA<br>CCGCTAACCCACTGGCTTCAATTGATTCTGCATTGTCAAAAGTGGACGCAGTTCGTTCTTCTC<br>TGGGGGCAATTCAAAACCGTTTTGATTCAGCCATTACCAACCTTGGCAATACGGTAACCAATC<br>TGAACTCCGCGCGTAGCCGTATCGAAGATGCTTAATAG |
| 0062 | Mutant 467<br>Mutant 467 | PRT | Artificial Sequence | MRGSHHHHHHGMASMTGGQQMGRDLYDLVPRGSAKDPMAQVINTNSLSLLTQNNLNKSQSSLS<br>SAIERLSSGLRINSAKDDAAGQAIANRFTSNIKGLTQASRNANDGISIAQTTEGALNEINNNLQRVR<br>ELSVQATNGTNSDSDLKSIQDEIQQRLEEIDRVSNQTQFNGVKVLSQDNQMKIQVGANDGETITID<br>LQKIDVKSLGLDGFNVNSPGISGGGGGILDSMGTLINEDAAAAKKSTANPLASIDSALSKVDAVRSS<br>LGAIQNRFDSAITNLGNTVTNLNSARSRIEDA |
| 0063 | Mutant 47CCT<br>CBLB502 | DNA | Artificial Sequence | ATGCGGGGTTCTCATCATCATCATCATCATGGTATGGCTAGCATGACTGGTGGACAGCAAATG<br>GGTCGGGATCTGTACGACGATGACGATAAGGATCCGATGGCACAAGTCATTAATACAAACAG<br>CCTGTCGCTGTTGACCCAGAATAACCTGAACAAATCTCAGTCCTCACTGAGTTCCGCTATTGA |

TABLE 1-continued

Illustrative Flagellin-Based Agents

| SEQ ID | Construct Name | DNA/ PRT | Species | Sequence |
|---|---|---|---|---|
| | | | | GCGTCTGTCCTCTGGTCTGCGTATCAACAGCGCGAAAGACGATGCGGCAGGCCAGGCGATT<br>GCTAACCGCTTCACTTCTAATATCAAAGGTCTGACTCAGGCTTCCCGTAACGCTAACGACGGC<br>ATTTCTATTGCGCAGACCACTGAAGGTGCGCTGAATGAAATCAACAACAACCTGCAGCGTGT<br>GCGTGAGTTGTCTGTTCAGGCCACTAACGGGACTAACTCTGATTCCGATCTGAAATCTATCCA<br>GGATGAAATTCAGCAACGTCTGGAAGAAATCGATCGCGTTTCTAATCAGACTCAATTTAACGG<br>TGTTAAAGTCCTGTCTCAGGACAACCAGATGAAAATCCAGGTTGGTGCTAACGATGGTGAAAC<br>CATTACCATCGATCTGCAAAAAATTGATGTGAAAAGCCTTGGCCTTGATGGGTTCAATGTTAAT<br>TCCCCGGGAATTTCCGGTGGTGGTGGTGGAATTCTAGACTCCATGGGTACATTAATCAATGAA<br>GACGCTGCCGCAGCCAAGAAAAGTACCGCTAACCCACTGGCTTCAATTGATTCTGCATTGTC<br>AAAAGTGGACGCAGTTCGTTCTTCTCTGGGGGCAATTCAAAACCGTTTTGATTCAGCCATTAC<br>CAACCTTGGCAATACGGTAACCAATCTGAACTCCGCGCGTAGCCGTATCGAAGATGCTGACT<br>ATGCAACGGAAGTTTCTAATATGTCTAAAGCGCAGATTCTGCAGCAGGCTGGTACTTCCGTTC<br>TGGCGCAGGCTAACCAGGTTCCGCAAAACGTCCTCTCTTTACTGCGTTAA |
| 0064 | Mutant 470CT<br>Forward Primer F470CT | DNA | Artificial Sequence | CGATAAGGATCATATGGCACAAGTCATTAATAC |
| 0065 | Mutant 470CT<br>Reverse Primer R470CT | DNA | Artificial Sequence | AGATCTGTCGACTTAACCATGATGATGATGATGATGAGAACCCCGCGGAACCAGTGCATAGT<br>CAGCATCTTCGATACG |
| 0066 | Mutant 470CT<br>Mutant 470CT | DNA | Artificial Sequence | TAATACGACTCACTATAGGGGAATTGTGAGCGGATAACAATTCCCCTCTAGAATAATTTTGTTT<br>AACTTTAAGAAGGAGATATACATATGGCACAAGTCATTAATACAAACAGCCTGTCGCTGTTGA<br>CCCAGAATAACCTGAACAAATCTCAGTCCTCACTGAGTTCCGCTATTGAGCGTCTGTCCTCTG<br>GTCTGCGTATCAACAGCGCGAAAGACGATGCGGCAGGCCAGGCGATTGCTAACCGCTTCAC<br>TTCTAATATCAAAGGTCTGACTCAGGCTTCCCGTAACGCTAACGACGGCATTTCTATTGCGCA<br>GACCACTGAAGGTGCGCTGAATGAAATCAACAACAACCTGCAGCGTGTGCGTGAGTTGTCTG<br>TTCAGGCCACTAACGGGACTAACTCTGATTCCGATCTGAAATCTATCCAGGATGAAATTCAGC<br>AACGTCTGGAAGAAATCGATCGCGTTTCTAATCAGACTCAATTTAACGGTGTTAAAGTCCTGT<br>CTCAGGACAACCAGATGAAAATCCAGGTTGGTGCTAACGATGGTGAAACCATTACCATCGATC<br>TGCAAAAAATTGATGTGAAAAGCCTTGGCCTTGATGGGTTCAATGTTAATTCCCCGGGAATTT<br>CCGGTGGTGGTGGTGGAATTCTAGACTCCATGGGTACATTAATCAATGAAGACGCTGCCGCA<br>GCCAAGAAAAGTACCGCTAACCCACTGGCTTCAATTGATTCTGCATTGTCAAAAGTGGACGCA<br>GTTCGTTCTTCTCTGGGGGCAATTCAAAACCGTTTTGATTCAGCCATTACCAACCTTGGCAAT<br>ACGGTAACCAATCTGAACTCCGCGCGTAGCCGTATCGAAGATGCTGACTATGCACTGGTTCC<br>GCGGGGTTCTCATCATCATCATCATCATGGTTAAGTCGAC |
| 0067 | Mutant 470CT<br>Mutant 470CT | PRT | Artificial Sequence | MAQVINTNSLSLLTQNNLNKSQSSLSSAIERLSSGLRINSAKDDAAGQAIANRFTSNIKGLTQASRN<br>ANDGISIAQTTEGALNEINNNLQRVRELSVQATNGTNSDSDLKSIQDEIQQRLEEIDRVSNQTQFN<br>GVKVLSQDNQMKIQVGANDGETITIDLQKIDVKSLGLDGFNVNSPGISGGGGGILDSMGTLINEDA<br>AAAKKSTANPLASIDSALSKVDAVRSSLGAIQNRFDSAITNLGNTVTNLNSARSRIEDADYALVPRG<br>SHHHHHHG |
| 0068 | Mutant 485CT<br>Reverse primer R485MC | DNA | Artificial Sequence | AGATCTCCGCGGAACCAGACCAGCCTGCTGCAGAATCTGC |
| 0069 | Mutant 485CT<br>DNA Sequence of 485CT | DNA | Artificial Sequence | TAATACGACTCACTATAGGGGAATTGTGAGCGGATAACAATTCCCCTCTAGAATAATTTTGTTT<br>AACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCG |

TABLE 1-continued

| Illustrative Flagellin-Based Agents | | | | |
|---|---|---|---|---|
| SEQ ID | Construct Name | DNA/ PRT | Species | Sequence |
| | | | | TAACGCTAACGACGGCATTTCTATTGCGCAGACCACTGAAGGTGCGCTGAATGAAATCAACAA CAACCTGCAGCGTGTGCGTGAGTTGTCTGTTCAGGCCACTAACGGGACTAACTCTGATTCCG ATCTGAAATCTATCCAGGATGAAATTCAGCAACGTCTGGAAGAAATCGATCGCGTTTCTAATC AGACTCAATTTAACGGTGTTAAAGTCCTGTCTCAGGACAACCAGATGAAAATCCAGGTTGGTG CTAACGATGGTGAAACCATTACCATCGATCTGCAAAAAATTGATGTGAAAAGCCTTGGCCTTG ATGGGTTCAATGTTAATTCCCCGGGAAGTACCGCTAACCCACTGGCTTCAATTGATTCTGCAT TGTCAAAAGTGGACGCAGTTCGTTCTTCTCTGGGGGCAATTCAAAACCGCTTTGATTCAGCCA TTACCAACCTTGGCAATACGGTAACCAATCTGAACTCCGCGCGTAGCCGTATCGAAGATGCT GACTATGCAACGGAAGTTTCTAATATGTCTAAAGCGCAGATTCTGCAGCAGGCTGGTCTGGTT CCGCGGGGTTCTCATCATCATCATCATCATGGTTAAGTCGAC |
| 0070 | Mutant 485CT Mutant 485CT | DNA | Artificial Sequence | ATGAGCGGGTTACGGATCAACAGCGCGAAAGACGATGCGGCAGGCCAGGCGATTGCTAACC GCTTCACTTCTAATATCAAAGGTCTGACTCAGGCTTCCCGTAACGCTAACGACGGCATTTCTA TTGCGCAGACCACTGAAGGTGCGCTGAATGAAATCAACAACAACCTGCAGCGTGTGCGTGAG TTGTCTGTTCAGGCCACTAACGGGACTAACTCTGATTCCGATCTGAAATCTATCCAGGATGAA ATTCAGCAACGTCTGGAAGAAATCGATCGCGTTTCTAATCAGACTCAATTTAACGGTGTTAAA GTCCTGTCTCAGGACAACCAGATGAAAATCCAGGTTGGTGCTAACGATGGTGAAACCATTAC CATCGATCTGCAAAAAATTGATGTGAAAAGCCTTGGCCTTGATGGGTTCAATGTTAATTCCCC GGGAAGTACCGCTAACCCACTGGCTTCAATTGATTCTGCATTGTCAAAAGTGGACGCAGTTC GTTCTTCTCTGGGGGCAATTCAAAACCGCTTTGATTCAGCCATTACCAACCTTGGCAATACGG TAACCAATCTGAACTCCGCGCGTAGCCGTATCGAAGATGCTGACTATGCAACGGAAGTTTCTA ATATGTCTAAAGCGCAGATTCTGCAGCAGGCTGGTCTGGTTCCGCGGGGTTCTCATCATCAT CATCATCATGGTTAA |
| 0071 | Mutant 485CT Mutant 485CT | PRT | Artificial Sequence | MSGLRINSAKDDAAGQAIANRFTSNIKGLTQASRNANDGISIAQTTEGALNEINNNLQRVRELSVQ ATNGTNSDSDLKSIQDEIQQRLEEIDRVSNQTQFNGVKVLSQDNQMKIQVGANDGETITIDLQKIDV KSLGLDGFNVNSPGSTANPLASIDSALSKVDAVRSSLGAIQNRFDSAITNLGNTVTNLNSARSRIED ADYATEVSNMSKAQILQQAGLVPRGSHHHHHHG |
| 0072 | Mutant 485D DNA template for deletion mutations from Mutant 485CT variant | DNA | Artificial Sequence | AACCCACTGGCTTCAATTGATTCTGCATTGTCAAAAGTGGACGCAGTTCGTTCTTCTCTGGGG GCAATTCAAAACCGTTTTGATTCAGCCATTACCGCCCTTGGCAATACGGTAACCAAT |
| 0073 | Mutant 485D PRT sequence for deletion mutations from Mutant 485CT variant | PRT | Artificial Sequence | NPLASIDSALSKVDAVRSSLGAIQNRFDSAITALGNTVTN |
| 0074 | Mutant 485D Forward Primer F485D | DNA | Artificial Sequence | GTTCGTTCTTCTCTGGGGGCAATTGATTCAGCCATTACCGCCCTTG |
| 0075 | Mutant 485D Reverse Primer R485D | DNA | Artificial Sequence | CAAGGGCGGTAATGGCTGAATCAATTGCCCCCAGAGAAGAACGAAC |
| 0076 | Mutant 485D DNA Sequence of 4850T_Delta construct | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG |

TABLE 1-continued

| SEQ ID | Construct Name | DNA/ PRT | Species | Sequence |
|---|---|---|---|---|
| Illustrative Flagellin-Based Agents | | | | |
| | | | | TAACGCTAACGACGGCATTTCTATTGCGCAGACCACTGAAGGTGCGCTGAATGAAATCAACAACAACCTGCAGCGTGTGCGTGAGTTGTCTGTTCAGGCCACTAACGGGACTAACTCTGATTCCGATCTGAAATCTATCCAGGATGAAATTCAGCAACGTCTGGAAGAAATCGATCGCGTTTCTAATCAGACTCAATTTAACGGTGTTAAAGTCCTGTCTCAGGACAACCAGATGAAAATCCAGGTTGGTGCTAACGATGGTGAAACCATTACCATCGATCTGCAAAAAATTGATGTGAAAAGCCTTGGCCTTGATGGGTTCAATGTTAATTCCCCGGGAAGTACCGCTAACCCACTGGCTTCAATTGATTCTGCATTGTCAAAAGTGGACGCAGTTCGTTCTTCTCTGGGGGCAATTGATTCAGCCATTACCGCCCTTGGCAATACGGTAACCAATCTGAACTCCGCGCGTAGCCGTATCGAAGATGCTGACTATGCAACGGAAGTTTCTAATATGTCTAAAGCGCAGATTCTGCAGCAGGCTGGTCTGGTTCCGCGGGGTTCTCATCATCATCATCATCATGGTTAAGTCGAC |
| 0077 | Mutant 485D Mutant 485D (CT_Delta 439-442) | PRT | Artificial Sequence | MSGLRINSAKDDAAGQAIANRFTSNIKGLTQASRNANDGISIAQTTEGALNEINNNLQRVRELSVQATNGTNSDSDLKSIQDEIQQRLEEIDRVSNQTQFNGVKVLSQDNQMKIQVGANDGETITIDLQKIDVKSLGLDGFNVNSPGSTANPLASIDSALSKVDAVRSSLGAIDSAITALGNTVTNLNSARSRIEDADYATEVSNMSKAQILQQAGLVPRGSHHHHHHG |
| 0078 | Mutant CGD1 Mutant SY3CT | DNA | Artificial Sequence | ATGAGCGGGTTACGGATCAACAGCGCGAAAGACGATGCGGCAGGCCAGGCGATTGCTAACCGCTTCACTTCTAATATCAAAGGTCTGACTCAGGCTTCCCGTAACGCTAACGACGGCATTTCTATTGCGCAGACCACTGAAGGTGCGCTGAATGAAATCAACAACAACCTGCAGCGTGTGCGTGAGTTGTCTGTTCAGGCCACTAACGGGACTAACTCTGATTCCGATCTGAAATCTATCCAGGATGAAATTCAGCAACGTCTGGAAGAAATCGATCGCGTTTCTAATCAGACTCAATTTAACGGTGTTAAAGTCCTGTCTCAGGACAACCAGATGAAAATCCAGGTTGGTGCTAACGATGGTGAAACCATTACCATCGATCTGCAAAAAATTGATGTGAAAAGCCTTGGCCTTGATGGGTTCAATGTTAATTCCCCGGGAAGTACCGCTAACCCACTGGCTTCAATTGATTCTGCATTGTCAAAAGTGGACGCAGTTCGTTCTTCTCTGGGGGCAATTCAAAACCGCTTTGATTCAGCCATTACCAACCTTGGCAATACGGTAACCAATCTGAACTCCGCGCGTAGCCGTATCGAAGATGCTGACTATGCACTGGTTCCGCGGGGTTCTCATCATCATCATCATCATGGTTAA |
| 0079 | Mutant CGD1 Mutant SY3CT | PRT | Artificial Sequence | MSGLRINSAKDDAAGQAIANRFTSNIKGLTQASRNANDGISIAQTTEGALNEINNNLQRVRELSVQATNGTNSDSDLKSIQDEIQQRLEEIDRVSNQTQFNGVKVLSQDNQMKIQVGANDGETITIDLQKIDVKSLGLDGFNVNSPGSTANPLASIDSALSKVDAVRSSLGAIQNRFDSAITNLGNTVTNLNSARSRIEDADYALVPRGSHHHHHHG |
| 0080 | Mutant CGD1 GFPuv4 | DNA | Artificial Sequence | ATGAGTAAAGGAGAAGAACTTTTCACTGGAGTTGTCCCAATTCTTGTTGAATTAGATGGTGATGTTAATGGGCACAAATTTTCTGTCAGTGGAGAGGGTGAAGGTGATGCAACATACGGAAAACTTACCCTTAAATTTATTTGCACTACTGGAAAACTACCTGTTCCATGGCCAACACTTGTCACTACTCTGACGTATGGTGTTCAATGCTTTTCCCGTTATCCGGATCATATGAAACGGCATGACTTTTTCAAGAGTGCCATGCCCGAAGGTTATGTACAGGAACGCACTATATCTTTCAAAGATGACGGGAACTACAAGACGCGTGCTGAAGTCAAGTTTGAAGGTGATACCCTTGTTAATCGTATCGAGTTAAAAGGTATTGATTTTAAAGAAGATGGAAACATTCTCGGACACAAACTCGAGTACAACTATAACTCACACAATGTATACATCACGGCAGACAAACAAAAGAATGGAATCAAAGCTAACTTCAAAATTCGCCACAACATTGAAGATGGATCCGTTCAACTAGCAGACCATTATCAACAAAATACTCCAATTGGCGATGGCCCTGTCCTTTTACCAGACAACCATTACCTGTCGACACAATCTGCCCTTTTGAAAGATCCCAACGAAAAGCGTGACCACATGGTCCTTCTTGAGTTTGTAACTGCTGCTGGGATTACACATGGCATGGATGAACTATACAAA |
| 0081 | Mutant CGD1 GFPuv4 | PRT | Artificial Sequence | MSKGEELFTGVVPILVELDGDVNGHKFSVSGEGEGDATYGKLTLKFICTTGKLPVPWPTLVTTLTYGVQCFSRYPDHMKRHDFFKSAMPEGYVQERTISFKDDGNYKTRAEVKFEGDTLVNRIELKGIDFK |

TABLE 1-continued

| Illustrative Flagellin-Based Agents | | | | |
|---|---|---|---|---|
| SEQ ID | Construct Name | DNA/PRT | Species | Sequence |
| | | | | EDGNILGHKLEYNYNSHNVYITADKQKNGIKANFKIRHNIEDGSVQLADHYQQNTPIGDGPVLLPD NHYLSTQSALLKDPNEKRDHMVLLEFVTAAGITHGMDELYK |
| 0082 | Mutant CGD1 GFPuv4 mutation of wt NdeI site | DNA | Artificial Sequence | ATGAGTAAAGGAGAAGAACTTTTCACTGGAGTTGTCCCAATTCTTGTTGAATTAGATGGTGAT GTTAATGGGCACAAATTTTCTGTCAGTGGAGAGGGTGAAGGTGATGCAACATACGGAAAACTT ACCCTTAAATTTATTTGCACTACTGGAAAACTACCTGTTCCATGGCCAACACTTGTCACTACTC TGACGTATGGTGTTCAATGCTTTTCCCGTTATCCGGATCACATGAAACGGCATGACTTTTTCAA GAGTGCCATGCCCGAAGGTTATGTACAGGAACGCACTATATCTTTCAAAGATGACGGGAACT ACAAGACGCGTGCTGAAGTCAAGTTTGAAGGTGATACCCTTGTTAATCGTATCGAGTTAAAAG GTATTGATTTTAAAGAAGATGGAAACATTCTCGGACACAAACTCGAGTACAACTATAACTCACA CAATGTATACATCACGGCAGACAAACAAAAGAATGGAATCAAAGCTAACTTCAAAATTCGCCA CAACATTGAAGATGGATCCGTTCAACTAGCAGACCATTATCAACAAAATACTCCAATTGGCGA TGGCCCTGTCCTTTTACCAGACAACCATTACCTGTCGACACAATCTGCCCTTTTGAAAGATCC CAACGAAAAGCGTGACCACATGGTCCTTCTTGAGTTTGTAACTGCTGCTGGGATTACACATGG CATGGATGAACTATACAAATAA |
| 0083 | Mutant CGD1 Forward primer FCGFP | DNA | Artificial Sequence | TCTAGACGGCCGATCTCAGGTAAGAATGGAATCAAAGCTAACTTCAAAATTCGC |
| 0084 | Mutant CGD1 PRT altered GFPuv4 sequence | PRT | Artificial Sequence | NVYIPISGKNGIKANFKIRH |
| 0085 | Mutant CGD1 Reverse RCGFP | DNA | Artificial Sequence | AGATCTCCGCGGTTTGTATAGTTCATCCATGCCATGTGTAATCCC |
| 0086 | Mutant CGD1 DNA Sequence of CGD1 construct | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG TAACGCTAACGACGGCATTTCTATTGCGCAGACCACTGAAGGTGCGCTGAATGAAATCAACAA CAACCTGCAGCGTGTGCGTGAGTTGTCTGTTCAGGCCACTAACGGGACTAACTCTGATTCCG ATCTGAAATCTATCCAGGATGAAATTCAGCAACGTCTGGAAGAAATCGATCGCGTTTCTAATC AGACTCAATTTAACGGTGTTAAAGTCCTGTCTCAGGACAACCAGATGAAAATCCAGGTTGGTG CTAACGATGGTGAAACCATTACCATCGATCTGCAAAAAATTGATGTGAAAAGCCTTGGCCTTG ATGGGTTCAATGTTAATTCCCCGGGAAGTACCGCTAACCCACTGGCTTCAATTGATTCTGCAT TGTCAAAAGTGGACGCAGTTCGTTCTTCTCTGGGGGCAATTCAAAACCGCTTTGATTCAGCCA TTACCAACCTTGGCAATACGGTAACCAATCTGAACTCCGCGCGTAGCCGTATCGAAGATGCT GACTATGCACTGGTTCCGCCGATCTCAGGTAAGAATGGAATCAAAGCTAACTTCAAAATTCGC CACAACATTGAAGATGGATCCGTTCAACTAGCAGACCATTATCAACAAAATACTCCAATTGGC GATGGCCCTGTCCTTTTACCAGACAACCATTACCTGTCGACACAATCTGCCCTTTTGAAAGAT CCCAACGAAAAGCGTGACCACATGGTCCTTCTTGAGTTTGTAACTGCTGCTGGGATTACACAT GGCATGGATGAACTATACAAACCGCGGGGTTCTCATCATCATCATCATCATGGTTAAGTCGAC |
| 0087 | Mutant CGD1 Expressed Mutant CGD1 | DNA | Artificial Sequence | ATGAGCGGGTTACGGATCAACAGCGCGAAAGACGATGCGGCAGGCCAGGCGATTGCTAACC GCTTCACTTCTAATATCAAAGGTCTGACTCAGGCTTCCCGTAACGCTAACGACGGCATTTCTA TTGCGCAGACCACTGAAGGTGCGCTGAATGAAATCAACAACAACCTGCAGCGTGTGCGTGAG TTGTCTGTTCAGGCCACTAACGGGACTAACTCTGATTCCGATCTGAAATCTATCCAGGATGAA ATTCAGCAACGTCTGGAAGAAATCGATCGCGTTTCTAATCAGACTCAATTTAACGGTGTTAAA |

TABLE 1-continued

Illustrative Flagellin-Based Agents

| SEQ ID | Construct Name | DNA/ PRT | Species | Sequence |
|---|---|---|---|---|
| | | | | GTCCTGTCTCAGGACAACCAGATGAAAATCCAGGTTGGTGCTAACGATGGTGAAACCATTAC CATCGATCTGCAAAAAATTGATGTGAAAAGCCTTGGCCTTGATGGGTTCAATGTTAATTCCCC GGGAAGTACCGCTAACCCACTGGCTTCAATTGATTCTGCATTGTCAAAAGTGGACGCAGTTC GTTCTTCTCTGGGGGCAATTCAAAACCGCTTTGATTCAGCCATTACCAACCTTGGCAATACGG TAACCAATCTGAACTCCGCGCGTAGCCGTATCGAAGATGCTGACTATGCACTGGTTCCGCCG ATCTCAGGTAAGAATGGAATCAAAGCTAACTTCAAAATTCGCCACAACATTGAAGATGGATCC GTTCAACTAGCAGACCATTATCAACAAAATACTCCAATTGGCGATGGCCCTGTCCTTTTACCA GACAACCATTACCTGTCGACACAATCTGCCCTTTTGAAAGATCCCAACGAAAAGCGTGACCAC ATGGTCCTTCTTGAGTTTGTAACTGCTGCTGGGATTACACATGGCATGGATGAACTATACAAA CCGCGGGGTTCTCATCATCATCATCATCATGGTTAA |
| 0088 | Mutant CGD1 Expressed Mutant CGD1 | PRT | Artificial Sequence | MSGLRINSAKDDAAGQAIANRFTSNIKGLTQASRNANDGISIAQTTEGALNEINNNLQRVRELSVQ ATNGTNSDSDLKSIQDEIQQRLEEIDRVSNQTQFNGVKVLSQDNQMKIQVGANDGETITIDLQKIDV KSLGLDGFNVNSPGSTANPLASIDSALSKVDAVRSSLGAIQNRFDSAITNLGNTVTNLNSARSRIED ADYALVPPISGKNGIKANFKIRHNIEDGSVQLADHYQQNTPIGDGPVLLPDNHYLSTQSALLKDPNE KRDHMVLLEFVTAAGITHGMDELYKPRGSHHHHHHG |
| 0089 | Mutant CPM194 Mutant CPM194 | DNA | Artificial Sequence | ATGAGTACCGCTAACCCACTGGCTTCAATTGATTCTGCATTGTCAAAAGTGGACGCAGTTCGT TCTTCTCTGGGGGCAATTCAAAACCGCTTTGATTCAGCCATTACCAACCTTGGCAATACGGTA ACCAATCTGAACTCCGCGCGTAGCCGTATCGAAGATGCTGACTATGCATCCCCGGGAAGCGG GTTACGGATCAACAGCGCGAAAGACGATGCGGCAGGCCAGGCGATTGCTAACCGCTTCACTT CTAATATCAAAGGTCTGACTCAGGCTTCCCGTAACGCTAACGACGGCATTTCTATTGCGCAGA CCACTGAAGGTGCGCTGAATGAAATCAACAACAACCTGCAGCGTGTGCGTGAGTTGTCTGTT CAGGCCACTAACGGGACTAACTCTGATTCCGATCTGAAATCTATCCAGGATGAAATTCAGCAA CGTCTGGAAGAAATCGATCGCGTTTCTAATCAGACTCAATTTAACGGTGTTAAAGTCCTGTCT CAGGACAACCAGATGAAAATCCAGGTTGGTGCTAACGATGGTCTGGTTCCGCGGGGTTCTCA TCATCATCATCATCATGGTTAA |
| 0090 | Mutant CPM194 Mutant CPM194 | PRT | Artificial Sequence | MSTANPLASIDSALSKVDAVRSSLGAIQNRFDSAITNLGNTVTNLNSARSRIEDADYASPGSGLRIN SAKDDAAGQAIANRFTSNIKGLTQASRNANDGISIAQTTEGALNEINNNLQRVRELSVQATNGTNS DSDLKSIQDEIQQRLEEIDRVSNQTQFNGVKVLSQDNQMKIQVGANDGLVPRGSHHHHHHG |
| 0091 | Mutant CPM194 Mutant CPM194 | DNA | Artificial Sequence | TAATACGACTCACTATAGGGGAATTGTGAGCGGATAACAATTCCCCTCTAGAATAATTTTGTTT AACTTTAAGAAGGAGATATACATATGAGTACCGCTAACCCACTGGCTTCAATTGATTCTGCATT GTCAAAAGTGGACGCAGTTCGTTCTTCTCTGGGGGCAATTCAAAACCGCTTTGATTCAGCCAT TACCAACCTTGGCAATACGGTAACCAATCTGAACTCCGCGCGTAGCCGTATCGAAGATGCTG ACTATGCATCCCCGGGAAGCGGGTTACGGATCAACAGCGCGAAAGACGATGCGGCAGGCCA GGCGATTGCTAACCGCTTCACTTCTAATATCAAAGGTCTGACTCAGGCTTCCCGTAACGCTAA CGACGGCATTTCTATTGCGCAGACCACTGAAGGTGCGCTGAATGAAATCAACAACAACCTGC AGCGTGTGCGTGAGTTGTCTGTTCAGGCCACTAACGGGACTAACTCTGATTCCGATCTGAAAT CTATCCAGGATGAAATTCAGCAACGTCTGGAAGAAATCGATCGCGTTTCTAATCAGACTCAAT TTAACGGTGTTAAAGTCCTGTCTCAGGACAACCAGATGAAAATCCAGGTTGGTGCTAACGATG GTCTGGTTCCGCGGGGTTCTCATCATCATCATCATCATGGTTAAGTCGAC |
| 0092 | Mutant CPM194 Forward primer FCD1 | DNA | Artificial Sequence | TCTAGACATATGAGTACCGCTAACCCACTGGCTTCAATTG |

TABLE 1-continued

Illustrative Flagellin-Based Agents

| SEQ ID | Construct Name | DNA/ PRT | Species | Sequence |
|---|---|---|---|---|
| 0093 | Mutant CPM194 Reverse primer RCD1J | DNA | Artificial Sequence | GCTTCCCGGGGATGCATAGTCAGCATCTTCGATACGGC |
| 0094 | Mutant CPM194 Forward primer FND1J | DNA | Artificial Sequence | GCATCCCCGGGAAGCGGGTTACGGATCAACAGCG |
| 0095 | Mutant CPM194 everse primer RND1 | DNA | Artificial Sequence | AGATCTCCGCGGAACCAGACCATCGTTAGCACCAACCTGGATTTTCATCT |
| 0096 | Mutant CPM217 Mutant CPM217 | DNA | Artificial Sequence | ATGAGTACCGCTAACCCACTGGCTTCAATTGATTCTGCATTGTCAAAAGTGGACGCAGTTCGT TCTTCTCTGGGGGCAATTCAAAACCGCTTTGATTCAGCCATTACCAACCTTGGCAATACGGTA ACCAATCTGAACTCCGCGCGTAGCCGTATCGAAGATGCTGACTATGCATCCCCGGGAAGCGG GTTACGGATCAACAGCGCGAAAGACGATGCGGCAGGCCAGGCGATTGCTAACCGCTTCACTT CTAATATCAAAGGTCTGACTCAGGCTTCCCGTAACGCTAACGACGGCATTTCTATTGCGCAGA CCACTGAAGGTGCGCTGAATGAAATCAACAACAACCTGCAGCGTGTGCGTGAGTTGTCTGTT CAGGCCACTAACGGGACTAACTCTGATTCCGATCTGAAATCTATCCAGGATGAAATTCAGCAA CGTCTGGAAGAAATCGATCGCGTTTCTAATCAGACTCAATTTAACGGTGTTAAAGTCCTGTCT CAGGACAACCAGATGAAAATCCAGGTTGGTGCTAACGATGGTGAAACCATTACCATCGATCT GCAAAAAATTGATGTGAAAAGCCTTGGCCTTGATGGGTTCAATGTTAATCTGGTTCCGCGGGG TTCTCATCATCATCATCATCATGGTTAA |
| 0097 | Mutant CPM217 Mutant CPM217 | PRT | Artificial Sequence | MSTANPLASIDSALSKVDAVRSSLGAIQNRFDSAITNLGNTVTNLNSARSRIEDADYASPGSGLRIN SAKDDAAGQAIANRFTSNIKGLTQASRNANDGISIAQTTEGALNEINNNLQRVRELSVQATNGTNS VDSDLKSIQDEIQQRLEEIDRVSNQTQFNGVKVLSQDNQMKIQVGANDGETITIDLQKIDVKSLGLDG FNVNLVPRGSHHHHHHG |
| 0098 | Mutant CPM217 Mutant CPM217 | DNA | Artificial Sequence | TAATACGACTCACTATAGGGGAATTGTGAGCGGATAACAATTCCCCTCTAGAATAATTTTGTTT AACTTTAAGAAGGAGATATACATATGAGTACCGCTAACCCACTGGCTTCAATTGATTCTGCATT GTCAAAAGTGGACGCAGTTCGTTCTTCTCTGGGGGCAATTCAAAACCGCTTTGATTCAGCCAT TACCAACCTTGGCAATACGGTAACCAATCTGAACTCCGCGCGTAGCCGTATCGAAGATGCTG ACTATGCATCCCCGGGAAGCGGGTTACGGATCAACAGCGCGAAAGACGATGCGGCAGGCCA GGCGATTGCTAACCGCTTCACTTCTAATATCAAAGGTCTGACTCAGGCTTCCCGTAACGCTAA CGACGGCATTTCTATTGCGCAGACCACTGAAGGTGCGCTGAATGAAATCAACAACAACCTGC AGCGTGTGCGTGAGTTGTCTGTTCAGGCCACTAACGGGACTAACTCTGATTCCGATCTGAAAT CTATCCAGGATGAAATTCAGCAACGTCTGGAAGAAATCGATCGCGTTTCTAATCAGACTCAAT TTAACGGTGTTAAAGTCCTGTCTCAGGACAACCAGATGAAAATCCAGGTTGGTGCTAACGATG GTGAAACCATTACCATCGATCTGCAAAAAATTGATGTGAAAAGCCTTGGCCTTGATGGGTTCA ATGTTAATCTGGTTCCGCGGGGTTCTCATCATCATCATCATCATGGTTAAGTCGAC |
| 0099 | Mutant CPM217 Reverse primer RCPM217 | DNA | Artificial Sequence | AGATCTCCGCGGAACCAGATTAACATTGAACCCATCAAGGCCAAG |
| 0100 | Mutant GD1G Forward Primer FGFP77 | DNA | Artificial Sequence | CCCGTTATCCGGATCACATGAAACGGCATGACTTTTTC |
| 0101 | Mutant GD1G Reverse Primer RGFP77 | DNA | Artificial Sequence | GAAAAAGTCATGCCGTTTCATGTGATCCGGATAACGGG |

TABLE 1-continued

| SEQ ID | Construct Name | DNA/ PRT | Species | Sequence |
|---|---|---|---|---|
| | | | | Illustrative Flagellin-Based Agents |
| 0102 | Mutant GD1G FGFP54 | DNA | Artificial Sequence | CTGTTCCATGGCCAACACTTG |
| 0103 | Mutant GD1G Forward primer FNGFP | DNA | Artificial Sequence | TCTAGACATATGAGTAAAGGAGAAGAACTTTTCACTGGAGTTGTCC |
| 0104 | Mutant GD1G altered GFP DNA sequence | DNA | Artificial Sequence | GGCCTATGCGGCCGCAGTAAAGGAGAAGAACTTTTCACTGGAGTTGTCCCAATTCTTGTTGAA |
| 0105 | Mutant GD1G Reverse RNGFP | DNA | Artificial Sequence | AGATCTATTAATGCGGCCTGATAGGCCTTGTTTGTCTGCCGTGATGTATACATTGTG |
| 0106 | Mutant GD1G altered GFP PRT sequence | PRT | Artificial Sequence | SHNVYITADKQGLSGRNM |
| 0107 | Mutant GD1G DNA Sequence of GD1G construct | DNA | Artificial Sequence | TAATACGACTCACTATAGGGGAATTGTGAGCGGATAACAATTCCCCTCTAGAATAATTTTGTTT AACTTTAAGAAGGAGATATACATATGAGTAAAGGAGAAGAACTTTTCACTGGAGTTGTCCCAA TTCTTGTTGAATTAGATGGTGATGTTAATGGGCACAAATTTTCTGTCAGTGGAGAGGGTGAAG GTGATGCAACATACGGAAAACTTACCCTTAAATTTATTTGCACTACTGGAAAACTACCTGTTCC ATGGCCAACACTTGTCACTACTCTGACGTATGGTGTTCAATGCTTTTCCCGTTATCCGGATCA CATGAAACGGCATGACTTTTTCAAGAGTGCCATGCCCGAAGGTTATGTACAGGAACGCACTAT ATCTTTCAAAGATGACGGGAACTACAAGACGCGTGCTGAAGTCAAGTTTGAAGGTGATACCCT TGTTAATCGTATCGAGTTAAAAGGTATTGATTTTAAAGAAGATGGAAACATTCTCGGACACAAA CTCGAGTACAACTATAACTCACACAATGTATACATCACGGCAGACAAACAAGGCCTATCAGGC CGCATTATGAGCGGGTTACGGATCAACAGCGCGAAAGACGATGCGGCAGGCCAGGCGATTG CTAACCGCTTCACTTCTAATATCAAAGGTCTGACTCAGGCTTCCCGTAACGCTAACGACGGCA TTTCTATTGCGCAGACCACTGAAGGTGCGCTGAATGAAATCAACAACAACCTGCAGCGTGTG CGTGAGTTGTCTGTTCAGGCCACTAACGGGACTAACTCTGATTCCGATCTGAAATCTATCCAG GATGAAATTCAGCAACGTCTGGAAGAAATCGATCGCGTTTCTAATCAGACTCAATTTAACGGT GTTAAAGTCCTGTCTCAGGACAACCAGATGAAAATCCAGGTTGGTGCTAACGATGGTGAAAC CATTACCATCGATCTGCAAAAAATTGATGTGAAAAGCCTTGGCCTTGATGGGTTCAATGTTAAT TCCCCGGGAAGTACCGCTAACCCACTGGCTTCAATTGATTCTGCATTGTCAAAAGTGGACGC AGTTCGTTCTTCTCTGGGGGCAATTCAAAACCGCTTTGATTCAGCCATTACCAACCTTGGCAA TACGGTAACCAATCTGAACTCCGCGCGTAGCCGTATCGAAGATGCTGACTATGCACTGGTTC CGCCGATCTCAGGTAAGAATGGAATCAAAGCTAACTTCAAAATTCGCCACAACATTGAAGATG GATCCGTTCAACTAGCAGACCATTATCAACAAAATACTCCAATTGGCGATGGCCCTGTCCTTT TACCAGACAACCATTACCTGTCGACACAATCTGCCCTTTTGAAAGATCCCAACGAAAAGCGTG ACCACATGGTCCTTCTTGAGTTTGTAACTGCTGCTGGGATTACACATGGCATGGATGAACTAT ACAAACCGCGGGGTTCTCATCATCATCATCATCATGGTTAAGTCGAC |
| 0108 | Mutant GD1G Expressed Mutant GD1G | DNA | Artificial Sequence | ATGAGTAAAGGAGAAGAACTTTTCACTGGAGTTGTCCCAATTCTTGTTGAATTAGATGGTGAT GTTAATGGGCACAAATTTTCTGTCAGTGGAGAGGGTGAAGGTGATGCAACATACGGAAAACTT ACCCTTAAATTTATTTGCACTACTGGAAAACTACCTGTTCCATGGCCAACACTTGTCACTACTC TGACGTATGGTGTTCAATGCTTTTCCCGTTATCCGGATCACATGAAACGGCATGACTTTTTCAA GAGTGCCATGCCCGAAGGTTATGTACAGGAACGCACTATATCTTTCAAAGATGACGGGAACT |

TABLE 1-continued

Illustrative Flagellin-Based Agents

| SEQ ID | Construct Name | DNA/ PRT | Species | Sequence |
|---|---|---|---|---|
| | | | | ACAAGACGCGTGCTGAAGTCAAGTTTGAAGGTGATACCCTTGTTAATCGTATCGAGTTAAAAG GTATTGATTTTAAAGAAGATGGAAACATTCTCGGACACAAACTCGAGTACAACTATAACTCACA CAATGTATACATCACGGCAGACAAACAAGGCCTATCAGGCCGCATTATGAGCGGGTTACGGA TCAACAGCGCGAAAGACGATGCGGCAGGCCAGGCGATTGCTAACCGCTTCACTTCTAATATC AAAGGTCTGACTCAGGCTTCCCGTAACGCTAACGACGGCATTTCTATTGCGCAGACCACTGA AGGTGCGCTGAATGAAATCAACAACAACCTGCAGCGTGTGCGTGAGTTGTCTGTTCAGGCCA CTAACGGGACTAACTCTGATTCCGATCTGAAATCTATCCAGGATGAAATTCAGCAACGTCTGG AAGAAATCGATCGCGTTTCTAATCAGACTCAATTTAACGGTGTTAAAGTCCTGTCTCAGGACA ACCAGATGAAAATCCAGGTTGGTGCTAACGATGGTGAAACCATTACCATCGATCTGCAAAAAA TTGATGTGAAAAGCCTTGGCCTTGATGGGTTCAATGTTAATTCCCCGGGAAGTACCGCTAACC CACTGGCTTCAATTGATTCTGCATTGTCAAAAGTGGACGCAGTTCGTTCTTCTCTGGGGGCAA TTCAAAACCGCTTTGATTCAGCCATTACCAACCTTGGCAATACGGTAACCAATCTGAACTCCG CGCGTAGCCGTATCGAAGATGCTGACTATGCACTGGTTCCGCCGATCTCAGGTAAGAATGGA ATCAAAGCTAACTTCAAAATTCGCCACAACATTGAAGATGGATCCGTTCAACTAGCAGACCAT TATCAACAAAATACTCCAATTGGCGATGGCCCTGTCCTTTTACCAGACAACCATTACCTGTCG ACACAATCTGCCCTTTTGAAAGATCCCAACGAAAAGCGTGACCACATGGTCCTTCTTGAGTTT GTAACTGCTGCTGGGATTACACATGGCATGGATGAACTATACAAACCGCGGGGTTCTCATCAT CATCATCATCATGGTTAA |
| 0109 | Mutant GD1G Expressed Mutant GD1G | PRT | Artificial Sequence | MSKGEELFTGVVPILVELDGDVNGHKFSVSGEGEGDATYGKLTLKFICTTGKLPVPWPTLVTTLTY GVQCFSRYPDHMKRHDFFKSAMPEGYVQERTISFKDDGNYKTRAEVKFEGDTLVNRIELKGIDFK EDGNILGHKLEYNYNSHNVYITADKQGLSGRIMSGLRINSAKDDAAGQAIANRFTSNIKGLTQASR NANDGISIAQTTEGALNEINNNLQRVRELSVQATNGTNSDSDLKSIQDEIQQRLEEIDRVSNQTQF NGVKVLSQDNQMKIQVGANDGETITIDLQKIDVKSLGLDGFNVNSPGSTANPLASIDSALSKVDAV RSSLGAIQNRFDSAITNLGNTVTNLNSARSRIEDADYALVPPISGKNGIKANFKIRHNIEDGSVQLAD HYQQNTPIGDGPVLLPDNHYLSTQSALLKDPNEKRDHMVLLEFVTAAGITHGMDELYKPRGSHHH HHHG |
| 0110 | Mutant MF227C mutant 470CT template | DNA | Artificial Sequence | CTTGGCCTTGATGGGTTCAATGTTAATTCCCCGGGAATTTCCGGTGGTGGTGGTGGAATTACA TTAATCAATGAAGACGCTGCCGCAGCCAAGAAAAGTACCGCTAACCCACTGGCTTCAATTG |
| 0111 | Mutant MF227C mutant 470CT template | PRT | Artificial Sequence | LGLDGFNVNSPGISGGGGGITLINEDAAAAKKSTANPLASI |
| 0112 | Mutant MF227C Reverse Primer R2YY | DNA | Artificial Sequence | AGATCTCCGCGGAACCAGTAAAGAGAGGACGTTTTGCGGAACCTGGTTTGCATAGTCAGCAT CTTCGATACG |
| 0113 | Mutant MF227C DNA sequence of Mutant MF227C | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG TAACGCTAACGACGGCATTTCTATTGCGCAGACCACTGAAGGTGCGCTGAATGAAATCAACAA CAACCTGCAGCGTGTGCGTGAGTTGTCTGTTCAGGCCACTAACGGGACTAACTCTGATTCCG ATCTGAAATCTATCCAGGATGAAATTCAGCAACGTCTGGAAGAAATCGATCGCGTTTCTAATC AGACTCAATTTAACGGTGTTAAAGTCCTGTCTCAGGACAACCAGATGAAAATCCAGGTTGGTG CTAACGATGGTGAAACCATTACCATCGATCTGCAAAAAATTGATGTGAAAAGCCTTGGCCTTG ATGGGTTCAATGTTAATTCCCCGGGAAGTACCGCTAACCCACTGGCTTCAATTGATTCTGCAT TGTCAAAAGTGGACGCAGTTCGTTCTTCTCTGGGGGCAATTCAAAACCGTTTTGATTCAGCCA TTACCAACCTTGGCAATACGGTAACCAATCTGAACTCCGCGCGTAGCCGTATCGAAGATGCT |

TABLE 1-continued

| Illustrative Flagellin-Based Agents | | | | |
|---|---|---|---|---|
| SEQ ID | Construct Name | DNA/ PRT | Species | Sequence |
| | | | | GACTATGCAAACCAGGTTCCGCAAAACGTCCTCTCTTTACTGGTTCCGCGGGGTTCTCATCAT CATCATCATCATGGTTAAGTCGAC |
| 0114 | Mutant MF227C Mutant MF227C | DNA | Artificial Sequence | ATGAGCGGGTTACGGATCAACAGCGCGAAAGACGATGCGGCAGGCCAGGCGATTGCTAACC GCTTCACTTCTAATATCAAAGGTCTGACTCAGGCTTCCCGTAACGCTAACGACGGCATTTCTA TTGCGCAGACCACTGAAGGTGCGCTGAATGAAATCAACAACAACCTGCAGCGTGTGCGTGAG TTGTCTGTTCAGGCCACTAACGGGACTAACTCTGATTCCGATCTGAAATCTATCCAGGATGAA ATTCAGCAACGTCTGGAAGAAATCGATCGCGTTTCTAATCAGACTCAATTTAACGGTGTTAAA GTCCTGTCTCAGGACAACCAGATGAAAATCCAGGTTGGTGCTAACGATGGTGAAACCATTAC CATCGATCTGCAAAAAATTGATGTGAAAAGCCTTGGCCTTGATGGGTTCAATGTTAATTCCCC GGGAAGTACCGCTAACCCACTGGCTTCAATTGATTCTGCATTGTCAAAAGTGGACGCAGTTC GTTCTTCTCTGGGGGCAATTCAAAACCGTTTTGATTCAGCCATTACCAACCTTGGCAATACGG TAACCAATCTGAACTCCGCGCGTAGCCGTATCGAAGATGCTGACTATGCAAACCAGGTTCCG CAAAACGTCCTCTCTTTACTGGTTCCGCGGGGTTCTCATCATCATCATCATCATGGTTAA |
| 0115 | Mutant MF227C Mutant MF227C | PRT | Artificial Sequence | MSGLRINSAKDDAAGQAIANRFTSNIKGLTQASRNANDGISIAQTTEGALNEINNNLQRVRELSVQ ATNGTNSDSDLKSIQDEIQQRLEEIDRVSNQTQFNGVKVLSQDNQMKIQVGANDGETITIDLQKIDV KSLGLDGFNVNSPGSTANPLASIDSALSKVDAVRSSLGAIQNRFDSAITNLGNTVTNLNSARSRIED ADYANQVPQNVLSLLVPRGSHHHHHHG |
| 0116 | Mutant MF227N Reverse Primer RMF227N | DNA | Artificial Sequence | AGATCTCCCGGGGAACCATCGTTAGCACCAACCTGGATTTTC |
| 0117 | Mutant MF227N DNA sequence of mutant MF227N | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG TAACGCTAACGACGGCATTTCTATTGCGCAGACCACTGAAGGTGCGCTGAATGAAATCAACAA CAACCTGCAGCGTGTGCGTGAGTTGTCTGTTCAGGCCACTAACGGGACTAACTCTGATTCCG ATCTGAAATCTATCCAGGATGAAATTCAGCAACGTCTGGAAGAAATCGATCGCGTTTCTAATC AGACTCAATTTAACGGTGTTAAAGTCCTGTCTCAGGACAACCAGATGAAAATCCAGGTTGGTG CTAACGATGGTTCCCCGGGAAGTACCGCTAACCCACTGGCTTCAATTGATTCTGCATTGTCAA AAGTGGACGCAGTTCGTTCTTCTCTGGGGGCAATTCAAAACCGCTTTGATTCAGCCATTACCA ACCTTGGCAATACGGTAACCAATCTGAACTCCGCGCGTAGCCGTATCGAAGATGCTGACTAT GCAACGGAAGTTTCTAATATGTCTAAAGCGCAGATTCTGCAGCAGGCTGGTACTTCCGTTCTG GCGCAGGCTAACCAGGTTCCGCAAAACGTCCTCTCTTTACTGGTTCCGCGGGGTTCTCATCA TCATCATCATCATGGTTAAGTCGAC |
| 0118 | Mutant MF227N mutant MF227N | DNA | Artificial Sequence | ATGAGCGGGTTACGGATCAACAGCGCGAAAGACGATGCGGCAGGCCAGGCGATTGCTAACC GCTTCACTTCTAATATCAAAGGTCTGACTCAGGCTTCCCGTAACGCTAACGACGGCATTTCTA TTGCGCAGACCACTGAAGGTGCGCTGAATGAAATCAACAACAACCTGCAGCGTGTGCGTGAG TTGTCTGTTCAGGCCACTAACGGGACTAACTCTGATTCCGATCTGAAATCTATCCAGGATGAA ATTCAGCAACGTCTGGAAGAAATCGATCGCGTTTCTAATCAGACTCAATTTAACGGTGTTAAA GTCCTGTCTCAGGACAACCAGATGAAAATCCAGGTTGGTGCTAACGATGGTTCCCCGGGAAG TACCGCTAACCCACTGGCTTCAATTGATTCTGCATTGTCAAAAGTGGACGCAGTTCGTTCTTC TCTGGGGGCAATTCAAAACCGCTTTGATTCAGCCATTACCAACCTTGGCAATACGGTAACCAA |

TABLE 1-continued

Illustrative Flagellin-Based Agents

| SEQ ID | Construct Name | DNA/ PRT | Species | Sequence |
|---|---|---|---|---|
| | | | | TCTGAACTCCGCGCGTAGCCGTATCGAAGATGCTGACTATGCAACGGAAGTTTCTAATATGTC TAAAGCGCAGATTCTGCAGCAGGCTGGTACTTCCGTTCTGGCGCAGGCTAACCAGGTTCCGC AAAACGTCCTCTCTTTACTGGTTCCGCGGGGTTCTCATCATCATCATCATCATGGTTAA |
| 0119 | Mutant MF227N mutant MF227N | PRT | Artificial Sequence | MSGLRINSAKDDAAGQAIANRFTSNIKGLTQASRNANDGISIAQTTEGALNEINNNLQRVRELSVQ ATNGTNSDSDLKSIQDEIQQRLEEIDRVSNQTQFNGVKVLSQDNQMKIQVGANDGSPGSTANPLA SIDSALSKVDAVRSSLGAIQNRFDSAITNLGNTVTNLNSARSRIEDADYATEVSNMSKAQILQQAGT SVLAQANQVPQNVLSLLVPRGSHHHHHHG |
| 0120 | Mutant MF233 Reverse primer RMF233 | DNA | Artificial Sequence | AGATCTCCGCGGAACCAGCAGGTTATTCTGGGTCAACAGCGACAGGCTGTTTGTATTAATGA CTTGTGCATAGTCAGCATCTTCGATACG |
| 0121 | Mutant MF233 DNA Sequence of construct MF233 | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG TAACGCTAACGACGGCATTTCTATTGCGCAGACCACTGAAGGTGCGCTGAATGAAATCAACAA CAACCTGCAGCGTGTGCGTGAGTTGTCTGTTCAGGCCACTAACGGGACTAACTCTGATTCCG ATCTGAAATCTATCCAGGATGAAATTCAGCAACGTCTGGAAGAAATCGATCGCGTTTCTAATC AGACTCAATTTAACGGTGTTAAAGTCCTGTCTCAGGACAACCAGATGAAAATCCAGGTTGGTG CTAACGATGGTGAAACCATTACCATCGATCTGCAAAAAATTGATGTGAAAAGCCTTGGCCTTG ATGGGTTCAATGTTAATTCCCCGGGAAGTACCGCTAACCCACTGGCTTCAATTGATTCTGCAT TGTCAAAAGTGGACGCAGTTCGTTCTTCTCTGGGGGCAATTCAAAACCGCTTTGATTCAGCCA TTACCAACCTTGGCAATACGGTAACCAATCTGAACTCCGCGCGTAGCCGTATCGAAGATGCT GACTATGCACAAGTCATTAATACAAACAGCCTGTCGCTGTTGACCCAGAATAACCTGCTGGTT CCGCGGGGTTCTCATCATCATCATCATCATGGTTAAGTCGAC |
| 0122 | Mutant MF233 MF233 | DNA | Artificial Sequence | ATGAGCGGGTTACGGATCAACAGCGCGAAAGACGATGCGGCAGGCCAGGCGATTGCTAACC GCTTCACTTCTAATATCAAAGGTCTGACTCAGGCTTCCCGTAACGCTAACGACGGCATTTCTA TTGCGCAGACCACTGAAGGTGCGCTGAATGAAATCAACAACAACCTGCAGCGTGTGCGTGAG TTGTCTGTTCAGGCCACTAACGGGACTAACTCTGATTCCGATCTGAAATCTATCCAGGATGAA ATTCAGCAACGTCTGGAAGAAATCGATCGCGTTTCTAATCAGACTCAATTTAACGGTGTTAAA GTCCTGTCTCAGGACAACCAGATGAAAATCCAGGTTGGTGCTAACGATGGTGAAACCATTAC CATCGATCTGCAAAAAATTGATGTGAAAAGCCTTGGCCTTGATGGGTTCAATGTTAATTCCCC GGGAAGTACCGCTAACCCACTGGCTTCAATTGATTCTGCATTGTCAAAAGTGGACGCAGTTC GTTCTTCTCTGGGGGCAATTCAAAACCGCTTTGATTCAGCCATTACCAACCTTGGCAATACGG TAACCAATCTGAACTCCGCGCGTAGCCGTATCGAAGATGCTGACTATGCACAAGTCATTAATA CAAACAGCCTGTCGCTGTTGACCCAGAATAACCTGCTGGTTCCGCGGGGTTCTCATCATCAT CATCATCATGGTTAA |
| 0123 | Mutant MF233 MF233 | PRT | Artificial | MSGLRINSAKDDAAGQAIANRFTSNIKGLTQASRNANDGISIAQTTEGALNEINNNLQRVRELSVQ SequenceATNGTNSDSDLKSIQDEIQQRLEEIDRVSNQTQFNGVKVLSQDNQMKIQVGANDGETITIDLQKIDV KSLGLDGFNVNSPGSTANPLASIDSALSKVDAVRSSLGAIQNRFDSAITNLGNTVTNLNSARSRIED ADYAQVINTNSLSLLTQNNLLVPRGSHHHHHHG |
| 0124 | Mutant MF471 Forward primer F471-77 | DNA | Artificial Sequence | GCTGACTATGCAACGGCAGTTTCTGCTATGTCTGCAGCGCAGATTCTGC |

TABLE 1-continued

| SEQ ID | Construct Name | DNA/ PRT | Species | Sequence |
|---|---|---|---|---|
| Illustrative Flagellin-Based Agents | | | | |
| 0125 | Mutant MF471 Reverse Primer R471-77 | DNA | Artificial Sequence | GCAGAATCTGCGCTGCAGACATAGCAGAAACTGCCGTTGCATAGTCAGC |
| 0126 | Mutant MF471 DNA Sequence of construct MF471 | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG TAACGCTAACGACGGCATTTCTATTGCGCAGACCACTGAAGGTGCGCTGAATGAAATCAACAA CAACCTGCAGCGTGTGCGTGAGTTGTCTGTTCAGGCCACTAACGGGACTAACTCTGATTCCG ATCTGAAATCTATCCAGGATGAAATTCAGCAACGTCTGGAAGAAATCGATCGCGTTTCTAATC AGACTCAATTTAACGGTGTTAAAGTCCTGTCTCAGGACAACCAGATGAAAATCCAGGTTGGTG CTAACGATGGTGAAACCATTACCATCGATCTGCAAAAAATTGATGTGAAAAGCCTTGGCCTTG ATGGGTTCAATGTTAATTCCCCGGGAAGTACCGCTAACCCACTGGCTTCAATTGATTCTGCAT TGTCAAAAGTGGACGCAGTTCGTTCTTCTCTGGGGGCAATTCAAAACCGCTTTGATTCAGCCA TTACCAACCTTGGCAATACGGTAACCAATCTGAACTCCGCGCGTAGCCGTATCGAAGATGCT GACTATGCAACGGCAGTTTCTGCTATGTCTGCAGCGCAGATTCTGCAGCAGGCTGGTCTGGT TCCGCGGGGTTCTCATCATCATCATCATCATGGTTAAGTCGAC |
| 0127 | Mutant MF471 MF471 | DNA | Artificial Sequence | ATGAGCGGGTTACGGATCAACAGCGCGAAAGACGATGCGGCAGGCCAGGCGATTGCTAACC GCTTCACTTCTAATATCAAAGGTCTGACTCAGGCTTCCCGTAACGCTAACGACGGCATTTCTA TTGCGCAGACCACTGAAGGTGCGCTGAATGAAATCAACAACAACCTGCAGCGTGTGCGTGAG TTGTCTGTTCAGGCCACTAACGGGACTAACTCTGATTCCGATCTGAAATCTATCCAGGATGAA ATTCAGCAACGTCTGGAAGAAATCGATCGCGTTTCTAATCAGACTCAATTTAACGGTGTTAAA GTCCTGTCTCAGGACAACCAGATGAAAATCCAGGTTGGTGCTAACGATGGTGAAACCATTAC CATCGATCTGCAAAAAATTGATGTGAAAAGCCTTGGCCTTGATGGGTTCAATGTTAATTCCCC GGGAAGTACCGCTAACCCACTGGCTTCAATTGATTCTGCATTGTCAAAAGTGGACGCAGTTC GTTCTTCTCTGGGGGCAATTCAAAACCGCTTTGATTCAGCCATTACCAACCTTGGCAATACGG TAACCAATCTGAACTCCGCGCGTAGCCGTATCGAAGATGCTGACTATGCAACGGCAGTTTCT GCTATGTCTGCAGCGCAGATTCTGCAGCAGGCTGGTCTGGTTCCGCGGGGTTCTCATCATCA TCATCATCATGGTTAA |
| 0128 | Mutant MF471 MF471 | PRT | Artificial Sequence | MSGLRINSAKDDAAGQAIANRFTSNIKGLTQASRNANDGISIAQTTEGALNEINNNLQRVRELSVQ ATNGTNSDSDLKSIQDEIQQRLEEIDRVSNQTQFNGVKVLSQDNQMKIQVGANDGETITIDLQKIDV KSLGLDGFNVNSPGSTANPLASIDSALSKVDAVRSSLGAIQNRFDSAITNLGNTVTNLNSARSRIED ADYATAVSAMSAAQILQQAGLVPRGSHHHHHHG |
| 0129 | Mutant MF479 Forward primer F479-83 | DNA | Artificial Sequence | GTTTCTAATATGTCTAAAGCGGCGATTCTGGGAGCGGCTGGTCTGGTTCCGCGG |
| 0130 | Mutant MF479 Reverse Primer R479-83 | DNA | Artificial Sequence | CCGCGGAACCAGACCAGCCGCTCCCAGAATCGCCGCTTTAGACATATTAGAAAC |
| 0131 | Mutant MF479 DNA Sequence of construct MF479 | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG TAACGCTAACGACGGCATTTCTATTGCGCAGACCACTGAAGGTGCGCTGAATGAAATCAACAA CAACCTGCAGCGTGTGCGTGAGTTGTCTGTTCAGGCCACTAACGGGACTAACTCTGATTCCG ATCTGAAATCTATCCAGGATGAAATTCAGCAACGTCTGGAAGAAATCGATCGCGTTTCTAATC AGACTCAATTTAACGGTGTTAAAGTCCTGTCTCAGGACAACCAGATGAAAATCCAGGTTGGTG |

TABLE 1-continued

| SEQ ID | Construct Name | DNA/ PRT | Species | Sequence |
|---|---|---|---|---|
| Illustrative Flagellin-Based Agents | | | | |
| | | | | CTAACGATGGTGAAACCATTACCATCGATCTGCAAAAAATTGATGTGAAAAGCCTTGGCCTTG ATGGGTTCAATGTTAATTCCCCGGGAAGTACCGCTAACCCACTGGCTTCAATTGATTCTGCAT TGTCAAAAGTGGACGCAGTTCGTTCTTCTCTGGGGGCAATTCAAAACCGCTTTGATTCAGCCA TTACCAACCTTGGCAATACGGTAACCAATCTGAACTCCGCGCGTAGCCGTATCGAAGATGCT GACTATGCAACGGAAGTTTCTAATATGTCTAAAGCGGCGATTCTGGGAGCGGCTGGTCTGGT TCCGCGGGGTTCTCATCATCATCATCATCATGGTTAAGTCGAC |
| 0132 | Mutant MF479 Mutant MF479 | DNA | Artificial Sequence | ATGAGCGGGTTACGGATCAACAGCGCGAAAGACGATGCGGCAGGCCAGGCGATTGCTAACC GCTTCACTTCTAATATCAAAGGTCTGACTCAGGCTTCCCGTAACGCTAACGACGGCATTTCTA TTGCGCAGACCACTGAAGGTGCGCTGAATGAAATCAACAACAACCTGCAGCGTGTGCGTGAG TTGTCTGTTCAGGCCACTAACGGGACTAACTCTGATTCCGATCTGAAATCTATCCAGGATGAA ATTCAGCAACGTCTGGAAGAAATCGATCGCGTTTCTAATCAGACTCAATTTAACGGTGTTAAA GTCCTGTCTCAGGACAACCAGATGAAAATCCAGGTTGGTGCTAACGATGGTGAAACCATTAC CATCGATCTGCAAAAAATTGATGTGAAAAGCCTTGGCCTTGATGGGTTCAATGTTAATTCCCC GGGAAGTACCGCTAACCCACTGGCTTCAATTGATTCTGCATTGTCAAAAGTGGACGCAGTTC GTTCTTCTCTGGGGGCAATTCAAAACCGCTTTGATTCAGCCATTACCAACCTTGGCAATACGG TAACCAATCTGAACTCCGCGCGTAGCCGTATCGAAGATGCTGACTATGCAACGGAAGTTTCTA ATATGTCTAAAGCGGCGATTCTGGGAGCGGCTGGTCTGGTTCCGCGGGGTTCTCATCATCAT CATCATCATGGTTAA |
| 0133 | Mutant MF479 Mutant MF479 | PRT | Artificial Sequence | MSGLRINSAKDDAAGQAIANRFTSNIKGLTQASRNANDGISIAQTTEGALNEINNNLQRVRELSVQ ATNGTNSDSDLKSIQDEIQQRLEEIDRVSNQTQFNGVKVLSQDNQMKIQVGANDGETITIDLQKIDV KSLGLDGFNVNSPGSTANPLASIDSALSKVDAVRSSLGAIQNRFDSAITNLGNTVTNLNSARSRIED ADYATEVSNMSKAAILGAAGLVPRGSHHHHHHG |
| 0134 | Mutant N45 Forward primer N45_F | DNA | Artificial Sequence | TCTAGAGGATCCGGCAGGCCAGGCG |
| 0135 | Mutant N45 Reverse R502D0 | DNA | Artificial Sequence | CGCAAGCTTGTCGACTTAACGC |
| 0136 | Mutant N45 DNA sequence of Mutant N45 | DNA | Artificial Sequence | TAATACGACTCACTATAGGGGAATTGTGAGCGGATAACAATTCCCCTCTAGAATAATTTTGTTT AACTTTAAGAAGGAGATATACATATGCGGGGTTCTCATCATCATCATCATCATGGTATGGCTA GCATGACTGGTGGACAGCAAATGGGTCGGGATCTGTACGACCTGGTTCCGCGCGGTAGCGC GAAGGATCCGGCAGGCCAGGCGATTGCTAACCGCTTCACTTCTAATATCAAAGGTCTGACTC AGGCTTCCCGTAACGCTAACGACGGCATTTCTATTGCGCAGACCACTGAAGGTGCGCTGAAT GAAATCAACAACAACCTGCAGCGTGTGCGTGAGTTGTCTGTTCAGGCCACTAACGGGACTAA CTCTGATTCCGATCTGAAATCTATCCAGGATGAAATTCAGCAACGTCTGGAAGAAATCGATCG CGTTTCTAATCAGACTCAATTTAACGGTGTTAAAGTCCTGTCTCAGGACAACCAGATGAAAATC CAGGTTGGTGCTAACGATGGTGAAACCATTACCATCGATCTGCAAAAAATTGATGTGAAAAGC CTTGGCCTTGATGGGTTCAATGTTAATTCCCCGGGAATTTCCGGTGGTGGTGGTGGAATTCTA GACTCCATGGGTACATTAATCAATGAAGACGCTGCCGCAGCCAAGAAAAGTACCGCTAACCC ACTGGCTTCAATTGATTCTGCATTGTCAAAAGTGGACGCAGTTCGTTCTTCTCTGGGGGCAAT TCAAAACCGTTTTGATTCAGCCATTACCAACCTTGGCAATACGGTAACCAATCTGAACTCCGC GCGTAGCCGTATCGAAGATGCTGACTATGCAACGGAAGTTTCTAATATGTCTAAAGCGCAGAT TCTGCAGCAGGCTGGTACTTCCGTTCTGGCGCAGGCTAACCAGGTTCCGCAAAACGTCCTCT CTTTACTGCGTTAAGTCGACAAGCTTGCGG |

TABLE 1-continued

| Illustrative Flagellin-Based Agents | | | | |
|---|---|---|---|---|
| SEQ ID | Construct Name | DNA/ PRT | Species | Sequence |
| 0137 | Mutant N45 Mutant N45 | PRT | Artificial Sequence | MRGSHHHHHHGMASMTGGQQMGRDLYDLVPRGSAKDPAGQAIANRFTSNIKGLTQASRNANDGISIAQTTEGALNEINNNLQRVRELSVQATNGTNSDSDLKSIQDEIQQRLEEIDRVSNQTQFNGVKVLSQDNQMKIQVGANDGETITIDLQKIDVKSLGLDGFNVNSPGISGGGGGILDSMGTLINEDAAAAKKSTANPLASIDSALSKVDAVRSSLGAIQNRFDSAITNLGNTVTNLNSARSRIEDADYATEVSNMSKAQILQQAGTSVLAQANQVPQNVLSLLR |
| 0138 | Mutant NGD1 DNA Sequence of NGD1 construct | DNA | Artificial Sequence | TAATACGACTCACTATAGGGGAATTGTGAGCGGATAACAATTCCCCTCTAGAATAATTTTGTTTAACTTTAAGAAGGAGATATACATATGAGTAAAGGAGAAGAACTTTTCACTGGAGTTGTCCCAATTCTTGTTGAATTAGATGGTGATGTTAATGGGCACAAATTTTCTGTCAGTGGAGAGGGTGAAGGTGATGCAACATACGGAAAACTTACCCTTAAATTTATTTGCACTACTGGAAAACTACCTGTTCCATGGCCAACACTTGTCACTACTCTGACGTATGGTGTTCAATGCTTTTCCCGTTATCCGGATCACATGAAACGGCATGACTTTTTCAAGAGTGCCATGCCCGAAGGTTATGTACAGGAACGCACTATATCTTTCAAAGATGACGGGAACTACAAGACGCGTGCTGAAGTCAAGTTTGAAGGTGATACCCTTGTTAATCGTATCGAGTTAAAAGGTATTGATTTTAAAGAAGATGGAAACATTCTCGGACACAAACTCGAGTACAACTATAACTCACACAATGTATACATCACGGCAGACAAACAAGGCCTATCAGGCCGCATTATGAGCGGGTTACGGATCAACAGCGCGAAAGACGATGCGGCAGGCCAGGCGATTGCTAACCGCTTCACTTCTAATATCAAAGGTCTGACTCAGGCTTCCCGTAACGCTAACGACGGCATTTCTATTGCGCAGACCACTGAAGGTGCGCTGAATGAAATCAACAACAACCTGCAGCGTGTGCGTGAGTTGTCTGTTCAGGCCACTAACGGGACTAACTCTGATTCCGATCTGAAATCTATCCAGGATGAAATTCAGCAACGTCTGGAAGAAATCGATCGCGTTTCTAATCAGACTCAATTTAACGGTGTTAAAGTCCTGTCTCAGGACAACCAGATGAAAATCCAGGTTGGTGCTAACGATGGTGAAACCATTACCATCGATCTGCAAAAAATTGATGTGAAAAGCCTTGGCCTTGATGGGTTCAATGTTAATTCCCCGGGAAGTACCGCTAACCCACTGGCTTCAATTGATTCTGCATTGTCAAAAGTGGACGCAGTTCGTTCTTCTCTGGGGGCAATTCAAAACCGCTTTGATTCAGCCATTACCAACCTTGGCAATACGGTAACCAATCTGAACTCCGCGCGTAGCCGTATCGAAGATGCTGACTATGCACTGGTTCCGCGGGGTTCTCATCATCATCATCATCATGGTTAAGTCGAC |
| 0139 | Mutant NGD1 Expressed Mutant SY3-GFP | DNA | Artificial Sequence | ATGAGTAAAGGAGAAGAACTTTTCACTGGAGTTGTCCCAATTCTTGTTGAATTAGATGGTGATGTTAATGGGCACAAATTTTCTGTCAGTGGAGAGGGTGAAGGTGATGCAACATACGGAAAACTTACCCTTAAATTTATTTGCACTACTGGAAAACTACCTGTTCCATGGCCAACACTTGTCACTACTCTGACGTATGGTGTTCAATGCTTTTCCCGTTATCCGGATCACATGAAACGGCATGACTTTTTCAAGAGTGCCATGCCCGAAGGTTATGTACAGGAACGCACTATATCTTTCAAAGATGACGGGAACTACAAGACGCGTGCTGAAGTCAAGTTTGAAGGTGATACCCTTGTTAATCGTATCGAGTTAAAAGGTATTGATTTTAAAGAAGATGGAAACATTCTCGGACACAAACTCGAGTACAACTATAACTCACACAATGTATACATCACGGCAGACAAACAAGGCCTATCAGGCCGCATTATGAGCGGGTTACGGATCAACAGCGCGAAAGACGATGCGGCAGGCCAGGCGATTGCTAACCGCTTCACTTCTAATATCAAAGGTCTGACTCAGGCTTCCCGTAACGCTAACGACGGCATTTCTATTGCGCAGACCACTGAAGGTGCGCTGAATGAAATCAACAACAACCTGCAGCGTGTGCGTGAGTTGTCTGTTCAGGCCACTAACGGGACTAACTCTGATTCCGATCTGAAATCTATCCAGGATGAAATTCAGCAACGTCTGGAAGAAATCGATCGCGTTTCTAATCAGACTCAATTTAACGGTGTTAAAGTCCTGTCTCAGGACAACCAGATGAAAATCCAGGTTGGTGCTAACGATGGTGAAACCATTACCATCGATCTGCAAAAAATTGATGTGAAAAGCCTTGGCCTTGATGGGTTCAATGTTAATTCCCCGGGAAGTACCGCTAACCCACTGGCTTCAATTGATTCTGCATTGTCAAAAGTGGACGCAGTTCGTTCTTCTCTGGGGGCAATTCAAAACCGCTTTGATTCAGCCATTACCAACCTTGGCAATACGGTAACCAATCTGAACTCCGCGCGTAGCCGTATCGAAGATGCTGACTATGCACTGGTTCCGCGGGGTTCTCATCATCATCATCATCATGGTTAA |

TABLE 1-continued

| Illustrative Flagellin-Based Agents | | | | |
|---|---|---|---|---|
| SEQ ID | Construct Name | DNA/ PRT | Species | Sequence |
| 0140 | Mutant NGD1 Expressed Mutant SY3-GFP/Mutant NGD1 | PRT | Artificial Sequence | MSKGEELFTGVVPILVELDGDVNGHKFSVSGEGEGDATYGKLTLKFICTTGKLPVPWPTLVTTLTY GVQCFSRYPDHMKRHDFFKSAMPEGYVQERTISFKDDGNYKTRAEVKFEGDTLVNRIELKGIDFK EDGNILGHKLEYNYNSHNVYITADKQGLSGRIMSGLRINSAKDDAAGQAIANRFTSNIKGLTQASR NANDGISIAQTTEGALNEINNNLQRVRELSVQATNGTNSDSDLKSIQDEIQQRLEEIDRVSNQTQF NGVKVLSQDNQMKIQVGANDGETITIDLQKIDVKSLGLDGFNVNSPGSTANPLASIDSALSKVDAV RSSLGAIQNRFDSAITNLGNTVTNLNSARSRIEDADYALVPRGSHHHHHHG |
| 0141 | Mutant S33 Forward F502_533 | DNA | Artificial Sequence | TCTAGAGGATCCGTCTGGTCTGCGTATCAACAGCGC |
| 0142 | Mutant S33 DNA sequence of Mutant S33 | DNA | Artificial Sequence | TAATACGACTCACTATAGGGGAATTGTGAGCGGATAACAATTCCCCTCTAGAATAATTTTGTTT AACTTTAAGAAGGAGATATACATATGCGGGGTTCTCATCATCATCATCATCATGGTATGGCTA GCATGACTGGTGGACAGCAAATGGGTCGGGATCTGTACGACCTGGTTCCGCGCGGTAGCGC GAAGGATCCGTCTGGTCTGCGTATCAACAGCGCGAAAGACGATGCGGCAGGCCAGGCGATT GCTAACCGCTTCACTTCTAATATCAAAGGTCTGACTCAGGCTTCCCGTAACGCTAACGACGGC ATTTCTATTGCGCAGACCACTGAAGGTGCGCTGAATGAAATCAACAACAACCTGCAGCGTGT GCGTGAGTTGTCTGTTCAGGCCACTAACGGGACTAACTCTGATTCCGATCTGAAATCTATCCA GGATGAAATTCAGCAACGTCTGGAAGAAATCGATCGCGTTTCTAATCAGACTCAATTTAACGG TGTTAAAGTCCTGTCTCAGGACAACCAGATGAAAATCCAGGTTGGTGCTAACGATGGTGAAAC CATTACCATCGATCTGCAAAAAATTGATGTGAAAAGCCTTGGCCTTGATGGGTTCAATGTTAAT TCCCCGGGAATTTCCGGTGGTGGTGGTGGAATTCTAGACTCCATGGGTACATTAATCAATGAA GACGCTGCCGCAGCCAAGAAAAGTACCGCTAACCCACTGGCTTCAATTGATTCTGCATTGTC AAAAGTGGACGCAGTTCGTTCTTCTCTGGGGGCAATTCAAAACCGTTTTGATTCAGCCATTAC CAACCTTGGCAATACGGTAACCAATCTGAACTCCGCGCGTAGCCGTATCGAAGATGCTGACT ATGCAACGGAAGTTTCTAATATGTCTAAAGCGCAGATTCTGCAGCAGGCTGGTACTTCCGTTC TGGCGCAGGCTAACCAGGTTCCGCAAAACGTCCTCTCTTTACTGCGTTAAGTCGAC |
| 0143 | Mutant S33 Mutant S33 | DNA | Artificial Sequence | ATGCGGGGTTCTCATCATCATCATCATCATGGTATGGCTAGCATGACTGGTGGACAGCAAATG GGTCGGGATCTGTACGACCTGGTTCCGCGCGGTAGCGCGAAGGATCCGTCTGGTCTGCGTA TCAACAGCGCGAAAGACGATGCGGCAGGCCAGGCGATTGCTAACCGCTTCACTTCTAATATC AAAGGTCTGACTCAGGCTTCCCGTAACGCTAACGACGGCATTTCTATTGCGCAGACCACTGA AGGTGCGCTGAATGAAATCAACAACAACCTGCAGCGTGTGCGTGAGTTGTCTGTTCAGGCCA CTAACGGGACTAACTCTGATTCCGATCTGAAATCTATCCAGGATGAAATTCAGCAACGTCTGG AAGAAATCGATCGCGTTTCTAATCAGACTCAATTTAACGGTGTTAAAGTCCTGTCTCAGGACA ACCAGATGAAAATCCAGGTTGGTGCTAACGATGGTGAAACCATTACCATCGATCTGCAAAAAA TTGATGTGAAAAGCCTTGGCCTTGATGGGTTCAATGTTAATTCCCCGGGAATTTCCGGTGGTG GTGGTGGAATTCTAGACTCCATGGGTACATTAATCAATGAAGACGCTGCCGCAGCCAAGAAA AGTACCGCTAACCCACTGGCTTCAATTGATTCTGCATTGTCAAAAGTGGACGCAGTTCGTTCT TCTCTGGGGGCAATTCAAAACCGTTTTGATTCAGCCATTACCAACCTTGGCAATACGGTAACC AATCTGAACTCCGCGCGTAGCCGTATCGAAGATGCTGACTATGCAACGGAAGTTTCTAATATG TCTAAAGCGCAGATTCTGCAGCAGGCTGGTACTTCCGTTCTGGCGCAGGCTAACCAGGTTCC GCAAAACGTCCTCTCTTTACTGCGTTAA |
| 0144 | Mutant S33 Mutant S33 | PRT | Artificial Sequence | MRGSHHHHHHGMASMTGGQQMGRDLYDLVPRGSAKDPSGLRINSAKDDAAGQAIANRFTSNIK GLTQASRNANDGISIAQTTEGALNEINNNLQRVRELSVQATNGTNSDSDLKSIQDEIQQRLEEIDRV SNQTQFNGVKVLSQDNQMKIQVGANDGETITIDLQKIDVKSLGLDGFNVNSPGISGGGGGILDSM GTLINEDAAAAKKSTANPLASIDSALSKVDAVRSSLGAIQNRFDSAITNLGNTVTNLNSARSRIEDA DYATEVSNMSKAQILQQAGTSVLAQANQVPQNVLSLLR |

TABLE 1-continued

| SEQ ID | Construct Name | DNA/ PRT | Species | Sequence |
| --- | --- | --- | --- | --- |
| | | | | Illustrative Flagellin-Based Agents |
| 0145 | Mutant SY3CT Reverse primer RSY3CT | DNA | Artificial Sequence | AGATCTCCGCGGAACCAGTGCATAGTCAGCATCTTCGATACGGC |
| 0146 | Mutant SY3CT DNA Sequence of SY3CT construct | DNA | Artificial Sequence | TAATACGACTCACTATAGGGGAATTGTGAGCGGATAACAATTCCCCTCTAGAATAATTTTGTTTAACTTTAAGAAGGAGATATACATATGAGCGGGTTACGGATCAACAGCGCGAAAGACGATGCGGCAGGCCAGGCGATTGCTAACCGCTTCACTTCTAATATCAAAGGTCTGACTCAGGCTTCCCGTAACGCTAACGACGGCATTTCTATTGCGCAGACCACTGAAGGTGCGCTGAATGAAATCAACAACAACCTGCAGCGTGTGCGTGAGTTGTCTGTTCAGGCCACTAACGGGACTAACTCTGATTCCGATCTGAAATCTATCCAGGATGAAATTCAGCAACGTCTGGAAGAAATCGATCGCGTTTCTAATCAGACTCAATTTAACGGTGTTAAAGTCCTGTCTCAGGACAACCAGATGAAAATCCAGGTTGGTGCTAACGATGGTGAAACCATTACCATCGATCTGCAAAAAATTGATGTGAAAAGCCTTGGCCTTGATGGGTTCAATGTTAATTCCCCGGGAAGTACCGCTAACCCACTGGCTTCAATTGATTCTGCATTGTCAAAAGTGGACGCAGTTCGTTCTTCTCTGGGGGCAATTCAAAACCGCTTTGATTCAGCCATTACCAACCTTGGCAATACGGTAACCAATCTGAACTCCGCGCGTAGCCGTATCGAAGATGCTGACTATGCACTGGTTCCGCGGGGTTCTCATCATCATCATCATCATGGTTAAGTCGAC |
| 0147 | Mutant SY3CT Expressed Mutant SY3CT | DNA | Artificial Sequence | ATGAGCGGGTTACGGATCAACAGCGCGAAAGACGATGCGGCAGGCCAGGCGATTGCTAACCGCTTCACTTCTAATATCAAAGGTCTGACTCAGGCTTCCCGTAACGCTAACGACGGCATTTCTATTGCGCAGACCACTGAAGGTGCGCTGAATGAAATCAACAACAACCTGCAGCGTGTGCGTGAGTTGTCTGTTCAGGCCACTAACGGGACTAACTCTGATTCCGATCTGAAATCTATCCAGGATGAAATTCAGCAACGTCTGGAAGAAATCGATCGCGTTTCTAATCAGACTCAATTTAACGGTGTTAAAGTCCTGTCTCAGGACAACCAGATGAAAATCCAGGTTGGTGCTAACGATGGTGAAACCATTACCATCGATCTGCAAAAAATTGATGTGAAAAGCCTTGGCCTTGATGGGTTCAATGTTAATTCCCCGGGAAGTACCGCTAACCCACTGGCTTCAATTGATTCTGCATTGTCAAAAGTGGACGCAGTTCGTTCTTCTCTGGGGGCAATTCAAAACCGCTTTGATTCAGCCATTACCAACCTTGGCAATACGGTAACCAATCTGAACTCCGCGCGTAGCCGTATCGAAGATGCTGACTATGCACTGGTTCCGCGGGGTTCTCATCATCATCATCATCATGGTTAA |
| 0148 | Mutant SY3CT Expressed Mutant SY3CT | PRT | Artificial Sequence | MSGLRINSAKDDAAGQAIANRFTSNIKGLTQASRNANDGISIAQTTEGALNEINNNLQRVRELSVQATNGTNSDSDLKSIQDEIQQRLEEIDRVSNQTQFNGVKVLSQDNQMKIQVGANDGETITIDLQKIDVKSLGLDGFNVNSPGSTANPLASIDSALSKVDAVRSSLGAIQNRFDSAITNLGNTVTNLNSARSRIEDADYALVPRGSHHHHHHG |
| 0149 | Mutant 33MX Mutant 33MX | DNA | Artificial Sequence | ATGAGCGGGTTACGGATCAACAGCGCGAAAGACGATGCGGCAGGCCAGGCGATTGCTAACCGCTTCACTTCTAATATCAAAGGTCTGACTCAGGCTTCCCGTAACGCTGCAGACGGCATTTCTATTGCGCAGACCACTGAAGGTGCGCTGAATGAAATCAACAACAACCTGCAGCGTGTGCGTGAGTTGTCTGTTCAGGCCACTGCCGGGGCTAACGCTGATGCCGCTCTGAAAGCTATCCAGGCTGAAATTCAGCAACGTCTGGAAGAAATCGATCGCGTTTCTCAGCAGACTCAAGCTGCCGCTGTTAAAGTCCTGTCTCAGGACAACGCAATGGCAATCCAGGTTGGTGCTAACGATGGTGCCGCTATTACCATCGATCTGCAAAAAATTGATGTGAAAAGCCTTGGCCTTGATGGGTTCAATGTTAATTCCCCGGGAAGTACCGCTAACCCACTGGCTTCAATTGATTCTGCATTGTCAAAAGTGGACGCAGTTCGTTCTTCTCTGGGGGCAATTCAAAACCGCTTTGATTCAGCCATTACCAACCTTGGCAATACGGTAACCAATCTGAACTCCGCGCGTAGCCGTATCGAAGATGCTGACTATGCAACGGAAGTTTCTCAAATGTCTAAAGCGCAGATTCTGCAGCAGGCTGGTACTTCCGTTCTGGCGCAGGCTAACCAGGTTCCGCAAAACGTCCTCTCTTTACTGGTTCCGCGGGGTTCTCATCATCATCATCATCATGGTTAA |

TABLE 1-continued

| Illustrative Flagellin-Based Agents | | | | |
|---|---|---|---|---|
| SEQ ID | Construct Name | DNA/ PRT | Species | Sequence |
| 0150 | Mutant 33MX Mutant 33MX | PRT | Artificial Sequence | MSGLRINSAKDDAAGQAIANRFTSNIKGLTQASRNAADGISIAQTTEGALNEINNNLQRVRELSVQA TAGANADAALKAIQAEIQQRLEEIDRVSQQTQAAAVKVLSQDNAMAIQVGANDGAAITIDLQKIDVK SLGLDGFNVNSPGSTANPLASIDSALSKVDAVRSSLGAIQNRFDSAITNLGNTVTNLNSARSRIEDA DYATEVSQMSKAQILQQAGTSVLAQANQVPQNVLSLLVPRGSHHHHHHG |
| 0151 | Mutant 33MX DNA sequence of 33MX | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG TAACGCTGCAGACGGCATTTCTATTGCGCAGACCACTGAAGGTGCGCTGAATGAAATCAACA ACAACCTGCAGCGTGTGCGTGAGTTGTCTGTTCAGGCCACTGCCGGGGCTAACGCTGATGC CGCTCTGAAAGCTATCCAGGCTGAAATTCAGCAACGTCTGGAAGAAATCGATCGCGTTTCTCA GCAGACTCAAGCTGCCGCTGTTAAAGTCCTGTCTCAGGACAACGCAATGGCAATCCAGGTTG GTGCTAACGATGGTGCCGCTATTACCATCGATCTGCAAAAAATTGATGTGAAAAGCCTTGGCC TTGATGGGTTCAATGTTAATTCCCCGGGAAGTACCGCTAACCCACTGGCTTCAATTGATTCTG CATTGTCAAAAGTGGACGCAGTTCGTTCTTCTCTGGGGGCAATTCAAAACCGCTTTGATTCAG CCATTACCAACCTTGGCAATACGGTAACCAATCTGAACTCCGCGCGTAGCCGTATCGAAGAT GCTGACTATGCAACGGAAGTTTCTCAAATGTCTAAAGCGCAGATTCTGCAGCAGGCTGGTACT TCCGTTCTGGCGCAGGCTAACCAGGTTCCGCAAAACGTCCTCTCTTTACTGGTTCCGCGGGG TTCTCATCATCATCATCATCATGGTTAAGTCGAC |
| 0152 | Mutant 485MX DNA Sequence of 485MX construct | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG TAACGCTGCAGACGGCATTTCTATTGCGCAGACCACTGAAGGTGCGCTGAATGAAATCAACA ACAACCTGCAGCGTGTGCGTGAGTTGTCTGTTCAGGCCACTGCCGGGGCTAACGCTGATGC CGCTCTGAAAGCTATCCAGGCTGAAATTCAGCAACGTCTGGAAGAAATCGATCGCGTTTCTCA GCAGACTCAAGCTGCCGCTGTTAAAGTCCTGTCTCAGGACAACGCAATGGCAATCCAGGTTG GTGCTAACGATGGTGCCGCTATTACCATCGATCTGCAAAAAATTGATGTGAAAAGCCTTGGCC TTGATGGGTTCAATGTTAATTCCCCGGGAAGTACCGCTAACCCACTGGCTTCAATTGATTCTG CATTGTCAAAAGTGGACGCAGTTCGTTCTTCTCTGGGGGCAATTCAAAACCGCTTTGATTCAG CCATTACCAACCTTGGCAATACGGTAACCAATCTGAACTCCGCGCGTAGCCGTATCGAAGAT GCTGACTATGCAACGGAAGTTTCTCAAATGTCTAAAGCGCAGATTCTGCAGCAGGCTGGTCT GGTTCCGCGGGGTTCTCATCATCATCATCATCATGGTTAAGTCGAC |
| 0153 | Mutant 485MX 485MX construct | DNA | Artificial Sequence | ATGAGCGGGTTACGGATCAACAGCGCGAAAGACGATGCGGCAGGCCAGGCGATTGCTAACC GCTTCACTTCTAATATCAAAGGTCTGACTCAGGCTTCCCGTAACGCTGCAGACGGCATTTCTA TTGCGCAGACCACTGAAGGTGCGCTGAATGAAATCAACAACAACCTGCAGCGTGTGCGTGAG TTGTCTGTTCAGGCCACTGCCGGGGCTAACGCTGATGCCGCTCTGAAAGCTATCCAGGCTGA AATTCAGCAACGTCTGGAAGAAATCGATCGCGTTTCTCAGCAGACTCAAGCTGCCGCTGTTAA AGTCCTGTCTCAGGACAACGCAATGGCAATCCAGGTTGGTGCTAACGATGGTGCCGCTATTA CCATCGATCTGCAAAAAATTGATGTGAAAAGCCTTGGCCTTGATGGGTTCAATGTTAATTCCC CGGGAAGTACCGCTAACCCACTGGCTTCAATTGATTCTGCATTGTCAAAAGTGGACGCAGTTC GTTCTTCTCTGGGGGCAATTCAAAACCGCTTTGATTCAGCCATTACCAACCTTGGCAATACGG TAACCAATCTGAACTCCGCGCGTAGCCGTATCGAAGATGCTGACTATGCAACGGAAGTTTCTC AAATGTCTAAAGCGCAGATTCTGCAGCAGGCTGGTCTGGTTCCGCGGGGTTCTCATCATCAT CATCATCATGGTTAA |

TABLE 1-continued

| Illustrative Flagellin-Based Agents | | | | |
|---|---|---|---|---|
| SEQ ID | Construct Name | DNA/ PRT | Species | Sequence |
| 0154 | Mutant 485MX 485MX construct | PRT | Artificial Sequence | MSGLRINSAKDDAAGQAIANRFTSNIKGLTQASRNAADGISIAQTTEGALNEINNNLQRVRELSVQA<br>TAGANADAALKAIQAEIQQRLEEIDRVSQQTQAAAVKVLSQDNAMAIQVGANDGAAITIDLQKIDVK<br>SLGLDGFNVNSPGSTANPLASIDSALSKVDAVRSSLGAIQNRFDSAITNLGNTVTNLNSARSRIEDA<br>DYATEVSQMSKAQILQQAGLVPRGSHHHHHHG |
| 0155 | Mutant MIM4 CBLB502 variant | DNA | Artificial Sequence | ATGCGGGGTTCTCATCATCATCATCATCATGGTATGGCTAGCATGACTGGTGGACAGCAAATG<br>GGTCGGGATCTGTACGACGATGACGATAAGGATCCGATGGCACAAGTCATTAATACAAACAG<br>CCTGTCGCTGTTGACCCAGAATAACCTGCAGAAATCTCAGTCCTCACTGAGTTCCGCTATTGA<br>GCGTCTGTCCTCTGGTCTGCGTATCAACAGCGCGAAAGACGATGCGGCAGGCCAGGCGATT<br>GCTAACCGCTTCACTTCTAATATCAAAGGTCTGACTCAGGCTTCCCGTAACGCTAACGACGGC<br>ATTTCTATTGCGCAGACCACTGAAGGTGCGCTGAATGAAATCAACAACAACCTGCAGCGTGT<br>GCGTGAGTTGTCTGTTCAGGCCACTCAAGGGACTAACTCTGATTCCGATCTGAAATCTATCCA<br>GGATGAAATTCAGCAACGTCTGGAAGAAATCGATCGCGTTTCTCAGCAGACTCAATTTAACGG<br>TGTTAAAGTCCTGTCTCAGGACAACCAGATGAAAATCCAGGTTGGTGCTAACGATGGTGAAAC<br>CATTACCATCGATCTGCAAAAAATTGATGTGAAAAGCCTTGGCCTTGATGGGTTCAATGTTAAT<br>TCCCCGGGAATTTCCGGTGGTGGTGGTGGAATTCTAGACTCCATGGGTACATTAATCAATGAA<br>GACGCTGCCGCAGCCAAGAAAAGTACCGCTAACCCACTGGCTTCAATTGATTCTGCATTGTC<br>AAAAGTGGACGCAGTTCGTTCTTCTCTGGGGGCAATTCAAAACCGTTTTGATTCAGCCATTAC<br>CAACCTTGGCAATACGGTAACCAATCTGAACTCCGCGCGTAGCCGTATCGAAGATGCTGACT<br>ATGCAACGGAAGTTTCTCAAATGTCTAAAGCGCAGATTCTGCAGCAGGCTGGTACTTCCGTTC<br>TGGCGCAGGCTAACCAGGTTCCGCAAAACGTCCTCTCTTTACTGCGTTAA |
| 0156 | Mutant MIM4 Primers design (for deletion aa Gln439; Asn440; Arg441; Phe442): | DNA | Artificial Sequence | AACCCACTGGCTTCAATTGATTCTGCATTGTCAAAAGTGGACGCAGTTCGTTCTTCTCTGGGG<br>GCAATTCAAAACCGTTTTGATTCAGCCATTACCGCCCTTGGCGCTACGGTAACCGCTCTGGC<br>CTCCGCGCGTAGCGCTATCGAAGATGCTGACTATGCAACGGAAGTTTCTCAAATG |
| 0157 | Mutant MIM4 Primers design (for deletion aa Gln439; Asn440; Arg441; Phe442): | PRT | Artificial Sequence | NPLASIDSALSKVDAVRSSLGAIQNRFDSAITALGATVTALASARSAIEDADYATEVSNM |
| 0158 | Mutant MIM4 Forward Primer MIM4 | DNA | Artificial Sequence | GCAGTTCGTTCTTCTCTGGGGGCAATTGATTCAGCCATTACCGCCCTTGG |
| 0159 | Mutant MIM4 Reverse Primer MIM4 | DNA | Artificial Sequence | CCAAGGGCGGTAATGGCTGAATCAATTGCCCCCAGAGAAGAACGAACTGC |
| 0160 | Mutant MIM4 MIM4 | DNA | Artificial Sequence | TAATACGACTCACTATAGGGGAATTGTGAGCGGATAACAATTCCCCTCTAGAAATAATTTTGTT<br>TAACTTTAAGAAGGAGATATACATATGCGGGGTTCTCATCATCATCATCATCATGGTATGGCTA<br>GCATGACTGGTGGACAGCAAATGGGTCGGGATCTGTACGACGATGACGATAAGGATCCGAT<br>GGCACAAGTCATTAATACAAACAGCCTGTCGCTGTTGACCCAGAATAACCTGAACAAATCTCA<br>GTCCTCACTGAGTTCCGCTATTGAGCGTCTGTCCTCTGGTCTGCGTATCAACAGCGCGAAAG<br>ACGATGCGGCAGGCCAGGCGATTGCTAACCGCTTCACTTCTAATATCAAAGGTCTGACTCAG<br>GCTTCCCGTAACGCTAACGACGGCATTTCTATTGCGCAGACCACTGAAGGTGCGCTGAATGA<br>AATCAACAACAACCTGCAGCGTGTGCGTGAGTTGTCTGTTCAGGCCACTAACGGGACTAACT |

TABLE 1-continued

| SEQ ID | Construct Name | DNA/ PRT | Species | Sequence |
|---|---|---|---|---|
| Illustrative Flagellin-Based Agents | | | | |
| | | | | CTGATTCCGATCTGAAATCTATCCAGGATGAAATTCAGCAACGTCTGGAAGAAATCGATCGCG TTTCTAATCAGACTCAATTTAACGGTGTTAAAGTCCTGTCTCAGGACAACCAGATGAAAATCCA GGTTGGTGCTAACGATGGTGAAACCATTACCATCGATCTGCAAAAAATTGATGTGAAAAGCCT TGGCCTTGATGGGTTCAATGTTAATTCCCCGGGAATTTCCGGTGGTGGTGGTGGAATTCTAG ACTCCATGGGTACATTAATCAATGAAGACGCTGCCGCAGCCAAGAAAAGTACCGCTAACCCA CTGGCTTCAATTGATTCTGCATTGTCAAAAGTGGACGCAGTTCGTTCTTCTCTGGGGGCAATT GATTCAGCCATTACCGCCCTTGGCGCTACGGTAACCGCTCTGGCCTCCGCGGCTAGCCGTAT CGAAGATGCTGACTATGCAACGGAAGTTTCTAATATGTCTAAAGCGCAGATTCTGCAGCAGGC TGGTACTTCCGTTCTGGCGCAGGCTAACCAGGTTCCGCAAAACGTCCTCTCTTTACTGCGTTA A |
| 0161 | Mutant MIM4 MIM4 | PRT | Artificial Sequence | MRGSHHHHHHGMASMTGGQQMGRDLYDDDDKDPMAQVINTNSLSLLTQNNLNKSQSSLSSAIE RLSSGLRINSAKDDAAGQAIANRFTSNIKGLTQASRNANDGISIAQTTEGALNEINNNLQRVRELSV QATNGTNSDSDLKSIQDEIQQRLEEIDRVSNQTQFNGVKVLSQDNQMKIQVGANDGETITIDLQKI DVKSLGLDGFNVNSPGISGGGGGILDSMGTLINEDAAAAKKSTANPLASIDSALSKVDAVRSSLGAI DSAITALGATVTALASAASRIEDADYATEVSNMSKAQILQQAGTSVLAQANQVPQNVLSLLR |
| 0162 | Mutant MIM5 Primers design (mutations Gln439Ala; Asn440Lys; Arg441Ala): | DNA | Artificial Sequence | AACCCACTGGCTTCAATTGATTCTGCATTGTCAAAAGTGGACGCAGTTCGTTCTTCTCTGGGG GCAATTGCAAAGGCTTTTGATTCAGCCATTACCGCCCTTGGCGCTACGGTAACCGCTCTGGC CTCCGCGCGTAGCGCTATCGAAGATGCTGACTATGCAACGGAAGTTTCTCAAATG |
| 0163 | Mutant MIM5 Primers design (mutations Gln439Ala; Asn440Lys; Arg441Ala): | PRT | Artificial Sequence | NPLASIDSALSKVDAVRSSLGAIAKAFDSAITALGATVTALASARSAIEDADYATEVSNM |
| 0164 | Mutant MIM5 Forward Primer MIM5 | DNA | Artificial Sequence | CGTTCTTCTCTGGGGGCAATTGCAAAGGCTTTTGATTCAGCCATTACCGC |
| 0165 | Mutant MIM5 Reverse Primer MIM5 | DNA | Artificial Sequence | GCGGTAATGGCTGAATCAAAAGCCTTTGCAATTGCCCCCAGAGAAGAACG |
| 0166 | Mutant MIM5 MIM5 | DNA | Artificial Sequence | TAATACGACTCACTATAGGGGAATTGTGAGCGGATAACAATTCCCCTCTAGAAATAATTTTGTT TAACTTTAAGAAGGAGATATACATATGCGGGGTTCTCATCATCATCATCATCATGGTATGGCTA GCATGACTGGTGGACAGCAAATGGGTCGGGATCTGTACGACGATGACGATAAGGATCCGAT GGCACAAGTCATTAATACAAACAGCCTGTCGCTGTTGACCCAGAATAACCTGAACAAATCTCA GTCCTCACTGAGTTCCGCTATTGAGCGTCTGTCCTCTGGTCTGCGTATCAACAGCGCGAAAG ACGATGCGGCAGGCCAGGCGATTGCTAACCGCTTCACTTCTAATATCAAAGGTCTGACTCAG GCTTCCCGTAACGCTAACGACGGCATTTCTATTGCGCAGACCACTGAAGGTGCGCTGAATGA AATCAACAACAACCTGCAGCGTGTGCGTGAGTTGTCTGTTCAGGCCACTAACGGGACTAACT CTGATTCCGATCTGAAATCTATCCAGGATGAAATTCAGCAACGTCTGGAAGAAATCGATCGCG TTTCTAATCAGACTCAATTTAACGGTGTTAAAGTCCTGTCTCAGGACAACCAGATGAAAATCCA GGTTGGTGCTAACGATGGTGAAACCATTACCATCGATCTGCAAAAAATTGATGTGAAAAGCCT TGGCCTTGATGGGTTCAATGTTAATTCCCCGGGAATTTCCGGTGGTGGTGGTGGAATTCTAG ACTCCATGGGTACATTAATCAATGAAGACGCTGCCGCAGCCAAGAAAAGTACCGCTAACCCA CTGGCTTCAATTGATTCTGCATTGTCAAAAGTGGACGCAGTTCGTTCTTCTCTGGGGGCAATT GCAAAGGCTTTTGATTCAGCCATTACCGCCCTTGGCGCTACGGTAACCGCTCTGGCCTCCGC |

TABLE 1-continued

| Illustrative Flagellin-Based Agents | | | | |
|---|---|---|---|---|
| SEQ ID | Construct Name | DNA/ PRT | Species | Sequence |
| | | | | GGCTAGCCGTATCGAAGATGCTGACTATGCAACGGAAGTTTCTAATATGTCTAAAGCGCAGAT<br>TCTGCAGCAGGCTGGTACTTCCGTTCTGGCGCAGGCTAACCAGGTTCCGCAAAACGTCCTCT<br>CTTTACTGCGTTAA |
| 0167 | Mutant MIM5<br>MIM5 | PRT | Artificial Sequence | MRGSHHHHHHGMASMTGGQQMGRDLYDDDDKDPMAQVINTNSLSLLTQNNLNKSQSSLSSAIE<br>RLSSGLRINSAKDDAAGQAIANRFTSNIKGLTQASRNANDGISIAQTTEGALNEINNNLQRVRELSV<br>QATNGTNSDSDLKSIQDEIQQRLEEIDRVSNQTQFNGVKVLSQDNQMKIQVGANDGETITIDLQKI<br>DVKSLGLDGFNVNSPGISGGGGGILDSMGTLINEDAAAAKKSTANPLASIDSALSKVDAVRSSLGAI<br>AKAFDSAITALGATVTALASAASRIEDADYATEVSNMSKAQILQQAGTSVLAQANQVPQNVLSLLR |
| 0168 | Mutant MIMX<br>Mutant 33MIMX | DNA | Artificial Sequence | ATGCGGGGTTCTCATCATCATCATCATCATGGTATGGCTAGCATGACTGGTGGACAGCAAATG<br>GGTCGGGATCTGTACGACCTGGTTCCGCGCGGTAGCGCGAAGGATCCGTCTGGTCTGCGTA<br>TCAACAGCGCGAAAGACGATGCGGCAGGCCAGGCGATTGCTAACCGCTTCACTTCTAATATC<br>AAAGGTCTGACTCAGGCTTCCCGTAACGCTGCAGACGGCATTTCTATTGCGCAGACCACTGA<br>AGGTGCGCTGAATGAAATCAACAACAACCTGCAGCGTGTGCGTGAGTTGTCTGTTCAGGCCA<br>CTAACGGGACTAACTCTGATTCCGATCTGAAATCTATCCAGGATGAAATTCAGCAACGTCTGG<br>AAGAAATCGATCGCGTTTCTAATCAGACTCAAGCTAACGGTGTTAAAGTCCTGTCTCAGGACA<br>ACGCAATGAAAATCCAGGTTGGTGCTAACGATGGTGCCGCTATTACCATCGATCTGCAAAAAA<br>TTGATGTGAAAAGCCTTGGCCTTGATGGGTTCAATGTTAATTCCCCGGGAATTTCCGGTGGTG<br>GTGGTGGAATTCTAGACTCCATGGGTACATTAATCAATGAAGACGCTGCCGCAGCCAAGAAA<br>AGTACCGCTAACCCACTGGCTTCAATTGATTCTGCATTGTCAAAAGTGGACGCAGTTCGTTCT<br>TCTCTGGGGGCAATTCAAGCTCGTTTTGCCGCGGCCATTGCTAACCTTGGCAATACGGTAAC<br>CAATCTGAACTCCGCGCGTAGCCGTATCGAAGATGCTGACTATGCAACGGAAGTTTCTAATAT<br>GTCTAAAGCGCAGATTCTGCAGCAGGCTGGTACTTCCGTTCTGGCGCAGGCTAACCAGGTTC<br>CGCAAAACGTCCTCTCTTTACTGCGTTAA |
| 0169 | Mutant MIMX<br>MIMx | PRT | Artificial Sequence | MRGSHHHHHHGMASMTGGQQMGRDLYDLVPRGSAKDPSGLRINSAKDDAAGQAIANRFTSNIK<br>GLTQASRNAADGISIAQTTEGALNEINNNLQRVRELSVQATNGTNSDSDLKSIQDEIQQRLEEIDRV<br>SNQTQANGVKVLSQDNAMKIQVGANDGAAITIDLQKIDVKSLGLDGFNVNSPGISGGGGGILDSM<br>GTLINEDAAAAKKSTANPLASIDSALSKVDAVRSSLGAIQARFAAAIANLGNTVTNLNSARSRIEDA<br>DYATEVSNMSKAQILQQAGTSVLAQANQVPQNVLSLLR |
| 0170 | Mutant MIMX<br>DNA sequence of 33MIMx | DNA | Artificial Sequence | TAATACGACTCACTATAGGGGAATTGTGAGCGGATAACAATTCCCCTCTAGAATAATTTTGTTT<br>AACTTTAAGAAGGAGATATACATATGCGGGGTTCTCATCATCATCATCATCATGGTATGGCTA<br>GCATGACTGGTGGACAGCAAATGGGTCGGGATCTGTACGACCTGGTTCCGCGCGGTAGCGC<br>GAAGGATCCGTCTGGTCTGCGTATCAACAGCGCGAAAGACGATGCGGCAGGCCAGGCGATT<br>GCTAACCGCTTCACTTCTAATATCAAAGGTCTGACTCAGGCTTCCCGTAACGCTGCAGACGG<br>CATTTCTATTGCGCAGACCACTGAAGGTGCGCTGAATGAAATCAACAACAACCTGCAGCGTGT<br>GCGTGAGTTGTCTGTTCAGGCCACTAACGGGACTAACTCTGATTCCGATCTGAAATCTATCCA<br>GGATGAAATTCAGCAACGTCTGGAAGAAATCGATCGCGTTTCTAATCAGACTCAAGCTAACGG<br>TGTTAAAGTCCTGTCTCAGGACAACGCAATGAAAATCCAGGTTGGTGCTAACGATGGTGCCG<br>CTATTACCATCGATCTGCAAAAAATTGATGTGAAAAGCCTTGGCCTTGATGGGTTCAATGTTAA<br>TTCCCCGGGAATTTCCGGTGGTGGTGGTGGAATTCTAGACTCCATGGGTACATTAATCAATGA<br>AGACGCTGCCGCAGCCAAGAAAAGTACCGCTAACCCACTGGCTTCAATTGATTCTGCATTGT<br>CAAAAGTGGACGCAGTTCGTTCTTCTCTGGGGGCAATTCAAGCTCGTTTTGCCGCGGCCATT<br>GCTAACCTTGGCAATACGGTAACCAATCTGAACTCCGCGCGTAGCCGTATCGAAGATGCTGA<br>CTATGCAACGGAAGTTTCTAATATGTCTAAAGCGCAGATTCTGCAGCAGGCTGGTACTTCCGT<br>TCTGGCGCAGGCTAACCAGGTTCCGCAAAACGTCCTCTCTTTACTGCGTTAAGTCGAC |

TABLE 1-continued

| SEQ ID | Construct Name | DNA/PRT | Species | Sequence |
|---|---|---|---|---|
| | | | | Illustrative Flagellin-Based Agents |
| 0171 | Mutant MIXC Reverse primer RMIXC | DNA | Artificial Sequence | AGATCTGTCGACTTAACCATGATGATGATGATGATGAGAACCCCGCGGAACCAGTAAAGAGA GGACGTTTTGCGGAACC |
| 0172 | Mutant MIXC DNA sequence of MIXC | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG TAACGCTAACGACGGCATTTCTATTGCGCAGACCACTGAAGGTGCGCTGAATGAAATCAACAA CAACCTGCAGCGTGTGCGTGAGTTGTCTGTTCAGGCCACTAACGGGACTAACTCTGATTCCG ATCTGAAATCTATCCAGGATGAAATTCAGCAACGTCTGGAAGAAATCGATCGCGTTTCTAATC AGACTCAATTTAACGGTGTTAAAGTCCTGTCTCAGGACAACCAGATGAAAATCCAGGTTGGTG CTAACGATGGTGAAACCATTACCATCGATCTGCAAAAAATTGATGTGAAAAGCCTTGGCCTTG ATGGGTTCAATGTTAATTCCCCGGGAAGTACCGCTAACCCACTGGCTTCAATTGATTCTGCAT TGTCAAAAGTGGACGCAGTTCGTTCTTCTCTGGGGGCAATTCAAGCTCGTTTTGCCGCGGCC ATTGCTAACCTTGGCAATACGGTAACCAATCTGAACTCCGCGCGTAGCCGTATCGAAGATGCT GACTATGCAACGGAAGTTTCTAATATGTCTAAAGCGCAGATTCTGCAGCAGGCTGGTACTTCC GTTCTGGCGCAGGCTAACCAGGTTCCGCAAAACGTCCTCTCTTTACTGGTTCCGCGGGGTTC TCATCATCATCATCATCATGGTTAAGTCGAC |
| 0173 | Mutant MIXC MIXC | PRT | Artificial Sequence | MSGLRINSAKDDAAGQAIANRFTSNIKGLTQASRNANDGISIAQTTEGALNEINNNLQRVRELSVQ ATNGTNSDSDLKSIQDEIQQRLEEIDRVSNQTQFNGVKVLSQDNQMKIQVGANDGETITIDLQKIDV KSLGLDGFNVNSPGSTANPLASIDSALSKVDAVRSSLGAIQARFAAAIANLGNTVTNLNSARSRIED ADYATEVSNMSKAQILQQAGTSVLAQANQVPQNVLSLLVPRGSHHHHHHG |
| 0174 | Mutant MIXN Forward primer FMIMxN | DNA | Artificial Sequence | AGATCTCATATGAGCGGGTTACGGATCAACAGCGCGAAAGACGATGC |
| 0175 | Mutant MIXN DNA sequence of MIX.N | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG TAACGCTGCAGACGGCATTTCTATTGCGCAGACCACTGAAGGTGCGCTGAATGAAATCAACA ACAACCTGCAGCGTGTGCGTGAGTTGTCTGTTCAGGCCACTAACGGGACTAACTCTGATTCC GATCTGAAATCTATCCAGGATGAAATTCAGCAACGTCTGGAAGAAATCGATCGCGTTTCTAAT CAGACTCAAGCTAACGGTGTTAAAGTCCTGTCTCAGGACAACGCAATGAAAATCCAGGTTGGT GCTAACGATGGTGCCGCTATTACCATCGATCTGCAAAAAATTGATGTGAAAAGCCTTGGCCTT GATGGGTTCAATGTTAATTCCCCGGGAAGTACCGCTAACCCACTGGCTTCAATTGATTCTGCA TTGTCAAAAGTGGACGCAGTTCGTTCTTCTCTGGGGGCAATTCAAAACCGCTTTGATTCAGCC ATTACCAACCTTGGCAATACGGTAACCAATCTGAACTCCGCGCGTAGCCGTATCGAAGATGCT GACTATGCAACGGAAGTTTCTAATATGTCTAAAGCGCAGATTCTGCAGCAGGCTGGTACTTCC GTTCTGGCGCAGGCTAACCAGGTTCCGCAAAACGTCCTCTCTTTACTGGTTCCGCGGGGTTC TCATCATCATCATCATCATGGTTAAGTCGAC |
| 0176 | Mutant MIXN Expressed Mutant MIX.N | PRT | Artificial Sequence | MSGLRINSAKDDAAGQAIANRFTSNIKGLTQASRNAADGISIAQTTEGALNEINNNLQRVRELSVQA TNGTNSDSDLKSIQDEIQQRLEEIDRVSNQTQANGVKVLSQDNAMKIQVGANDGAAITIDLQKIDVK SLGLDGFNVNSPGSTANPLASIDSALSKVDAVRSSLGAIQNRFDSAITNLGNTVTNLNSARSRIEDA DYATEVSNMSKAQILQQAGTSVLAQANQVPQNVLSLLVPRGSHHHHHHG |

TABLE 1-continued

Illustrative Flagellin-Based Agents

| SEQ ID | Construct Name | DNA/ PRT | Species | Sequence |
|---|---|---|---|---|
| 0177 | Mutants MIM1; MIM2 and MIM3 502 Mutants MIM1; MIM2 and MIM3 C-terminal part of CBLB502 | DNA | Artificial Sequence | AACCCACTGGCTTCAATTGATTCTGCATTGTCAAAAGTGGACGCAGTTCGTTCTTCTCTGGGG GCAATTCAAAACCGTTTTGATTCAGCCATTACCAACCTTGGCAATACGGTAACCAATCTGAACT CCGCGCGTAGCCGTATCGAAGATGCTGACTATGCAACGGAAGTTTCTCAAATGTCTAAAGCG CAGATTCTGCAGCAGGCTGGTACTTCCGTTCTGGCGCAGGCTAACCAGGTTCCGCAAAACGT CCTCTCTTTACTGCGTTAA |
| 0178 | Mutants MIM1; MIM2 and MIM3 Primers design (mutant MIM1) | DNA | Artificial Sequence | ATTACCAACCTTGGCAATACGGTAACCAATCTGAACTCCGCGCGTAGCCGTATCGAAGAT |
| 0179 | Mutants MIM1; MIM2 and MIM3 Primers design (mutant MIM1) | PRT | Artificial Sequence | ITNLGNTVTNLNSARSRIED |
| 0180 | Mutants MIM1; MIM2 and MIM3 Forward Primer 455-57 | DNA | Artificial Sequence | CCTTGGCAATACGGTAACCGCTCTGGCCTCCGCGCGTAGCCGTATC |
| 0181 | Mutants MIM1; MIM2 and MIM3 Reverse Primer 455-57 | DNA | Artificial Sequence | GATACGGCTACGCGCGGAGGCCAGAGCGGTTACCGTATTGCCAAGG |
| 0182 | Mutants MIM1; MIM2 and MIM3 Primers design (mutant MIM2_MIM1 plus R460A) | DNA | Artificial Sequence | ACGGTAACCGCTCTGGCCTCCGCGCGTAGCCGTATCGAAGATGCTGACTATGCAACGGAA |
| 0183 | Mutants MIM1; MIM2 and MIM3 Primers design (mutant MIM2_MIM1 plus R460A) | PRT | Artificial Sequence | TVTALASARSRIEDADYATE |
| 0184 | Mutants MIM1; MIM2 and MIM3 Forward Primer 460 | DNA | Artificial Sequence | GCTCTGGCCTCCGCGGCTAGCCGTATCGAAGATG |
| 0185 | Mutants MIM1; MIM2 and MIM3 Reverse Primer 460 | DNA | Artificial Sequence | CATCTTCGATACGGCTAGCCGCGGAGGCCAGAGC |

TABLE 1-continued

| Illustrative Flagellin-Based Agents | | | | |
|---|---|---|---|---|
| SEQ ID | Construct Name | DNA/ PRT | Species | Sequence |
| 0186 | Mutants MIM1; MIM2 and MIM3 Primers design (mutant MIM3_MIM2 plus N448A; N451A) | DNA | Artificial Sequence | CAAAACCGTTTTGATTCAGCCATTACCAACCTTGGCAATACGGTAACCGCTCTGGCCTCC |
| 0187 | Mutants MIM1; MIM2 and MIM3 Primers design (mutant MIM3_MIM2 plus N448A; N451A) | PRT | Artificial Sequence | QNRFDSAITNLGNTVTALAS |
| 0188 | Mutants MIM1; MIM2 and MIM3 Forward Primer 448-51 | DNA | Artificial Sequence | GTTTTGATTCAGCCATTACCGCCCTTGGCGCTACGGTAACCGCTCTGG |
| 0189 | Mutants MIM1; MIM2 and MIM3 Reverse Primer 448-51 | DNA | Artificial Sequence | CCAGAGCGGTTACCGTAGCGCCAAGGGCGGTAATGGCTGAATCAAAAC |
| 0190 | Mutant ME42 Forward Primer ME42 | DNA | Artificial Sequence | CAACAGCGCGAAAGCCGATGCGGGAGGCCAGGCGATTGC |
| 0191 | Mutant ME42 Reverse Primer ME42 | DNA | Artificial Sequence | GCAATCGCCTGGCCTCCCGCATCGGCTTTCGCGCTGTTG |
| 0192 | Mutant ME42 Sequence of ME42 construct | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGCCGATGCG GGAGGCCAGGCGATTGCTAACCGCTTCACTTCTAATATCAAAGGTCTGACTCAGGCTTCCCG TAACGCTAACGACGGCATTTCTATTGCGCAGACCACTGAAGGTGCGCTGAATGAAATCAACAA CAACCTGCAGCGTGTGCGTGAGTTGTCTGTTCAGGCCACTAACGGGACTAACTCTGATTCCG ATCTGAAATCTATCCAGGATGAAATTCAGCAACGTCTGGAAGAAATCGATCGCGTTTCTAATC AGACTCAATTTAACGGTGTTAAAGTCCTGTCTCAGGACAACCAGATGAAAATCCAGGTTGGTG CTAACGATGGTGAAACCATTACCATCGATCTGCAAAAAATTGATGTGAAAAGCCTTGGCCTTG ATGGGTTCAATGTTAATTCCCCGGGAAGTACCGCTAACCCACTGGCTTCAATTGATTCTGCAT TGTCAAAAGTGGACGCAGTTCGTTCTTCTCTGGGGGCAATTCAAAACCGCTTTGATTCAGCCA TTACCAACCTTGGCAATACGGTAACCAATCTGAACTCCGCGCGTAGCCGTATCGAAGATGCT GACTATGCAACGGAAGTTTCTAATATGTCTAAAGCGCAGATTCTGCAGCAGGCTGGTACTTCC GTTCTGGCGCAGGCTAACCAGGTTCCGCAAAACGTCCTCTCTTTACTGGTTCCGCGGGGTTC TCATCATCATCATCATCATGGTTAAGTCGAC |
| 0193 | Mutant ME42 Mutant ME42 | PRT | Artificial Sequence | MSGLRINSAKADAGGQAIANRFTSNIKGLTQASRNANDGISIAQTTEGALNEINNNLQRVRELSVQ ATNGTNSDSDLKSIQDEIQQRLEEIDRVSNQTQFNGVKVLSQDNQMKIQVGANDGETITIDLQKIDV KSLGLDGFNVNSPGSTANPLASIDSALSKVDAVRSSLGAIQNRFDSAITNLGNTVTNLNSARSRIED ADYATEVSNMSKAQILQQAGTSVLAQANQVPQNVLSLLVPRGSHHHHHHG |
| 0194 | Mutant ME110 Forward Primer ME100 | DNA | Artificial Sequence | GTCTGTTCAGGCCACTGCCGGGGCTAACTCTGATTCCGATCTG |

TABLE 1-continued

| Illustrative Flagellin-Based Agents | | | | |
|---|---|---|---|---|
| SEQ ID | Construct Name | DNA/ PRT | Species | Sequence |
| 0195 | Mutant ME110 Reverse Primer ME100 | DNA | Artificial Sequence | CAGATCGGAATCAGAGTTAGCCCCGGCAGTGGCCTGAACAGAC |
| 0196 | Mutant ME110 Sequence of ME100 construct | DNA | Artificial Sequence | TAATACGACTCACTATAGGGGAATTGTGAGCGGATAACAATTCCCCTCTAGAATAATTTTGTTT<br>AACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCG<br>TAACGCTAACGACGGCATTTCTATTGCGCAGACCACTGAAGGTGCGCTGAATGAAATCAACAA<br>CAACCTGCAGCGTGTGCGTGAGTTGTCTGTTCAGGCCACTGCCGGGGCTAACTCTGATTCCG<br>ATCTGAAATCTATCCAGGATGAAATTCAGCAACGTCTGGAAGAAATCGATCGCGTTTCTAATC<br>AGACTCAATTTAACGGTGTTAAAGTCCTGTCTCAGGACAACCAGATGAAAATCCAGGTTGGTG<br>CTAACGATGGTGAAACCATTACCATCGATCTGCAAAAAATTGATGTGAAAAGCCTTGGCCTTG<br>ATGGGTTCAATGTTAATTCCCCGGGAAGTACCGCTAACCCACTGGCTTCAATTGATTCTGCAT<br>TGTCAAAAGTGGACGCAGTTCGTTCTTCTCTGGGGGCAATTCAAAACCGCTTTGATTCAGCCA<br>TTACCAACCTTGGCAATACGGTAACCAATCTGAACTCCGCGCGTAGCCGTATCGAAGATGCT<br>GACTATGCAACGGAAGTTTCTAATATGTCTAAAGCGCAGATTCTGCAGCAGGCTGGTACTTCC<br>GTTCTGGCGCAGGCTAACCAGGTTCCGCAAAACGTCCTCTCTTTACTGGTTCCGCGGGGTTC<br>TCATCATCATCATCATCATGGTTAAGTCGAC |
| 0197 | Mutant ME110 Mutant ME110 | PRT | Artificial Sequence | MSGLRINSAKDDAAGQAIANRFTSNIKGLTQASRNANDGISIAQTTEGALNEINNNLQRVRELSVQ<br>ATAGANSDSDLKSIQDEIQQRLEEIDRVSNQTQFNGVKVLSQDNQMKIQVGANDGETITIDLQKIDV<br>KSLGLDGFNVNSPGSTANPLASIDSALSKVDAVRSSLGAIQNRFDSAITNLGNTVTNLNSARSRIED<br>ADYATEVSNMSKAQILQQAGTSVLAQANQVPQNVLSLLVPRGSHHHHHHG |
| 0198 | Mutant ME100/110 Forward Primer ME110 | DNA | Artificial Sequence | CTGATTCCGATCTGAAAGCTATCCAGGCTGAAATTCAGCAACGTC |
| 0199 | Mutant ME100/110 Reverse Primer ME110 | DNA | Artificial Sequence | GACGTTGCTGAATTTCAGCCTGGATAGCTTTCAGATCGGAATCAG |
| 0200 | Mutant ME100/110 Sequence of ME100/110 construct | DNA | Artificial Sequence | TAATACGACTCACTATAGGGGAATTGTGAGCGGATAACAATTCCCCTCTAGAATAATTTTGTTT<br>AACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCG<br>TAACGCTAACGACGGCATTTCTATTGCGCAGACCACTGAAGGTGCGCTGAATGAAATCAACAA<br>CAACCTGCAGCGTGTGCGTGAGTTGTCTGTTCAGGCCACTGCCGGGGCTAACTCTGATTCCG<br>ATCTGAAAGCTATCCAGGCTGAAATTCAGCAACGTCTGGAAGAAATCGATCGCGTTTCTAATC<br>AGACTCAATTTAACGGTGTTAAAGTCCTGTCTCAGGACAACCAGATGAAAATCCAGGTTGGTG<br>CTAACGATGGTGAAACCATTACCATCGATCTGCAAAAAATTGATGTGAAAAGCCTTGGCCTTG<br>ATGGGTTCAATGTTAATTCCCCGGGAAGTACCGCTAACCCACTGGCTTCAATTGATTCTGCAT<br>TGTCAAAAGTGGACGCAGTTCGTTCTTCTCTGGGGGCAATTCAAAACCGCTTTGATTCAGCCA<br>TTACCAACCTTGGCAATACGGTAACCAATCTGAACTCCGCGCGTAGCCGTATCGAAGATGCT<br>GACTATGCAACGGAAGTTTCTAATATGTCTAAAGCGCAGATTCTGCAGCAGGCTGGTACTTCC<br>GTTCTGGCGCAGGCTAACCAGGTTCCGCAAAACGTCCTCTCTTTACTGGTTCCGCGGGGTTC<br>TCATCATCATCATCATCATGGTTAAGTCGAC |
| 0201 | Mutant ME104N Intermediate Mutant ME100/110 | DNA | Artificial Sequence | ATGAGCGGGTTACGGATCAACAGCGCGAAAGACGATGCGGCAGGCCAGGCGATTGCTAACC<br>GCTTCACTTCTAATATCAAAGGTCTGACTCAGGCTTCCCGTAACGCTAACGACGGCATTTCTA<br>TTGCGCAGACCACTGAAGGTGCGCTGAATGAAATCAACAACAACCTGCAGCGTGTGCGTGAG |

TABLE 1-continued

| SEQ ID | Construct Name | DNA/ PRT | Species | Sequence |
|---|---|---|---|---|
| Illustrative Flagellin-Based Agents | | | | |
| | | | | TTGTCTGTTCAGGCCACTGCCGGGGCTAACTCTGATTCCGATCTGAAAGCTATCCAGGCTGA AATTCAGCAACGTCTGGAAGAAATCGATCGCGTTTCTAATCAGACTCAATTTAACGGTGTTAAA GTCCTGTCTCAGGACAACCAGATGAAAATCCAGGTTGGTGCTAACGATGGTGAAACCATTAC CATCGATCTGCAAAAAATTGATGTGAAAAGCCTTGGCCTTGATGGGTTCAATGTTAATTCCCC GGGAAGTACCGCTAACCCACTGGCTTCAATTGATTCTGCATTGTCAAAAGTGGACGCAGTTC GTTCTTCTCTGGGGGCAATTCAAAACCGCTTTGATTCAGCCATTACCAACCTTGGCAATACGG TAACCAATCTGAACTCCGCGCGTAGCCGTATCGAAGATGCTGACTATGCAACGGAAGTTTCTA ATATGTCTAAAGCGCAGATTCTGCAGCAGGCTGGTACTTCCGTTCTGGCGCAGGCTAACCAG GTTCCGCAAAACGTCCTCTCTTTACTGGTTCCGCGGGGTTCTCATCATCATCATCATCATGGT TAA |
| 0202 | Mutant ME100/110 Mutant ME110/110 | PRT | Artificial Sequence | MSGLRINSAKDDAAGQAIANRFTSNIKGLTQASRNANDGISIAQTTEGALNEINNNLQRVRELSVQ ATAGANSDSDLKAIQAEIQQRLEEIDRVSNQTQFNGVKVLSQDNQMKIQVGANDGETITIDLQKIDV KSLGLDGFNVNSPGSTANPLASIDSALSKVDAVRSSLGAIQNRFDSAITNLGNTVTNLNSARSRIED ADYATEVSNMSKAQILQQAGTSVLAQANQVPQNVLSLLVPRGSHHHHHHG |
| 0203 | Mutant ME104 Forward Primer ME104 | DNA | Artificial Sequence | GCCACTAACGGGACTAACGCTGATGCCGCTCTGAAATCTATCCAG |
| 0204 | Mutant ME104 Reverse Primer ME104 | DNA | Artificial Sequence | CTGGATAGATTTCAGAGCGGCATCAGCGTTAGTCCCGTTAGTGGC |
| 0205 | Mutant ME104 Sequence of ME104 construct | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG TAACGCTAACGACGGCATTTCTATTGCGCAGACCACTGAAGGTGCGCTGAATGAAATCAACAA CAACCTGCAGCGTGTGCGTGAGTTGTCTGTTCAGGCCACTAACGGGACTAACGCTGATGCCG CTCTGAAATCTATCCAGGATGAAATTCAGCAACGTCTGGAAGAAATCGATCGCGTTTCTAATC AGACTCAATTTAACGGTGTTAAAGTCCTGTCTCAGGACAACCAGATGAAAATCCAGGTTGGTG CTAACGATGGTGAAACCATTACCATCGATCTGCAAAAAATTGATGTGAAAAGCCTTGGCCTTG ATGGGTTCAATGTTAATTCCCCGGGAAGTACCGCTAACCCACTGGCTTCAATTGATTCTGCAT TGTCAAAAGTGGACGCAGTTCGTTCTTCTCTGGGGGCAATTCAAAACCGCTTTGATTCAGCCA TTACCAACCTTGGCAATACGGTAACCAATCTGAACTCCGCGCGTAGCCGTATCGAAGATGCT GACTATGCAACGGAAGTTTCTAATATGTCTAAAGCGCAGATTCTGCAGCAGGCTGGTACTTCC GTTCTGGCGCAGGCTAACCAGGTTCCGCAAAACGTCCTCTCTTTACTGGTTCCGCGGGGTTC TCATCATCATCATCATCATGGTTAAGTCGAC |
| 0206 | Mutant ME104 Mutant ME104 | PRT | Artificial Sequence | MSGLRINSAKDDAAGQAIANRFTSNIKGLTQASRNANDGISIAQTTEGALNEINNNLQRVRELSVQ ATNGTNADAALKSIQDEIQQRLEEIDRVSNQTQFNGVKVLSQDNQMKIQVGANDGETITIDLQKIDV KSLGLDGFNVNSPGSTANPLASIDSALSKVDAVRSSLGAIQNRFDSAITNLGNTVTNLNSARSRIED ADYATEVSNMSKAQILQQAGTSVLAQANQVPQNVLSLLVPRGSHHHHHHG |
| 0207 | Mutant ME104N Primer FME104New | DNA | Artificial Sequence | GCCACTGCCGGGGCTAACGCTGATGCCGCTCTGAAAGCTATCCAG |
| 0208 | Mutant ME104N Primer RME104New | DNA | Artificial Sequence | CTGGATAGCTTTCAGAGCGGCATCAGCGTTAGCCCCGGCAGTGGC |

TABLE 1-continued

| SEQ ID | Construct Name | DNA/ PRT | Species | Sequence |
|---|---|---|---|---|
| Illustrative Flagellin-Based Agents | | | | |
| 0209 | Mutant ME104N Sequence of construct ME104New | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG TAACGCTAACGACGGCATTTCTATTGCGCAGACCACTGAAGGTGCGCTGAATGAAATCAACAA CAACCTGCAGCGTGTGCGTGAGTTGTCTGTTCAGGCCACTGCCGGGGCTAACGCTGATGCC GCTCTGAAAGCTATCCAGGCTGAAATTCAGCAACGTCTGGAAGAAATCGATCGCGTTTCTAAT CAGACTCAATTTAACGGTGTTAAAGTCCTGTCTCAGGACAACCAGATGAAAATCCAGGTTGGT GCTAACGATGGTGAAACCATTACCATCGATCTGCAAAAAATTGATGTGAAAAGCCTTGGCCTT GATGGGTTCAATGTTAATTCCCCGGGAAGTACCGCTAACCCACTGGCTTCAATTGATTCTGCA TTGTCAAAAGTGGACGCAGTTCGTTCTTCTCTGGGGGCAATTCAAAACCGCTTTGATTCAGCC ATTACCAACCTTGGCAATACGGTAACCAATCTGAACTCCGCGCGTAGCCGTATCGAAGATGCT GACTATGCAACGGAAGTTTCTAATATGTCTAAAGCGCAGATTCTGCAGCAGGCTGGTACTTCC GTTCTGGCGCAGGCTAACCAGGTTCCGCAAAACGTCCTCTCTTTACTGGTTCCGCGGGGTTC TCATCATCATCATCATCATGGTTAAGTCGAC |
| 0210 | Mutant ME104N Mutant ME104N | PRT | Artificial Sequence | MSGLRINSAKDDAAGQAIANRFTSNIKGLTQASRNANDGISIAQTTEGALNEINNNLQRVRELSVQ ATAGANADAALKAIQAEIQQRLEEIDRVSNQTQFNGVKVLSQDNQMKIQVGANDGETITIDLQKIDV KSLGLDGFNVNSPGSTANPLASIDSALSKVDAVRSSLGAIQNRFDSAITNLGNTVTNLNSARSRIED ADYATEVSNMSKAQILQQAGTSVLAQANQVPQNVLSLLVPRGSHHHHHHG |
| 0211 | Mutant ME110 Sequence of ME110 construct | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG TAACGCTAACGACGGCATTTCTATTGCGCAGACCACTGAAGGTGCGCTGAATGAAATCAACAA CAACCTGCAGCGTGTGCGTGAGTTGTCTGTTCAGGCCACTAACGGGACTAACTCTGATTCCG ATCTGAAAGCTATCCAGGCTGAAATTCAGCAACGTCTGGAAGAAATCGATCGCGTTTCTAATC AGACTCAATTTAACGGTGTTAAAGTCCTGTCTCAGGACAACCAGATGAAAATCCAGGTTGGTG CTAACGATGGTGAAACCATTACCATCGATCTGCAAAAAATTGATGTGAAAAGCCTTGGCCTTG ATGGGTTCAATGTTAATTCCCCGGGAAGTACCGCTAACCCACTGGCTTCAATTGATTCTGCAT TGTCAAAAGTGGACGCAGTTCGTTCTTCTCTGGGGGCAATTCAAAACCGCTTTGATTCAGCCA TTACCAACCTTGGCAATACGGTAACCAATCTGAACTCCGCGCGTAGCCGTATCGAAGATGCT GACTATGCAACGGAAGTTTCTAATATGTCTAAAGCGCAGATTCTGCAGCAGGCTGGTACTTCC GTTCTGGCGCAGGCTAACCAGGTTCCGCAAAACGTCCTCTCTTTACTGGTTCCGCGGGGTTC TCATCATCATCATCATCATGGTTAAGTCGAC |
| 0212 | Mutant ME110 Mutant ME110 | PRT | Artificial Sequence | MSGLRINSAKDDAAGQAIANRFTSNIKGLTQASRNANDGISIAQTTEGALNEINNNLQRVRELSVQ ATNGTNSDSDLKAIQAEIQQRLEEIDRVSNQTQFNGVKVLSQDNQMKIQVGANDGETITIDLQKIDV KSLGLDGFNVNSPGSTANPLASIDSALSKVDAVRSSLGAIQNRFDSAITNLGNTVTNLNSARSRIED ADYATEVSNMSKAQILQQAGTSVLAQANQVPQNVLSLLVPRGSHHHHHHG |
| 0213 | Mutant ME117 Forward Primer ME117 | DNA | Artificial Sequence | CTATCCAGGATGAAATTCAGGCACGTCTGGCAGAAATCGATCGCG |
| 0214 | Mutant ME117 Reverse Primer ME117 | DNA | Artificial Sequence | CGCGATCGATTTCTGCCAGACGTGCCTGAATTTCATCCTGGATAG |
| 0215 | Mutant ME117 Sequence of 33ML | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG |

TABLE 1-continued

| Illustrative Flagellin-Based Agents | | | | |
|---|---|---|---|---|
| SEQ ID | Construct Name | DNA/ PRT | Species | Sequence |
| | construct (should this say ME117?) | | | GCAGGCCAGGCGATTGCTAACCGCTTCACTTCTAATATCAAAGGTCTGACTCAGGCTTCCCG<br>TAACGCTAACGACGGCATTTCTATTGCGCAGACCACTGAAGGTGCGCTGAATGAAATCAACAA<br>CAACCTGCAGCGTGTGCGTGAGTTGTCTGTTCAGGCCACTAACGGGACTAACTCTGATTCCG<br>ATCTGAAATCTATCCAGGATGAAATTCAGGCACGTCTGGCAGAAATCGATCGCGTTTCTAATC<br>AGACTCAATTTAACGGTGTTAAAGTCCTGTCTCAGGACAACCAGATGAAAATCCAGGTTGGTG<br>CTAACGATGGTGAAACCATTACCATCGATCTGCAAAAAATTGATGTGAAAAGCCTTGGCCTTG<br>ATGGGTTCAATGTTAATTCCCCGGGAAGTACCGCTAACCCACTGGCTTCAATTGATTCTGCAT<br>TGTCAAAAGTGGACGCAGTTCGTTCTTCTCTGGGGGCAATTCAAAACCGCTTTGATTCAGCCA<br>TTACCAACCTTGGCAATACGGTAACCAATCTGAACTCCGCGCGTAGCCGTATCGAAGATGCT<br>GACTATGCAACGGAAGTTTCTAATATGTCTAAAGCGCAGATTCTGCAGCAGGCTGGTACTTCC<br>GTTCTGGCGCAGGCTAACCAGGTTCCGCAAAACGTCCTCTCTTTACTGGTTCCGCGGGGTTC<br>TCATCATCATCATCATCATGGTTAAGTCGAC |
| 0216 | Mutant ME117 Mutant ME117 | PRT | Artificial Sequence | MSGLRINSAKDDAAGQAIANRFTSNIKGLTQASRNANDGISIAQTTEGALNEINNNLQRVRELSVQ<br>ATNGTNSDSDLKSIQDEIQARLAEIDRVSNQTQFNGVKVLSQDNQMKIQVGANDGETITIDLQKIDV<br>KSLGLDGFNVNSPGSTANPLASIDSALSKVDAVRSSLGAIQNRFDSAITNLGNTVTNLNSARSRIED<br>ADYATEVSNMSKAQILQQAGTSVLAQANQVPQNVLSLLVPRGSHHHHHHG |
| 0217 | Mutant ME124 Forward Primer ME104 | DNA | Artificial Sequence | GGAAGAAATCGATGCCGTTTCTGCTGCGACTCAATTTAACGGTGTTAAAGTCCTGTCTC |
| 0218 | Mutant ME124 Reverse Primer ME104 | DNA | Artificial Sequence | GAGACAGGACTTTAACACCGTTAAATTGAGTCGCAGCAGAAACGGCATCGATTTCTTCC |
| 0219 | Mutant ME124 Sequence of ME124 construct | DNA | Artificial Sequence | TAATACGACTCACTATAGGGGAATTGTGAGCGGATAACAATTCCCCTCTAGAATAATTTTGTTT<br>AACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCG<br>TAACGCTAACGACGGCATTTCTATTGCGCAGACCACTGAAGGTGCGCTGAATGAAATCAACAA<br>CAACCTGCAGCGTGTGCGTGAGTTGTCTGTTCAGGCCACTAACGGGACTAACTCTGATTCCG<br>ATCTGAAATCTATCCAGGATGAAATTCAGCAACGTCTGGAAGAAATCGATGCCGTTTCTGCTG<br>CGACTCAATTTAACGGTGTTAAAGTCCTGTCTCAGGACAACCAGATGAAAATCCAGGTTGGTG<br>CTAACGATGGTGAAACCATTACCATCGATCTGCAAAAAATTGATGTGAAAAGCCTTGGCCTTG<br>ATGGGTTCAATGTTAATTCCCCGGGAAGTACCGCTAACCCACTGGCTTCAATTGATTCTGCAT<br>TGTCAAAAGTGGACGCAGTTCGTTCTTCTCTGGGGGCAATTCAAAACCGCTTTGATTCAGCCA<br>TTACCAACCTTGGCAATACGGTAACCAATCTGAACTCCGCGCGTAGCCGTATCGAAGATGCT<br>GACTATGCAACGGAAGTTTCTAATATGTCTAAAGCGCAGATTCTGCAGCAGGCTGGTACTTCC<br>GTTCTGGCGCAGGCTAACCAGGTTCCGCAAAACGTCCTCTCTTTACTGGTTCCGCGGGGTTC<br>TCATCATCATCATCATCATGGTTAAGTCGAC |
| 0220 | Mutant ME124 Mutant ME124 | PRT | Artificial Sequence | MSGLRINSAKDDAAGQAIANRFTSNIKGLTQASRNANDGISIAQTTEGALNEINNNLQRVRELSVQ<br>ATNGTNSDSDLKSIQDEIQQRLEEIDAVSAATQFNGVKVLSQDNQMKIQVGANDGETITIDLQKIDV<br>KSLGLDGFNVNSPGSTANPLASIDSALSKVDAVRSSLGAIQNRFDSAITNLGNTVTNLNSARSRIED<br>ADYATEVSNMSKAQILQQAGTSVLAQANQVPQNVLSLLVPRGSHHHHHHG |
| 0221 | Mutant ME124P Forward Primer ME124P | DNA | Artificial Sequence | CAGCAACGTCTGGAAGAAATCGATGCCGTTTCTAATCAGACTCAATTTAACGG |

TABLE 1-continued

Illustrative Flagellin-Based Agents

| SEQ ID | Construct Name | DNA/ PRT | Species | Sequence |
|---|---|---|---|---|
| 0222 | Mutant ME124P Reverse Primer ME124P | DNA | Artificial Sequence | CCGTTAAATTGAGTCTGATTAGAAACGGCATCGATTTCTTCCAGACGTTGCTG |
| 0223 | Mutant ME124 Expressed Mutant ME124P | DNA | Artificial Sequence | ATGAGCGGGTTACGGATCAACAGCGCGAAAGACGATGCGGCAGGCCAGGCGATTGCTAACC<br>GCTTCACTTCTAATATCAAAGGTCTGACTCAGGCTTCCCGTAACGCTAACGACGGCATTTCTA<br>TTGCGCAGACCACTGAAGGTGCGCTGAATGAAATCAACAACAACCTGCAGCGTGTGCGTGAG<br>TTGTCTGTTCAGGCCACTAACGGGACTAACTCTGATTCCGATCTGAAATCTATCCAGGATGAA<br>ATTCAGCAACGTCTGGAAGAAATCGATGCCGTTTCTAATCAGACTCAATTTAACGGTGTTAAA<br>GTCCTGTCTCAGGACAACCAGATGAAAATCCAGGTTGGTGCTAACGATGGTGAAACCATTAC<br>CATCGATCTGCAAAAAATTGATGTGAAAAGCCTTGGCCTTGATGGGTTCAATGTTAATTCCCC<br>GGGAAGTACCGCTAACCCACTGGCTTCAATTGATTCTGCATTGTCAAAAGTGGACGCAGTTC<br>GTTCTTCTCTGGGGGCAATTCAAAACCGCTTTGATTCAGCCATTACCAACCTTGGCAATACGG<br>TAACCAATCTGAACTCCGCGCGTAGCCGTATCGAAGATGCTGACTATGCAACGGAAGTTTCTA<br>ATATGTCTAAAGCGCAGATTCTGCAGCAGGCTGGTACTTCCGTTCTGGCGCAGGCTAACCAG<br>GTTCCGCAAAACGTCCTCTCTTTACTGGTTCCGCGGGGTTCTCATCATCATCATCATCATGGT<br>TAA |
| 0224 | Mutant ME124P ME124P | DNA | Artificial Sequence | TAATACGACTCACTATAGGGGAATTGTGAGCGGATAACAATTCCCCTCTAGAATAATTTTGTTT<br>AACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCG<br>TAACGCTAACGACGGCATTTCTATTGCGCAGACCACTGAAGGTGCGCTGAATGAAATCAACAA<br>CAACCTGCAGCGTGTGCGTGAGTTGTCTGTTCAGGCCACTAACGGGACTAACTCTGATTCCG<br>ATCTGAAATCTATCCAGGATGAAATTCAGCAACGTCTGGAAGAAATCGATGCCGTTTCTAATC<br>AGACTCAATTTAACGGTGTTAAAGTCCTGTCTCAGGACAACCAGATGAAAATCCAGGTTGGTG<br>CTAACGATGGTGAAACCATTACCATCGATCTGCAAAAAATTGATGTGAAAAGCCTTGGCCTTG<br>ATGGGTTCAATGTTAATTCCCCGGGAAGTACCGCTAACCCACTGGCTTCAATTGATTCTGCAT<br>TGTCAAAAGTGGACGCAGTTCGTTCTTCTCTGGGGGCAATTCAAAACCGCTTTGATTCAGCCA<br>TTACCAACCTTGGCAATACGGTAACCAATCTGAACTCCGCGCGTAGCCGTATCGAAGATGCT<br>GACTATGCAACGGAAGTTTCTAATATGTCTAAAGCGCAGATTCTGCAGCAGGCTGGTACTTCC<br>GTTCTGGCGCAGGCTAACCAGGTTCCGCAAAACGTCCTCTCTTTACTGGTTCCGCGGGGTTC<br>TCATCATCATCATCATCATGGTTAAGTCGAC |
| 0225 | Mutant ME124P ME124P | PRT | Artificial Sequence | MSGLRINSAKDDAAGQAIANRFTSNIKGLTQASRNANDGISIAQTTEGALNEINNNLQRVRELSVQ<br>ATNGTNSDSDLKSIQDEIQQRLEEIDAVSNQTQFNGVKVLSQDNQMKIQVGANDGETITIDLQKIDV<br>KSLGLDGFNVNSPGSTANPLASIDSALSKVDAVRSSLGAIQNRFDSAITNLGNTVTNLNSARSRIED<br>ADYATEVSNMSKAQILQQAGTSVLAQANQVPQNVLSLLVPRGSHHHHHHG |
| 0226 | Mutant ME132 Forward Primer ME132 | DNA | Artificial Sequence | CGTTTCTAATCAGACTCAATTTGCCGCTGTTAAAGTCCTGTCTCAGGACAACC |
| 0227 | Mutant ME132 Reverse Primer ME132 | DNA | Artificial Sequence | GGTTGTCCTGAGACAGGACTTTAACAGCGGCAAATTGAGTCTGATTAGAAACG |
| 0228 | Mutant ME132 Sequence of ME132 construct | DNA | Artificial Sequence | TAATACGACTCACTATAGGGGAATTGTGAGCGGATAACAATTCCCCTCTAGAATAATTTTGTTT<br>AACTTTAAGAAGGAGATATACATATGAGCGGGTTACGGATCAACAGCGCGAAAGACGATGCG<br>GCAGGCCAGGCGATTGCTAACCGCTTCACTTCTAATATCAAAGGTCTGACTCAGGCTTCCCG<br>TAACGCTAACGACGGCATTTCTATTGCGCAGACCACTGAAGGTGCGCTGAATGAAATCAACAA<br>CAACCTGCAGCGTGTGCGTGAGTTGTCTGTTCAGGCCACTAACGGGACTAACTCTGATTCCG |

TABLE 1-continued

Illustrative Flagellin-Based Agents

| SEQ ID | Construct Name | DNA/ PRT | Species | Sequence |
|---|---|---|---|---|
| | | | | ATCTGAAATCTATCCAGGATGAAATTCAGCAACGTCTGGAAGAAATCGATCGCGTTTCTAATC AGACTCAATTTGCCGCTGTTAAAGTCCTGTCTCAGGACAACCAGATGAAAATCCAGGTTGGTG CTAACGATGGTGAAACCATTACCATCGATCTGCAAAAAATTGATGTGAAAAGCCTTGGCCTTG ATGGGTTCAATGTTAATTCCCCGGGAAGTACCGCTAACCCACTGGCTTCAATTGATTCTGCAT TGTCAAAAGTGGACGCAGTTCGTTCTTCTCTGGGGGCAATTCAAAACCGCTTTGATTCAGCCA TTACCAACCTTGGCAATACGGTAACCAATCTGAACTCCGCGCGTAGCCGTATCGAAGATGCT GACTATGCAACGGAAGTTTCTAATATGTCTAAAGCGCAGATTCTGCAGCAGGCTGGTACTTCC GTTCTGGCGCAGGCTAACCAGGTTCCGCAAAACGTCCTCTCTTTACTGGTTCCGCGGGGTTC TCATCATCATCATCATCATGGTTAAGTCGAC |
| 0229 | Mutant ME132 Mutant ME117 (ME132?) | PRT | Artificial Sequence | MSGLRINSAKDDAAGQAIANRFTSNIKGLTQASRNANDGISIAQTTEGALNEINNNLQRVRELSVQ ATNGTNSDSDLKSIQDEIQQRLEEIDRVSNQTQFAAVKVLSQDNQMKIQVGANDGETITIDLQKIDV KSLGLDGFNVNSPGSTANPLASIDSALSKVDAVRSSLGAIQNRFDSAITNLGNTVTNLNSARSRIED ADYATEVSNMSKAQILQQAGTSVLAQANQVPQNVLSLLVPRGSHHHHHHG |
| 0230 | Mutant ME142 Forward Primer ME142 | DNA | Artificial Sequence | GTTAAAGTCCTGTCTCAGGACAACGCGATGGCAATCCAGGTTGGTGCTAACG |
| 0231 | Mutant ME142 Reverse Primer ME142 | DNA | Artificial Sequence | CGTTAGCACCAACCTGGATTGCCATCGCGTTGTCCTGAGACAGGACTTTAAC |
| 0232 | Mutant ME142 Sequence of ME142 construct | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGTTACGGATCAACAGCGCGAAAGACGATGCG GCAGGCCAGGCGATTGCTAACCGCTTCACTTCTAATATCAAAGGTCTGACTCAGGCTTCCCG TAACGCTAACGACGGCATTTCTATTGCGCAGACCACTGAAGGTGCGCTGAATGAAATCAACAA CAACCTGCAGCGTGTGCGTGAGTTGTCTGTTCAGGCCACTAACGGGACTAACTCTGATTCCG ATCTGAAATCTATCCAGGATGAAATTCAGCAACGTCTGGAAGAAATCGATCGCGTTTCTAATC AGACTCAATTTAACGGTGTTAAAGTCCTGTCTCAGGACAACGCGATGGCAATCCAGGTTGGT GCTAACGATGGTGAAACCATTACCATCGATCTGCAAAAAATTGATGTGAAAAGCCTTGGCCTT GATGGGTTCAATGTTAATTCCCCGGGAAGTACCGCTAACCCACTGGCTTCAATTGATTCTGCA TTGTCAAAAGTGGACGCAGTTCGTTCTTCTCTGGGGGCAATTCAAAACCGCTTTGATTCAGCC ATTACCAACCTTGGCAATACGGTAACCAATCTGAACTCCGCGCGTAGCCGTATCGAAGATGCT GACTATGCAACGGAAGTTTCTAATATGTCTAAAGCGCAGATTCTGCAGCAGGCTGGTACTTCC GTTCTGGCGCAGGCTAACCAGGTTCCGCAAAACGTCCTCTCTTTACTGGTTCCGCGGGGTTC TCATCATCATCATCATCATGGTTAAGTCGAC |
| 0233 | Mutant ME142 Mutant ME142 | PRT | Artificial Sequence | MSGLRINSAKDDAAGQAIANRFTSNIKGLTQASRNANDGISIAQTTEGALNEINNNLQRVRELSVQ ATNGTNSDSDLKSIQDEIQQRLEEIDRVSNQTQFNGVKVLSQDNAMAIQVGANDGETITIDLQKIDV KSLGLDGFNVNSPGSTANPLASIDSALSKVDAVRSSLGAIQNRFDSAITNLGNTVTNLNSARSRIED ADYATEVSNMSKAQILQQAGTSVLAQANQVPQNVLSLLVPRGSHHHHHHG |
| 0234 | Mutant ME150 Forward Primer ME150 | DNA | Artificial Sequence | GATGAAAATCCAGGTTGGTGCTAGCGCTGCTGAAACCATTACCATCGATCTGC |
| 0235 | Mutant ME150 Reverse Primer ME150 | DNA | Artificial Sequence | GCAGATCGATGGTAATGGTTTCAGCAGCGCTAGCACCAACCTGGATTTTCATC |

TABLE 1-continued

| Illustrative Flagellin-Based Agents | | | | |
|---|---|---|---|---|
| SEQ ID | Construct Name | DNA/ PRT | Species | Sequence |
| 0236 | Mutant ME150 Sequence of ME150 construct | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG TAACGCTAACGACGGCATTTCTATTGCGCAGACCACTGAAGGTGCGCTGAATGAAATCAACAA CAACCTGCAGCGTGTGCGTGAGTTGTCTGTTCAGGCCACTAACGGGACTAACTCTGATTCCG ATCTGAAATCTATCCAGGATGAAATTCAGCAACGTCTGGAAGAAATCGATCGCGTTTCTAATC AGACTCAATTTAACGGTGTTAAAGTCCTGTCTCAGGACAACCAGATGAAAATCCAGGTTGGTG CTAGCGCTGCTGAAACCATTACCATCGATCTGCAAAAAATTGATGTGAAAAGCCTTGGCCTTG ATGGGTTCAATGTTAATTCCCCGGGAAGTACCGCTAACCCACTGGCTTCAATTGATTCTGCAT TGTCAAAAGTGGACGCAGTTCGTTCTTCTCTGGGGGCAATTCAAAACCGCTTTGATTCAGCCA TTACCAACCTTGGCAATACGGTAACCAATCTGAACTCCGCGCGTAGCCGTATCGAAGATGCT GACTATGCAACGGAAGTTTCTAATATGTCTAAAGCGCAGATTCTGCAGCAGGCTGGTACTTCC GTTCTGGCGCAGGCTAACCAGGTTCCGCAAAACGTCCTCTCTTTACTGGTTCCGCGGGGTTC TCATCATCATCATCATCATGGTTAAGTCGAC |
| 0237 | Mutant ME150 Mutant ME150 | PRT | Artificial Sequence | MSGLRINSAKDDAAGQAIANRFTSNIKGLTQASRNANDGISIAQTTEGALNEINNNLQRVRELSVQ ATNGTNSDSDLKSIQDEIQQRLEEIDRVSNQTQFNGVKVLSQDNQMKIQVGASAAETITIDLQKIDV KSLGLDGFNVNSPGSTANPLASIDSALSKVDAVRSSLGAIQNRFDSAITNLGNTVTNLNSARSRIED ADYATEVSNMSKAQILQQAGTSVLAQANQVPQNVLSLLVPRGSHHHHHHG |
| 0238 | Mutant ME468 Forward Primer ME468 | DNA | Artificial Sequence | GCCGTATCGAAGATGCTGACGCTGGAGCGGAAGTTGCTAATATGTCTAAAGCGCAG |
| 0239 | Mutant ME468 Reverse Primer ME468 | DNA | Artificial Sequence | CTGCGCTTTAGACATATTAGCAACTTCCGCTCCAGCGTCAGCATCTTCGATACGGC |
| 0240 | Mutant ME468 Sequence of ME468 construct | DNA | Artificial Sequence | TAATACGACTCACTATAGGGGAATTGTGAGCGGATAACAATTCCCCTCTAGAATAATTTTGTTT AACTTTAAGAAGGAGATATACATATGAGCGGGTTACGGATCAACAGCGCGAAAGACGATGCG GCAGGCCAGGCGATTGCTAACCGCTTCACTTCTAATATCAAAGGTCTGACTCAGGCTTCCCG TAACGCTAACGACGGCATTTCTATTGCGCAGACCACTGAAGGTGCGCTGAATGAAATCAACAA CAACCTGCAGCGTGTGCGTGAGTTGTCTGTTCAGGCCACTAACGGGACTAACTCTGATTCCG ATCTGAAATCTATCCAGGATGAAATTCAGCAACGTCTGGAAGAAATCGATCGCGTTTCTAATC AGACTCAATTTAACGGTGTTAAAGTCCTGTCTCAGGACAACCAGATGAAAATCCAGGTTGGTG CTAACGATGGTGAAACCATTACCATCGATCTGCAAAAAATTGATGTGAAAAGCCTTGGCCTTG ATGGGTTCAATGTTAATTCCCCGGGAAGTACCGCTAACCCACTGGCTTCAATTGATTCTGCAT TGTCAAAAGTGGACGCAGTTCGTTCTTCTCTGGGGGCAATTCAAAACCGCTTTGATTCAGCCA TTACCAACCTTGGCAATACGGTAACCAATCTGAACTCCGCGCGTAGCCGTATCGAAGATGCT GACGCTGGAGCGGAAGTTGCTAATATGTCTAAAGCGCAGATTCTGCAGCAGGCTGGTACTTC CGTTCTGGCGCAGGCTAACCAGGTTCCGCAAAACGTCCTCTCTTTACTGGTTCCGCGGGGTT CTCATCATCATCATCATCATGGTTAAGTCGAC |
| 0241 | Mutant ME468 Mutant ME468 | PRT | Artificial Sequence | MSGLRINSAKDDAAGQAIANRFTSNIKGLTQASRNANDGISIAQTTEGALNEINNNLQRVRELSVQ ATNGTNSDSDLKSIQDEIQQRLEEIDRVSNQTQFNGVKVLSQDNQMKIQVGANDGETITIDLQKIDV KSLGLDGFNVNSPGSTANPLASIDSALSKVDAVRSSLGAIQNRFDSAITNLGNTVTNLNSARSRIED ADAGAEVANMSKAQILQQAGTSVLAQANQVPQNVLSLLVPRGSHHHHHHG |
| 0242 | Linker | PRT | Artificial Sequence | SPG |

TABLE 1-continued

| Illustrative Flagellin-Based Agents | | | | |
|---|---|---|---|---|
| SEQ ID | Construct Name | DNA/ PRT | Species | Sequence |
| 0243 | Lru283 | PRT | Artificial Sequence | mghhhhhhsgMEEFNMRINTNVAAMNTYSRLTAANTAKSNSLAKLSSGLRINKAGDDAAGLAISEKMKSQIGGLTQAKRNAQDGISLVQTAEGALNETHSILERMRDLAVQGSNGTLTSSDRGSINKELKALHQELTRISNTTEFNTQKLFSQTKQKSVTFTFQIGANAGQTLSVAITAMSGEALLVSTDAKFSLNAAGTNAGAMIKSIDAAIAKVSDQRADLGAVQNRLEHTINNLTATNENLSDANSRIRDVDMAEEMMTFTKSNILSQAATSMLAQANAMPNSVLNLLQG |
| 0244 | Tpe270 | PRT | Artificial Sequence | mghhhhhhsgMRINHNISALNAWRNIDQTQYSMSKTLERLSSGLRINRAGDDAAGLAISEKMRGQIKGLNMAIKNAQDAISLIQTAEGALTEVHSILQRMRELAVQAASDTNTNVDREQIQKEIDQLREEIDRIARTTEFNTKKLLDGKLEGFRSQVDAKVVTGGNINVQLGTVSSKAVEGTYVIEVGaAERAIMVVDAAIHRVSTARAALGAIQNRLEHTISNLGVAAENLTAAESRIRDADMAKEMMEFTKQQILLQSSMAMLAQSNTLPQNVLQLMR |
| 0245 | Tpe159w | PRT | Artificial Sequence | mghhhhhhsGLNMAIKNAQDAISLIQTAEGALTEVHSILQRMRELAVQAASDTNTNVDREQIQKEIDQLREEIDRIARTTEFNTKKLLDGKLEGFRSQVDAKVVTGGNINVQLGTVSSKAVEGTYVIEVGaAERAIMVVDAAIHRVSTARAALGAIQNRLEHTISNLG |
| 0246 | Chy275 | PRT | Artificial Sequence | mghhhhhhsgMSLRINNNIEALNAWRALNSTSNALQKSMEKLSSGLRINRAGDDAAGLAISEKLRAQIRGLNQAIRNAQDGISLIQTAEGGLSEIQNILQRMRELGVQAANGTLNNQDISAITTELNQLFNEIDRIAGATEFNTKNLLAVSTGLVVTLQVGANAGQVIAFTIDNAGTASLGLSSADLAINDNASASAFISKVDSALQKVSTYRANLGSIQNRLEHTIANLGIASENLSASESRIRDVDMAAEMMNFTKNQILQQAGVAILAQANQAPQAVLQLLR |
| 0247 | Chy162w | PRT | Artificial Sequence | mghhhhhhsGLNQAIRNAQDGISLIQTAEGGLSEIQNILQRMRELGVQAANGTLNNQDISAITTELNQLFNEIDRIAGATEFNTKNLLAVSTGLVVTLQVGANAGQVIAFTIDNAGTASLGLSSADLAINDNASASAFISKVDSALQKVSTYRANLGSIQNRLEHTIANLG |
| 0248 | ChyU137 | PRT | Artificial Sequence | mghhhhhhsGLNQAIRNAQDGISLIQTAEGGLSEIQNILQRMRELGVQAANGTLNNQDISAITTELNQLFNEIDRIAGATEFNTKNLLAAGTASLGLSSADLAINDNASASAFISKVDSALQKVSTYRANLGSIQNRLEHTIANLG |
| 0249 | ChyN108 | PRT | Artificial Sequence | mghhhhhhSASAFISKVDSALQKVSTYRANLGSIQNRLEHTIANLGpdGLNQAIRNAQDGISLIQTAEGGLSEIQNILQRMRELGVQAANGTLNNQDISAITTELNQLFNEIDRIA |
| 0250 | ChyZ94 | PRT | Artificial Sequence | mghhhhhhsNNQDISAITTELNQLFNEIDRIAGATgsGGLSEIQNILQRMRELGVQAANGTLNggSASAFISKVDSALQKVSTYRANLGSIQNRLEHTIANLG |
| 0251 | Fir161B | PRT | Artificial Sequence | mghhhhhhsGLAQASRNAQDAISIAQTAEGALDETQSILQRVRELGVQGANGTLTADDINALQAEVDQLIAEIDRIAGATEFNTQNLLDGSFTTKAFQVGANSGQNMTLTIGKMDTTTLGLSSADLAINDNAFANGAISTVDSALQKVSAERAKLGAIQNRLEHTIANLG |
| 0252 | Fir161MNB | PRT | Artificial Sequence | mghhhhhhsGLAQASRQAQDAISIAQTAEGALDETQSILQRVRELGVQGADGTLTADDIDALQAEVDQLIAEIDRIAGATEFATQKLLDGSFTTKAFQVGAASGQDVTLTIGKVDTTTLGLSSADLAIDSAAFADGAISTVDSALQKVSAERAKLGAIQNRLEHTIAQLG |

In some embodiments, the aluminum gel or salt is selected from aluminum hydroxide, aluminum phosphate, and potassium aluminum sulfate, AS04 (which is composed of aluminum salt and MPL), and ALHYDROGEL. In some embodiments, the aluminum gel or salt is a formulation or mixture with any of the additional adjuvants described herein.

In some embodiments, adjuvants in addition to the described flagellin-based agent and an aluminum gel or salt find use in the present invention. In some embodiments, the additional adjuvant is selected from, oil-in-water emulsion formulations, saponin adjuvants, ovalbumin, Freunds Adjuvant, cytokines, and chitosans. Illustrative additional adjuvants include, but are not limited to: (1) ovalbumin (e.g. ENDOFIT), which is often used for biochemical studies; (2) oil-in-water emulsion formulations (with or without other specific immunostimulating agents such as muramyl peptides or bacterial cell wall components), such as for example (a) MF59 (PCT Publ. No. WO 90/14837), containing 5% Squalene, 0.5% Tween 80, and 0.5% Span 85 (optionally containing various amounts of MTP-PE) formulated into submicron particles using a microfluidizer such as, for example, Model HOy microfluidizer (Microfluidics, Newton, Mass.), (b) SAF, containing 10% Squalane, 0.4% Tween 80, 5% pluronic-blocked polymer L121, and thr-MDP either microfluidized into a submicron emulsion or vortexed to generate a larger particle size emulsion, (c) RIBI adjuvant system (RAS), (RIBI IMMUNOCHEM, Hamilton, Mo.) containing 2% Squalene, 0.2% Tween 80, and, optionally, one or more bacterial cell wall components from the group of monophosphorylipid A (MPL), trehalose dimycolate (TDM), and cell wall skeleton (CWS), including MPL+CWS (DETOX™); and (d) ADDAVAX (Invitrogen); (3) saponin adjuvants, such as STIMULON (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (by way of non-limiting example, IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; (6) chitosans and other derivatives of chitin or poly-N-acetyl-D-glucosamine in which the greater proportion of the N-acetyl groups have been removed through hydrolysis (see, e.g., European Patent Application 460 020, which is hereby incorporated by reference in its entirety, disclosing pharmaceutical formulations including chitosans as mucosal absorption enhancers; and (7) other substances that act as immunostimulating agents to enhance the effectiveness of the composition, e.g., monophosphoryl lipid A. In other embodiments, the additional adjuvant is one or more of a flagellin-based agent (e.g. CBLB502 or any of the agents of Table 1), an aluminium salt or gel, a pattern recognition receptors (PRR) agonist, CpG ODNs and imidazoquinolines. In some embodiments, the additional adjuvant is one or more of cyclic [G(3',5')pA(3',5')p] (e.g. 3'3'-cGAMP VACCIGRADE); cyclic [G(2',5')pA(3',5')p]2'3' (e.g. 2'3' cGAMP VACCIGRADE); cyclic [G(2',5')pA(2',5')p] (e.g. 2'2'-cGAMP VACCIGRADE), cyclic diadenylate monophosphate (e.g. c-di-AMP VACCIGRADE); cyclic diguanylate monophosphate (e.g. c-di-GMP VACCIGRADE); TLR7 agonist-imidazoquinolines compound (e.g. TLR7 agonists, such as, for example, Gardiquimod VACCIGRADE, Imiquimod VACCIGRADE, R848 VACCIGRADE); lipopolysaccharides (e.g. TLR4 agonists), such as that from *E. coli* 0111:B4 strain (e.g. LPS-EB VACCIGRADE); monophosphoryl lipid A (e.g. MPLA-SM VACCIGRADE and MPLA Synthetic VACCIGRADE); N-glycolylated muramyldipeptide (e.g. N-Glycolyl-MDP VACCIGRADE); CpG ODN, class A and/oror CpG ODN, class B and/or CpG ODN, class C (e.g. ODN 1585 VACCIGRADE, ODN 1826 VACCIGRADE, ODN 2006 VACCIGRADE, ODN 2395 VACCIGRADE), a triacylated lipoprotein (e.g. Pam3CSK4 VACCIGRADE); Polyinosine-polycytidylic acid (e.g. Poly(I:C) (HMW) VACCIGRADE); and cord factor (i.e. mycobacterial cell wall component trehalose 6,6' dimycolate (TDM)) or an analog thereof (e.g. TDB VACCIGRADE, TDB-HS15 VACCIGRADE). In some emobodiments, the additional adjuvant is a TLR agonist (e.g. TLR1, and/or TLR2, and/or TLR3, and/or TLR4, and/or TLR5, and/or TLR6, and/or TLR7, and/or TLR8, and/or TLR9, and/or TLR10, and/or TLR11, and/or TLR12, and/or TLR13), a nucleotide-binding oligomerization domain (NOD) agonist, a stimulator of interferon genes (STING) ligand, or related agent.

In some embodiments, the additional adjuvants is one or more of a mineral adjuvant, gel-based adjuvant, tensoactive agent, bacterial product, oil emulsion, particulated adjuvant, fusion protein, and lipopeptide. Other mineral salt adjuvants, besides the aluminum adjuvants described elsewhere, include salts of calcium (e.g. calcium phosphate), iron and zirconium. Other gel-based adjuvants, besides the aluminum gel-based adjuvants described elsewhere, include Acemannan. Tensoactive agents include Quil A, saponin derived from an aqueous extract from the bark of *Quillaja saponaria*; saponins, tensoactive glycosides containing a hydrophobic nucleus of triterpenoid structure with carbohydrate chains linked to the nucleus, and QS-21. Bacterial products include cell wall peptidoglycan or lipopolysaccharide of Gram-negative bacteria (e.g. from *Mycobacterium* spp., *Corynebacterium parvum, C. granulosum, Bordetella pertussis* and *Neisseria meningitidis*), N-acetyl muramyl-L-alanyl-D-isoglutamine (MDP), different compounds derived from MDP (e.g. threonyl-MDP), lipopolysaccharides (LPS) (e.g. from the cell wall of Gram-negative bacteria), trehalose dimycolate (TDM), and DNA containing CpG motifs. Oil emulsions include FIA, Montanide, Adjuvant 65, Lipovant, the montanide family of oil-based adjuvants, and various liposomes. Among particulated and polymeric systems, poly (DL-lactide-coglycolide) microspheres have been extensively studied and find use herein.

Further, in some embodiments, cytokines are an adjuvant of the present invention (e.g. IFN-γ and granulocyte-macrophage colony stimulating factor (GM-CSF)). Also carbohydrate adjuvants (e.g. inulin-derived adjuvants, such as, gamma inulin, algammulin (a combination of γ-inulin and aluminum hydroxide), and polysaccharides based on glucose and mannose, such as glucans, dextrans, lentinans, glucomannans and galactomannans) find use in the present invention. In some embodiments, adjuvant formulations are useful in the present invention and include alum salts in combination with other adjuvants such as Lipid A, algammulin, immunostimulatory complexes (ISCOMS), which are virus like particles of 30-40 nm and dodecahedric structure, composed of Quil A, lipids, and cholesterol.

In some embodiments, the additional adjuvants are described in Jennings et al. Adjuvants and Delivery Systems for Viral Vaccines-Mechanisms and Potential. In: Brown F, Haaheim L R, (eds). *Modulation of the Immune Response to Vaccine Antigens. Dev. Biol. Stand*, Vol. 92. Basel: Karger 1998; 19-28 and/or Sayers et al. J Biomed Biotechnol. 2012; 2012: 831486, and/or Petrovsky and Aguilar, Immunology and Cell Biology (2004) 82, 488-496 the contents of which are hereby incorporated by reference in their entireties.

In various embodiments, the present adjuvants (e.g. flagellin-based agent and an aluminum gel or salt) may be part of live and attenuated, or killed or inactivated, or toxoid, or subunit or conjugate vaccines.

In various embodiments, the present adjuvants (e.g. flagellin-based agent and an aluminum gel or salt) may be part of one or more approved vaccines and/or the antigens of one or more approved vaccines may be the antigens of the present invention. In some embodiments, the approved vaccines include: Adenovirus; Anthrax (Biothrax); BCG (Tice); DT (Sanofi); DTaP (Daptacel); DTaP (Infanrix); DTaP-HepB-IPV (Pediarix); DTaP-IPV (Kinrix); DTaP-IPV/Hib (Pentacel); Hib (ActHIB); Hib (Hiberix); Hib (PedvaxHIB); Hib/Hep B (Comvax); Hib/lMening. CY (MenHibrix); Hep A (Havrix); Hep A (Havrix); Hep B (Engerix-B); Hep B (Recombivax); Hep A/Hep B (Twinrix); Human Papillomavirus (HPV) (Cerverix); Human Papillomavirus (HPV) (Gardasil); Influenza (Afluria); Influenza (Agriflu); Influenza (Fluarix); Influenza (Flublok); Influenza (Flucelvax); Influenza (Fluvirin); Influenza (Flulaval); Influenza (Fluzone: Standard, High-Dose, & Intradermal); Influenza (FluMist); Japanese Encephalitis (Ixiaro); Meningococcal (MCV4-Menactra); Meningococcal (MCV4-Menveo); Meningococcal (MPSV4-Menomune); MMR (MMR-II); MMRV (ProQuad); Pneumococcal (PCV13-Prevnar 13); Pneumococcal (PPSV-23-Pneumovax); Polio (IPV-Ipol); Rabies (Imovax); Rabies (RabAvert); Rotavirus (RotaTeq); Rotavirus (Rotarix); Smallpox (Vaccinia-ACAM2000); Td (Decavac); Td (Tenivac); Td (Mass Biologics); Tdap (Adacel); Tdap (Boostrix); Typhoid (inactivated-Typhim Vi); Typhoid (oral-Ty21a); Varicella (Varivax); Yellow Fever (YF-Vax); and Zoster (Shingles-Zostavax).

In various embodiments, the present adjuvants (e.g. flagellin-based agent and an aluminum gel or salt) may be part of one or more illustrative vaccines and/or the antigens of one or more illustrative vaccines may be the antigens of the present invention. Illustrative vaccines include, by way of example, subunit vaccine and inactivated or "killed" vaccine (e.g. Infanrix-IPV/Hib (*Bordetella pertussis*), Infanrix-IPV/Hib (*Haemophilus influenzae*), Infanrix-IPV/Hib (Poliovirus), Infanrix-IPV/Hib (*Clostridium tetani*), Infanrix-IPV/Hib (*Corynebacterium diphtheriae*), Infanrix-hexa (*Bordetella pertussis*), Infanrix-hexa (*Haemophilus influenzae*), Infanrix-hexa (Poliovirus), Infanrix-hexa (Hepatitis B virus), Infanrix-hexa (*Clostridium tetani*), Infanrix-hexa (*Corynebacterium diphtheriae*), Infanrix-IPV (*Bordetella pertussis*), Infanrix-IPV (Poliovirus), Infanrix-IPV (*Clostridium tetani*), Infanrix-IPV (*Corynebacterium diphtheriae*), Infanrix/Hib (*Corynebacterium diphtheriae*), Pediarix (*Clostridium tetani*), Pediarix (Poliovirus), Pediarix (Hepatitis B virus), ViVaxim (*Salmonella* spp.), ViVaxim (Hepatitis A virus); subunit vaccines (e.g. 5CVMB (*Neisseria meningitidis*), *B. pertussis* CyaA protein vaccine (*Bordetella pertussis*), *B. pertussis* PTx protein vaccine (*Bordetella pertussis*), Cancer VEGFA protein vaccine (Cancer), *E. coli* vaccine using intimin polypeptide (*Escherichia coli*), Engerix-B (Hepatitis B virus), *H. pylori* VacA protein vaccine (*Helicobacter* pylon), HC of type C and D (*Clostridium botulinum*), Infanrix/Hib (*Bordetella pertussis*), Infanrix/Hib (*Haemophilus influenzae*), Infanrix/Hib (*Clostridium tetani*), *M. gallisepticum* TM-1 Protein Subunit Vaccine (*Mycoplasma gallisepticum*), MDA-modified human apo B-100 peptide Vaccine (Atherosclerosis), MSP3-LSP with aluminium hydroxide (*Plasmodium* spp.), Mumps HN Protein Subunit Vaccine (Mumps virus), *N. miningitidis* TBP2 Protein Vaccine (*Neisseria meningitidis*), *P. aeruginosa* Oprl Protein Vaccine (*Pseudomonas aeruginosa*), *P. falciparum* Subunit SE36 Protein Vaccine (*Plasmodium* spp.), *Phleum pratense* Allergy Phl p 12 Subunit Vaccine (Allergy), Recombivax HB (Hepatitis B virus), *S. pneumoniae* ClpP protein Vaccine (*Streptococcus pneumoniae*); toxoid vaccine (e.g. BoNT/F(Hc) (*Clostridium botulinum*), DAPTACEL (*Corynebacterium diphtheriae*), Infanrix (*Bordetella pertussis*), Infanrix (*Clostridium tetani*), KINRIX (*Clostridium tetani*), PBT (*Clostridium botulinum*), Pediarix (*Bordetella pertussis*), inactivated or "killed" vaccines (e.g. Avaxim (Hepatitis A virus), Avaxim-Pediatric (Hepatitis A virus), FSME-IMMUN (Tick-borne Encephalitis Virus (TBEV)), Infanrix (*Corynebacterium diphtheriae*), Ixiaro (Japanese encephalitis virus), KINRIX (*Corynebacterium diphtheriae*), and Pediarix (*Corynebacterium diphtheriae*)); and conjugate vaccines (e.g., Arabinomannan-tetanus toxoid conjugate (*Mycobacterium tuberculosis*)), CCPS-P64kR (*Neisseria meningitidis*), COMVAX (*Haemophilus influenzae*), Menjugate (*Neisseria meningitidis*), Neisvac-C (*Neisseria meningitidis*), and PedvaxHIB (*Haemophilus influenzae*)).

In some embodiments, the present adjuvants (e.g. flagellin-based agent and an aluminum gel or salt) are combined in a vaccine targeting a substance abuse. For example, in one embodiment, the present adjuvants are used in vaccines against addition to fentanyl, heroin, morphine, opium, oxycodone, hydrocodone, ketamine, PCP, barbiturates, benzodiazepines, flunitrazepam, GHB, methaqualone, hashish, marijuana, LSD, mescaline, psilocybin, amphetamine, cocaine, MDMA, methamphetamine, methylphenidate, and nicotine (e.g. TA-CD (Celtic Pharma), those described in US Patent Publication No. 2013/0011432, the contents of which are hereby incorporated by reference (e.g. using 6-(2R,3S)-3-(benzoyloxy)-8-methyl-8-azabicyclo [3.2.1]octane-2-carbonyloxy-hexanoic acid (GNC) or 6-((2R,3S)-3-(benzoyloxy)-8-methyl-8-azabicyclo [3.2.1] octane-2-carboxamido) hexanoic acid) (GNE) as the antigen, and TA-NIC (Celtic Pharma)).

In some embodiments, the present adjuvants (e.g. flagellin-based agent and an aluminum gel or salt) and/or the present vaccines may comprise any one of the adjuvants or antigens annotated in the VIOLIN or Vaxjo databases (as described in He et al. *Nucleic Acids Research.* 2014. 42 (D1): D1124-D1132 and Xiang et al. *Nucleic Acids Res.* 2008 January; 36: D923-8, the contents of which are hereby incorporated by reference in their entirety).

In various embodiments, the present adjuvants (e.g. flagellin-based agent and an aluminum gel or salt) may be part of one or more cancer vaccines and/or the antigens of one or more cancer vaccines may be the antigens of the present invention. Illustrative cancer vaccines include therapeutic and preventative vaccines. For instance, cancer vaccines include ONCOPHAGE (ANTIGENICS INC., approved in Russia in 2008 for kidney cancer), APC8015/Sipuleucel-T/PROVENGE (DENDREON, for, e.g. metastatic hormone-refractory prostate cancer), CANCERVAX (CANVAXIN), GENITOPE CORP (MYVAX personalized immunotherapy), and FAVRILLE INC (FAVID), preventive vaccines which attack the cancer-causing viruses human papillomavirus (e.g. CERVARIX (GSK) and GARDASIL (MERCK)), hepatitis A virus (e.g. CERVARIX (GSK) and GARDASIL (MERCK)), and hepatitis B virus (e.g. RECOMBIVAX HB (MERCK), ENGERIX-B (GSK), ELOVAC B (HUMAN BIOLOGICALS INSTITUTE), GENEVAC B (SERUM INSTITUTE), SHANVAC B, etc.

In various embodiments, the present adjuvants (e.g. flagellin-based agent and an aluminum gel or salt) may be part of one or more allergen vaccines and/or the antigens of one or more allergen vaccines may be the antigens of the present invention. For instance, subcutaneous immunotherapy (SCIT) allergen compositions and methods are applicable to the present invention (e.g. "allergy shots"). For example, vaccinations for allergic rhinitis and conjunctivitis (e.g. pollen (including ragweed), dust mites, animal dander and airborne mold spores); allergic or extrinsic bronchial asthma (e.g. house dust mites, pollen, animal dander, mold (*Cladosporium*), latex); and insect venom hypersensitivity. Allergens include pollen (e.g. tree, grass, weed), pet dander (e.g. cat pelt), dust mites, airborne molds, occupational aeroallergens, honey bee venom, yellow jacket venom, hornet venom, wasp venom, and fire anti venom.

In various embodiments, the antigens of the present vaccines may be the antigens of live and attenuated or killed or inactivated or toxoid or a subunit or conjugate vaccines. In various embodiments, the antigen of the present vaccines is an antigen of any of the vaccines described herein. For example, in some embodiments, the present antigen is that of one or more of the following vaccines: DTP (diphtheria-tetanus-pertussis vaccine), DTaP (diphtheria-tetanus-acellular pertussis vaccine), Hib (*Haemophilus influenzae* type b) conjugate vaccines, Pneumococcal conjugate vaccine, Hepatitis A vaccines, Poliomyelitis vaccines, Yellow fever vaccines, Hepatitis B vaccines, combination DTaP, Tdap, Hib, Human Papillomavirus (HPV) vaccine, Anthrax vaccine, *Bacillus* Calmette-Guerin (Tb), and Rabies vaccine.

In various embodiments, the flagellin-based agent and antigen are adsorbed to the aluminum gel or salt. In some embodiments, the flagellin-based agent and aluminum gel or salt are mixed to form a stable complex. In some embodiments, the flagellin-based agent and aluminum gel or salt are mixed in a ratio that is substantially below a loading capacity of the aluminum salt. In some embodiments, the flagellin-based agent and aluminum gel or salt are present in a ratio that is substantially below a loading capacity of the aluminum salt. In various embodiments, the flagellin-based agent and aluminum gel or salt are mixed or present in a ratio (w/w) of about 1:500, or about 1:600, or about 1:700, or about 1:800, or about 1:900, or about 1:1000, or about 1:2000, or about 1:5000, or about 1:6000, or about 1:7000, or about 1:8000, or about 1:9000, or about 1:10000. In some embodiments, the flagellin-based agent and aluminum gel or salt are mixed in a ratio (w/w) of about 1:500 or less. In some embodiments, the flagellin-based agent and aluminum gel or salt are present in a ratio that is substantially below a loading capacity of the aluminum salt even in the presence of anitigen.

The loading (or adsorption) capacity of the adjuvant (e.g. the aluminum gel or salt) can be measured using a variety of analytical methods. In general, it is done by comparing the protein content in the aqueous phase of the agent being loaded or adsorbed (e.g. flagellin-based agent and/or antigen solution) before and after adsorption onto the adjuvant. For instance, the Ramon flocculation test may be used (as is used to determine the adsorption of diphtheria and tetanus toxoid). Further, loading can be measured using immunoprecipitation techniques (e.g. quantitative immunoelectrophoresis or single radial immunodiffusion) or spectrophotometric techniques (e.g. the BCA method) ELISA methods may also be used as can immunoelectrophoresis or HPLC. The aluminum content in the final vaccine can be monitored using a number of known techniques, including spectrometric methods, such as for example atomic adsorption spectrometry.

In some embodiments, the amount of aluminum gel or salt in the vaccines and/or adjuvants described herein is about 0.05 to about 1.0 mg/dose, or about 0.125 to about 0.625 mg/dose. In some embodiments, the amount of aluminum gel or salt in the vaccines and/or adjuvants described herein is about 0.05, or about 0.10, or about 0.15, or about 0.20, or about 0.25, or about 0.30, or about 0.35, or about 0.40, or about 0.45, or about 0.50, or about 0.55, or about 0.60, or about 0.65, or about 0.70, or about 0.75, or about 0.80, or about 0.85, or about 0.90, or about 0.95, or about 1.0 mg/dose.

In some embodiments, the amount of flagellin-based agent is about 0.03 to about 5 μg/dose (e.g. about 0.03 μg/dose, about 0.1 μg/dose, about 0.3 μg/dose, about 0.5 μg/dose about 1.0 μg/dose, about 1.5 μg/dose, about 2.0 μg/dose, about 2.5 μg/dose, about 3.0 μg/dose, about 4.0 μg/dose, about 4.5 μg/dose, about 5.0 μg/dose). In various embodiments, the present compositions and methods comprise doses of flagellin-based agent that are less than about 5 μg/dose, or less than 4 μg/dose, or less than 3 μg/dose, or less than 2 μg/dose, or less than 1 μg/dose, or less than 0.5 μg/dose. In some embodiments, the present compositions and methods comprise low doses of flagellin-based agent.

In various embodiments, the present compositions and methods do not involve covalently attaching an antigen to the flagellin-based agent either as a fusion protein or via chemical conjugation. In various embodiments, the present compositions do not have either equimolar ratio of antigen to flagellin-based agent (as in a fusion) or several molecules of hapten per one molecule of flagellin-based agent (as in chemical conjugates). In various embodiments, the amount of flagellin-based agent in any of the present vaccines is less than the amount of antigen. In various embodiments, the amount of flagellin-based agent in any of the present vaccines is less than the amount of antigen. In various embodiments, the amount of flagellin-based agent in any of the present vaccines is substantially less than the amount of antigen. In various embodiments, the amount of flagellin-based agent in any of the present vaccines is about 500-fold, or about 450-fold, or about 400-fold, or about 350-fold, or about 325-fold, or about 300-fold, or about 250-fold, or about 200-fold, or about 150-fold, or about 100-fold, or about 50-fold less than the amount of antigen.

In various embodiments, the combination of flagellin-based agent and alum do not substatially effect TLR5 interaction by the flagellin-based agent.

In various embodiments, the present compositions and methods do not induce production of TNFα.

In various embodiments the present combination of flagellin-based agent and alum is subtantially stable at low temperatures for about one week (e.g. at about 4° C. for about 3 days, or about 5 days, or about 6 days, or about 7 days, or about 10 days).

In another aspect, the present invention relates to a method of vaccinating a subject against a disorder, comprising administering an effective amount of a vaccine comprising an adjuvant comprising a flagellin-based agent and an aluminum gel or salt and an antigen associated with the disorder. In another aspect, the invention relates to a use of vaccine comprising an adjuvant comprising a flagellin-based agent and an aluminum gel or salt and an antigen associated with a disorder for vaccinating a subject against the disorder. In another aspect, the invention relates to a use of an effective amount of vaccine comprising an adjuvant comprising a flagellin-based agent and an aluminum gel or salt and an antigen associated with a disorder in the manufacture of a medicament for vaccinating a subject against the disorder.

In another aspect, the present invention relates to a method of immunostimulating a subject in advance of or concurrent with vaccination, comprising administering an effective amount of an adjuvant comprising a flagellin-based agent and an aluminum gel or salt, wherein both $T_{H1}$ and $T_{H2}$-mediated immune responses are immunostimulated. In another aspect, the invention relates to a use of an effective amount of an adjuvant comprising a flagellin-based agent and an aluminum gel or salt for immunostimulating a subject in advance of or concurrent with vaccination. In another aspect, the invention relates to a use of an effective amount of an adjuvant comprising a flagellin-based agent and an aluminum gel or salt in the manufacture of a medicament for immunostimulating a subject in advance of or concurrent with vaccination.

In various embodiments, the vaccine described herein causes an improvement in adjuvant properties relative to a vaccine comprising the antigen and the aluminum gel or salt alone (or flagellin-based agent and antigen alone). In various embodiments, the vaccine and/or adjuvant described herein causes a broader, more diverse, more robust and longer lasting immunostimulatory effect than the vaccine comprising the antigen and the aluminum gel or salt alone (or flagellin-based agent and antigen alone) and/or the adjuvant comprising the aluminum gel or salt alone (or the adjuvant comprising the flagellin-based agent alone).

In some embodiments, the described vaccine and/or described adjuvant causes an increase in titer of 1 or more of, or 2 or more of, or 3 or more of, or all of IgG1, IgG2a, IgG2b, and IgG3 antibodies (e.g. relative to the adjuvant comprising the aluminum gel or salt or flagellin-based agent alone, or relative to the vaccine comprising the antigen and the aluminum gel or salt alone or flagellin-based agent alone)). In some embodiments, the described vaccine and/or described adjuvant causes a relative increase in the titer of all of IgG1, IgG2a, IgG2b, and IgG3 antibodies. In some embodiments, the described vaccine and/or described adjuvant causes a relative increase in the titer of more IgG3 antibodies than the described vaccine and/or described adjuvant in the absence of a flagellin-based agent (or the described vaccine and/or described adjuvant in the absence of an aluminum gel or salt alone).

In some embodiments, the antigen is administered simultaneously with or sequentially to the adjuvant.

In some embodiments, the disorder is selected from infectious diseases, cancer, allergy, and autoimmune diseases.

In some embodiments, the disorder is selected from diphtheria, tetanus, pertussis, influenza, pneumonia, hepatitis A, hepatitis B, polio, yellow fever, Human Papillomavirus (HPV) infection, anthrax, rabies, Japanese Encephalitis, meningitis, measles, mumps, rubella, gastroenteritis, smallpox, typhoid fever, varicella (chickenpox), rotavirus, and shingles.

In some embodiments, the disorder is a cancer is selected from, but not limited to, a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In some embodiments, the disorder is an allergy, selected from, by way of non-limiting example, allergic rhinitis and conjunctivitis, allergic or extrinsic bronchial asthma, and insect venom hypersensitivity.

In some embodiments, the disorder is a substance abuse disorder (e.g. of fentanyl, heroin, morphine, opium, oxycodone, hydrocodone, ketamine, PCP, barbiturates, benzodiazepines, flunitrazepam, GHB, methaqualone, hashish, marijuana, LSD, mescaline, psilocybin, amphetamine, cocaine, MDMA, methamphetamine, methylphenidate, and nicotine).

In some embodiments, the compositions of the present invention (e.g. the described adjuvants and vaccines) can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, Journal of Pharmaceutical Science, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compositions of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, the compositions of the present invention (e.g. the described adjuvants and vaccines) described herein are in the form of a pharmaceutically acceptable salt.

In some embodiments, the compositions of the present invention (e.g. the described adjuvants and vaccines) may comprise a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any composition described herein, if desired, can also comprise minor amounts of wetting or emulsifying agents, or pH buffering agents.

The present invention includes the compositions of the present invention (e.g. the described adjuvants and vaccines) in various formulations. Any composition of the present invention can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described in Remington's Pharmaceutical Sciences 1447-1676 (Alfonso R. Gennaro eds., 19th ed. 1995), incorporated herein by reference.

Where necessary, the compositions of the present invention can also include a solubilizing agent. Also, the agents can be delivered with a suitable vehicle or delivery device as known in the art. Combination therapies outlined herein can be co-delivered in a single delivery vehicle or delivery device. Compositions for administration can optionally include a local anesthetic such as, for example, lignocaine to lessen pain at the site of the injection.

The formulations comprising the compositions of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In one embodiment, any composition of the present invention is formulated in accordance with routine procedures as a composition adapted for a mode of administration described herein.

Routes of administration include intramuscular, e.g. by injection or infusion. In some embodiments, the described adjuvant of a flagellin-based agent (e.g. CBLB502) and aluminum gel or salt may prevent systemic delivery of the flagellin-based agent and induce localized delivery. In other embodiments, routes of administration include nasal, oral, and sublingual delivery.

Routes of administration may also be intradermal, intramuscular, intraperitoneal, intravenous, subcutaneous, intranasal, oral, sublingual, intranasal, transdermal, or by inhalation. In some embodiments, the administering is effected orally or by parenteral injection. The mode of administration can be left to the discretion of the practitioner, and depends in-part upon the site of the medical condition. In most instances, administration results in the release of any agent described herein into the bloodstream.

Any composition of the present invention (e.g. the described adjuvants and vaccines) can be administered orally. Such compositions can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art.

The dosage of any composition of the present invention (e.g. the described adjuvants and vaccines) as well as the dosing schedule can depend on various parameters, including, but not limited to, the disorder being treated, the subject's general health, and the administering physician's discretion.

In vitro or in vivo assays can be employed to help identify optimal dosage ranges. For example, doses may be determined with reference Physicians' Desk Reference, 66th Edition, PDR Network; 2012 Edition (Dec. 27, 2011), the contents of which are incorporated by reference in its entirety.

For administration of a composition of the present invention (e.g. the described adjuvants and vaccines) by parenteral injection, the dosage is normally about 0.1 mg to about 250 mg per day, about 1 mg to about 20 mg per day, or about 3 mg to about 5 mg per day. Injections may be given up to four times daily. Generally, when orally or parenterally administered, the dosage of any agent described herein is normally about 0.1 mg to about 1500 mg per day, or about 0.5 mg to about 10 mg per day, or about 0.5 mg to about 5 mg per day. A dosage of up to about 3000 mg per day can be administered.

In another embodiment, delivery can be in a vesicle, in particular a liposome (see Langer, 1990, *Science* 249:1527-1533; Treat et al., in *Liposomes in the Therapy of Infectious Disease and Cancer*, Lopez-Berestein and Fidler (eds.), Liss, New York, pp. 353-365 (1989).

Any composition of the present invention (e.g. the described adjuvants and vaccines) can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105).

In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, Science 249:1527-1533) may be used.

Administration of a composition of the present invention (e.g. the described adjuvants and vaccines) can, independently, be once per patient or may be used in a booster strategy. Administration may be about one to about four times daily or about one to about four times per month or about one to about six times per year or once every two, three, four or five years. Administration can be for the duration of about one day or about one month, about two months, about three months, about six months, about one year, about two years, about three years, and may even be for the life of the subject. The dosage may be administered as a single dose or divided into multiple doses.

The dosage regimen utilizing any flagellin related composition (and/or additional agents) described herein can be selected in accordance with a variety of factors including type, species, age, weight, sex and medical condition of the subject; the severity of the condition to be treated; the route of administration; the renal or hepatic function of the subject; the pharmacogenomic makeup of the individual; and the specific compound of the invention employed. Any flagellin related composition (and/or additional agents) described herein can be administered in a single daily dose, or the total daily dosage can be administered in divided doses of two, three or four times daily. Furthermore, any flagellin related composition (and/or additional agents) described herein can be administered continuously rather than intermittently throughout the dosage regimen.

In some embodiments, the composition of the present invention (e.g. the described adjuvants and vaccines) may be used in conjunction with one or more additional agents. In some embodiments, the invention pertains to co-administration and/or co-formulation. Any of the compositions described herein may be co-formulated and/or co-administered.

In some embodiments, any composition described herein acts synergistically when co-administered with another agent and is administered at doses that are lower than the doses commonly employed when such agents are used as monotherapy. In various embodiments, any agent referenced herein may be used in combination with any of the composition described herein.

In some embodiments, the present invention pertains to additional agents described elsewhere herein. In one embodiment, any flagellin-related agent or composition comprising the same may be used with agents that stimulate NOD receptors (e.g. NOD1 and NOD2 agonists, such as peptidoglycan, C12-iE-DAP and L18-MDP) and as described in Infect Immun. October 2013; 81(10): 3855-3864, the contents of which are hereby incorporated by reference in their entirety.

In some embodiments, the present invention pertains to chemotherapeutic agents as additional agents.

Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; def of amine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

In some embodiments, the flagellin-based agents (and/or additional agents) described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of turicamycin, etc. Additionally, the derivative can contain one or more non-classical amino acids.

In still other embodiments, the flagellin-based agents (and/or additional agents) described herein further comprise a cytotoxic agent, comprising, in illustrative embodiments, a toxin, a chemotherapeutic agent, a radioisotope, and an agent that causes apoptosis or cell death. Such agents may be conjugated to a composition described herein.

The flagellin-based agents (and/or additional agents) described herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Illustrative cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the *vinca* alkaloids, vincristine and vinblastine. Other cytotoxic agents include paclitaxel (taxol), ricin, *pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, *vinca* alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux, Avastin, Pertuzumab, anti-CD20 antibodies, Rituxan, ocrelizumab, ofatumumab, DXL625, HERCEPTIN®, or any combination thereof. Toxic enzymes from plants and bacteria such as ricin, diphtheria toxin and *Pseudomonas* toxin may be conjugated to the therapeutic agents (e.g. antibodies) to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the antibody, or binding fragments thereof, with or without the use of a complex-forming agent. Such radionuclides include beta-emitters such as Phosphorus-32, Scandium-47, Copper-67, Gallium-67, Yttrium-88, Yttrium-90, Iodine-125, Iodine-131, Samarium-153, Lutetium-177, Rhenium-186 or Rhenium-188, and alpha-emitters such as Astatine-211, Lead-212, Bismuth-212, Bismuth-213 or Actinium-225.

Illustrative detectable moieties further include, but are not limited to, horseradish peroxidase, acetylcholinesterase, alkaline phosphatase, beta-galactosidase and luciferase. Further illustrative fluorescent materials include, but are not limited to, rhodamine, fluorescein, fluorescein isothiocyanate, umbelliferone, dichlorotriazinylamine, phycoerythrin and dansyl chloride. Further illustrative chemiluminescent moieties include, but are not limited to, luminol. Further illustrative bioluminescent materials include, but are not limited to, luciferin and aequorin. Further illustrative radioactive materials include, but are not limited to, lodine-125, Carbon-14, Sulfur-35, Tritium and Phosphorus-32.

In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g. GFP). In some embodiments, the subject and/or animal is a transgenic animal comprising a fluorescent cell.

In some embodiments, the subject and/or animal is a human. In some embodiments, the human is a pediatric human. In other embodiments, the human is an adult human. In other embodiments, the human is a geriatric human. In other embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In other embodiments, the subject is a non-human animal, and therefore the invention pertains to veterinary use. In a specific embodiment, the non-human animal is a household pet. In another specific embodiment, the non-human animal is a livestock animal.

The invention provides kits that can simplify the administration of any agent described herein. An illustrative kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of a composition of the invention and an effective amount of another composition, such those described herein.

The following definitions are used in connection with the invention disclosed herein. Unless defined otherwise, all technical and scientific terms used herein have the same meaning as commonly understood to one of skill in the art to which this invention belongs.

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

An "effective amount," when used in connection with medical uses is an amount that is effective for providing a measurable treatment, prevention, or reduction in the rate of pathogenesis of a disease of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified.

As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents (e.g. flagellin-based agents, flagellin-based agents (and/or additional agents) described herein) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. For example, administration of therapeutic agents to a patient suffering from cancer provides a therapeutic benefit not only when the underlying condition is eradicated or ameliorated, but also when the patient reports a decrease in the severity or duration of the symptoms associated with the disease, e.g., a decrease in tumor burden, a decrease in circulating tumor cells, an increase in progression free survival. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

In certain embodiments, a pharmacologically effective amount that will treat cancer will modulate the symptoms typically by at least about 10%, at least about 20%, at least about 30%, at least about 40%, or at least about 50%. In illustrative embodiments, such modulations will result in, for example, statistically significant and quantifiable changes in the numbers of cancerous cells.

This invention is further illustrated by the following non-limiting examples.

EXAMPLES

Example 1: Preparation of the Model Vaccine

Alum adjuvant (IMJECT ALUM, THERMO) was used in combination with CBLB502 to challenge the mice with a model antigen, ovalbumin (OVA). Vaccine was comprised of the following components as shown in

TABLE A

| Component | Amount (per mouse) |
|---|---|
| Ovalbumin | 10 mg |
| CBLB502 | 1 ug/10 ug |
| Alum Adjuvant | 500 ug |

To achieve excellent absorption CBLB502 (either 1 μg or 10 ug) was mixed with 10 mg of OVA and 500 μg of Alum adjuvant for 30 minutes at 300 rpm at room temperature.

Example 2: Mouse Immunization Study

C57Bl/6 male mice (10 weeks of age, n=6 for each experiment) were used for injection. Mice were divided into five groups with six animals in each group (n=6). Mice were injected with 100 μl of above described vaccine in each of the hind legs (200 μl total per mouse) as shown in TABLE B.

| | Ovalbumin | CBLB502 | Alum Adjuvant |
|---|---|---|---|
| Group 1 | | | |
| Group 2 | 10 mg | | |
| Group 3 | 10 mg | | 500 ug |
| Group 4 | 10 mg | 1 ug | 500 ug |
| Group 5 | 10 mg | 10 ug | 500 ug |

Figure 3:
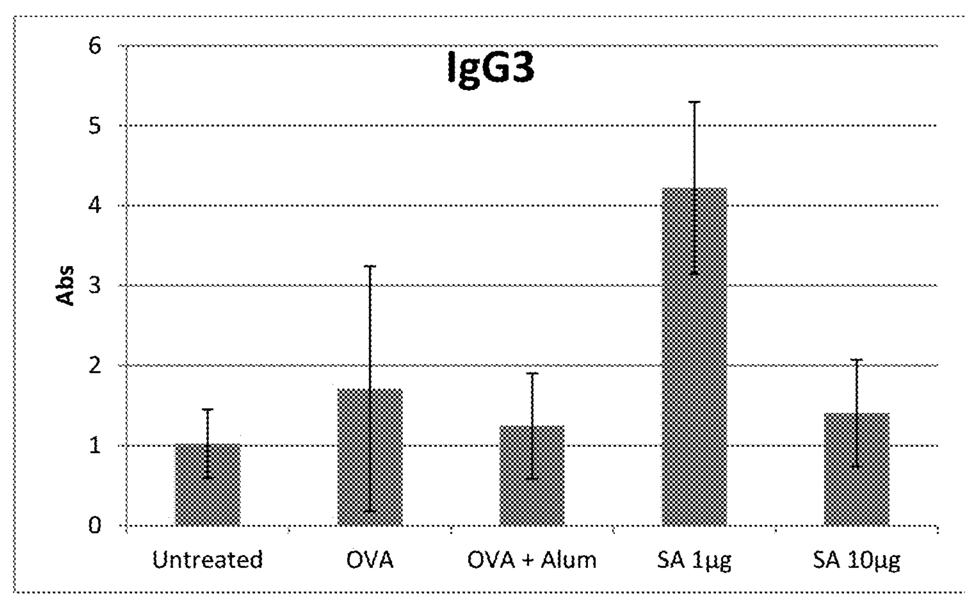
FIG. 3 shows ELISA data for the average response of five mouse treatment groups at the time point of 2 weeks post-boost. Panel A is total IgG, Panel B is IgG1, Panel C is IgG2a, Panel D is IgG2b and Panel E is IgG3. Groups 1-5 are defined in TABLE B (Example 2): Group 1 is also called "Untreated;" Group 2 is also called "OVA," Groups 3 is also called "OVA+Alum," Group 4 is also called "SA 1 μg," and Group 5 is also called "SA 10 μg."

Two weeks after the initial immunization mice were challenged with an additional booster following the same setup as the original injection. Plasma was collected one, two and four weeks after booster via mandibular vein. Using an ELISA based assay total IgG, IgG1, IgG2a, IgG2b and IgG3 were measured. Results are shown in FIGS. 2-3. In the figures, Group 1 is also called "Untreated;" Group 2 is also called "OVA," Groups 3 is also called "OVA+Alum," Group 4 is also called "SA 1 μg," and Group 5 is also called "SA 10 μg."

Figure 4:
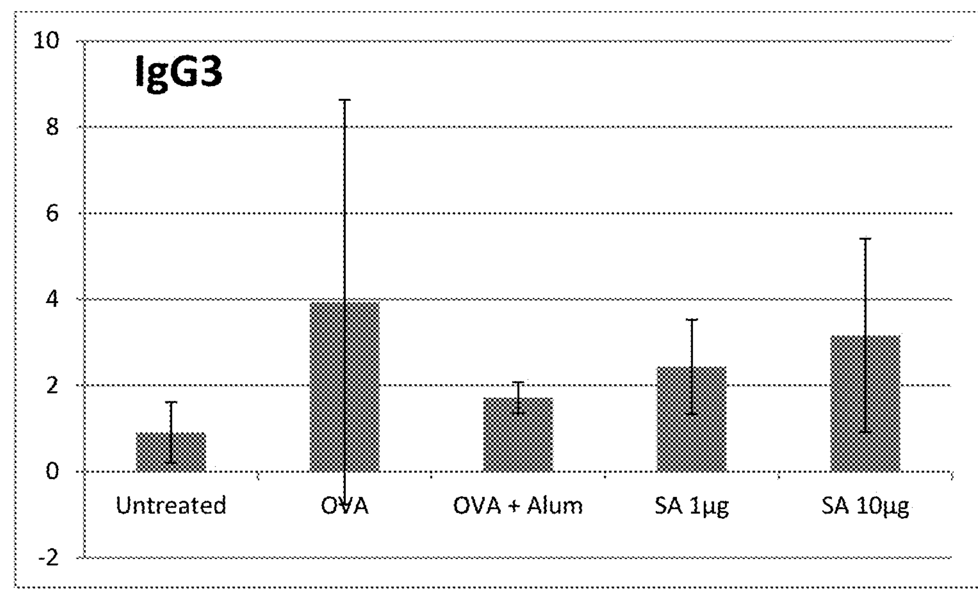
FIG. 4 shows ELISA data for the average response of five mouse treatment groups at the time point of 4 weeks post-boost. Panel A is total IgG, Panel B is IgG1, Panel C is IgG2a, Panel D is IgG2b and Panel E is IgG3. Groups 1-5 are defined in TABLE B (Example 2): Group 1 is also called "Untreated;" Group 2 is also called "OVA," Groups 3 is also called "OVA+Alum," Group 4 is also called "SA 1 μg," and Group 5 is also called "SA 10 μg."

FIG. 2 shows ELISA data for the average response of the five aforementioned mouse treatment groups at the time point of 1 week post-boost. FIG. 3 shows ELISA data for the average response of the five aforementioned mouse treatment groups at the time point of 2 weeks post-boost. FIG. 4 shows ELISA data for the average response of the five aforementioned mouse treatment groups at the time point of 4 weeks post-boost.

Example 3: Evaluation of CBLB502 Binding to ALHYDROGEL

The binding capacity of ALHYDROGEL for CBLB502 was evaluated. ALHYDROGEL adjuvant 2%, aluminium hydroxide wet gel (colloidal) suspension (INVIVIGEN Catalog # vac-alu-250), was mixed with CBLB502 at different volume ratios, resulting in 10 to 52% ALHYDROGEL suspension in the reaction. CBLB502 concentration was maintained at 10 μg/ml, corresponding to a 1 μg/100 μl inoculation dose (100 μl inoculation volume is the recommended maximum volume for subcutaneous injection of antigen/adjuvant mixtures per injection site for mice). After overnight incubation at 4° C., the tubes were centrifuged to sediment ALHYDROGEL and unbound CBLB502, remaining in solution was measured by ELISA. The amounts of adsorbed CBLB502 were calculated as difference between total protein added to the mixture and unbound CBLB502 (TABLE C). The maximum adsorption of CBLB502, more than 99.9% bound, was observed when the reactions were formulated with 40 to 52 μl ALHYDROGEL/100 μl; at lower ratios, the binding efficiency decreased gradually to about 83% at 10 μl/100 μl ALHYDROGEL suspension.

TABLE C

CBLB502 adsorption at different ALHYDROGEL 2% volume ratios. The binding reactions were composed of CBLB502, PBS and the indicated volumes of ALHYDROGEI adjuvant 2%.

| | ALHYDROGEL 2% μl/100 μl | CBLB502 dose μg/100 μl | Total CBLB502 ng/ml | Unbound ng/ml | Bound ng/ml | Bound (%) |
|---|---|---|---|---|---|---|
| 1 | 52 | 1 | 10000 | 2.1 | 9997.9 | 99.98 |
| 2 | 50 | 1 | 10000 | 1.6 | 9998.4 | 99.98 |
| 3 | 40 | 1 | 10000 | 2.9 | 9997.1 | 99.97 |
| 4 | 30 | 1 | 10000 | 22.7 | 9977.3 | 99.77 |
| 5 | 20 | 1 | 10000 | 173.4 | 9826.6 | 98.27 |
| 6 | 10 | 1 | 10000 | 1692.5 | 8307.5 | 83.07 |

CBLB502 binding to ALHYDROGEL was also evaluated at different CBLB502 doses. Adsorption of CBLB502 to ALHYDROGEL (52 μl/100 μl ALHYDROGEL adjuvant 2%) was determined at CBLB502 doses, ranging from approximately 0.02 to 20 μg per 100 μl. The reactions were incubated as described above and unbound CBLB502 was measured by ELISA. The results (TABLE D) demonstrated that almost complete binding of the drug to ALHYDROGEL, 99.82 to 99.99% bound, was accomplished at all tested CBLB502 concentrations.

TABLE D

Efficiency of CBLB502 binding to ALHYDROGEl in PBS. The incubations were performed with CBLB502 at the indicated doses in PBS and 52 μl/100 μl ALHYDROGEL adjuvant 2%.

| | CBLB502 dose μg/100 μl | Total CBLB502 ng/ml | Unbound ng/ml | Bound ng/ml | Bound (%) |
|---|---|---|---|---|---|
| 1 | 20 | 200000 | 199.3 | 199800.7 | 99.90 |
| 2 | 5 | 50000 | 90.6 | 49909.4 | 99.82 |
| 3 | 1.25 | 12500 | 0.79 | 12499.2 | 99.99 |
| 4 | 0.31 | 3125.0 | 0.029 | 3124.97 | 99.99 |
| 5 | 0.078 | 781.25 | 0.023 | 781.23 | 99.99 |
| 6 | 0.02 | 195.31 | 0.011 | 195.30 | 99.99 |

CBLB502 binding to ALHYDROGEL in the presence of TT-SMA vaccine was evaluated. Binding efficiency of CBLB502 to ALHYDROGEL was tested in the presence of a vaccine candidate TT-SMA, succinyl methamphetamine (SMA) hapten conjugated to tetanus toxoid. In a separate study, shown below, this vaccine was administered to mice at a 32 μg/100 μl dose to compare efficacy with and without CBLB502. This TT-SMA dose was co-incubated with CBLB502 (0.02 to 20 μg/100 μl) and ALHYDROGEL (52 μl/100 μl) under standard conditions and unbound CBLB502 was measured by ELISA. The binding efficiency was 99.7 to 99.9% at all tested CBLB502 concentrations, indicating that CBLB502 adsorption to ALHYDROGEL was unaffected with addition of TT-SMA to the reaction mixture

TABLE E

CBLB502 binding to ALHYDROGEL in the presence of TT-SMA. The incubations were performed with CBLB502 at the indicated doses in PBS, 52 μl/100 μl ALHYDROGEL adjuvant 2% and 32 μg/100 μl TT-SMA conjugate.

| | CBLB502 dose μg/100 μl | Total CBLB502 ng/ml | Unbound ng/ml | Bound ng/ml | Bound (%) |
|---|---|---|---|---|---|
| 1 | 20 | 200000 | 668.88 | 199331.1 | 99.67 |
| 2 | 5 | 50000 | 50.21 | 49949.8 | 99.90 |

TABLE E-continued

CBLB502 binding to ALHYDROGEL in the presence of TT-SMA. The incubations were performed with CBLB502 at the indicated doses in PBS, 52 μl/100 μl ALHYDROGEL adjuvant 2% and 32 μg/100 μl TT-SMA conjugate.

| | CBLB502 dose μg/100 μl | Total CBLB502 ng/ml | Unbound ng/ml | Bound ng/ml | Bound (%) |
|---|---|---|---|---|---|
| 3 | 1.25 | 12500 | 11.44 | 12488.6 | 99.91 |
| 4 | 0.31 | 3125.0 | 1.65 | 3123.4 | 99.95 |

TABLE E-continued

CBLB502 binding to ALHYDROGEL in the presence of TT-SMA. The incubations were performed with CBLB502 at the indicated doses in PBS, 52 μl/100 μl ALHYDROGEL adjuvant 2% and 32 μg/100 μl TT-SMA conjugate.

| | CBLB502 dose μg/100 μl | Total CBLB502 ng/ml | Unbound ng/ml | Bound ng/ml | Bound (%) |
|---|---|---|---|---|---|
| 5 | 0.078 | 781.25 | 0.13 | 781.1 | 99.98 |
| 6 | 0.02 | 195.31 | 0.06 | 195.2 | 99.96 |

Example 4: Analysis of In Vitro CBLB502 Activity after Adsorption to ALHYDROGEL An activity assay of CBLB502/ALHYDROGEL using 293-hTLR5-LacZ reporter cells was undertaken. Biological activity of CBLB502 after adsorption to ALHYDROGEL was tested using an in vitro assay which measures activation of a NF-κB-controlled reporter enzyme, β-galactosidase, in HEK293-hTLR5:NF-κB-lacZ (293-hTLR5-LacZ) cells. Since 293-hTLR5-LacZ cells express only one cell membrane-bound toll-like receptor, human TLR5, CBLB502 activity could be determined without interference from other toll-like receptor ligands such as LPS (endotoxin).

Figure 5:
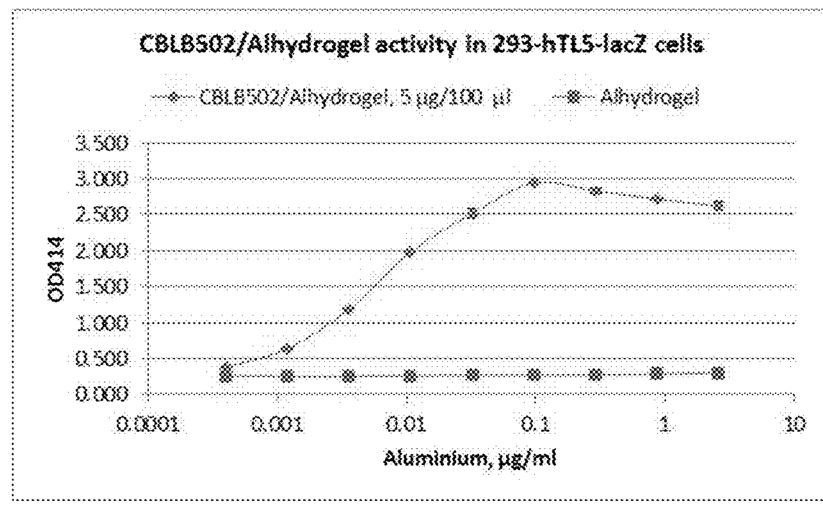
FIG. 5 shows a determination of CBLB502/ALHYDROGEL activity using a cell-based NF-κB activation assay. CBLB502/ALHYDROGEL formulation (5 μg/100 μl) and ALHYDROGEL control were serially diluted in assay media 2000- to 13122000-fold (2.6-0.0004 μg/ml aluminium) and incubated with 293-hTLR5-LacZ cells for 20 hr. Activity of β-galactosidase was measured after addition of cell lysis buffer and ONPG substrate and expressed as optical density at 414 nm (OD414).

Specific induction of the β-galactosidase reporter by CBLB502/ALHYDROGEL was demonstrated after incubating the cells with a serially diluted CBLB502/ALHYDROGEL formulation (5 μg/100 μl), starting with a 2000-fold dilution in cell growth media and resulting in the concentration range of ALHYDROGEL-adsorbed CBLB502 from 25 to 0.004 ng/ml (FIG. 5). The maximum β-galactosidase activity was observed at 0.93 ng/ml ALHYDROGEL-adsorbed CBLB502; this value was consistent with typical results of the assay using soluble CBLB502 where the reporter enzyme activity would normally peak around 1 ng/ml. ALHYDROGEL alone tested at same dilutions did not induce the reporter. Therefore, it could be concluded, inter alia, that CBLB502 retains its biological activity after adsorption to ALHYDROGEL and becomes readily available for interaction with its target receptor (TLR5) under regular cell culture conditions.

Figure 6:
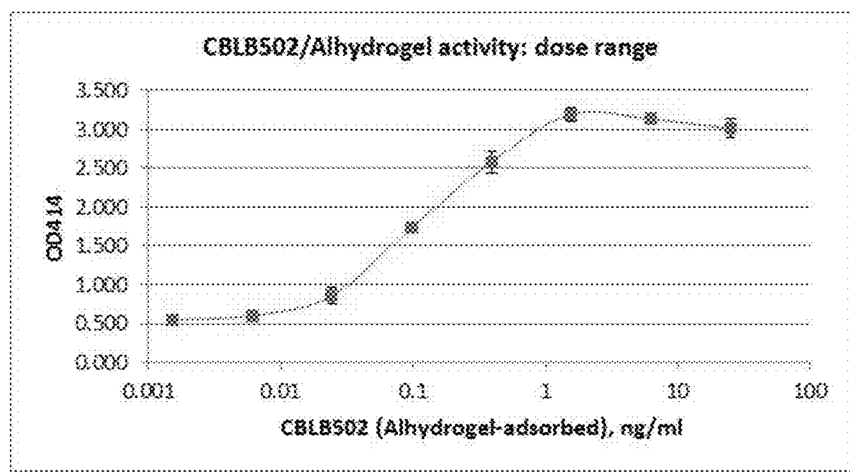
FIG. 6 shows NF-κB-inducing activity of CBLB502/ALHYDROGEL formulated with different CBLB502 doses. 293-hTLR5-LacZ cells were incubated with CBLB502/ALHYDROGEL suspensions prepared at CBLB502 doses ranging from 2.5 to 0.00015 μg/100 μl and diluted 200-fold with media. Activity of β-galactosidase reporter enzyme was measured after 20 hr incubation.

Next, CBLB502/ALHYDROGEL suspensions were prepared at CBLB502 inoculation doses ranging from 2.5 to 0.00015 μg/100 μl and were added to 293-hTLR5-LacZ cells at 200-fold dilution (FIG. 6). NF-κB-inducing activity followed a typical dose-response pattern and was measured at sub-nanogram doses of CBLB502/ALHYDROGEL (less than 0.001 μg/100 μl), indicating that at such low doses, CBLB502 was not irreversibly bound to the alum adjuvant and remained active.

Figure 7:
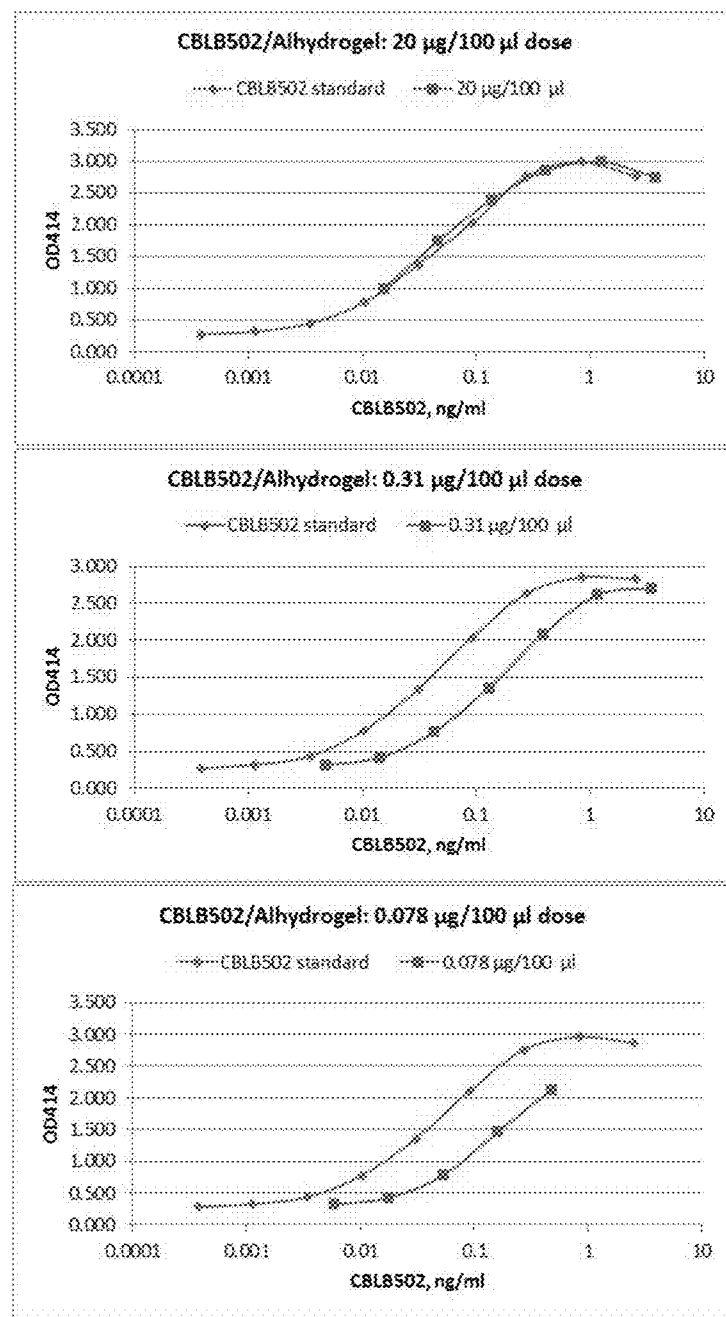
FIG. 7 shows dose-response titration curves CBLB502/ALHYDROGEL generated with 293-hTLR5-LacZ reporter cells. CBLB502 was adsorbed to ALHYDROGEL at indicated doses (20 μg/100 μl: top panel, 0.31 μg/100 μl: middle panel and 0.078 μg/100 μl: bottom panel), serially diluted with media and assayed together with soluble CBLB502 standards.

An activity titration of CBLB502/ALHYDROGEL at different CBLB502 doses was undertaken. CBLB502/ALHYDROGEL suspensions were titrated in cell culture media and incubated with 293-hTLR5-LacZ cells. CBLB502 standards were included in the assay to compare the recovered activity. The resulting reporter enzyme activity was plotted against theoretical concentrations of ALHYDROGEL-bound CBLB502, assuming that the protein was completely available (FIG. 7).

The results of titration assay demonstrated that at a formulation dose of 20 μg/100 μl, the activity of CBLB502 followed the expected concentrations, essentially matching the activity of soluble standards. However, reduction of the dose 64- and 256-fold to respectively, about 0.31 and 0.078 μg/100 μl, resulted in lower relative recovery of NF-κB-inducing activity to approximately 15-30%. This apparent loss of CBLB502 activity could be due to stronger binding of the particular amounts of the protein relative to the amounts of alum in the formulation. These fixed amounts could represent a small fraction of total CBLB502 at the higher doses such as 20 μg/100 μl and would not affect significantly the measured activity. However, at lower doses, this tightly adsorbed fraction may become substantial compared to the total protein, leading to a lower measurable activity of CBLB502

Example 5: Assessment of CBLB502/ALHYDROGEL Short-Term Storage Stability at 4° C.

Figure 8:
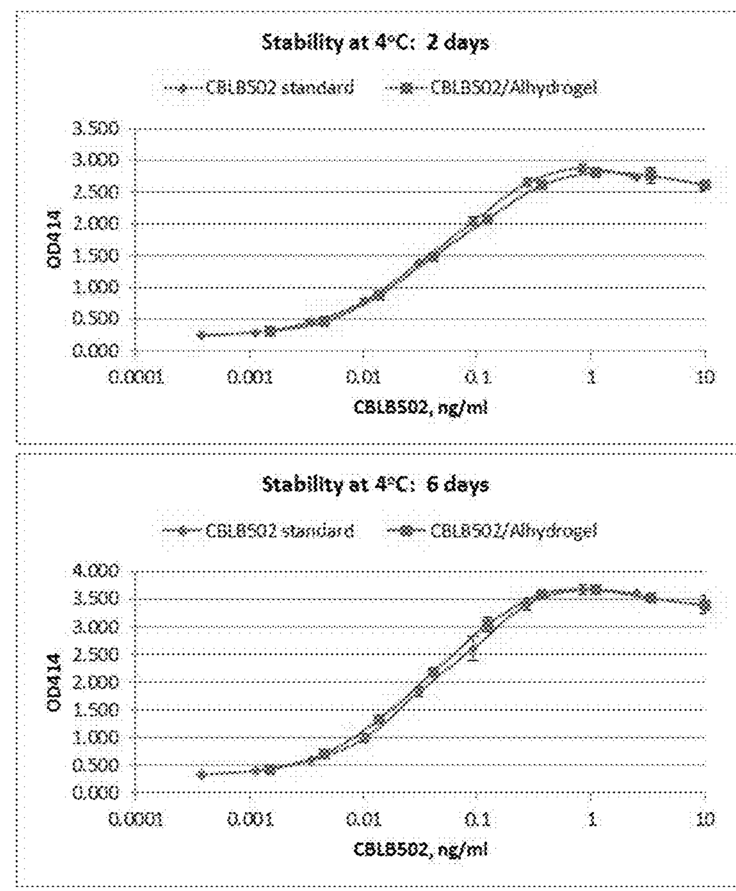
FIG. 8 shows the activity of CBLB502/ALHYDROGEL (1 μg/100 μl dose) stored at 4° C. for 2 and 6 days. NF-κB-inducing activity was measured using 293-hTLR5-LacZ reporter cell assay.

A formulation of 1 μg/100 μl CBLB502 (52 μl/100 μl ALHYDROGEL 2%) was prepared and tested for activity after 2 and 6 days storage at 4° C. The results of CBLB502 activity assay using 293-hTLR5-LacZ reporter cells are shown in FIG. 8. Based on comparison with the soluble CBLB502 standard, in can be concluded that NF-κB-inducing activity of ALHYDROGEL-adsorbed CBLB502 remained unchanged after 6 days under the storage conditions.

Example 6: Evaluation of CBLB502 Dissociation from ALHYDROGEL in PBS and Cell Media Aliquots of CBLB502/ALHYDROGEL (1 μg/100 μl dose; 52 μl/100 μl ALHYDROGEL 2%) were re-suspended in PBS or cell media (DMEM supplemented with 10% FBS) and incubated for 3 hr at 22° C. and 37° C. After centrifugation to remove ALHYDROGEL, dissociated CBLB502 was measured in supernatants by ELISA. The calculation of CBLB502 amounts that were recovered during incubation demonstrated that the protein remained stably associated with ALHYDROGEL in PBS; however, in cell media, 28 and 53% CBLB502 was released from the complex at 22° C. and 37° C., respectively (TABLE F). Such rapid dissociation from ALHYDROGEL in media may be facilitated by serum proteins which could displace CBLB502 from the complex with alum, explaining how the protein becomes readily available in the cell-based activity assay.

TABLE F

CBLB502 recovery from ALHYDROGEL after incubation in PBS and cell media

| | | | 22° C. | | 37° C. | |
|---|---|---|---|---|---|---|
| Incubation conditions | CBLB502 dose μg/100 μl | Total CBLB502 ng/ml | Recovered ng/ml | Desorption (%) | Recovered ng/ml | Desorption (%) |
| PBS | 1 | 10000 | 2.3 | 0.02 | 33.2 | 0.33 |
| Media | 1 | 10000 | 2807.6 | 28.1 | 5300.9 | 53.0 |

Example 7: Quantitation of CBLB502 and Cytokine Levels in Mouse Serum after Subcutaneous Administration of CBLB502/ALHYDROGEL An animal study was conducted to evaluate feasibility of methods to determine the levels of CBLB502 and cytokines in serum after administration of a CBLB502/ALHYDROGEL formulation. The study design is presented in TABLE G. In this study, mice were injected subcutaneously with a 1 μg dose CBLB502 adsorbed to 52 μl/100 μl ALHYDROGEL 2% and serum samples were collected between 0.5 and 24 hr post inoculation.

TABLE G

Study design.

| Group No. | Group Size | Age Strain Sex | Treatment | Injection volume, μl | Time Point, blood collection | Evaluation |
|---|---|---|---|---|---|---|
| 1 | 3 | 8 wk old | ALHYDROGEL/PBS, sc | 100 | 1 hr | Serum prepared from |
| 2 | 3 | C57BL/6 | ALHYDROGEL/PBS/CBLB502, | 100 | 30 min | collected blood and |
| 3 | 3 | Female | (1 μg/100 μl CBLB502; 52 μl/ | 100 | 1 h | analyzed for |
| 4 | 3 | | 100 μl ALHYDROGEL 2%) | 100 | 2 h | entolimod |
| 5 | 3 | | sc | 100 | 4 h | concentration and |
| 6 | 3 | | | 100 | 8 h | cytokine levels by |
| 7 | 3 | | | 100 | 24 h | ELISA |

Figure 9:
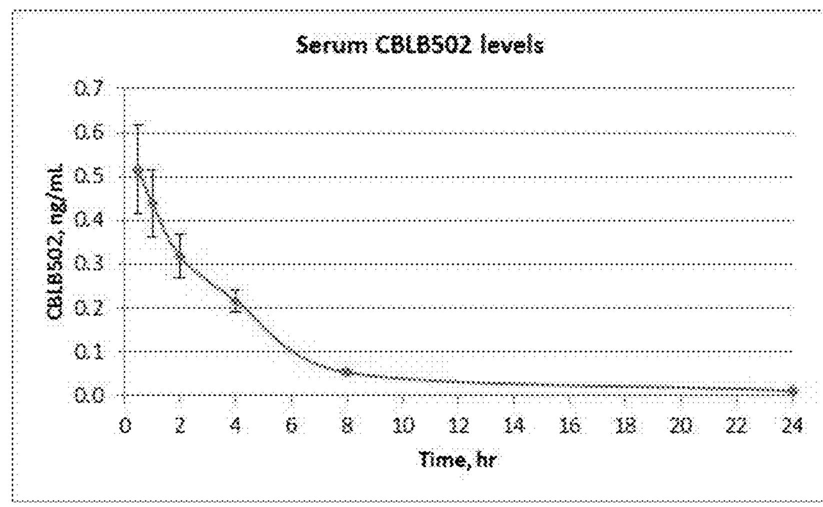
FIG. 9 shows pharmacokinetics of CBLB502 in mouse serum after subcutaneous injection of a 1 μg dose of CBLB502 adsorbed to ALHYDROGEL 2%. The graph shows per-group mean serum CBLB502 concentrations and SEM (standard error of the mean) for each time point.

Serum concentrations of CBLB502 were determined by ELISA and were found at measurable levels in all groups of animals inoculated with CBLB502/ALHYDROGEL. The pharmacokinetic profile representing per-group mean serum CBLB502 concentrations is shown in FIG. 9. The maximum mean CBLB502 concentration, 0.516 ng/ml, was observed at the first blood collection time point, 0.5 hr post administration; the minimum concentration was 0.012 ng/ml at 24 hr. Half-time elimination of CBLB502 was calculated at 2.4 hr. As discussed above, CBLB502 dissociated rapidly from the complex with ALHYDROGEL after incubation in cell media, containing 10% fetal bovine serum. Therefore, it should be expected to see the protein released from alum into animal bloodstream shortly after inoculation.

Figure 10:
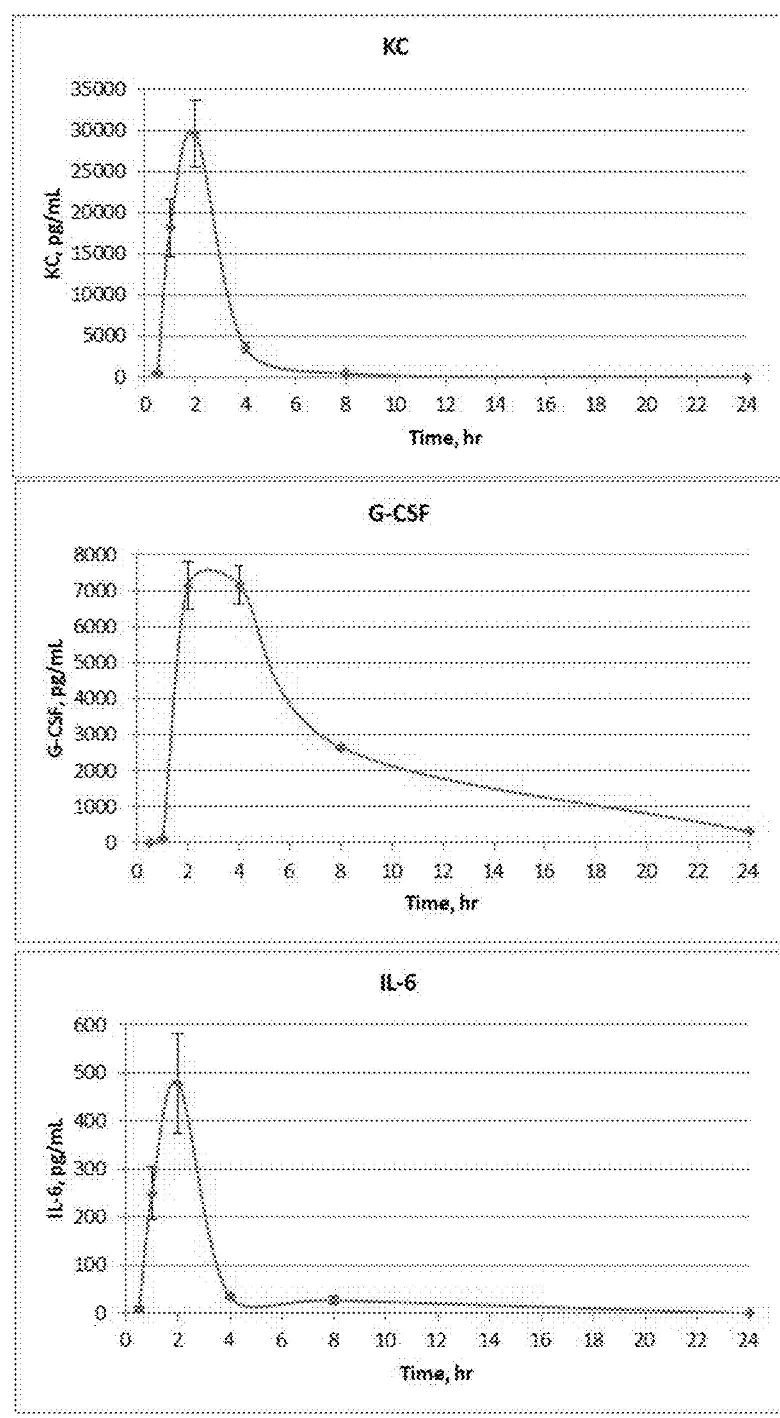
FIG. 10 shows induction of KC, G-CSF and IL-6 following s.c. administration of a 1 μg dose of CBLB502 adsorbed to ALHYDROGEL 2%. Serum concentrations of the cytokines were determined using R&D Systems DuoSet kits DY453 (KC, top panel), DY414 (G-CSF, middle panel) and DY406 (IL-6, bottom panel). The graphs show per-group mean serum cytokine concentrations and SEM (standard error of the mean) for each time point.

The concentrations of three cytokines, KC, G-CSF and IL-6, were measured in the collected mouse serum samples by ELISA (FIG. 10). Rapid induction of KC and IL-6 was detected 1 hr after CBLB502/ALHYDROGEL administration; the maximum per-group mean concentrations, 29624 and 479 μg/ml, respectively, were determined at 2 hr time point. After reaching maximum, the blood levels of these cytokines decreased to baseline at 4 to 8 hr post injection. The serum G-CSF concentration increased about an hour later compared to KC and IL-6 and was maximal between 2 and 4 hr after CBLB502/ALHYDROGEL administration (7141 and 7169 μg/ml per-group mean concentrations at 2 and 4 hr, respectively). However, CBLB502-induced G-CSF level was decreasing at a slower rate, remaining above baseline at 24 hr time point. In general, the kinetics of cytokine induction after CBLB502/ALHYDROGEL administration was similar to the kinetics observed after injection of the soluble CBLB502 preparations, suggesting consistent effects of this drug formulation.

Example 8: CBLB502 Adjuvant with Methamphetamine Vaccine

This study evaluated CBLB502 adjuvant at a 32 μg dose of human methamphetamine vaccine (SMA-TT) to achieve high and long lasting levels of anti-MA antibody in mice. A low to high dose of CBLB502 ranging from 0.03 to 20 μg with TT-SMA and alum was studied. Ten groups (n=5) of Balb/c female mice were employed to test 0, 0.03, 0.1, 0.3, 1, 3, 10, 20 μg of 502 in combination with 32 μg of TT-SMA and 1.5 mg alum compared to unvaccinated controls and TT-SMA with 502 alone. All vaccinated groups were administered two boosters, at 3 and 6 weeks after the initial vaccination. Levels of anti-MA IgG were assessed by ELISA in pooled sera samples collected at 2, 4, and 6 weeks after initial vaccination. The antibody levels were higher at 0.03 to 0.3 μg 502 in comparison to the higher doses (1 to 20 μg) of 502. In this experiment, antibody levels were 2 fold higher in the groups with 0.1 μg of 502 in combination with TT-SMA and alum (group 4) than in the comparison group with TT-SMA and alum alone (group 1) and approx. 4 fold higher when compared to a group with TT-SMA and 502 alone (group 2), as demonstrated in FIG. 11 (panel A). Anti-502 antibodies in the same sera sample were also evaluated. As shown in FIG. 11 (panel B), the level of anti-502 antibodies was minimal at the low dose range of 502 and increases at higher doses of 502.

Example 9: Generation of Vaccines with Various Antigens

In this Example, the composition of an adjuvant component for adjuvant-enhanced vaccine is established by testing a range of doses of CBLB502 and CBLB502 optionally combined with an antigen, such as, by way of non-limitation, NOD1 agonist C12-iE-DAP. Additionally, characterization of the effects of these agents on humoral immune response to a model antigen (ovalbumin) is undertaken.

As shown above, aluminum hydroxide and CBLB502 form a complex which, without wishing to be bound by theory, is stabilized by electrostatic forces as substances with opposite charges in aqueous medium. To test relative efficacy of different compositions of the adjuvant component of the vaccine, a standard dose of aluminum is used (1.5 μg per injection) loaded with a range of doses of CBLB502 (up to 30 μg and including 10 μg, 3 μg, 1 μg, 0.3 μg and 0.1 μg). CBLB502 in aqueous solution is added to the alum suspension in PBS and stirred for 10 min at room temperature. Aluminum hydroxide is then spun down by centrifugation and traces of CBLB502 in supernatants are determined using two quantitative analytical assays: (i) ELISA-based and (ii) reporter cell based (TLR5-positive 293 cells carrying NF-kB responsive reporter and calibrated for detection of CBLB 502 in the medium). In light of, inter alia, the above Examples, it is expected that a substantial fraction of CBLB 502 will be stably bound to alum under these conditions and within the chosen range of doses of TLR5 agonists.

To determine whether this adjuvant remains localized at the vaccine injection site, adult BALB/c female mice (n=10) carrying in their germ line firefly luciferase cDNA under the control of NF-kB-responsive promoter will be used. These "NF-kB reporter mice" are a sensitive tool for the detection of release of CBLB502 from the injection site by monitoring the luciferase activity in TLR5-positive tissues such as liver or small intestine. Only one dose of CBLB502-containing adjuvant formulation will be used that corresponds to the highest dose that demonstrated stability as a composition with Alum in vitro (presumably 30 μg). Two doses of free CBLB502 (1 and 3 μg in aqueous solution, s.c. injection) will be used for comparison as positive controls of systemically distributed TLR5 agonist. Luciferase detection will be done using a luminescent imager in vivo following luciferin injection at 2, 4, 6 and 18 hours post injection of the adjuvant. For a more accurate and sensitive detection, 3 animals from each group are sacrificed 6 hours post injection of the adjuvant formulation and tissues will be collected from the injection site, lymph nodes nearest to injection site and the liver. The level of luciferase activity indicative of the presence of CBLB 502 is quantitated in these tissue samples following tissue lysis. In addition to functional detection of CBLB 502 based on its expected NF-kB-inducing activity, an alternative analytical method of an established sensitive ELISA assay for direct detection of CBLB502 in tissue extracts is used.

Adjuvant formulations containing the above-described range of doses of CBLB502 are mixed with 10 mg of ovalbumin and vaccination is performed, as described herein, followed by the ELISA determination of titers of different classes of anti-albumin IgG (IgG1, IgG2a, IgG2b and IgG3) antibodies. The results are compared with "Alum only" control. Determination of the effects on different IgG types provides definition of the degrees of engagement of different immunization paths (e.g. $T_{H1}$- versus $T_{H2}$-mediated routes) by the adjuvant.

After determination of the composition of the adjuvant (in terms of anti-ovalbumin antibody inducing efficacy), additional enhancement of immunization is tested by adding into the formulation a NOD1 agonist, C12-iE-DAP.

Also, determination of vaccine efficacy at different CBLB 502 doses to generate antibodies to antigen is undertaken in mice. Female mice are chosen because they have stronger immune responses than male mice and BALB/c mice are a commonly used strain in immunological studies due to their robust immune responses. At the beginning of the study, mice weigh about 25 g and are group-housed (5 per cage) in standard acrylic cages (7"×11"×5") with corncob bedding polycarbonate and tops. Mice will have ad libitum access to food (Harlan) and water. The vivarium will be maintained at 22±1° C. and on a 12:12 light/dark cycle (lights on at 6 AM). All experimental procedures are approved by the Institutional Animal Care and Use Committee (IACUC) and are within the guidelines delineated in the Guide for the Care and Use of Laboratory Animals.

Mice are intramuscularly injected with the vaccine in the gluteal muscle. Each group is optionally immunized with a booster dose with the same vaccine formulation at 3 and 6 weeks post initial immunization. If persistent antibody levels are not maintained for at least 4 weeks, an additional immunization will be given at week 10.

Blood is drawn at 14, 28, 42, 56 and 84 days post initial immunization and allowed to clot at room temperature for 2 hours. Serum is collected after centrifugation at 4000 rpm for 15 min. Samples are stored at −80 degrees until ready to run the enzyme linked immunosorbent assays (ELISA). In the context of a vaccine with antigen X, anti-antigen X specific antibodies are assessed by ELISAs. To measure the antibodies, ELISA plates (Immulon 2HB, Daigger, Vernon Hills, Ill.) are coated overnight in carbonate buffer (0.05 M; pH 9.6) using fish gelatin, which is a heterologous carrier protein, as the conjugate partner for SMA. Pooled or individual serum samples are added to plates in 2 fold serial dilutions starting at 1K in phosphate buffered saline (PBS)-Tween (0.1%) and incubated for 2 hours. Plates are washed with PBS-Tween prior to adding goat anti-mouse IgG conjugated to horse-radish peroxidase (HRP) (Southern Biotech, Birmingham, Ala.). Plates are incubated for another 30 min and washed before adding substrate (Tetramethylbenzidine, Sigma, St. Louis, Mo.). Plates are incubated for 45 min in the dark prior to stopping the reaction with 1M HCl. The optical density (OD) of the resulting dark spots on the plates from the antibody with antigen X linking are used to measure titer levels on a microplate reader (iMark Microplate Absorbance Reader) using Microplate Manager v 6.1 software.

ELISA data is analyzed using SigmaPlot (Systat Software Inc.) and background antibody binding to the carrier alone will be subtracted from each sample. Comparisons are made in each plate with a standard curve of purified mouse IgG (Sigma) bound directly in the wells in serial dilution.

Example 10: Comparison of CBLB502-Based Adjuvants/Vaccines with Flagellin-Based Adjuvants/Vaccines The CBLB502/alum adjuvant of the above Examples is tested head to head against a flagellin/alum adjuvant using the methods and study design of, for instance, Example 9 (optionally with an antigen). Further, the alum binding and dissociation studies, as well as the mouse evaluation studies, all described in the above Examples, are repeated with a flagellin/alum adjuvant for comparison to the CBLB502/alum adjuvant. The efficacy of the CBLB502 variant, i.e., CBLB502-S33MX is also tested.

In one comparison experiment, a group of mice (n=6) is immunized with TT-SMA, which is a methamphetamine vaccine and is used illustratively, co-adsorbed onto Alhydrogel with either flagellin, CBLB502, or CBLB502-S33MX. Immunication is carried out on days 0, 14, and 28 of the study. Each immunization dose includes 32 μg of TT-SMA and adjuvants as follows: Group 1: 0.03 μg flagellin, Group 2: 0.1 μg flagellin, Group 3: 0.3 μg flagellin, Group 4: 1 μg flagellin, Group 5: 0.03 μg CBLB502, Group 6: 0.1 μg CBLB502, Group 7: 0.3 μg CBLB502, Group 8: 1 μg CBLB502, Group 9: 0.03 μg CBLB502-S33MX, Group 10: 0.1 μg CBLB502-S33MX, Group 11: 0.3 μg CBLB502-S33MX, and Group 12: 1 μg CBLB502-S33MX.

Serum samples are collected and analyzed on days −1 (pre-immune serum), 14 (post-prime), 28 (post first boost), and 35 (post second boost). For example, the serum samples are analyzed for the levels of anti-methamphetamine and anti-entolimod antibodies. Analysis indicates that CBLB502/alum and CBLB502-S33MX/alum cause a broader, more diverse, more robust and longer immunostimulatory effect than flagellin/alum. In addition, CBLB502/alum and CBLB502-S33MX/alum activate both $T_{H1}$ and $T_{H2}$-mediated immune response and a greater $T_{H1}$-mediated immune response than flagellin/alum.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

REFERENCES

1. Yoon S I, Kurnasov O, Natarajan V, Hong M, Gudkov A V, Osterman A L, Wilson I A., 2012. Structural Basis of TLR5-Flagellin Recognition and Signaling. Science 335: 859-864 (PMID: 22344444)
2. Smith K D, Andersen-Nissen E, Hayashi F, Strobe K, Bergman M A, Barrett S L, Cookson B T, Aderem A. 2003. Toll-like receptor 5 recognizes a conserved site on flagellin required for protofilament formation and bacterial motility. Nat Immunol. 4:1247-53 (PMID: 14625549)
3. Mizel, S. B., A. P. West, R. R. Hantgan. 2003. Identification of a sequence in human Toll-like receptor 5 required for the binding of Gram-negative flagellin. J. Biol. Chem. 278:23624-23629 (PMID: 12711596)
4. Murthy, K. G., Deb, A., Goonesekera, S., Szabo, C. & Salzman, A. L. (2004) J. Biol. Chem. 279:5667-5675 (PMID: 14634022)
5. Andersen-Nissen E., Smith K. D., Strobe K. L., Barrett S. L., Cookson B. T., Logan S. M., Aderem A. (2005) Evasion of Toll-like receptor 5 by flagellated bacteria. Proc. Natl. Acad. Sci. U.S.A. 102: 9247-9252 (PMID: 15956202)
6. Andersen-Nissen E, Smith K D, Bonneau R, Strong R K, Aderem A. 2007. A conserved surface on Toll-like receptor 5 recognizes bacterial flagellin. J Exp Med. 204:393-403 (PMID: 17283206)
7. Burdelya L G, Krivokrysenko V I, Tallant T C, Strom E, Gleiberman A S, Gupta D, Kurnasov O V, Fort F L, Osterman A L, Didonato J A, Feinstein E, Gudkov A V., 2008. An agonist of Toll-like receptor 5 has radioprotective activity in mouse and primate models. Science 320: 226-230 (PMID: 18403709).
8. Huleatt J W, Nakaar V, Desai P, Huang Y, Hewitt D, Jacobs A, Tang J, McDonald W, Song L, Evans R K et al. 2008. Potent immunogenicity and efficacy of a universal influenza vaccine candidate comprising a recombinant fusion protein linking influenza M2e to the TRL5 ligand flagellin. Vaccine. 26:201-214.

What is claimed is:

1. A method of vaccinating a subject against influenza, comprising administering an effective amount of a vaccine comprising:

(a) an adjuvant comprising a flagellin-based agent having TLR5 agonist activity and an aluminum gel or salt and (b) an antigen which stimulates protective immunity against influenza, wherein the antigen is a constituent of an influenza infectious agent selected from a live and attenuated, killed, inactivated, and toxoid influenza infectious agent.

2. The method of claim 1, wherein the flagellin-based agent comprises an amino acid sequence having at least 95% identity with SEQ ID NO: 2.

3. The method of claim 1, wherein the flagellin-based agent is the amino sequence of SEQ ID NO: 2.

4. The method of claim 1, wherein the flagellin-based agent comprises an amino acid sequence having at least 95% identity with one or more of CBLB502-S33 (SEQ ID NO: 17), CBLB502-S33ML (SEQ ID NO: 35), CBLB502-485CT (CBLB533, SEQ ID NO: 71), and CBLB502-S33MX (SEQ ID NO: 150).

5. The method of claim 1, wherein the flagellin-based agent inhibits and abrogates the ability of neutralizing anti-flagellin antibodies to neutralize the adjuvant.

6. The method of claim 1, wherein the aluminum gel or salt is selected from aluminum hydroxide, aluminum phosphate, and aluminum sulfate.

7. The method of claim 1, wherein one or more of the flagellin-based agent and/or the antigen is adsorbed to the aluminum gel or salt.

8. The method of claim 1, wherein the flagellin-based agent and aluminum gel or salt are mixed to form a stable complex.

9. The method of claim 1, wherein the flagellin-based agent and aluminum gel or salt are mixed in a ratio that is substantially below a loading capacity of the aluminum salt.

10. The method of claim 8, wherein the flagellin-based agent and aluminum gel or salt are mixed in a ratio (w/w) of about 1:500, or about 1:600, or about 1:700, or about 1:800, or about 1:900, or about 1:1000, or about 1:2000, or about 1:5000, or about 1:10000.

11. The method of claim 1, wherein the antigen is a constituent of an inactivated influenza virus.

12. The method of claim 1, wherein the vaccine further comprises an additional adjuvant selected from oil-in-water emulsion formulations, saponin adjuvants, ovalbumin, Freund's Adjuvant, cytokines, and chitosans.

13. The method of claim 1, wherein the vaccine and/or adjuvant causes immunostimulation of one or more of a $T_{H1}$ and $T_{H2}$-mediated immune response.

14. The method of claim 1, wherein the administering is orally or by parenteral injection.

15. The method of claim 1, wherein the administering takes place by controlled-release or sustained-release.

16. The method of claim 1, wherein the vaccine is administered once per subject or is used in a booster strategy.

* * * * *